(12) United States Patent
Song et al.

(10) Patent No.: US 7,678,913 B2
(45) Date of Patent: Mar. 16, 2010

(54) UREAS AS FACTOR XA INHIBITORS

(75) Inventors: Yonghong Song, Foster City, CA (US);
Bing-Yan Zhu, Palo Alto, CA (US);
Shumei Wang, Foster City, CA (US);
Chhaya Bhakta, Hayward, CA (US);
Robert M. Scarborough, Half Moon Bay, CA (US)

(73) Assignee: Portola Pharmaceuticals, Inc., South San Francisco, CA (US)

( * ) Notice: Subject to any disclaimer, the term of this patent is extended or adjusted under 35 U.S.C. 154(b) by 1133 days.

(21) Appl. No.: 11/298,317

(22) Filed: Dec. 7, 2005

(65) Prior Publication Data
US 2006/0160821 A1 Jul. 20, 2006

Related U.S. Application Data

(60) Provisional application No. 60/634,201, filed on Dec. 7, 2004.

(51) Int. Cl.
*A61K 31/48* (2006.01)
*C07D 207/40* (2006.01)
*C07D 215/38* (2006.01)

(52) U.S. Cl. ..................... 546/158; 548/546
(58) Field of Classification Search ............ 514/211.02; 548/546; 546/158
See application file for complete search history.

(56) References Cited

U.S. PATENT DOCUMENTS

| 4,588,587 | A | 5/1986 | Gasic |
| 6,362,177 | B1 | 3/2002 | Shiota et al. |
| 6,534,694 | B2 * | 3/2003 | Kling et al. ............. 604/366 |
| 7,405,209 | B2 * | 7/2008 | Marquis et al. ........ 514/211.03 |
| 2004/0038858 | A1 | 2/2004 | Dorsch et al. |
| 2005/0137230 | A1 | 6/2005 | Dorsch et al. |
| 2006/0160790 | A1 | 7/2006 | Song et al. |

FOREIGN PATENT DOCUMENTS

| EP | 0798295 | 10/1997 |
| WO | WO94/13693 | 6/1994 |
| WO | WO 97/14689 A1 | 4/1997 |
| WO | WO98/28269 | 7/1998 |
| WO | WO99/10316 | 3/1999 |
| WO | WO97/21437 | 4/2002 |
| WO | WO02/48099 | 6/2002 |
| WO | WO 2004/024679 A1 | 3/2004 |
| WO | WO 2005/056528 A1 | 6/2005 |

OTHER PUBLICATIONS

Berge et al., "Pharmaceutical Salts," *Journal of Pharmaceutical Sciences*, Jan. 1977, vol. 66, No. 1, pp. 1-19.

Claeson, Goran, "Synthetic Peptides and Peptidomimetics as Substrates and Inhibitors of Thrombin and Other Proteases in the Blood Coagulation System", *Blood Coagulation Fibrinolysis*, 1994, vol. 5, pp. 411-436.

Elõdi et al., "Optimization of Conditions for the Catalytic Effect of the Factor IXa-Factor VIII Complex: Probable Role of the Complex in the Amplification of Blood Coagulation", *Thrombosis Research*, 1979, vol. 15, pp. 617-629.

Fressinaud et al., "Therapeutic monitoring of Von Willebrand Disease: Interest and Limits of a Platelet Function Analyser at High Shear Rates", *British Journal of Haematology*, 1999, vol. 106, No. 3, pp. 777-783.

Hauptmann et al., "Comparison of the Anticoagulant and Antithrombotic Effects of Synthetic Thrombin and Factor Xa Inhibitors", *Thrombosis and Haemostasis*, 1990, vol. 63, pp. 220-223.

Hitomi et al., "Inhibitory Effect of New Synthetic Protease Inhibitor (fut-175) on the Coagulation System", *Haemostasis*, 1985, vol. 15, pp. 164-168.

Kam et al., "Mechanism Based Isocoumarin Inhibitors for Trypsin and Blood Coagulation Serine Proteases: New Anticoagulants", *Biochemistry*, 1988, vol. 27, pp. 2547-2557.

Maugeri, et al., "Transcellular Metabolism of Arachidonic Acid: Increased Platelet Thromboxane Generation in the Presence of Activated Polymorphonuclear Leukocytes", *Blood*, 1992, vol. 80, No. 2, pp. 447-451.

Nutt et al., "The Amino Acid sequence of Antistasin, a Potent Inhibitor of Factor Xa Reveals a Repeated Internal Structure", *Journal Biological Chemistry*, 1988, vol. 263, No. 21, pp. 10162-10167.

Rocca et al., "Cyclooxygenase-2 Expression is Induced During Human Megakaryopoiesis and Characterizes Newly Formed Platelets", *Proceedings of National Academy of Sciences*, 2002, vol. 99, No. 11, pp. 7634-7639.

Sturzebecher et al., "Synthetic Inhibitors of Bovine Factor Xa and Thrombin. Comparison of Their Anticoagulant Efficiency", *Thrombosis Research*, 1989, vol. 54, pp. 245-252.

Tidwell et al., "Strategies for Anticoagulation With Synthetic Protease Inhibitors. Xa Inhibitors Versus Thrombin Inhibitors", *Thrombosis Research*, 1980, vol. 19, pp. 339-349.

Turner et al., "p-Amidino Esters as Irreversible Inhibitors of Factor IXa and Xa and Thrombin", *Biochemistry*, 1986, vol. 25, pp. 4929-4935.

Valles et al., "Erythrocytes Metabolically Enhance Collagen-Induced Platelet Responsiveness Via Increased Thromboxane Production, Adenosine Diphosphate Release, and Recruitment", *Blood*, 1991, vol. 78, No. 1, pp. 154-162.

(Continued)

*Primary Examiner*—D. Margaret Seaman
(74) *Attorney, Agent, or Firm*—Townsend and Townsend and Crew LLP

(57) ABSTRACT

The present invention is directed to compounds represented by Formula I and pharmaceutically acceptable salts, solvates, hydrates, and prodrugs thereof which are inhibitors of Factor Xa. The present invention is also directed to and intermediates used in making such compounds, pharmaceutical compositions containing such compounds, methods to prevent or treat a number of conditions characterized by undesired thrombosis and methods of inhibiting the coagulation of a blood sample.

34 Claims, 23 Drawing Sheets

OTHER PUBLICATIONS

Wang et al., "Immunological Characterization of Urinary 8-epi-Prostaglandin F2 Alpha Excretion in Man", *Journal of Pharmacology and Experimental Therapeutics*, 1995, vol. 275, No. 1, pp. 94-100.

Wang et al., "Incidence of Aspirin Nonresponsiveness Using the Ultegra Rapid Platelet Function Assay-ASA", *American Journal of Cardioliology*, 2003, vol. 92, No. 12, pp. 1492-1494.

Waxman et al., "Tick Anticoagulant peptide (TAP) is a Novel Inhibitor of Blood Coagulation Factor Xa", *Science*, 1990, vol. 248, pp. 593-596.

Yin et al., "Antiaggregatory Activity of 8-Epi-Prostaglandin F2 Alpha and Other F-Series Prostanoids and Their Binding to Thromboxane A2/Prostaglandin H2 Receptors in Human Platelets", *The Journal of Pharmacology and Experimental Therapeutics*. 1994, vol. 270, No. 3, pp. 1192-1196.

Patani, et al. "Bioisosterism: A Rational Approach in Drug Design," Chem. Rev., 1996, vol. 96, pp. 3147-3176.

Wolff, Manfred, et al. "Burger's Medicinal Chemistry, 5ed, Part I," John Wiley & sons, 1995, pp. 975-977.

West, Anthony, R. Solid State Chemistry and it's Applications, Wiley, New York, 1988, pp. 358-365.

* cited by examiner

UREAS AS FACTOR XA INHIBITORS

CROSS-REFERENCES TO RELATED APPLICATIONS

This application claims the benefit of U.S. Patent Application Ser. No. 60/634,201, filed Dec. 7, 2004, the content of which is incorporated herein by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfunction or other disruption. Although platelets and blood coagulation are both involved in thrombus formation, certain components of the coagulation cascade are primarily responsible for the amplification or acceleration of the processes involved in platelet aggregation and fibrin deposition.

Thrombin is a key enzyme in the coagulation cascade as well as in hemostasis. Thrombin plays a central role in thrombosis through its ability to catalyze the conversion of fibrinogen into fibrin and through its potent platelet activation activity. Direct or indirect inhibition of thrombin activity has been the focus of a variety of recent anticoagulant strategies as reviewed by Claeson, G., "Synthetic Peptides and Peptidomimetics as Substrates and Inhibitors of Thrombin and Other Proteases in the Blood Coagulation System", *Blood Coag. Fibrinol.*, 5:411-436 (1994). Several classes of anticoagulants currently used in the clinic directly or indirectly affect thrombin (i.e. heparins, low-molecular weight heparins, heparin-like compounds and coumarins).

A prothrombinase complex, including Factor Xa (a serine protease, the activated form of its Factor X precursor and a member of the calcium ion binding, gamma carboxyglutamyl (Gla)-containing, vitamin K dependent, blood coagulation glycoprotein family), converts the zymogen prothrombin into the active procoagulant thrombin. Unlike thrombin, which acts on a variety of protein substrates as well as at a specific receptor, factor Xa appears to have a single physiologic substrate, namely prothrombin. Since one molecule of factor Xa may be able to generate up to 138 molecules of thrombin (Elodi et al., *Thromb. Res.* 15:617-619 (1979)), direct inhibition of factor Xa as a way of indirectly inhibiting the formation of thrombin may be an efficient anticoagulant strategy. Therefore, it has been suggested that compounds which selectively inhibit factor Xa may be useful as in vitro diagnostic agents, or for therapeutic administration in certain thrombotic disorders, see e.g., WO 94/13693.

Polypeptides derived from hematophagous organisms have been reported which are highly potent and specific inhibitors of factor Xa. U.S. Pat. No. 4,588,587 describes anticoagulant activity in the saliva of the Mexican leech, *Haementeria officinalis*. A principal component of this saliva was shown to be the polypeptide factor Xa inhibitor, antistasin (ATS), by Nutt, E. et al., "The Amino Acid Sequence of Antistasin, a Potent Inhibitor of Factor Xa Reveals a Repeated Internal Structure", *J. Biol. Chem.*, 263:10162-10167 (1988). Another potent and highly specific inhibitor of Factor Xa, called tick anticoagulant peptide (TAP), has been isolated from the whole body extract of the soft tick *Ornithidoros moubata*, as reported by Waxman, L., et al., "Tick Anticoagulant Peptide (TAP) is a Novel Inhibitor of Blood Coagulation Factor Xa", *Science*, 248:593-596 (1990).

Factor Xa inhibitory compounds which are not large polypeptide-type inhibitors have also been reported (see e.g. Tidwell, R. R. et al., "Strategies for Anticoagulation With Synthetic Protease Inhibitors. Xa Inhibitors Versus Thrombin Inhibitors", *Thromb. Res.*, 19:339-349 (1980); Turner, A. D. et al., "p-Amidino Esters as Irreversible Inhibitors of Factor IXa and Xa and Thrombin", *Biochemistry*, 25:4929-4935 (1986); Hitomi, Y. et al., "Inhibitory Effect of New Synthetic Protease Inhibitor (FUT-175) on the Coagulation System", *Haemostasis*, 15:164-168 (1985); Sturzebecher, J. et al., "Synthetic Inhibitors of Bovine Factor Xa and Thrombin. Comparison of Their Anticoagulant Efficiency", *Thromb. Res.*, 54:245-252 (1989); Kam, C. M. et al., "Mechanism Based Isocoumarin Inhibitors for Trypsin and Blood Coagulation Serine Proteases: New Anticoagulants", *Biochemistry*, 27:2547-2557 (1988); Hauptmann, J. et al., "Comparison of the Anticoagulant and Antithrombotic Effects of Synthetic Thrombin and Factor Xa Inhibitors", *Thromb. Haemost.*, 63:220-223 (1990)).

Others have reported Factor Xa inhibitors which are small molecule organic compounds, such as nitrogen containing heterocyclic compounds which have amidino substituent groups, wherein two functional groups of the compounds can bind to Factor Xa at two of its active sites. For example, WO 98/28269 describes pyrazole compounds having a terminal C(=NH)—NH$_2$ group; WO 97/21437 describes benzimidazole compounds substituted by a basic radical which are connected to a naphthyl group via a straight or branched chain alkylene, C(O) or SO$_2$ bridging group; WO 99/10316 describes compounds having a 4-phenyl-N-alkylamidino-piperidine and 4-phenoxy-N-alkylamidino-piperidine group connected to a 3-amidinophenyl group via a carboxamidealkyleneamino bridge; and EP 798295 describes compounds having a 4-phenoxy-N-alkylamidino-piperidine group connected to an amidinonaphthyl group via a substituted or unsubstituted sulfonamide or carboxamide bridging group.

There exists a need for effective therapeutic agents for the regulation of hemostasis, and for the prevention and treatment of thrombus formation and other pathological processes in the vasculature induced by thrombin such as restenosis and inflammation. In particular, there continues to be a need for compounds which selectively inhibit factor Xa or its precursors. Compounds that have different combinations of bridging groups and functional groups than compounds previously discovered are needed, particularly compounds which selectively or preferentially bind to Factor Xa. Compounds with a higher degree of binding to Factor Xa than to thrombin are desired, especially those compounds having good bioavailability and/or solubility.

BRIEF SUMMARY OF THE INVENTION

In one aspect, the present invention provides compounds having the formula:

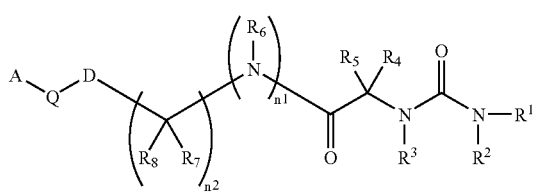

and pharmaceutically acceptable salts, hydrates, solvates and prodrugs thereof. In formula (I), each $R^1$ represents a member selected from the group consisting of: hydrogen, —$C_{1-6}$alkyl, —$C_{0-6}$alkyl-aryl, heteroaryl and —$C_{2-6}$alkenyl.

The symbol $R^2$ represents a member selected from the group consisting of: —$C_{0-6}$alkyl-aryl, —$C_{3-8}$cycloalkyaryl, heteroaryl, —$C_{3-8}$cycloalkylheteroaryl, —$C_{3-8}$cycloalkyl, —$C_{3-8}$cycloalkenyl, heteromonocyclyl, fused heterobicyclyl and unfused heterobicyclyl, optionally substituted with from 1 to 3 $R^{2a}$ substituents, wherein each heterocyclyl comprises 5 to 12 ring atoms, 1 to 4 of which are members independently selected from the group consisting of N, O and S.

The symbol $R^3$ represents a member selected from the group consisting of: hydrogen, $C_{1-6}$alkyl, heteroaryl, $C_{2-6}$alkenyl, —$C_{0-4}$alkyl-$C_{3-8}$-cycloalkyl, —$C_{0-6}$alkyl-aryl, —$C_{0-6}$alkyl-heteroaryl, —$C_{0-6}$alkyl-heterocyclyl, —$C_{0-6}$alkyl-CO—$OR^{3a}$, —$C_{1-6}$alkyl-N($^{3a}R^{3b}$), —$C_{1-6}$alkyl-O—$R^{3a}$, —$C_{1-6}$alkyl-S—$R^{3a}$, —$C_{0-6}$alkyl-C(O)—N($R^{3a}$ $R^{3b}$) and —$C_{1-6}$alkyl-N($R^{3a}$)—C(O)$R^{3b}$.

Each $R^4$ and $R^5$ is a member independently selected from the group consisting of: hydrogen, —$C_{1-6}$alkyl, —$C_{2-6}$alkenyl, —$C_{2-6}$alkynyl, —$C_{3-8}$cycloalkyl, —$C_{0-4}$alkyl-$C_{3-8}$-cycloalkyl, $C_{1-6}$haloalkyl, —$C_{0-6}$alkyl-heteroaryl, —$C_{0-6}$alkyl-heterocyclyl, —$C_{0-6}$alkyl-CN, —$C_{0-6}$alkyl-$NO_2$, —$C_{1-6}$alkyl-O—$R^{4a}$, —$C_{1-6}$alkyl-S—$R^{4a}$, —$C_{1-6}$alkyl-$SO_2$—$R^{4a}$, —$C_{1-6}$alkyl-S(O)—$R^{4a}$, —$C_{0-6}$alkyl-CO—$OR^{4a}$, —$C_{0-6}$alkyl-C(O)—N($R^{4a}$ $R^{4b}$), —$C_{0-6}$alkyl-C(O)$R^{4a}$, —$C_{1-6}$alkyl-N($R^{4a}R^{4b}$), —$C_{1-6}$alkyl-N($R^{4a}$)—C(O)$R^{4b}$, —$C_{1-6}$alkyl-N($R^{4a}$)—C(O)—N($R^{4b}R^{4c}$), —$C_{1-6}$alkyl-N($R^{4a}$)—$SO_2$—$R^{4b}$, —$C_{1-6}$alkyl-$SO_2$—N($R^{4a}R^{4b}$), —$C_{0-6}$alkyl-PO(—$OR^{4a}$)(—$OR^{4b}$), —$C_{1-6}$alkyl-N($R^{4a}$)—PO(—$OR^{4b}$)(—$OR^{4c}$), —$C_{0-6}$alkyl-aryl, —$C_{0-6}$alkyl-heteroaryl, and —$C_{0-6}$alkyl-heterocyclyl; or $R^4$ and $R^5$ can be taken together with the carbon atom to which they are attached to form a 3 to 8 membered cycloalkyl or heterocyclyl group; wherein each heterocyclyl is a 3 to 8 membered monocyclic ring or a 8-12 membered bicyclic ring, each comprising from 1 to 4 heteroatoms selected from the group consisting of O, N and S, and wherein 1 to 3 carbon or nitrogen atoms of aryl, heteroaryl and heterocyclyl are substituted with 1 to 3 $R^{4d}$ substituents.

The letter D is a member selected from the group consisting of: a direct bond, aryl, heteroaryl, $C_{3-8}$cycloalkyl, $C_{3-8}$cycloalkenyl, heteromonocyclyl, unfused heterobicyclyl, and fused heterobicyclyl; optionally substituted with 1 to 3 $R^9$ substituents, wherein each heterocyclyl comprises from 5 to 10 ring atoms, 1-4 of which are selected from the group consisting of N, O and S.

The symbol Q is selected from the group consisting of: a direct bond, —C($R^{10a}R^{10b}$)—, —C(O)—, —C(S)—, —C(=$NR^{10a}$)—, —O—, —S—, —N($R^{10a}$)—, —N($R^{10a}$)$CH_2$—, —$CH_2$N($R^{10a}$)—, —C(O)N($R^{10a}$)—, —N($R^{10a}$)C(O)—, —$SO_2$—, —SO—, —$SO_2$N($R^{10a}$)—, and —N($R^{10a}$)—$SO_2$—; and at least one of D and Q is not a direct bond.

The symbol A is selected from the group consisting of: —$NR^{11c}R^{11d}$, —C(=$NR^{11c}$)$NR^{11a}R^{11b}$, —C(=$NR^{11e}R^{11f}$)$NR^{11a}R^{11b}$, —N($R^{11d}$)C(=$NR^{11c}$)$NR^{11a}R^{11b}$, —N($R^{11d}$)C(=$NR^{11c}$)$R^{11a}$, —N($R^{11c}$)$NR^{11a}R^{11b}$, —N($R^{11c}$)$OR^{11d}$, $C_{1-6}$alkyl, $C_{2-6}$alkenyl, and pyridyl-oxide optionally substituted with 1 to 3 $R^{11g}$.

Each $R^{2a}$, $R^{4d}$, $R^9$ and $R^{11g}$ is a member independently selected from the group consisting of: H, halo, $C_{1-6}$alkyl, $C_{2-6}$alkenyl, $C_{2-6}$alkynyl, $C_{0-4}$alkyl$C_{3-8}$cycloalkyl, —$C_{1-4}$alkoxy, —O—$CO_{0-2}$alkyl-$CF_3$, —$C_{0-2}$alkyl-$CF_3$, —$C_{0-2}$alkyl-CN, —$C_{0-2}$alkyl-$NO_2$, —$C_{0-2}$alkyl-$NR^{12a}R^{12b}$, —$C_{0-2}$alkyl-$SO_2NR^{12a}R^{12b}$, —$C_{0-2}$alkyl-$SO_2R^{12a}$, —$C_{0-2}$alkyl-$SO_2R^{12a}$, —$C_{0-2}$alkyl-$CF_3$, —$C_{0-2}$alkyl-$OR^{12a}$, —$C_{0-2}$alkyl-$SR^{12a}$, —O—$CH_2$—$CH_2$—$OR^{12a}$, —O—$CH_2$—$CO_2R^{12a}$, —N($R^{12a}$)—$CH_2$—$CH_2$—$OR^{12b}$, —$C_{0-2}$alkyl-C(O)$NR^{12a}R^{12b}$, —$C_{0-2}$alkyl-$CO_2R^{12a}$, —$C_{0-2}$alkyl-N($R^{12a}$)—C(O)$R^{12b}$, —$C_{0-2}$alkyl-N($R^{12c}$)—C(O)$NR^{12a}R^{12b}$, —$C_{0-2}$alkyl-C(=$NR^{12c}$)$NR^{12a}R^{12b}$, —$C_{0-2}$alkyl-C(=$NR^{12a}$)$R^{12b}$, —$C_{0-2}$alkyl-N($R^{12d}$)C(=$NR^{12c}$)$NR^{12a}R^{12b}$, —$C_{0-2}$alkyl-N($R^{12a}$)—$SO_2$—$R^{12b}$, =O, =S, =$NR^{12a}$, 5- or 6-membered aryl, 5- or 6-membered heteroaryl and 5- to 7-membered heterocyclyl, each of which is optionally substituted with a member independently selected from the group consisting of halo, $CF_3$, $OCF_3$, $SCF_3$, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —$CONR^{12a}R^{12b}$, =O, =S —OH, —CN and —$NO_2$; wherein each heteroaryl or heterocyclyl comprises 1 to 4 heteroatoms, independently selected from the group consisting of N, O and S.

Each of the symbols $R^{3a}$, $R^{3b}$, $R^{4a}$, $R^{4b}$, $R^{12a}$, $R^{12b}$, $R^{12c}$ and $R^{12d}$ are members independently selected from the group consisting of: H, $C_{1-6}$alkyl, $C_{2-6}$alkenyl, $C_{2-6}$alkynyl, $C_{0-4}$alkyl$C_{3-8}$cycloalkyl, $C_{0-4}$alkylaryl, $C_{0-4}$alkyl-heteroaryl, —$C_{0-6}$alkyl-$COC_{1-4}$alkyl, —$C_{0-6}$alkyl-$CO_2C_{1-4}$alkyl, —$C_{0-6}$alkyl-$SO_2$—$C_{1-4}$alkyl, —$C_{0-6}$alkyl-$SO_2$—N($C_{,1-4}$alkyl, —$C_{0-6}$alkyl-N($C_{1-4}$alkyl, $C_{1-4}$alkyl) and —$C_{1-6}$alkyl-O—$C_{0-6}$alkyl, wherein 1-3 hydrogen atoms on the aryl or heteroaryl ring may be independently replaced with a member selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —CON($C_{1-4}$alkyl, $C_{1-4}$alkyl), —OH, —CN and $NO_2$; or can be taken together with the nitrogen atom to which they are attached to form a 3-8 membered heterocyclyl group, comprising 1 to 4 heteroatoms selected from the group consisting of N, O and S, optionally substituted with 1 to 4 $R^{13}$ substituents selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —CON($C_{1-4}$alkyl, $C_{1-4}$alkyl), =O, =S, —OH, —CN and $NO_2$.

Each of the symbols $R^6$, $R^7$, $R^8$, $R^{10a}$ and $R^{10b}$ is a member independently selected from the group consisting of: hydrogen, $C_{1-6}$alkyl, $C_{2-6}$alkenyl, $C_{2-6}$alkynyl, $C_{3-8}$cycloalkyl and $C_{0-4}$alkyl$C_{3-8}$cycloalkyl, —$C_{0-6}$alkyl-aryl, hetaryl and —$C_{0-6}$alkyl-heteroaryl, or $R^4$ and $R^6$ can be taken together with the atoms to which they are attached to form a 5 to 12 membered heterocyclyl group; wherein each heterocyclyl is a 5 to 8 membered monocyclic ring or a 8-12 membered bicyclic ring, each comprising from 1 to 4 heteroatoms selected from the group consisting of O, N and S, and wherein 1 to 3 carbon or nitrogen atoms of aryl, heteroaryl and heterocyclyl are substituted with 1 to 3 $R^{4d}$ substituents.

Each of the symbols $R^{11a}$, $R^{11b}$, $R^{11c}$, $R^{11d}$, $R^{11e}$ and $R^{11f}$ are members independently selected from the group consisting of: H, $C_{1-6}$alkyl, $C_{2-6}$alkenyl, $C_{2-6}$alkynyl, $C_{0-4}$alkyl $C_{3-8}$cycloalkyl, $C_{0-4}$alkylaryl, $C_{0-4}$alkyl-heteroaryl, —$C_{0-6}$alkyl-$COC_{1-4}$alkyl, —$C_{0-6}$alkyl-$CO_2C_{1-4}$alkyl, —$C_{0-6}$alkyl-$SO_2$—$C_{1-4}$alkyl, —$C_{0-6}$alkyl-$SO_2$—$NR^{12a}R^{12b}$, —$C_{0-6}$alkyl-$NR^{12a}R^{12b}$ and —$C_{1-6}$alkyl-O—$C_{0-6}$alkyl, wherein 1-3 hydrogen atoms on the aryl or heteroaryl ring may be independently replaced with a member selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —$CON(C_{1-4}$alkyl, $C_{1-4}$alkyl), —OH, —CN and $NO_2$; or each $R^{11a}$ and $R^{11b}$ can be taken together with the nitrogen atom to which they are attached to form a 3-8 membered heterocyclyl group, comprising 1 to 4 heteroatoms selected from the group consisting of N, O and S, optionally substituted with 1 to 4 $R^{13}$ substituents selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —$CON(C_{1-4}$alkyl, $C_{1-4}$alkyl), =O, =S, —OH, —CN and $NO_2$; or each $R^{11e}$ and $R^{11f}$ can be taken together with the nitrogen atom to which they are attached to form a 3-8 membered heterocyclyl group, comprising 1 to 4 heteroatoms selected from the group consisting of N, O and S, optionally substituted with 1 to 4 $R^{13}$ substituents selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —$CON(C_{1-4}$alkyl, $C_{1-4}$alkyl), =O, =S, —OH, —CN and $NO_2$.

Each of the subscripts n1 and n2 is an integer of 0 to 1.

In one aspect, the present invention provides compounds having the formula:

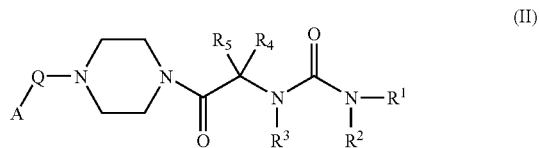

(II)

and pharmaceutically acceptable salts, hydrates, solvates and prodrugs thereof. In formula (II), $R^1$ is a member selected from the group consisting of: hydrogen, —$C_{0-6}$alkyl, —$C_{0-6}$alkyl-aryl, heteroaryl and —$C_{2-6}$alkenyl.

The symbol $R^2$ is a member selected from the group consisting of: —$C_{0-6}$alkyl-aryl, —$C_{3-8}$cycloalkylaryl, heteroaryl, —$C_{3-8}$cycloalkylheteroaryl, —$C_{3-8}$cycloalkyl, —$C_{3-8}$cycloalkenyl, heteromonocyclyl, fused heterobicyclyl and unfused heterobicyclyl, optionally substituted with from 1 to 3 $R^{2a}$ substituents, wherein each heterocyclyl comprises 5 to 12 ring atoms, 1 to 4 of which are members independently selected from the group consisting of N, O and S.

The symbol $R^3$ is a member selected from the group consisting of: hydrogen, $C_{1-6}$alkyl, heteroaryl, $C_{2-6}$alkenyl, —$C_{3-8}$cycloalkyl, —$C_{0-4}$alkyl-$C_{3-8}$-cycloalkyl, —$C_{0-6}$alkyl-aryl, —$C_{0-6}$alkyl-heteroaryl, —$C_{0-6}$alkyl-heterocyclyl, —$C_{0-6}$alkyl-CO—$OR^{3a}$, —$C_{1-6}$alkyl-N($R^{3a}R^{3b}$), —$C_{1-6}$alkyl-O—$R^{3a}$, —$C_{1-6}$alkyl-S—$R^{3a}$, —$C_{0-6}$alkyl-C(O)—N($R^{3a}R^{3b}$) and —$C_{1-6}$alkyl-N($R^{3a}$)—C(O)$R^{3b}$.

Each $R^4$ and $R^5$ is a member independently selected from the group consisting of: hydrogen, —$C_{1-6}$alkyl, —$C_{2-6}$alkenyl, —$C_{2-6}$alkynyl, —$C_{3-8}$cycloalkyl, —$C_{0-4}$alkyl-$C_{3-8}$-cycloalkyl, $C_{1-6}$haloalkyl, —$C_{0-6}$alkyl-heterocyclyl, —$C_{0-6}$alkyl-heterocyclyl, —$C_{0-6}$alkyl-CN, —$C_{0-6}$alkyl-$NO_2$, —$C_{1-6}$alkyl-O-$R^{4a}$, —$C_{1-6}$alkyl-S—$R^{4a}$, —$C_{1-6}$alkyl-$SO_2$—$R^{4a}$, —$C_{1-6}$alkyl-S(O)—$R^{4a}$, —$C_{0-6}$alkyl-CO—$OR^{4a}$, —$CO$—$C_{0-6}$alkyl-C(O)—N($R^{4a}R^{4b}$), —$C_{0-6}$alkyl-C(O)$R^{4a}$, —$C_{1-6}$alkyl-N($R^{4a}R^{4b}$), —$C_{1-6}$alkyl-N($R^{4a}$)—C(O)—N($R^{4b}R^{4c}$) —$C_{1-6}$alkyl-N($R^{4a}$)—$SO_2$—$R^{4b}$, —$C_{1-6}$alkyl-$SO_2$—N($R^{4a}R^{4b}$), —$C_0$-6alkyl-PO(—$OR^{4a}$)(—$OR^{4b}$), —$C_{1-6}$alkyl-N($R^{4a}$)—PO(—$OR^{4b}$)(—$OR^{4c}$), —$C_{0-6}$alkyl-aryl, —$C_{0-6}$alkyl-heteroaryl, and —$C_{0-6}$alkyl-heterocyclyl; or $R^4$ and $R^5$ can be taken together with the carbon atom to which they are attached to form a 3 to 8 membered heterocyclyl group; wherein each heterocyclyl is a 3 to 8 membered monocyclic ring or a 8-12 membered bicyclic ring, each comprising from 1 to 4 heteroatoms selected from the group consisting of O, N and S, and wherein 1 to 3 carbon or nitrogen atoms of aryl, heteroaryl and heterocyclyl are substituted with 1 to 3 $R^{4d}$ substituents.

The symbol Q is selected from the group consisting of: a direct bond, —C($R^{10a}R^{10b}$)—, —C(O)—, —C(S)—, —C(=$NR^{10a}$), —N($R^{10a}$)C(O)—, —$SO_2$—, and —N($R^{10a}$)—$SO_2$—.

The symbol A is selected from the group consisting of: —$NR^{11c}R^{11d}$, —C(=$NR^{11c}$)$NR^{11a}R^{11b}$, —C(=$NR^{11e}R^{11f}$)$NR^{11a}R^{11b}$, —N($R^{11d}$)C(=$NR^{11a}R^{11b}$, —N($R^{11d}$)C(=$NR^{11c}$)$R^{11a}$, —N($R^{11c}$)$NR^{11a}R^{11b}$, —N($R^{11c}$)$OR^{11d}$; $C_{1-6}$alkyl, $C_{2-6}$alkenyl, aryl, heteroaryl, —$C_{3-8}$cycloalkyl, —$C_{3-8}$cycloalkenyl, heteromonocyclyl, and fused heterobicyclyl; each of aryl, heteroaryl, heteromonocyclyl and fused heterobicyclyl, optionally substituted with 1 to 3 $R^{11g}$; wherein each hetercyclyl comprises from 5 to 10 ring atoms, 1-4 of which are selected from the group consisting of N, O and S.

Each $R^{2a}$, $R^{4d}$, $R^9$ and $R^{11g}$ is a member independently selected from the group consisting of: H, halo, $C_{1-6}$alkyl, $C_{2-6}$alkenyl, $C_{2-6}$alkynyl, $C_{0-4}$alkyl$C_{3-8}$cycloalkyl, —$C_{1-4}$alkoxy, —O—$C_{0-2}$alkyl-$CF_3$, —$C_{0-2}$alkyl-$CF_3$, —$C_{0-2}$alkyl-CN, —$C_{0-2}$alkyl-$NO_2$, —$C_{0-2}$alkyl-$NR^{12a}R^{12b}$, —$C_{0-2}$alkyl-$SO_2NR^{12a}R^{12b}$, —$C_{0-2}$alkyl-$SO_2R^{12a}$, —$C_{0-2}$alkyl-$SOR^{12a}$, —$C_{0-2}$alkyl-$CF_3$, —$C_{0-2}$alkyl-$OR^{12a}$, —$C_{0-2}$alkyl-$SR^{12a}$, —O—$CH_2$—$CH_2$—$OR^{12a}$, —O—$CH_2$—$CO_2R^{12a}$, —N($R^{12a}$)—$CH_2$—$CH_2$—$OR^{12b}$, —$C_{0-2}$alkyl-C(O)$NR^{12a}R^{12b}$, —$C_{0-2}$alkyl-$CO_2R^{12a}$, —$C_{0-2}$alkyl-N($R^{12a}$)—C(O)$R^{12b}$, —$C_{0-2}$alkyl-N($R^{12c}$)—C(O)$NR^{12a}R^{12b}$, —$C_{0-2}$alkyl-C(=$NR^{12c}$)$NR^{12a}R^{12b}$, —$C_{0-2}$alkyl-C(=$NR^{12a}$)$R^{12b}$, —$C_{0-2}$alkyl-N($R^{12d}$)C(=$NR^{12c}$)$NR^{12a}R^{12b}$, —$C_{0-2}$alkyl-N($R^{12a}$)—$SO_2$—$R^{12b}$, =O, =S, =$NR^{12a}$, 5- or 6-membered aryl, 5- or 6-membered heteroaryl and 5- to 7-membered heterocyclyl, each of which is optionally substituted with a member independently selected from the group consisting of halo, $CF_3$, $OCF_3$, $SCF_3$, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2C_{1-4}$alkyl, —$CONR^{12a}R^{12b}$, =O, =S, —OH, —CN and —$NO_2$; wherein each heteroaryl or heterocyclyl comprises 1 to 4 heteroatoms, independently selected from the group consisting of N, O and S.

Each of the symbols $R^{3a}$, $R^{3b}$, $R^{4a}$, $R^{4b}$, $R^{4c}$, $R^{11a}$, $R^{11b}$, $R^{11c}$, $R^{11d}$, $R^{11e}$, $R^{11f}R^{12a}$, $R^{12b}$, $R^{12c}$ and $R^{12d}$ are members independently selected from the group consisting of: H, $C_{1-6}$alkyl, $C_{2-6}$alkenyl, $C_{2-6}$alkynyl, $C_{0-4}$alkyl$C_{3-8}$cycloalkyl, $C_{0-4}$alkylaryl, $C_{0-4}$alkyl-heteroaryl, —$C_{0-6}$alkyl-$COC_{1-4}$alkyl, —$C_{0-6}$alkyl-$SO_2$—$C_{1-4}$alkyl, —$C_{0-6}$alkyl-$SO_2$—N($C_{1-4}$alkyl, $C_{1-4}$alkyl), —$C_{0-6}$alkyl-N($C_{1-4}$alkyl, $C_{1-4}$alkyl) and —$C_{1-6}$alkyl-O—$C_{0-6}$alkyl, wherein 1-3 hydrogen atoms on the aryl or heteroaryl ring may be independently replaced with a member selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$C_{0-2}C_{1-4}$alkyl, —$CON(C_{1-4}$alkyl, $C_{1-4}$alkyl), —OH, —CN and $NO_2$; or can be taken together with the nitrogen atom to which they are attached to form a 3-8 membered heterocyclyl group, comprising 1 to 4 heteroatoms selected from the group consisting of N, O and S, optionally substituted with 1 to 4 $R^{13}$ substituents selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —$CON(C_{1-4}$alkyl, $C_{1-4}$alkyl), =O, =S, —OH, —CN and $NO_2$.

Each of the symbols $R^{10a}$ and $R^{10b}$ is a member independently selected from the group consisting of: hydrogen, $C_{1-6}$alkyl, $C_{2-6}$alkenyl, $C_{2-6}$alkynyl, $C_{3-8}$cycloalkyl and $C_{0-4}$alkyl$C_{3-8}$cycloalkyl, —$C_{0-6}$alkyl-aryl, hetaryl and —$C_{0-6}$alkyl-heteroaryl; and wherein 1 to 3 carbon or nitrogen atoms of aryl and heteroaryl are substituted with 1 to 3 $R^{4d}$ substituents.

In one aspect, the present invention provides compounds having the formula:

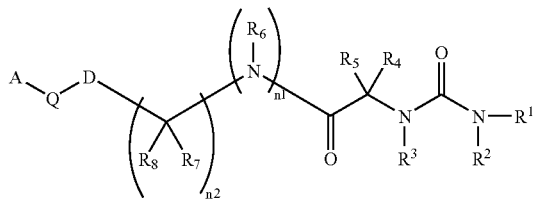

and pharmaceutically acceptable salts, hydrates, solvates and prodrugs thereof. In formula (III), $R^1$ is a member selected from the group consisting of: hydrogen, —$C_{1-6}$alkyl, —$C_{0-6}$alkyl-aryl, heteroaryl and —$C_{2-6}$alkenyl.

The symbol $R^2$ is a member selected from the group consisting of: —$C_{0-6}$alkyl-aryl, —$C_{3-8}$cycloalkylaryl, heteroaryl, —$C_{3-8}$cycloalkylheteroaryl, —$C_{3-8}$cycloalkyl, —$C_{3-8}$cycloalkenyl, heteromonocyclyl, fused heterobicyclyl and unfused heterobicyclyl, optionally substituted with from 1 to 3 $R^{2a}$ substituents, wherein each heterocyclyl comprises 5 to 12 ring atoms, 1 to 4 of which are members independently selected from the group consisting of N, O and S.

The symbol $R^3$ is a member selected from the group consisting of: hydrogen, $C_{1-6}$alkyl, heteroaryl, $C_{2-6}$alkenyl, —$C_{3-8}$cycloalkyl, —$C_{0-4}$alkyl-$C_{3-8}$-cycloalkyl, —$C_{0-6}$alkyl-aryl, —$C_{0-6}$alkyl-heteroaryl, —$C_{0-6}$alkyl-heterocyclyl, —$C_{0-6}$alkyl-CO—$OR^{3a}$, —$C_{1-6}$alkyl-$N(R^{3a}R^{3b})$, —$C_{1-6}$alkyl-O—R, —$C_{1-6}$alkyl-S—$R^{3a}$, —$C_{0-6}$alkyl-C(O)—$N(R^{3a}R^{3b})$ and —$C_{1-6}$alkyl-$N(R^{3a})$—$C(O)R^{3b}$.

Each $R^4$ and $R^5$ is a member independently selected from the group consisting of: hydrogen, —$C_{1-6}$alkyl, —$C_{2-6}$alkenyl, —$C_{2-6}$alkynyl, —$C_{3-8}$cycloalkyl, —$C_{0-4}$alkyl-$C_{3-8}$cycloalkyl, $C_{1-6}$haloalkyl, —$C_{0-6}$alkyl-heteroaryl, —$C_{0-6}$alkyl-heterocyclyl, —$C_{0-6}$alkyl-CN, —$C_{0-6}$alkyl-CN, —$C_{0-6}$alkyl-$NO_2$, —$C_{1-6}$alkyl-O—$R^{4a}$, —$C_{1-6}$alkyl-S—$R^{4a}$, —$C_{1-6}$alkyl-$SO_2$—$R^{4a}$, —$C_{1-6}$alkyl-S(O)—$R^{4a}$, —$C_{0-6}$alkyl-CO—$OR^{4a}$, —$C_{0-6}$alkyl-C(O)—$N(R^{4a}R^{4b})$, —$C_{0-6}$alkyl-$C(O)R^{4a}$, —$C_{1-6}$alkyl-$N(R^{4a}R^{4b})$, —$C_{1-6}$alkyl-$N(R^{4a})$—$C(O)R^{4b}$, —$C_{1-6}$alkyl-$N(R^{4a})$—C(O)—$N(R^{4b}R^{4c})$, —$C_{1-6}$alkyl-$N(R^{4a})$—$SO_2$—$R^{4b}$, —$C_{1-6}$alkyl-$SO_2$—$N(R^{4a}R^{4b})$, —$C_{0-6}$alkyl-PO(—$OR^{4a}$)(—$OR^{4b}$), —$C_{1-6}$alkyl-$N(R^{4a})$—PO(—$OR^{4b}$)(—$OR^{4c}$), —$C_{0-6}$alkyl-aryl, —$C_{0-6}$alkyl-heteroaryl, and —$C_{0-6}$alkyl-heterocyclyl; or $R^4$ and $R^5$ can be taken together with the carbon atom to which they are attached to form a 3 to 8 membered cycloalkyl or heterocyclyl group; wherein each heterocyclyl is a 3 to 8 membered monocyclic ring or a 8-12 membered bicyclic ring, each comprising from 1 to 4 heteroatoms selected from the group consisting of O, N and S, and wherein 1 to 3 carbon or nitrogen atoms of aryl, heteroaryl and heterocyclyl are substituted with 1 to 3 $R^{4d}$ substituents.

The letter D is a member selected from the group consisting of: a direct bond, aryl, heteroaryl, $C_{3-8}$cycloalkyl, $C_{3-8}$cycloalkenyl, heteromonocyclyl, unfused heterobicyclyl, and fused heterobicyclyl; optionally substituted with 1 to 3 $R^9$ substituents, wherein each heterocyclyl comprises from 5 to 10 ring atoms, 1-4 of which are selected from the group consisting of N, O and S.

The symbol Q is selected from the group consisting of: a direct bond, —$C(R^{10a}R^{10b})$—, —C(O)—, —C(S)—, —$C(=NR^{10a})$—, —O—, —S—, —$N(R^{10a})$—, —$N(R^{10a})CH_2$—, —$CH_2N(R^{10a})$—, —$C(O)N(R^{10a})$—, —$N(R^{10a})C(O)$—, —$SO_2$—, —SO—, —$SO_2N(R^{10a})$—, and —$N(R^{10a})$—$SO_2$—; and at least one of D and Q is not a direct bond.

In one embodiment the symbol A is dihydroimidazolyl, 1,4-diazepanyl, thiazolyl, oxazolyl, imidazolyl, pyrid-4-yl or 3-oxo-morpholin-4-yl, each optionally substituted with 1 to 3 $R^{11g}$. In another embodiment the symbol A is pyridinyl, pyrrolidinyl, homopiperazinyl, piperazinyl or morpholinyl each optionally substituted with 1 to 3 $R^{11g}$.

Each $R^{2a}$, $R^{4d}$, $R^9$ and $R^{11g}$ is a member independently selected from the group consisting of: H, halo, $C_{1-6}$alkyl, $C_{2-6}$alkenyl, $C_{2-6}$alkynyl, $C_{0-4}$alkyl$C_{3-8}$cycloalkyl, —$C_{1-4}$alkoxy, —O—$C_{0-2}$alkyl-$CF_3$, —$C_{0-2}$alkyl-$CF_3$, —$C_{0-2}$alkyl-CN, —$C_{0-2}$alkyl-$NO_2$, —$C_{0-2}$alkyl-$NR^{12a}R^{12b}$, —$C_{0-2}$alkyl-$SO_2NR^{12a}R^{12b}$, —$C_{0-2}$alkyl-$SO_2R^{12a}$, —$C_{0-2}$alkyl-$SOR^{12a}$, —$C_{0-2}$alkyl-$CF_3$, —$C_{0-2}$alkyl-$OR^{12a}$, —$C_{0-2}$alkyl-$SR^{12a}$, —O—$CH_2$—$CH_2$—$OR^{12a}$, —O—$CH_2$—$CO_2R^{12a}$, —$N(R^{12a})$—$CH_2$—$CH_2$—$OR^{12b}$, —$C_{0-2}$alkyl-$C(O)NR^{12a}R^{12b}$, —$C_{0-2}$alkyl-$CO_2R^{12a}$, —$C_{0-2}$alkyl-$N(R^{12a})$—$C(O)R^{12b}$, —$C_{0-2}$alkyl-$N(R^{12c})$—$C(O)NR^{12a}R^{12b}$, —$C_{0-2}$alkyl-$C(=NR^{12c})NR^{12a}R^{12b}$, —$C_{0-2}$alkyl-$C(=NR^{12a})R^{12b}$, —$C_{0-2}$alkyl-$N(R^{12d})C(=NR^{12c})NR^{12a}R^{12b}$, —$C_{0-2}$alkyl-$N(R^{12a})$—$SO_2$—$R^{12b}$, =O, =S, =$NR^{12a}$, 5- or 6-membered aryl, 5- or 6-membered heteroaryl and 5- to 7-membered heterocyclyl, each of which is optionally substituted with a member independently selected from the group consisting of halo, $CF_3$, $OCF_3$, $SCF_3$, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —$CONR^{12a}R^{12b}$, =O, =S, —OH, —CN and —$NO_2$; wherein each heteroaryl or heterocyclyl comprises 1 to 4 heteroatoms, independently selected from the group consisting of N, O and S.

Each of the symbols $R^{3a}$, $R^{3b}$, $R^{4a}$, $R^{4b}$, $R^{4c}$, $R^{12a}$, $R^{12b}$, $R^{12c}$ and $R^{12d}$ are members independently selected from the group consisting of: H, $C_{1-6}$alkyl, $C_{2-6}$alkenyl, $C_{2-6}$alkynyl, $C_{0-4}$alkyl$C_{3-8}$cycloalkyl, $C_{0-4}$alkylaryl, $C_{0-4}$alkyl-heteroaryl, —$C_{0-6}$alkyl-$COC_{1-4}$alkyl, —$C_{0-6}$alkyl-$CO_2C_{1-4}$alkyl, —$C_{0-6}$alkyl-$SO_2$—$C_{1-4}$alkyl, —$C_{0-6}$alkyl-$SO_2$-$N(C_{1-4}$alkyl, $C_{1-4}$alkyl), —$C_{0-6}$alkyl-$N(C_{1-4}$alkyl, $C_{1-4}$alkyl) and —$C_{1-6}$alkyl-O—$C_{0-6}$alkyl, wherein 1-3 hydrogen atoms on the aryl or heteroaryl ring may be independently replaced with a member selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —$CON(C_{1-4}$alkyl, $C_{1-4}$alkyl), —OH, —CN and $NO_2$; or can be taken together with the nitrogen atom to which they are attached to form a 3-8 membered heterocyclyl group, comprising 1 to 4 heteroatoms selected from the group consisting of N, O and S, optionally substituted with 1 to 4 $R^{13}$ substituents selected from the group consisting of: halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —$CON(C_{1-4}$alkyl, $C_{1-4}$alkyl), =O, =S, —OH, —CN and $NO_2$.

Each of the symbols $R^6$, $R^7$, $R^8$, $R^{10a}$ and $R^{10b}$ is a member independently selected from the group consisting of: hydrogen, $C_{1-6}$alkyl, $C_{2-6}$alkenyl, $C_{2-6}$alkynyl, $C_{3-8}$cycloalkyl and $C_{0-4}$alkyl$C_{3-8}$cycloalkyl, —$C_{0-6}$alkyl-aryl, hetaryl and —$C_{0-6}$alkyl-heteroaryl, or $R^4$ and $R^6$ can be taken together with the atoms to which they are attached to form a 5 to 12 membered heterocyclyl group; wherein each heterocyclyl is a 5 to 8 membered monocyclic ring or a 8-12 membered bicyclic ring, each comprising from 1 to 4 heteroatoms selected from the group consisting of O, N and S, and wherein 1 to 3 carbon or nitrogen atoms of aryl, heteroaryl and heterocyclyl are substituted with 1 to 3 $R^{4d}$ substituents.

Each of the subscripts n1 and n2 is an integer of 0 to 1.

The present invention further provides chemical intermediates, pharmaceutical compositions and methods for preventing or treating a condition in a mammal characterized by undesired thrombosis comprising the step of administering to said mammal a therapeutically effective amount of a compound of the present invention. Such conditions include but are not limited to acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like.

The present invention further provides methods for inhibiting the coagulation of a blood sample comprising contacting said sample with a compound of the present invention.

DETAILED DESCRIPTION OF THE INVENTION

Abbreviations and Definitions

Figure 1A:
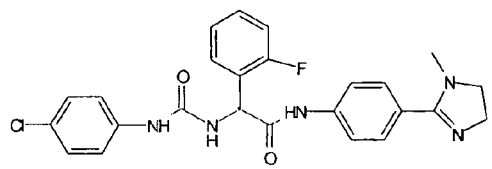
FIG. 1A-W illustrates a variety of embodiments of compounds of the invention.
Figure 1A:
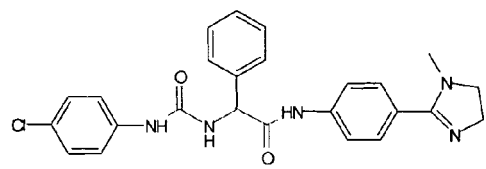
Figure 1A:
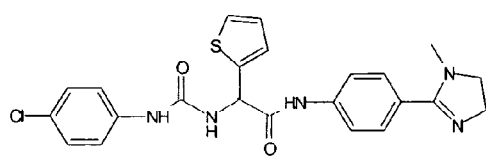
Figure 1A:
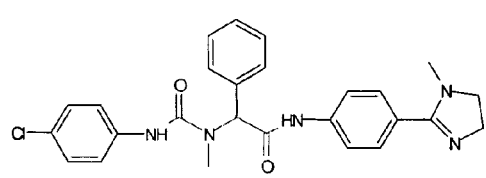
Figure 1A:
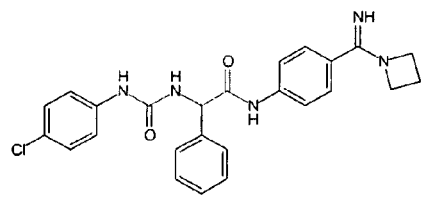
Figure 1A:
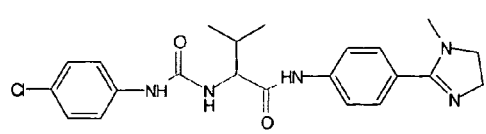
Figure 1A:
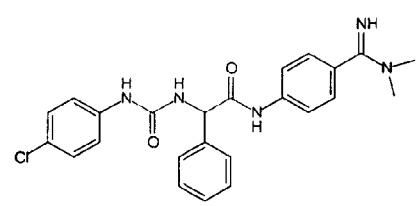
Figure 1A:
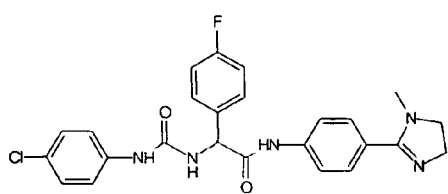
Figure 1A:
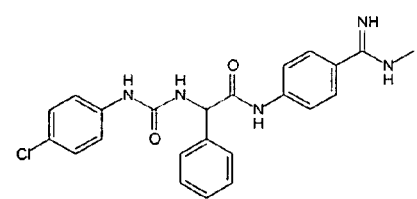
Figure 1B:
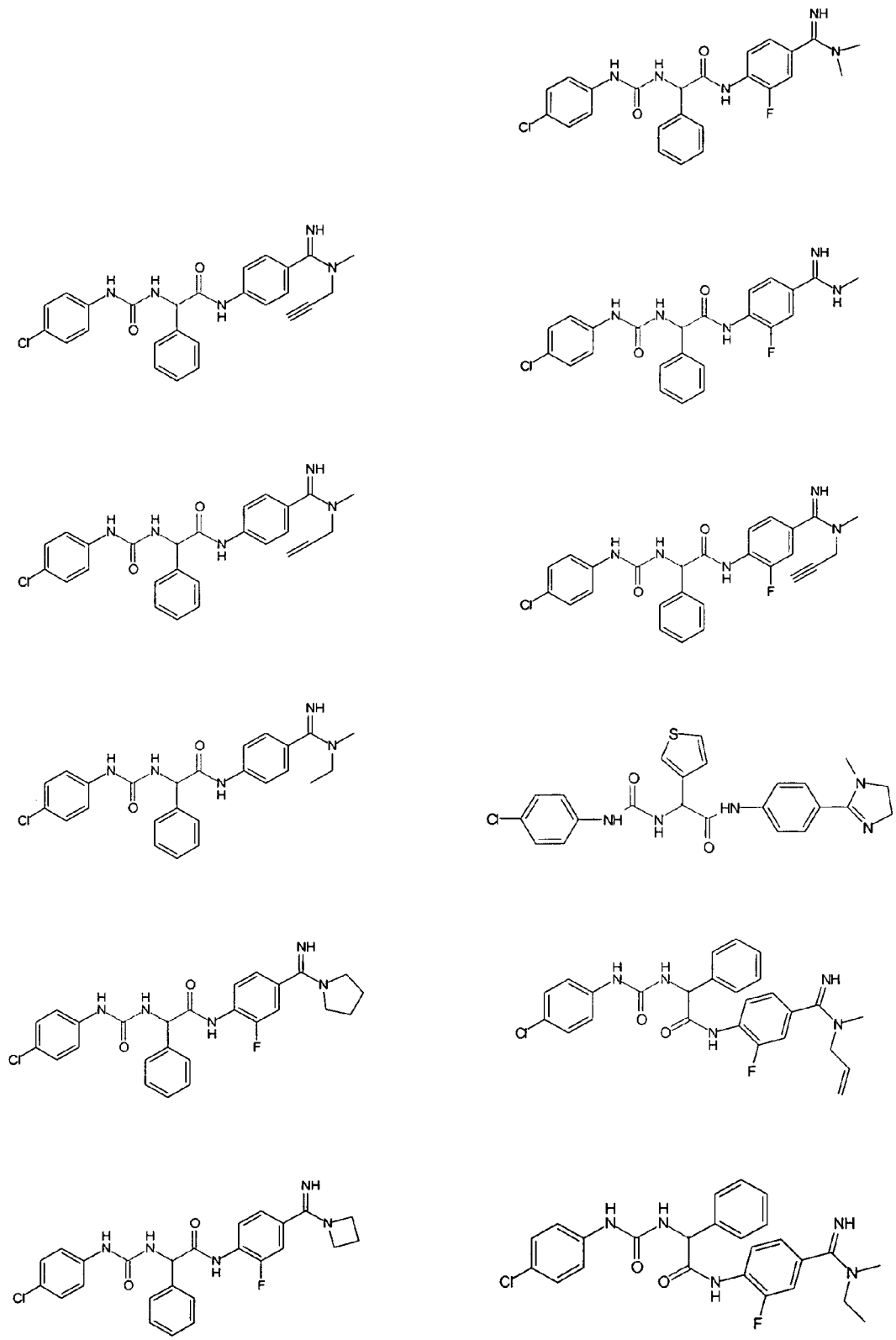
Figure 1C:
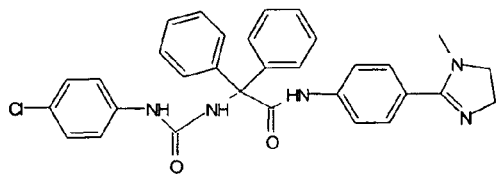
Figure 1C:
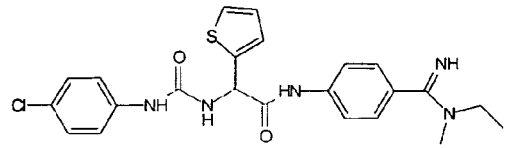
Figure 1C:
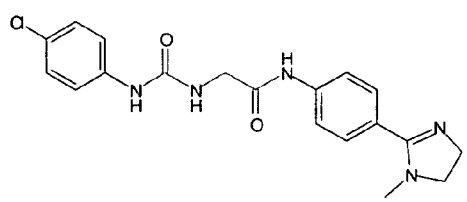
Figure 1C:
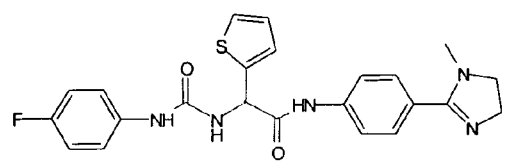
Figure 1C:
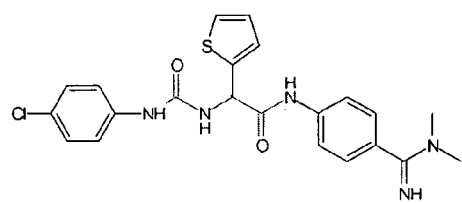
Figure 1C:
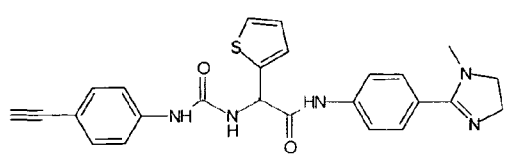
Figure 1C:
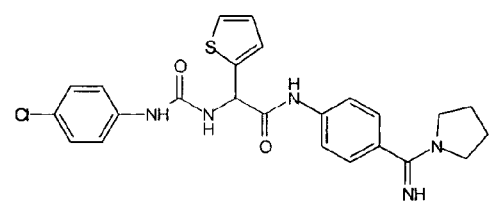
Figure 1C:
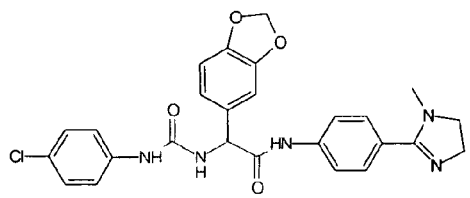
Figure 1C:
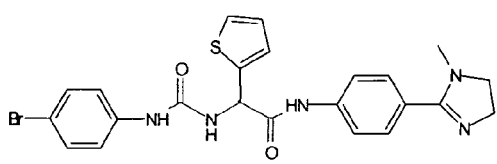
Figure 1C:
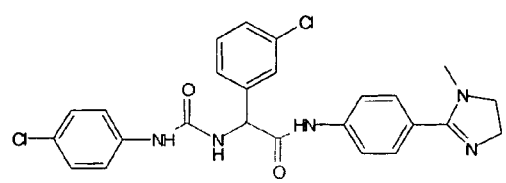
Figure 1C:
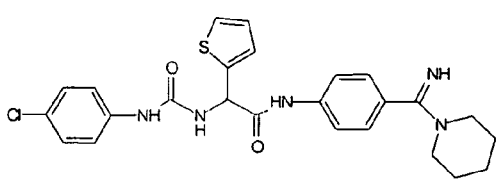
Figure 1C:
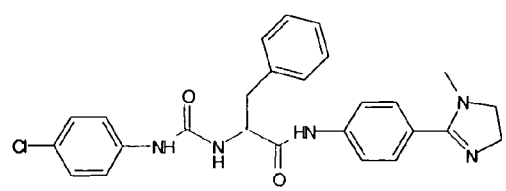
Figure 1D:
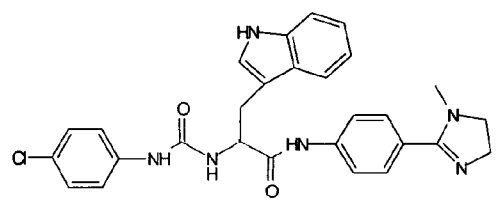
Figure 1D:
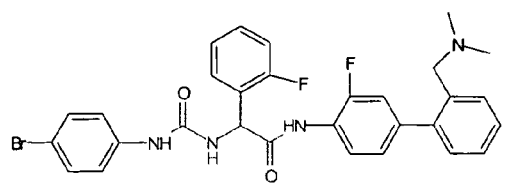
Figure 1D:
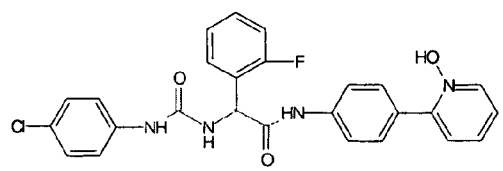
Figure 1D:
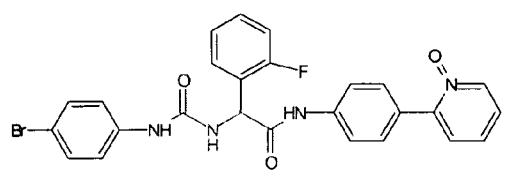
Figure 1D:
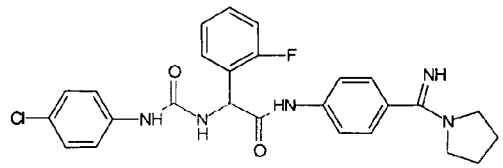
Figure 1D:
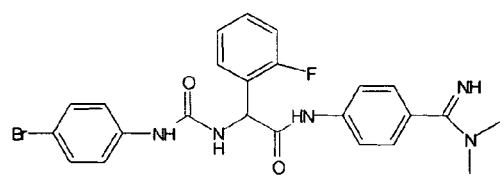
Figure 1D:
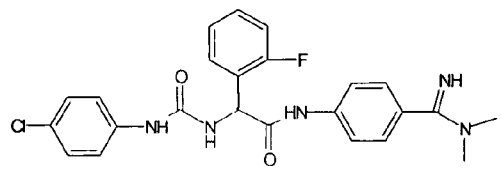
Figure 1D:
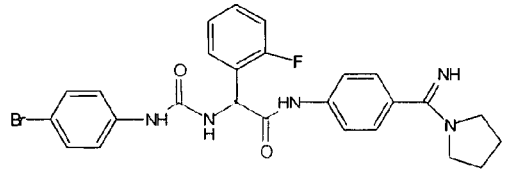
Figure 1D:
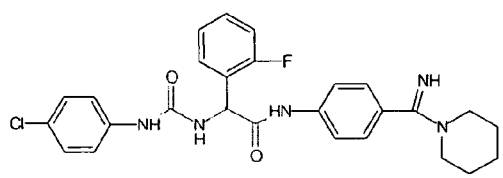
Figure 1D:
Figure 1D:
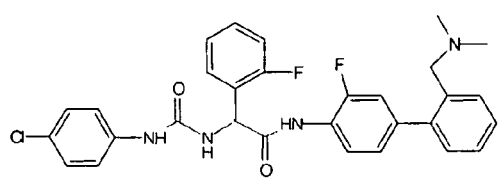
Figure 1E:
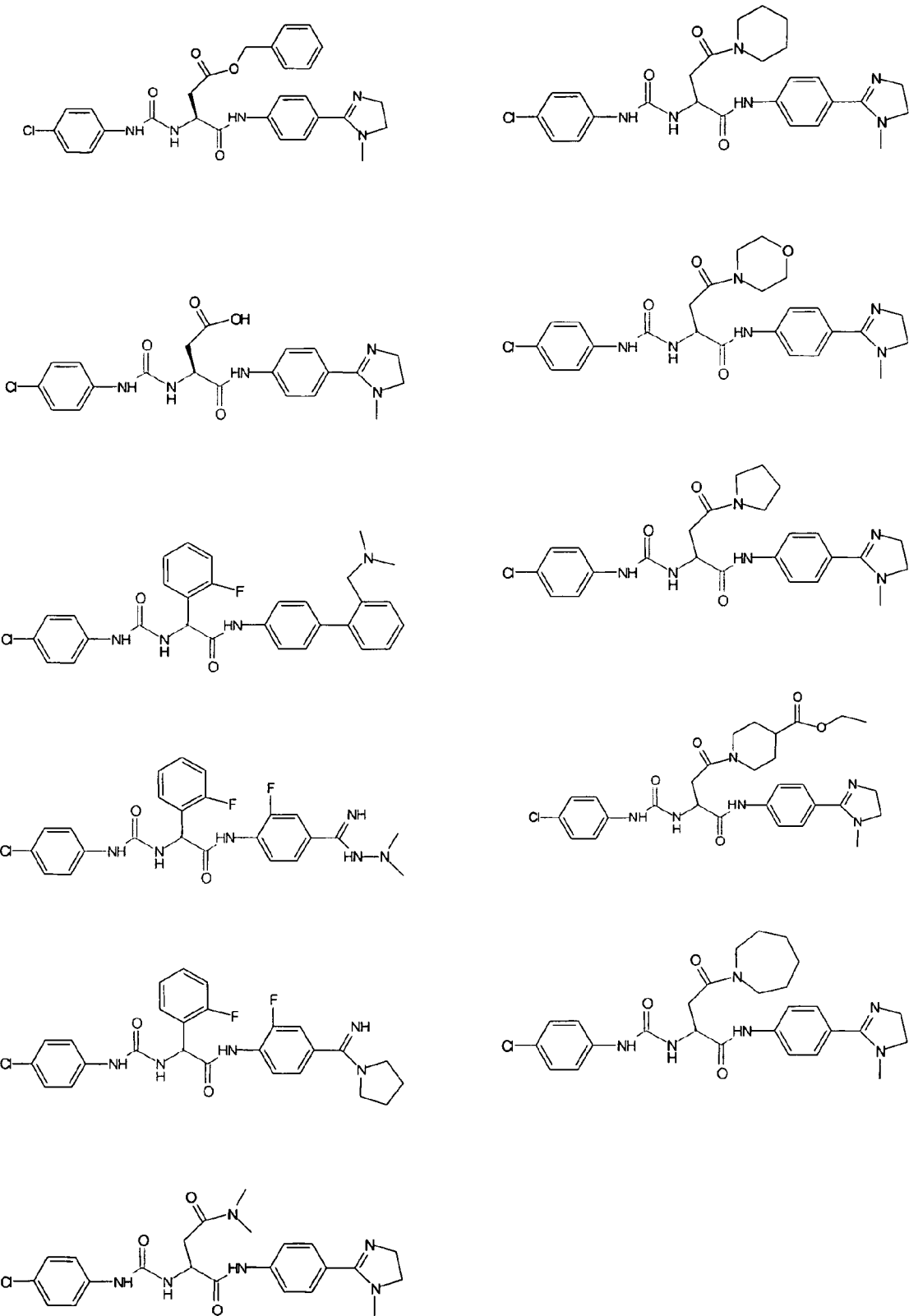
Figure 1F:
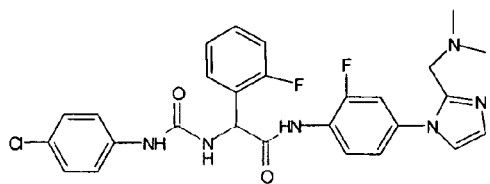
Figure 1F:
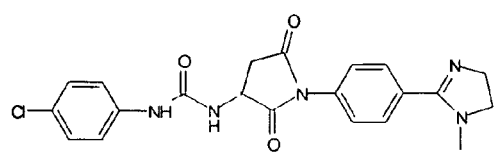
Figure 1F:
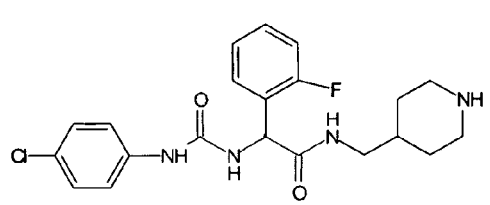
Figure 1F:
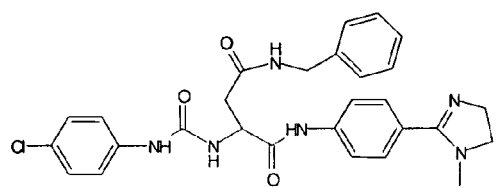
Figure 1F:
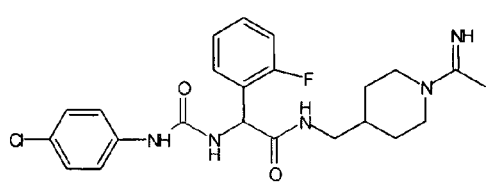
Figure 1F:
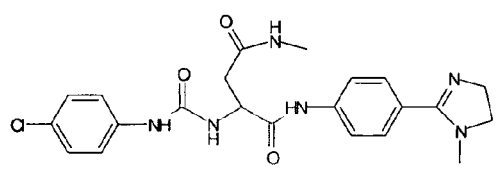
Figure 1F:
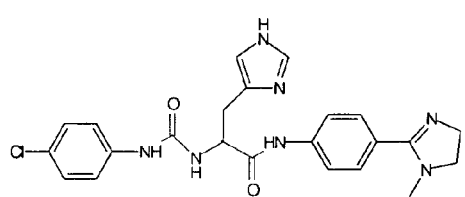
Figure 1F:
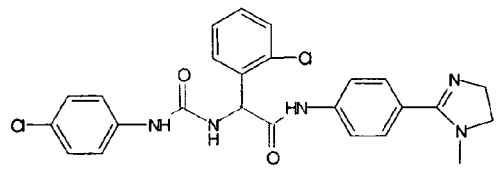
Figure 1F:
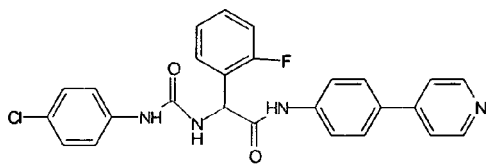
Figure 1F:
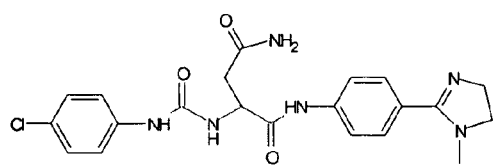
Figure 1F:
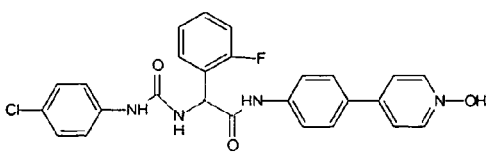
Figure 1F:
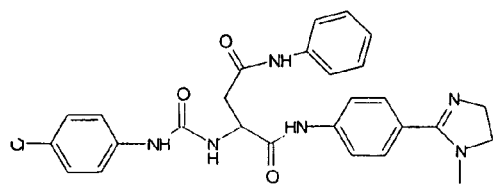
Figure 1G:
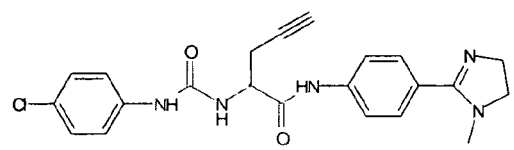
Figure 1G:
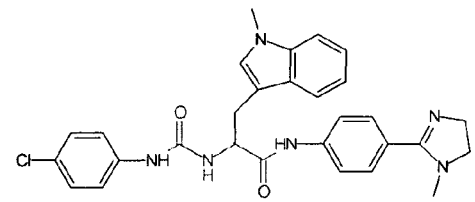
Figure 1G:
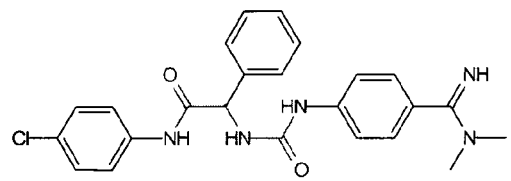
Figure 1G:
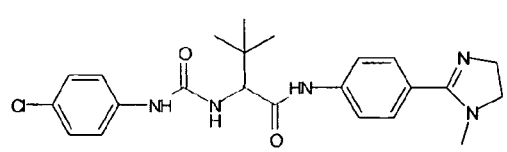
Figure 1G:
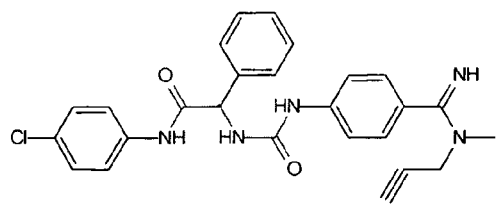
Figure 1G:
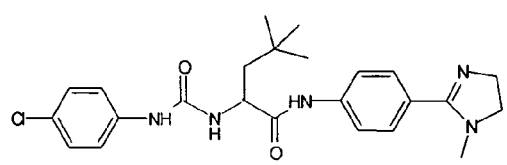
Figure 1G:
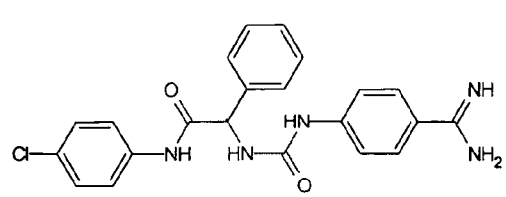
Figure 1H:
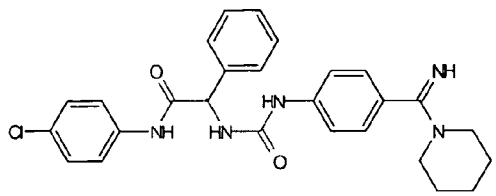
Figure 1H:
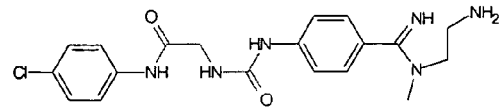
Figure 1H:
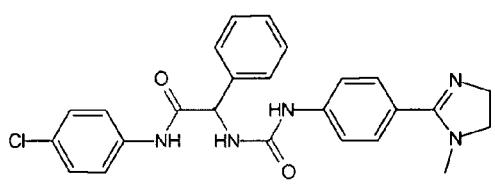
Figure 1H:
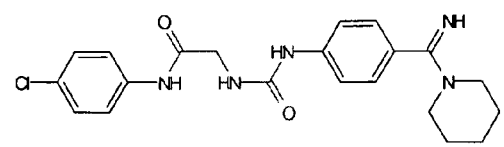
Figure 1H:
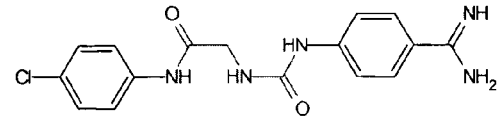
Figure 1H:
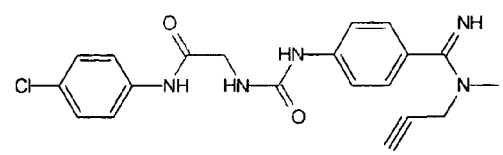
Figure 1H:
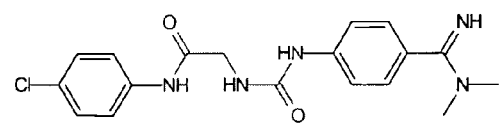
Figure 1H:
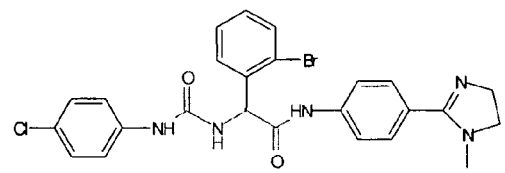
Figure 1H:
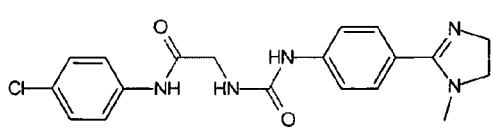
Figure 1H:
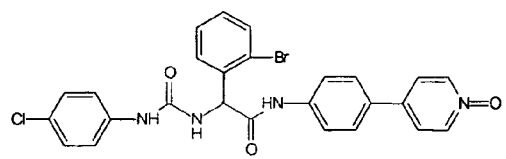
Figure 1I:
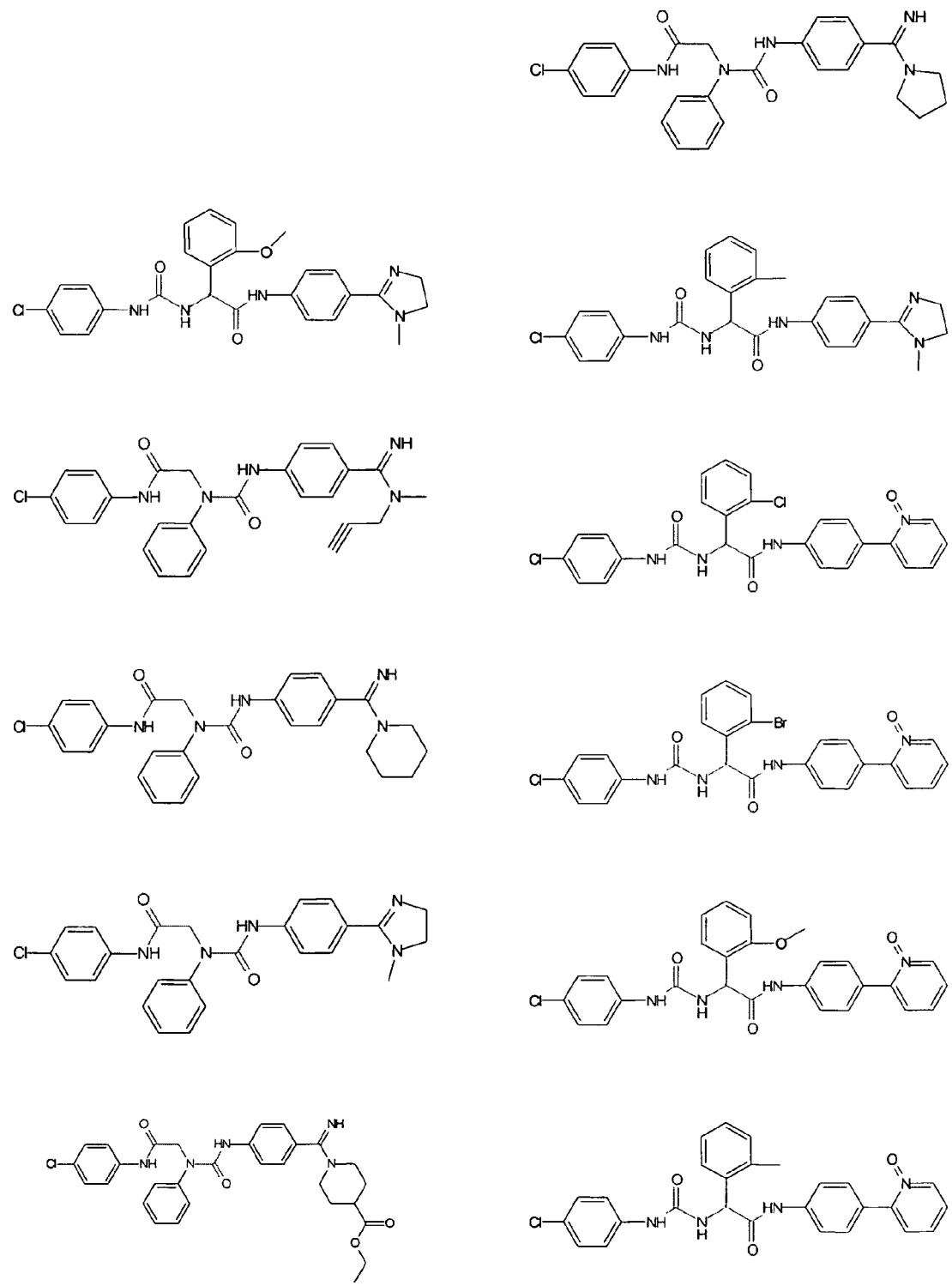
Figure 1J:
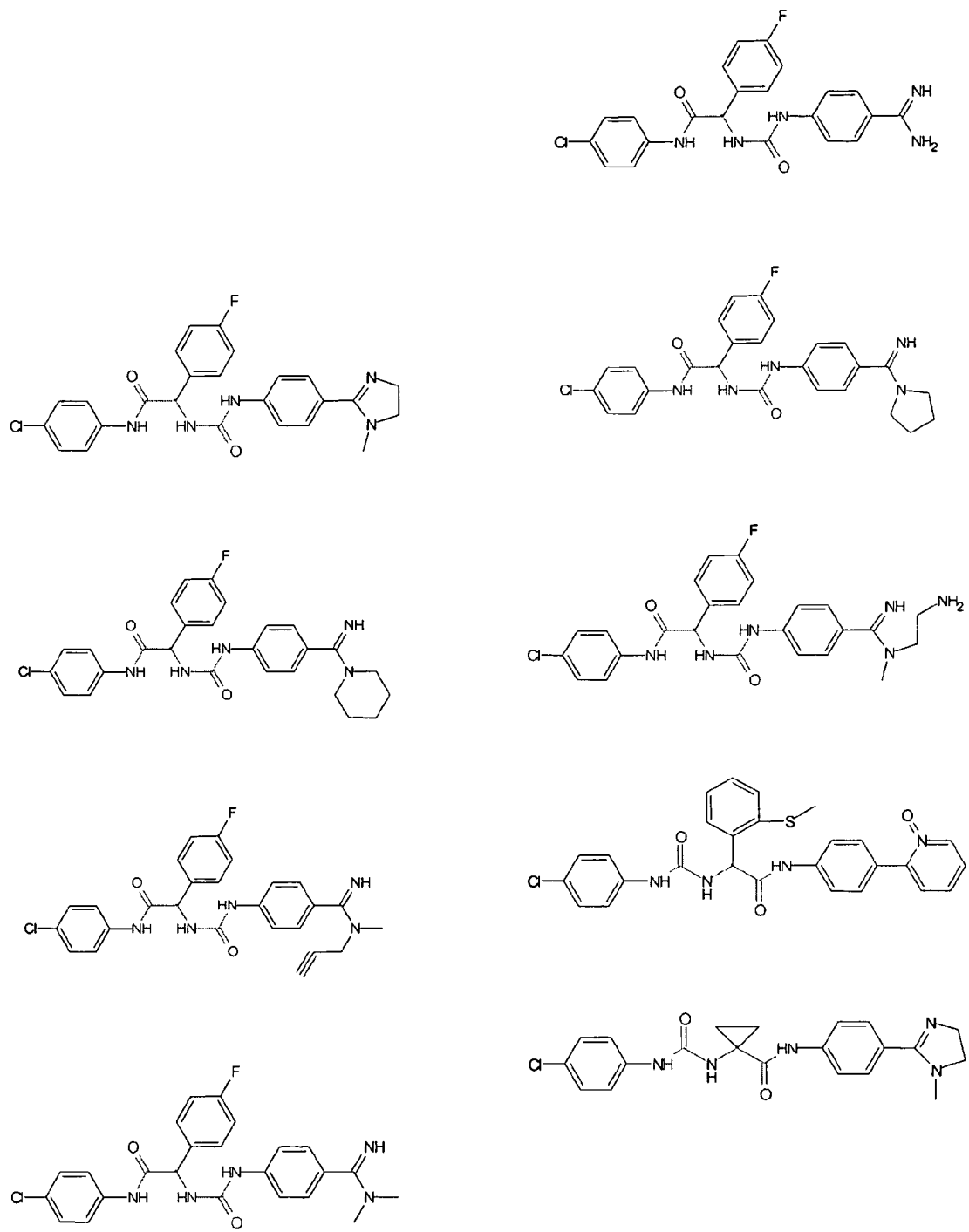
Figure 1K:
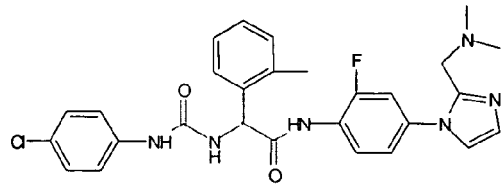
Figure 1K:
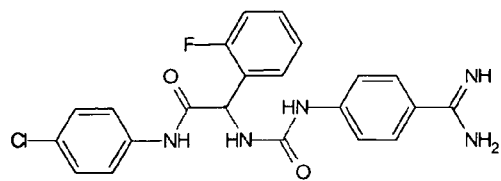
Figure 1K:
Figure 1K:
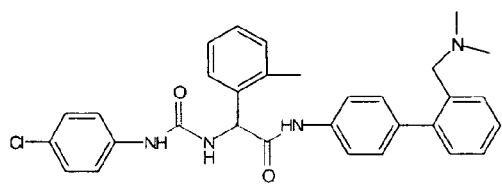
Figure 1K:
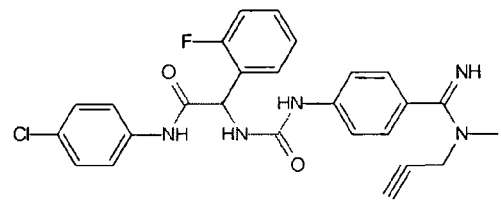
Figure 1K:
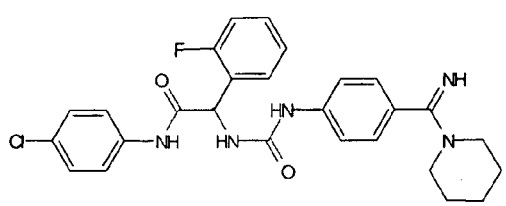
Figure 1K:
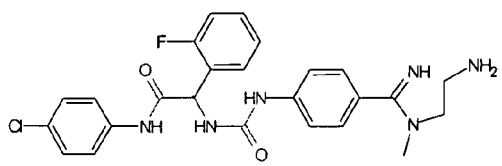
Figure 1K:
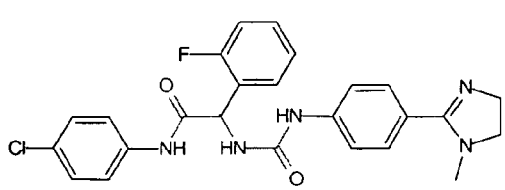
Figure 1K:
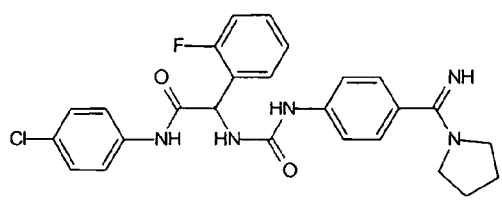
Figure 1K:
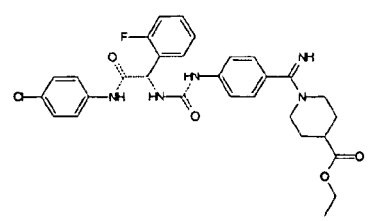
Figure 1L:
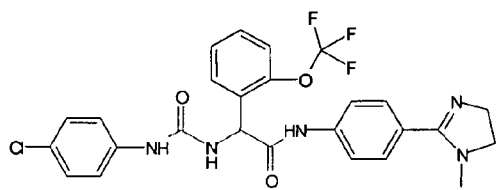
Figure 1L:
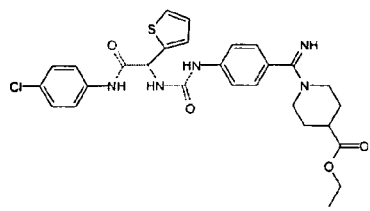
Figure 1L:
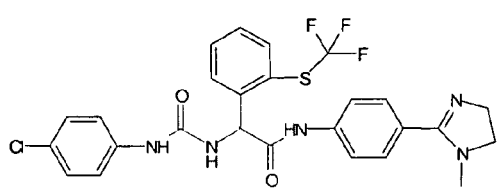
Figure 1L:
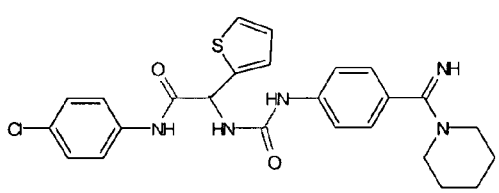
Figure 1L:
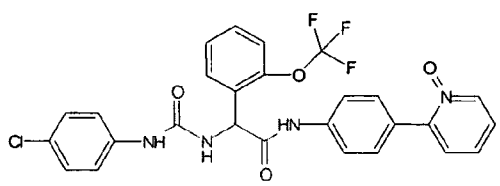
Figure 1L:
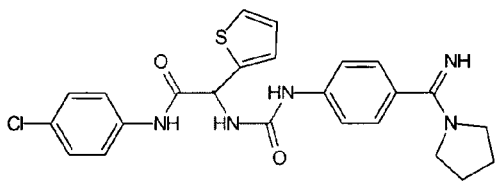
Figure 1L:
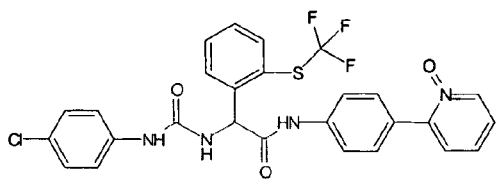
Figure 1L:
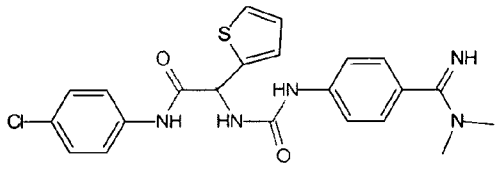
Figure 1L:
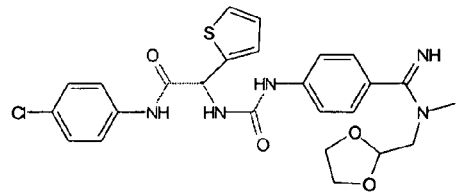
Figure 1L:
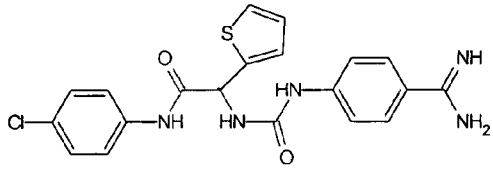
Figure 1L:
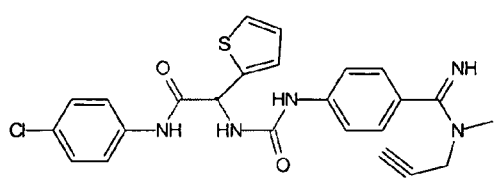
Figure 1L:
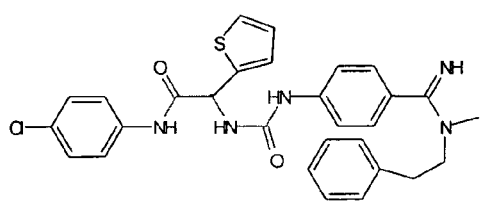
Figure 1M:
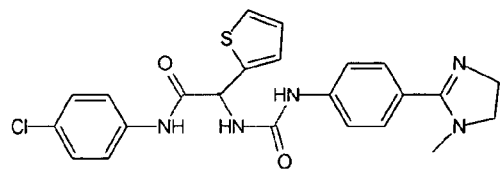
Figure 1M:
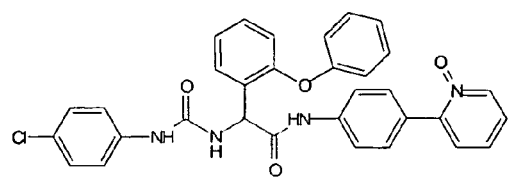
Figure 1M:
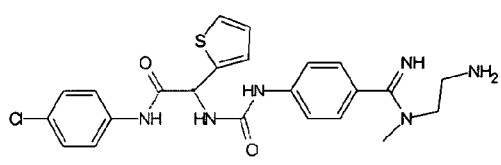
Figure 1M:
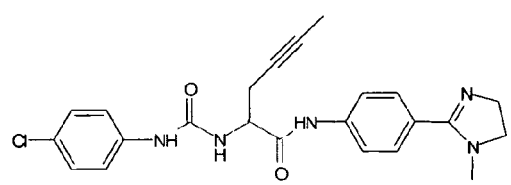
Figure 1M:
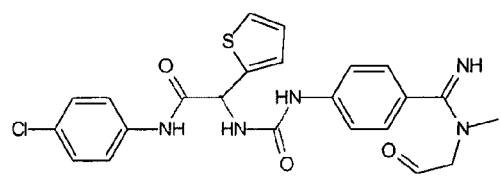
Figure 1M:
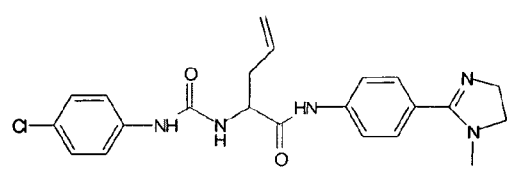
Figure 1M:
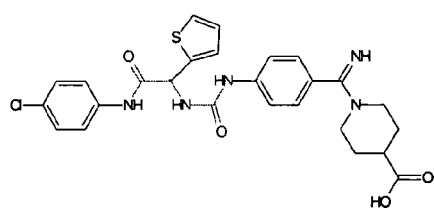
Figure 1M:
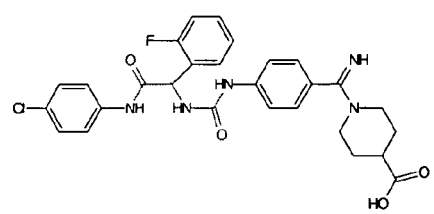
Figure 1M:
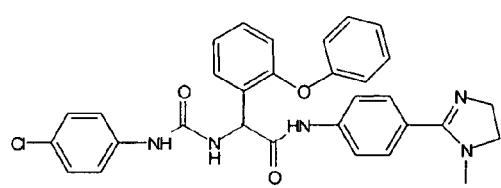
Figure 1N:
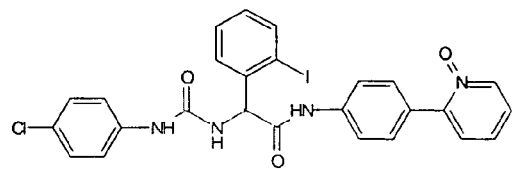
Figure 1N:
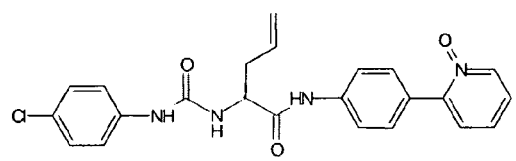
Figure 1N:
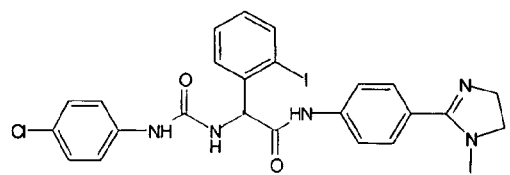
Figure 1N:
Figure 1N:
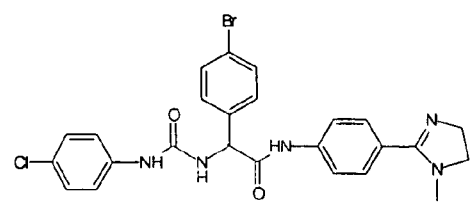
Figure 1N:
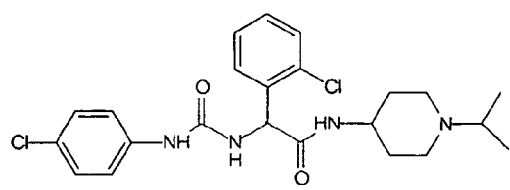
Figure 1O:
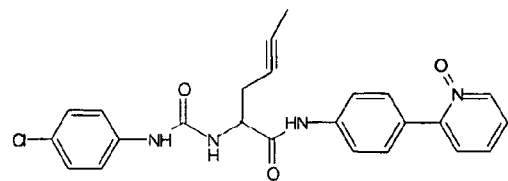
Figure 1O:
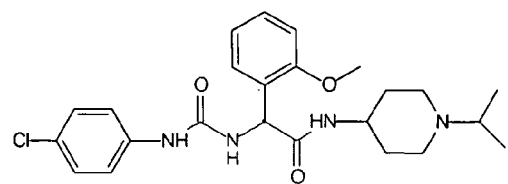
Figure 1O:
Figure 1O:
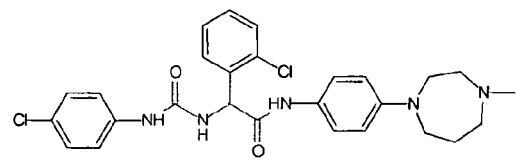
Figure 1O:
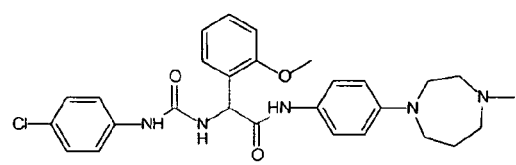
Figure 1P:
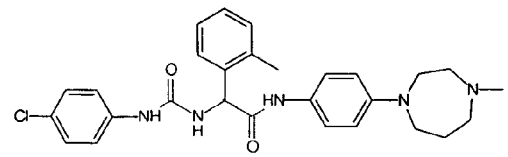
Figure 1P:
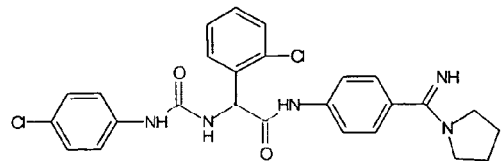
Figure 1P:
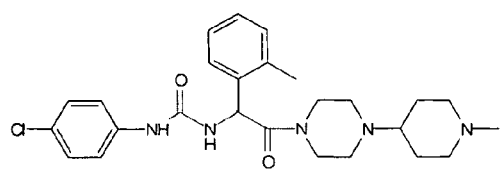
Figure 1P:
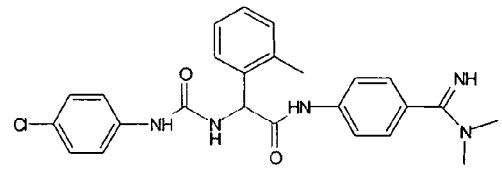
Figure 1P:
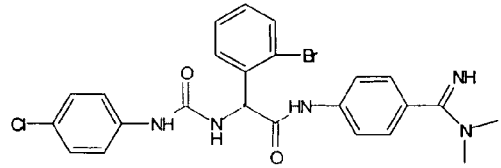
Figure 1P:
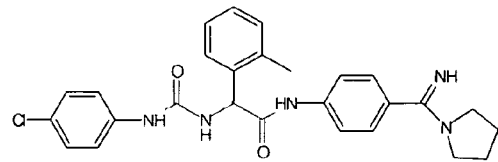
Figure 1P:
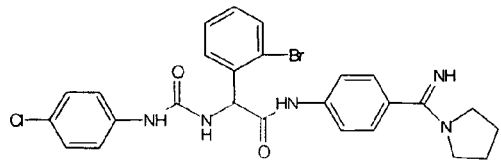
Figure 1P:
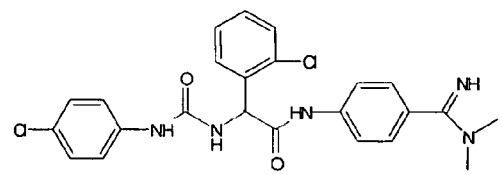
Figure 1P:
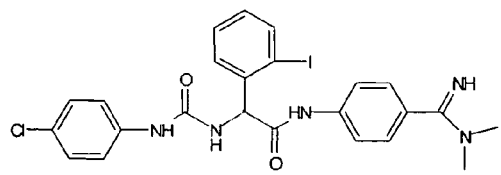
Figure 1Q:
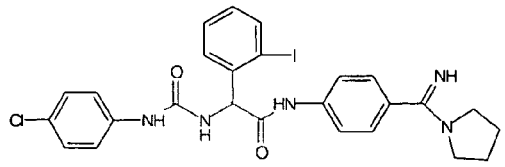
Figure 1Q:
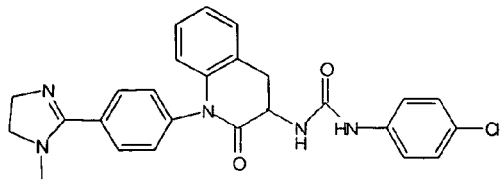
Figure 1Q:
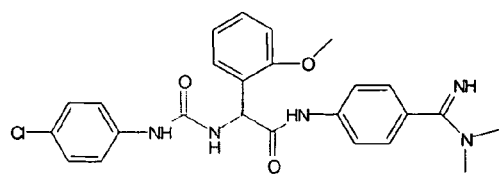
Figure 1Q:
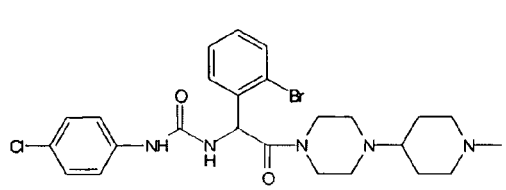
Figure 1Q:
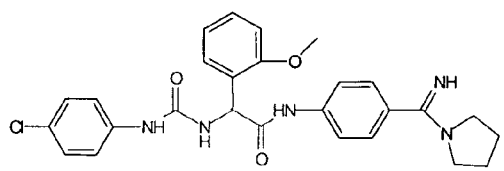
Figure 1Q:
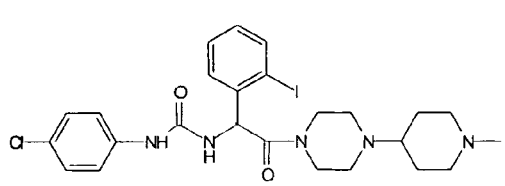
Figure 1Q:
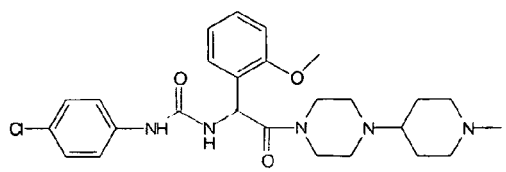
Figure 1Q:
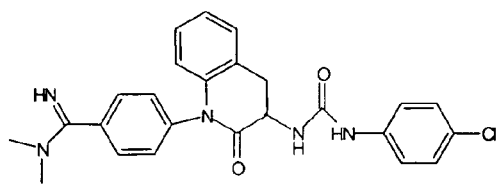
Figure 1Q:
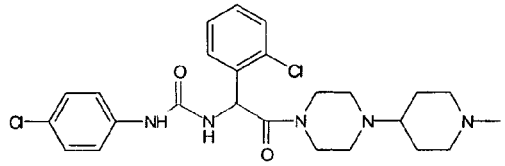
Figure 1Q:
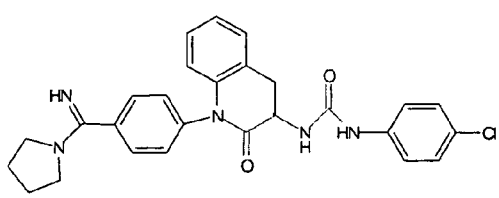
Figure 1R:
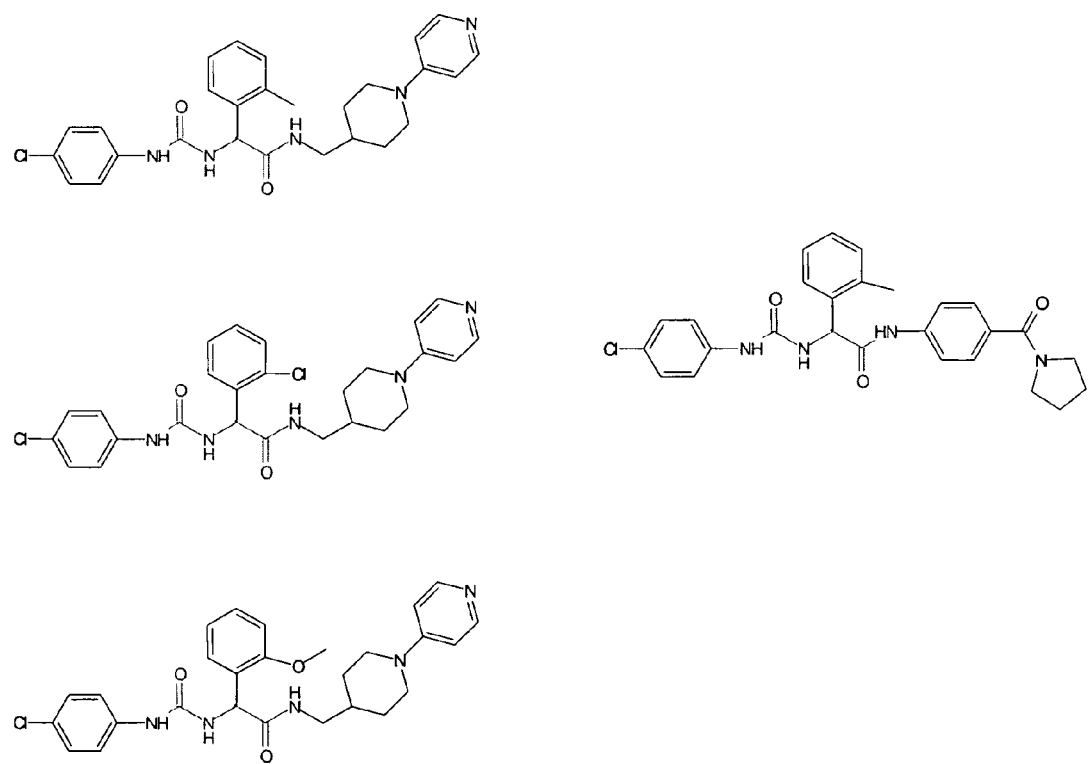
Figure 1S:
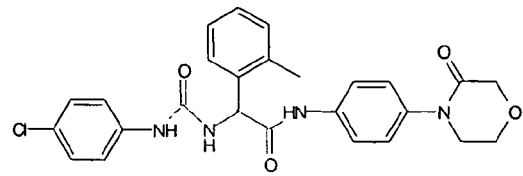
Figure 1S:
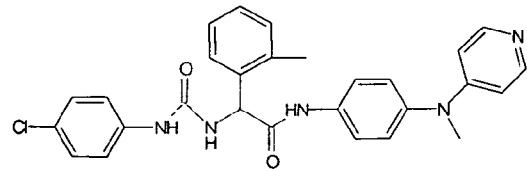
Figure 1S:
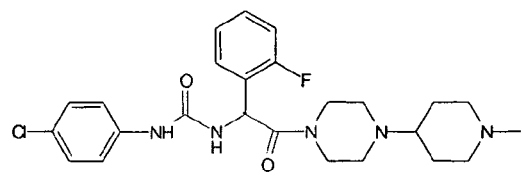
Figure 1S:
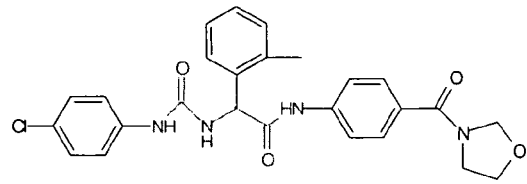
Figure 1S:
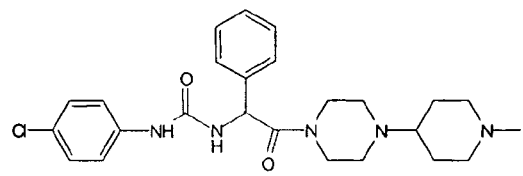
Figure 1S:
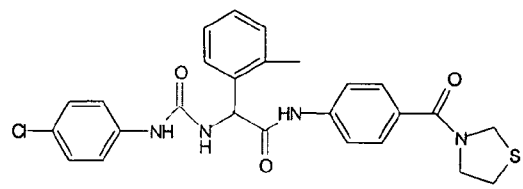
Figure 1T:
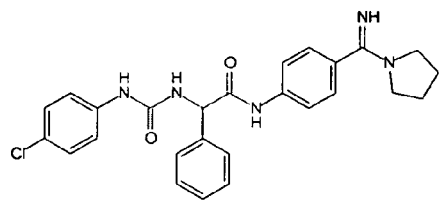
Figure 1T:
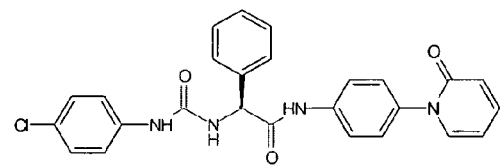
Figure 1T:
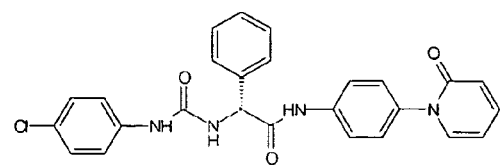
Figure 1U:
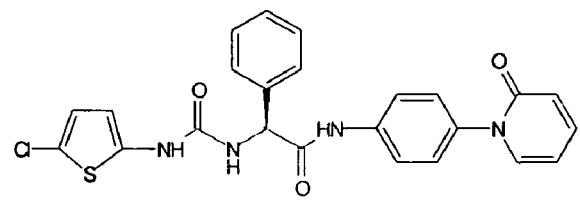
Figure 1U:
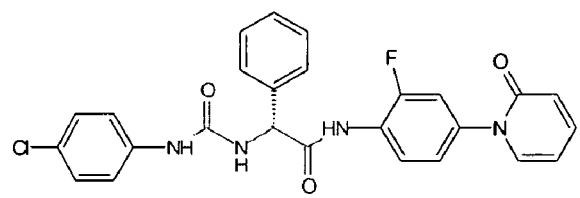
Figure 1U:
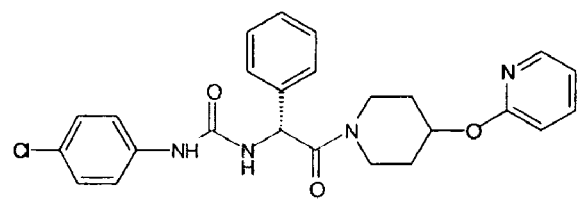
Figure 1U:
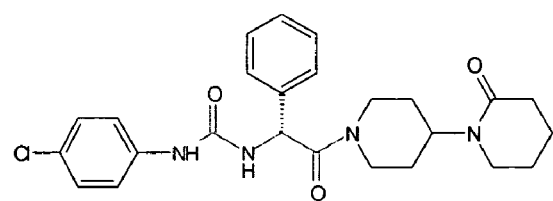
Figure 1V:
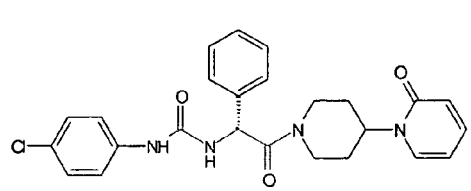
Figure 1V:
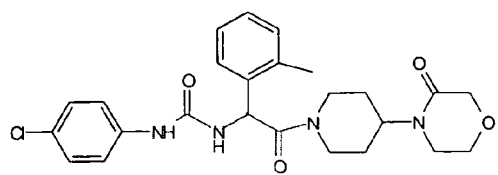
Figure 1V:
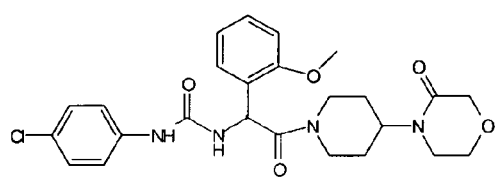
Figure 1V:
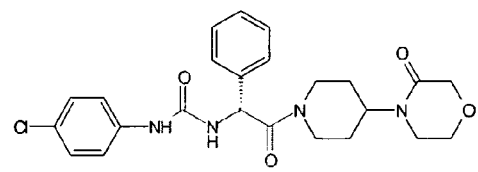
Figure 1V:
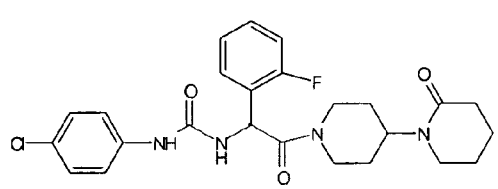
Figure 1V:
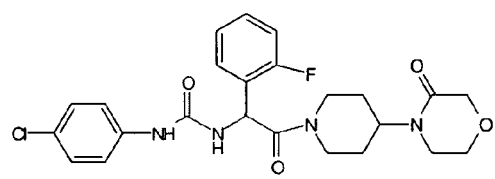
Figure 1V:
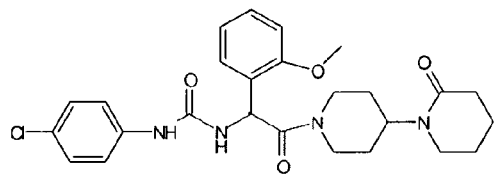
Figure 1V:
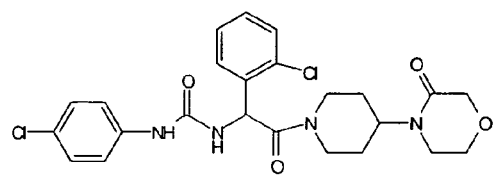
Figure 1V:
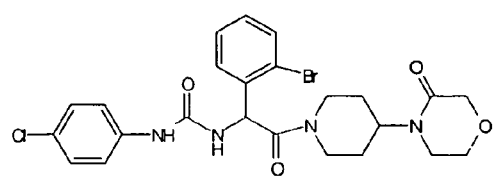
Figure 1W:
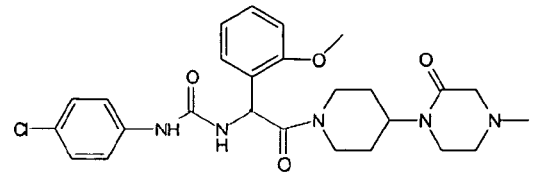
Figure 1W:
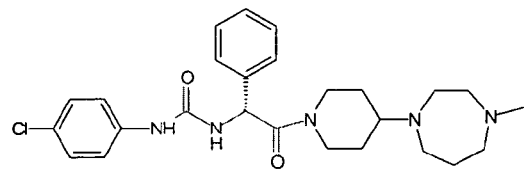
Figure 1W:
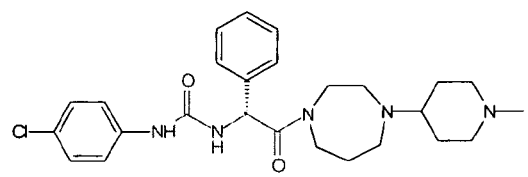
Figure 1W:
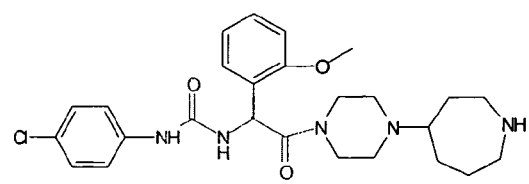
Figure 1W:
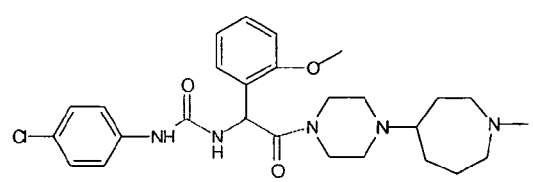
Figure 1W:
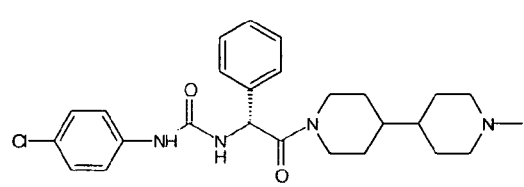

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group is one having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. When "cycloalkyl" is used in combination with "alkyl", as in $C_{3-5}$cycloalkyl-alkyl, the cycloalkyl portion is meant to have from three to five carbon atoms, while the alkyl portion is an alkylene moiety having from one to three carbon atoms (e.g., —$CH_2$—, —$CH_2CH_2$— or —$CH_2CH_2CH_2$—).

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups (typically provided as —$NR^aR^b$ or a variant thereof), the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom or through a carbon atom. Non-limiting examples of aryl groups include phenyl, naphthyl and biphenyl, while non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, benzopyrazolyl, 5-indolyl, 1-isoquinolyl, 5-isoquinolyl, 2-quinoxalinyl, 5-quinoxalinyl, 3-quinolyl, and 6-quinolyl. If not specifically stated, substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like).

The terms "heterocycle" and "heterocyclyl" refers to a saturated or unsaturated non-aromatic cyclic group containing at least one sulfur, nitrogen or oxygen heteroatom. Each heterocycle can be attached at any available ring carbon or heteroatom. Each heterocycle may have one ("heteromonocyclyl") or more rings (e.g. "heterobicyclyl"). When multiple rings are present, they can be fused together or linked covalently. Each heterocycle must contain at least one heteroatom (typically 1 to 5 heteroatoms) selected from nitrogen, oxygen or sulfur. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Non-limiting examples of heterocycle groups include pyrrolidine, piperidine, imidazolidine, pyrazolidine, butyrolactam, valerolactam, imidazolidinone, hydantoin, dioxolane, phthalimide, 1,4-dioxane, morpholine, thiomorpholine, thiomorpholine-S,S-dioxide, piperazine, pyran, pyridone, 3-pyrroline, thiopyran, pyrone, tetrahydrofuran, tetrahydrothiophene and the like.

The above terms (e.g., "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below.

Substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"CO$_2$R', —NR'—C(O)NR"R'", —NH—C(NH$_2$)=NH, —NR'C(NH$_2$)=NH, —NH—C(NH$_2$)=NR', —S(O)R', —SO$_2$R', —SO$_2$NR'R", —NR'SO$_2$R", —N$_3$, perfluoro(C$_1$-C$_4$)alkoxy, and perfluoro(C$_1$-C$_4$)alkyl, in a number ranging from zero to the total number of open valences on the aromatic ring system; and where R', R"and R'" is independently selected from hydrogen, C$_{1-8}$alkyl, C$_{3-6}$cycloalkyl, C$_{2-8}$alkenyl, C$_{2-8}$alkynyl, unsubstituted aryl and heteroaryl, (unsubstituted aryl)-C$_{1-4}$alkyl, and unsubstituted aryloxy-C$_{1-4}$alkyl. Other suitable substituents include each of the above aryl substituents attached to a ring atom by an alkylene tether of from 1-4 carbon atoms.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, e.g., Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

General

Embodiments of the Invention

Compounds

In one aspect, the present invention provides compounds having the formula:

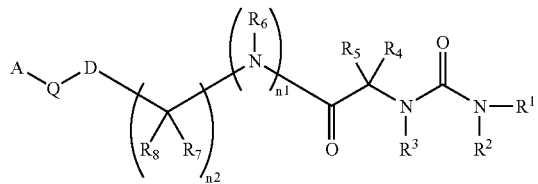

and pharmaceutically acceptable salts, hydrates, solvates and prodrugs thereof. In formula (I), each $R^1$ represents a member selected from the group consisting of: hydrogen, —$C_{1-6}$alkyl, —$C_{0-6}$alkyl-aryl, heteroaryl and —$C_{2-6}$alkenyl.

The symbol $R^2$ represents a member selected from the group consisting of: —$C_{0-6}$alkyl-aryl, —$C_{3-8}$cycloalkyaryl, heteroaryl, —$C_{3-8}$cycloalkylheteroaryl, —$C_{3-8}$cycloalkyl, —$C_{3-8}$cycloalkenyl, heteromonocyclyl, fused heterobicyclyl and unfused heterobicyclyl, optionally substituted with from 1 to 3 $R^{2a}$ substituents, wherein each heterocyclyl comprises 5 to 12 ring atoms, 1 to 4 of which are members independently selected from the group consisting of N, O and S.

The symbol $R^3$ represents a member selected from the group consisting of: hydrogen, $C_{1-6}$alkyl, heteroaryl, $C_{2-6}$alkenyl, —$C_{3-8}$cycloalkyl, —$C_{0-4}$alkyl-$C_{3-8}$-cycloalkyl, —$C_{0-6}$alkyl-aryl, —$C_{0-6}$alkyl-heteroaryl, —$C_{0-6}$alkyl-heterocyclyl, —$C_{0-6}$alkyl-CO-OR$^{3a}$, —$C_{1-6}$alkyl-N(R$^{3a}$R$^{3b}$), —$C_{1-6}$alkyl-O—R$^{3a}$, —$C_{1-6}$alkyl-S—R$^{3a}$, —$C_{0-6}$alkyl-C(O)—N(R$^{3a}$R$^{3b}$) and —$C_{1-6}$alkyl-N(R$^{3a}$)—C(O)R$^{3b}$.

Each $R^4$ and $R^5$ is a member independently selected from the group consisting of: hydrogen, —$C_{1-6}$alkyl, —$C_{2-6}$alkenyl, —$C_{2-6}$alkynyl, —$C_{3-8}$cycloalkyl, —$C_{0-4}$alkyl-$C_{3-8}$-cycloalkyl, $C_{1-6}$haloalkyl, —$C_{0-6}$alkyl-heteroaryl, —$C_{0-6}$alkyl-heterocyclyl, —$C_{0-6}$alkyl-CN, —$C_{0-6}$alkyl-NO$_2$, —$C_{1-6}$alkyl-O—R$^{4a}$, —$C_{1-6}$alkyl-S—R$^{4a}$, —$C_{1-6}$alkyl-SO$_2$—R$^{4a}$, —$C_{1-6}$alkyl-S(O)—R$^{4a}$, —$C_{0-6}$alkyl-CO—OR$^{4a}$, —$C_{0-6}$alkyl-C(O)—N(R$^{4a}$R$^{4b}$), —$C_{0-6}$alkyl-C(O)R$^{4a}$, —$C_{1-6}$alkyl-N)R$^{4a}$R$^{4b}$), —$C_{1-6}$alkyl-N(R$^{4a}$)—C(O)R$^{4b}$, —$C_{1-6}$alkyl-N(R$^{4a}$)—C(O)—N(R$^{4b}$R$^{4c}$), —$C_{1-6}$alkyl-N(R$^{4a}$)—SO$_2$—R$^{4b}$, —$C_{1-6}$alkyl-SO$_2$—N(R$^{4a}$R$^{4b}$), —$C_{0-6}$alkyl-PO(—OR$^{4a}$)(—OR$^{4b}$), —$C_{1-6}$alkyl-N(R$^{4a}$)—PO(—OR$^{4b}$)(—OR$^{4c}$), —$C_{0-6}$alkyl-aryl, —$C_{0-6}$alkyl-heteroaryl, and —$C_{0-6}$alkyl-heterocyclyl; or $R^4$ and $R^5$ can be taken together with the carbon atom to which they are attached to form a 3 to 8 membered cycloalkyl or heterocyclyl group; wherein each heterocyclyl is a 3 to 8 membered monocyclic ring or a 8-12 membered bicyclic ring, each comprising from 1 to 4 heteroatoms selected from the group consisting of O, N and S, and wherein 1 to 3 carbon or nitrogen atoms of aryl, heteroaryl and heterocyclyl are substituted with 1 to 3 $R^{4d}$ substituents.

The letter D is a member selected from the group consisting of: a direct bond, aryl, heteroaryl, $C_{3-8}$cycloalkyl, $C_{3-8}$cycloalkenyl, heteromonocyclyl, unfused heterobicyclyl, and fused heterobicyclyl; optionally substituted with 1 to 3 $R^9$ substituents, wherein each heterocyclyl comprises from 5 to 10 ring atoms, 1-4 of which are selected from the group consisting of N, O and S.

The symbol Q is selected from the group consisting of: a direct bond, —C(R$^{10a}$R$^{10b}$)—, —C(O)—, —C(S)—, —C(=NR$^{10a}$)—, —O—, —S—, —N(R$^{10a}$)—, —N(R$^{10a}$)CH$_2$—, —CH$_2$N(R$^{10a}$)—, —C(O)N(R$^{10a}$)—, —N(R$^{10a}$)C(O)—, —SO$_2$—, —SO—, —SO$_2$N(R$^{10a}$)—, and —N(R$^{10a}$)—SO$_2$—; and at least one of D and Q is not a direct bond.

The symbol A is selected from the group consisting of: —NR$^{11c}$R$^{11d}$, —C(=NR$^{11c}$)NR$^{11a}$R$^{11b}$, —C(=NR$^{11e}$R$^{11f}$)NR$^{11a}$R$^{11b}$, —N(R$^{11d}$)C(=NR$^{11c}$)NR$^{11a}$R$^{11b}$, —N(R$^{11d}$)C(=NR$^{11c}$)R$^{11a}$, —N(R$^{11c}$)NR$^{11a}$R$^{11b}$, —N(R$^{11c}$)OR$^{11d}$, $C_{1-6}$alkyl, $C_{2-6}$alkenyl, and pyridyl-oxide, optionally substituted with 1 to 3 $R^{11g}$. In another embodiment the symbol A is pyridinyl, pyrrolidinyl, homopiperazinyl, piperazinyl or morpholinyl each optionally substituted with 1 to 3 $R^{11g}$.

Each $R^{2a}$, $R^{4d}$, $R^9$ and $R^{11g}$ is a member independently selected from the group consisting of: H, halo, $C_{1-6}$alkyl, $C_{2-6}$alkenyl, $C_{2-6}$alkynyl, $C_{0-4}$alkylC$_{3-8}$cycloalkyl, —$C_{1-4}$alkoxy, —O—$C_{0-2}$alkyl-CF$_3$, —$C_{0-2}$alkyl-CF$_3$, —$C_{0-2}$alkyl-CN, —$C_{0-2}$alkyl-NO$_2$, —$C_{0-2}$alkyl-NR$^{12a}$R$^{12b}$, —$C_{0-2}$alkyl-SO$_2$NR$^{12a}$R$^{12b}$, —$C_{0-2}$alkyl-SO$_2$R$^{12a}$, —$C_{0-2}$alkyl-SOR$^{12a}$, —$C_{0-2}$alkyl-CF$_3$, —$C_{0-2}$alkyl-OR$^{12a}$, —$C_{0-2}$alkyl-SR$^{12a}$, —O—CH$_2$—CH$_2$—OR$^{12a}$, —O—CH$_2$—CO$_2$R$^{12a}$, —N(R$^{12a}$)—CH$_2$—CH$_2$—OR$^{12b}$, —$C_{0-2}$alkyl-C(O)NR$^{12a}$R$^{12b}$, —$C_{0-2}$alkyl-CO$_2$R$^{12a}$, —$C_{0-2}$alkyl-N(R$^{12a}$)—C(O)R$^{12b}$, —$C_{0-2}$alkyl-N(R$^{12c}$)—C(O)NR$^{12a}$R$^{12b}$, —$C_{0-2}$alkyl-C(=NR$^{12c}$)NR$^{12a}$R$^{12b}$, —$C_{0-2}$alkyl-C(=NR$^{12a}$)R$^{12b}$, —$C_{0-2}$alkyl-N(R$^{12d}$)C(NR$^{12c}$)NR$^{12a}$R$^{12b}$, —$C_{0-2}$alkyl-N(R$^{12a}$)—SO$_2$R$^{12b}$, =O, =S, =NR$^{12a}$, 5- or 6-membered aryl, 5- or 6-membered heteroaryl and 5- to 7-membered heterocyclyl, each of which is optionally substituted with a member independently selected from the group consisting of halo, CF$_3$, OCF$_3$, SCF$_3$, $C_{1-6}$alkyl, $C_{2-6}$alkenyl, $C_{2-6}$alkynyl, $C_{0-4}$alkylC$_{3-8}$cycloalkyl, $C_{1-4}$alkoxy, —CO$_2$H, —CO$_2$C$_{1-4}$alkyl, —CONR$^{12a}$R$^{12b}$, =O, =X, —OH, —CN and —NO$_2$; wherein each heteroaryl or heterocyclyl comprises 1 to 4 heteroatoms, independently selected from the group consisting of N, O and S.

Each of the symbols $R^{3a}$, $R^{3b}$, $R^{4a}$, $R^{4b}$, $R^{4c}$, $R^{12a}$, $R^{12b}$, $R^{12c}$ and $R^{12d}$ are members independently selected from the group consisting of: H, $C_{1-6}$alkyl, $C_{2-6}$alkenyl, $C_{2-6}$alkynyl, $C_{0-4}$alkylC$_{3-8}$cycloalkyl, $C_{0-4}$alkylaryl, $C_{0-4}$alkyl-heteroaryl, —$C_{0-6}$alkyl-COC$_{1-4}$alkyl, —$C_{0-6}$alkyl-CO$_2$C$_{1-4}$alkyl, —$C_{0-6}$alkyl-SO$_2$—C$_{1-4}$alkyl, —$C_{0-6}$alkyl-SO$_2$—N(C$_{1-4}$alkyl, C$_{1-4}$alkyl), —$C_{0-6}$alkyl-N(C$_{1-4}$alkyl, C$_{1-4}$alkyl) and —$C_{1-6}$alkyl-O—$C_{0-6}$alkyl, wherein 1-3 hydrogen atoms on the aryl or heteroaryl ring may be independently replaced with a member selected from the group consisting of halo, $C_{1-6}$alkyl, $C_{2-6}$alkenyl, $C_{2-6}$alkynyl, $C_{0-4}$alkylC$_{3-8}$cycloalkyl, $C_{1-4}$alkoxy, —CO$_2$H, —CO$_2$C$_{1-4}$alkyl, —CON(C$_{1-4}$alkyl, C$_{1-4}$alkyl), —OH, —CN and NO$_2$; or can be taken together with the nitrogen atom to which they are attached to form a 3-8 membered heterocyclyl group, comprising 1 to 4 heteroatoms selected from the group consisting of N, O and S, optionally substituted with 1 to 4 $R^{13}$ substituents selected from the group consisting of halo, $C_{1-6}$alkyl, $C_{2-6}$alkenyl, $C_{2-6}$alkynyl, $C_{0-4}$alkylC$_{3-8}$cycloalkyl, $C_{1-4}$alkoxy, —CO$_2$H, —CO$_2$C$_{1-4}$alkyl, —CON(C$_{1-4}$alkyl, C$_{1-4}$alkyl), =O, =S, —OH, —CN and NO$_2$.

Each of the symbols $R^6$, $R^7$, $R^8$, $R^{10a}$ and $R^{10b}$ is a member independently selected from the group consisting of: hydrogen, $C_{1-6}$alkyl, $C_{2-6}$alkenyl, $C_{2-6}$alkynyl, $C_{3-8}$cycloalkyl and $C_{0-4}$alkylC$_{3-8}$cycloalkyl, —$C_{0-6}$alkyl-aryl and —$C_{0-6}$alkyl-heteroaryl, or $R^4$ and $R^6$ can be taken together with the atoms to which they are attached to form a 5 to 12 membered heterocyclyl group; wherein each heterocyclyl is a 5 to 8 membered monocyclic ring or a 8-12 membered bicyclic ring, each comprising from 1 to 4 heteroatoms selected from the group consisting of O, N and S, and wherein 1 to 3 carbon or nitrogen atoms of aryl, heteroaryl and heterocyclyl are substituted with 1 to 3 $R^{4d}$ substituents.

Each of the symbols $R^{11a}$, $R^{11b}$, $R^{11c}$, $R^{11d}$, $R^{11e}$ and $R^{11f}$ are members independently selected from the group consisting of: H, $C_{1-6}$alkyl, $C_{2-6}$alkenyl, $C_{2-6}$alkynyl, $C_{0-4}$alkyl $C_{3-8}$cycloalkyl, $C_{0-4}$alkylaryl, $C_{0-4}$alkyl-heteroaryl, —$C_{0-6}$alkyl-COC$_{1-4}$alkyl, —$C_{0-6}$alkyl-CO$_2$C$_{1-4}$alkyl, —$C_{0-6}$alkyl-SO$_2$—C$_{1-4}$alkyl, —$C_{0-6}$alkyl-SO$_2$—NR$^{12a}$R$^{12b}$ and —$C_{1-6}$alkyl-O—$C_{0-6}$alkyl, wherein 1-3 hydrogen atoms on the aryl or heteroaryl ring may be independently replaced with a member selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —$CON(C_{1-4}$alkyl, $C_{1-4}$alkyl), —OH, —CN and $NO_2$; or each $R^{11a}$ and $R^{11b}$ can be taken together with the nitrogen atom to which they are attached to form a 3-8 membered heterocyclyl group, comprising 1 to 4 heteroatoms selected from the group consisting of N, O and S, optionally substituted with 1 to 4 $R^{13}$ substituents selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —$CON(C_{1-4}$alkyl, $C_{1-4}$alkyl), =O, =S, —OH, —CN and $NO_2$; or each $R^{11e}$ and $R^{11f}$ can be taken together with the nitrogen atom to which they are attached to form a 3-8 membered heterocyclyl group, comprising 1 to 4 heteroatoms selected from the group consisting of N, O and S, optionally substituted with 1 to 4 $R^{13}$ substituents selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —$CON(C_{1-4}$alkyl, $C_{1-4}$alkyl), =O, =S, —OH, —CN and $NO_2$.

Each of the subscripts n1 and n2 is an integer of 0 to 1.

With the above formula are a number of specific embodiments of the invention. In one group of embodiments, $R^1$ and $R^3$ is H. In a specific group of embodiments, $R^2$ is aryl, optionally substituted with 1 to 3 $R^{2a}$. More preferably, $R^2$ is phenyl or thiophenyl. More preferably, $R^{2a}$ is independently selected from the group consisting of halo and $C_{2-6}$alkynyl. For these embodiments, a preferred group of embodiments are those in which $R^{2a}$ is attached to the phenyl ring at a position para to the rest of the molecule.

In one group of embodiments, $R^4$ and $R^5$ is a member independently selected from the group consisting of: hydrogen, —$C_{0-6}$ alkyl-heteroaryl, —$C_{0-6}$alkyl-aryl and —$C_{2-6}$alkynyl, wherein each heterocyclyl is a 3 to 8 membered monocyclic ring or a 8-12 membered bicyclic ring, each comprising from 1 to 4 heteroatoms selected from the group consisting of O, N and S, and wherein 1 to 3 carbon or nitrogen atoms of aryl and heteroaryl are substituted with 1 to 3 $R^{4d}$ substituents. More preferably $R^4$ is hydrogen and $R^5$ is a member independently selected from the group consisting of hydrogen, 2-thiophenyl, phenyl and 2-butynyl. In a specific group of embodiments when $R^4$ and $R^5$ are different, the carbon bearing $R^5$ has the R-configuration. In another group of embodiments when $R^4$ and $R^5$ are different, the carbon bearing $R^5$ has the S-configuration. In another group of embodiments each $R^{4d}$ is a member independently selected from the group consisting of halogen, —$C_{1-6}$alkyl, —O—$C_{0-2}$alkyl-$CF_3$ and $C_{0-2}$alkyl-$OR^{12a}$; and $R^{12a}$ is $C_{1-6}$alkyl or $C_{0-4}$alkylaryl.

In one group of embodiments, the subscript n1 is 0. In another group of embodiments the subscript n1 is 1.

In a specific group of embodiments $R^6$ is H or $R^4$ and $R^6$ can be taken together with the atoms to which they are attached to form a 5 to 12 membered heterocyclyl group; wherein each heterocyclyl is a 5 to 8 membered monocyclic ring or a 8-12 membered bicyclic ring, each comprising from 1 to 4 heteroatoms selected from the group consisting of O, N and S, and wherein 1 to 3 carbon or nitrogen atoms of aryl, heteroaryl and heterocyclyl are substituted with 1 to 3 $R^{4d}$ substituents. Within this embodiment, $R^4$ and $R^6$ are taken together with the atoms to which they are attached selected from the group having the formula:

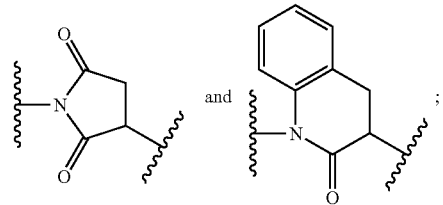

optionally substituted with 1 to 3 $R^{4d}$ substituents. In one group of embodiments, the subscript n2 is 0. In another group of embodiments the subscript n2 is 1. In another group of embodiments, each $R^7$ and $R^8$ is H.

In one group of embodiments, D is aryl or heteromonocyclyl, wherein each heteromonocyclyl comprises from 5 to 7 ring atoms, 1 to 2 of which are N or O. More preferably, D is phenyl, piperidinyl or piperazinyl.

In another group of embodiments, Q is selected from the group consisting of a direct bond, —C(=NH)—, C(O)— and —N($R^{10a}$)—; and $R^{10a}$ is $C_{1-6}$alkyl. More preferably, Q is attached to the phenyl, piperidinyl or piperazinyl ring at a position para to the rest of the molecule.

In another group of embodiments, A is selected from the group consisting of: —$NR^{11c}R^{11d}$, —C(=$NR^{11c}$)$NR^{11a}R^{11b}$, —C(=$NR^{11e}R^{11f}$)$NR^{11a}R^{11b}$, —N($R^{11c}$)$NR^{11a}R^{11b}$, $C_{1-6}$alkyl and pyridyl-oxide. In another embodiment the symbol A is pyridinyl, pyrrolidinyl, homopiperazinyl, piperazinyl or morpholinyl each optionally substituted with 1 to 3 $R^{11g}$.

More preferably, each $R^{11a}$ and $R^{11b}$ is independently selected from the group consisting of H, $C_{1-6}$alkyl, $C_{2-6}$alkenyl, $C_{2-6}$alkynyl and —$C_{0-6}$alkyl-$NR^{12a}R^{12b}$ or each $R^{11a}$ and $R^{11b}$ can be taken together with the nitrogen atom to which they are attached to form a 3-8 membered heterocyclyl group, comprising 1 to 4 heteroatoms selected from the group consisting of N, O and S.

Other embodiments are in which A-Q-D-($CR^7R^8$)$_{n2}$—$NR^6_{n1}$ is selected from the group consisting of:

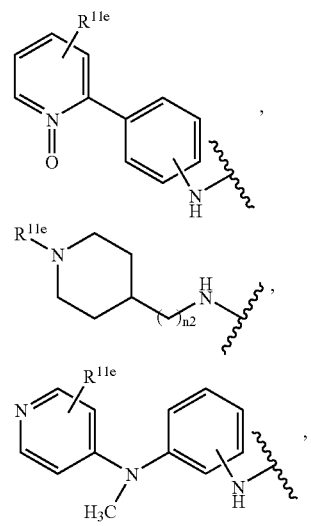

-continued

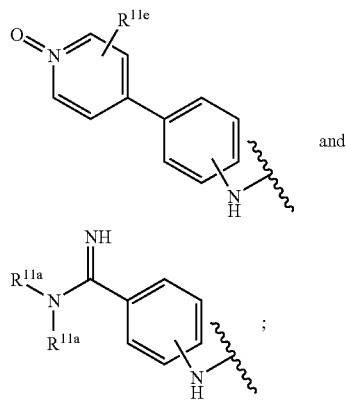

and wherein the wavy line indicates the point of attachment to the rest of the molecule. Other embodiments are in which A-Q-D-$(CR^7R^8)_{n2}$—$NR^6_{n1}$ is selected from the group consisting of:

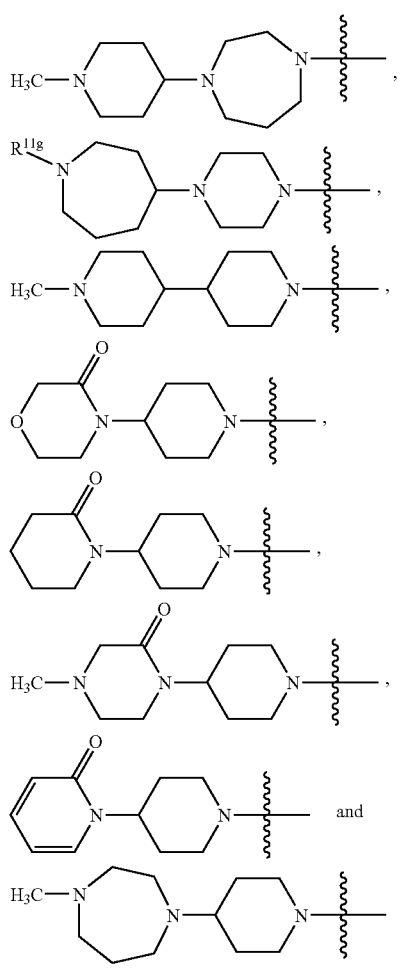

wherein the wavy line indicates the point of attachment to the rest of the molecule. Other embodiments are in wherein A-Q- is selected from the group consisting of:

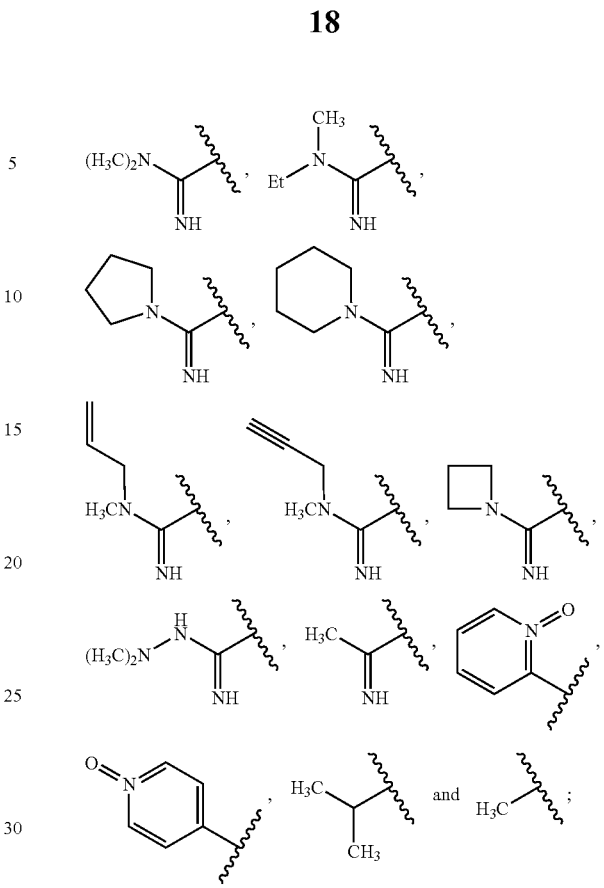

wherein the wavy line indicates the point of attachment to the rest of the molecule. Other embodiments are in wherein A-Q- is selected from the group consisting of:

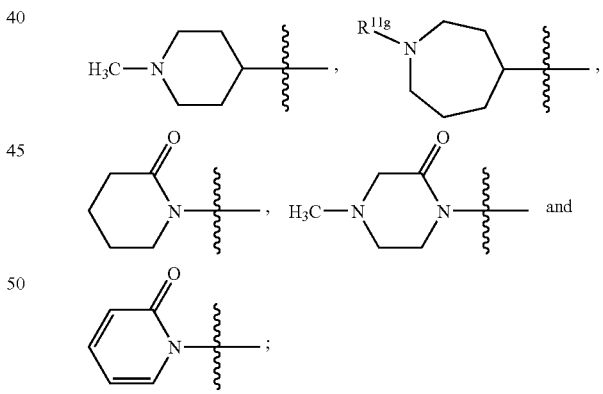

wherein the wavy line indicates the point of attachment to the rest of the molecule. Other embodiments are wherein $R^{11a}$ and $R^{11b}$ is independently selected from the group consisting of H, $C_{1-6}$alkyl, $C_{2-6}$alkenyl, $C_{2-6}$alkynyl and —$C_{0-6}$alkyl-$NR^{12a}R^{12b}$ or each $R^{11a}$ and $R^{11b}$ can be taken together with the nitrogen atom to which they are attached to form a 3-8 membered heterocyclyl group, comprising 1 to 4 heteroatoms selected from the group consisting of N, O and S.

In other embodiments, compounds of formula I are provided which have the formula:

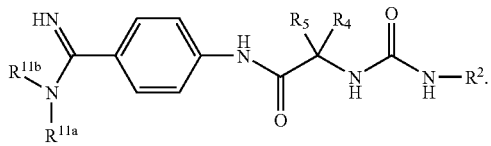

Within this group, specific embodiments are provided in which $R^2$ is aryl, optionally substituted with 1 to 3 $R^{2a}$; and preferably phenyl. Preferably, the optional substituent $R^{2a}$ is halo. Still further preferred are embodiments, wherein $R^{2a}$ is attached to the phenyl ring at a position para to the rest of the molecule. Yet another group of embodiments are those in which each $R^4$ and $R^5$ is a member independently selected from the group consisting of: hydrogen, —$C_{0-6}$alkyl-heteroaryl and —$C_{0-6}$alkyl-aryl, wherein each heterocyclyl is a 3 to 8 membered monocyclic ring or a 8-12 membered bicyclic ring, each comprising from 1 to 4 heteroatoms selected from the group consisting of O, N and S, and wherein 1 to 3 carbon or nitrogen atoms of aryl and heteroaryl are substituted with 1 to 3 $R^{4d}$ substituents. More preferably $R^4$ is hydrogen and $R^5$ is a member independently selected from the group consisting of hydrogen, 2-thiophenyl and phenyl. In a specific group of embodiments when $R^4$ and $R^5$ are different, the carbon bearing $R^5$ has the R-configuration. In another group of embodiments when $R^4$ and $R^5$ are different, the carbon bearing $R^5$ has the S-configuration.

In other embodiments, each $R^{11a}$ and $R^{11b}$ is independently selected from the group consisting of H, $C_{1-6}$alkyl, $C_{2-6}$alkenyl, $C_{2-6}$alkynyl and —$C_{0-6}$alkyl-$NR^{12a}R^{12b}$ or each $R^{11a}$ and $R^{11b}$ can be taken together with the nitrogen atom to which they are attached to form a 3-8 membered heterocyclyl group, comprising 1 to 4 heteroatoms selected from the group consisting of N, O and S.

In one aspect, the present invention provides compounds having the formula:

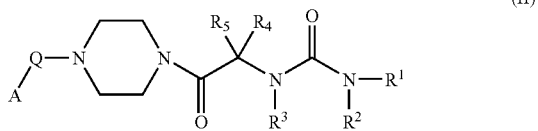

(II)

and pharmaceutically acceptable salts, hydrates, solvates and prodrugs thereof. In formula (II), $R^1$ is a member selected from the group consisting of: hydrogen, —$C_{1-6}$alkyl, —$C_{0-6}$alkyl-aryl, heteroaryl and —$C_{2-6}$alkenyl.

The symbol $R^2$ is a member selected from the group consisting of: —$C_{0-6}$alkyl-aryl, —$C_{3-8}$cycloalkylaryl, heteroaryl, —$C_{3-8}$cycloalkylheteroaryl, —$C_{3-8}$cycloalkyl, —$C_{3-8}$cycloalkenyl, heteromonocyclyl, fused heterobicyclyl and unfused heterobicyclyl, optionally substituted with from 1 to 3 $R^{2a}$ substituents, wherein each heterocyclyl comprises 5 to 12 ring atoms, 1 to 4 of which are members independently selected from the group consisting of N, O and S.

The symbol $R^3$ is a member selected from the group consisting of: hydrogen, $C_{1-6}$alkyl, $C_{2-6}$alkenyl, —$C_{3-8}$cycloalkyl, —$C_{0-4}$alkyl-$C_{3-8}$-cycloalkyl, —$C_{0-6}$alkyl-aryl, —$C_{0-6}$alkyl-heteroaryl, —$C_{0-6}$alkyl-heterocyclyl, —$C_{0-6}$alkyl-CO—$OR^{3a}$, —$C_{1-6}$alkyl-N($R^{3a}R^{3b}$), —$C_{1-6}$alkyl-O—$R^{3a}$, —$C_{1-6}$alkyl-S—$R^{3a}$, —$C_{0-6}$alkyl-C(O)—N($R^{3a}R^{3b}$) and —$C_{1-6}$alkyl-N($R^{3a}$)—C(O)$R^{3b}$.

Each $R^4$ and $R^5$ is a member independently selected from the group consisting of: hydrogen, —$C_{1-6}$alkyl, —$C_{2-6}$alkenyl, —$C_{2-6}$alkynyl, —$C_{3-8}$cycloalkyl, —$C_{0-4}$alkyl-$C_{3-8}$-cycloalkyl, $C_{1-6}$haloalkyl, —$C_{0-6}$alkyl-heteroaryl, —$C_{0-6}$alkyl-heterocyclyl, —$C_{0-6}$alkyl-CN, —$C_{0-6}$alkyl-$NO_2$, —$C_{1-6}$alkyl-O—$R^{4a}$, —$C_{1-6}$alkyl-S—$R^{4a}$, —$C_{1-6}$alkyl-$SO_2$—$R^{4a}$, —$C_{1-6}$alkyl-S(O)—$R^{4a}$, —$C_{0-6}$alkyl-O—$OR^{4a}$, —$C_{0-6}$alkyl-C(O)—N($R^{4a}R^{4b}$), —$C_{0-6}$alkyl-C(O)$R^{4a}$, —$C_{1-6}$alkyl-N($R^{4a}R^{4b}$), —$C_{1-6}$alkyl-N($R^{4a}$)—C(O)$R^{4b}$, —$C_{1-6}$alkyl-N($R^{4a}$)—C(O)—N($R^{4b}R^{4c}$) —$C_{1-6}$alkyl-N($R^{4a}$)—$SO_2$—$R^{4b}$, —$C_{1-6}$alkyl-$SO_2$—N($R^{4a}R^{4b}$), —$C_{0-6}$alkyl-PO(—$OR^{4a}$)(—$OR^{4b}$), —$C_{1-6}$alkyl-N($R^{4a}$)—PO(—$OR^{4b}$)(—$OR^{4c}$) and —$C_{0-6}$alkyl-aryl; or $R^4$ and $R^5$ can be taken together with the carbon atom to which they are attached to form a 3 to 8 membered heterocyclyl group; wherein each heterocyclyl is a 3 to 8 membered monocyclic ring or a 8-12 membered bicyclic ring, each comprising from 1 to 4 heteroatoms selected from the group consisting of O, N and S, and wherein 1 to 3 carbon or nitrogen atoms of aryl, heteroaryl and heterocyclyl are substituted with 1 to 3 $R^{4d}$ substituents.

The symbol Q is selected from the group consisting of: a direct bond, —$C(R^{10a}R^{10b})$—, —C(O)—, —C(S)—, —C(=$NR^{10a}$)—, —N($R^{10a}$)C(O)—, —$SO_2$—, —SO—, and —N($R^{10a}$)—$SO_2$.

The symbol A is selected from the group consisting of: —$NR^{11c}R^{11d}$, —C(=$NR^{11c}$)$NR^{11a}R^{11b}$, —C(=$NR^{11e}R^{11f}$)$NR^{11a}R^{11b}$, —N($R^{11d}$)C(=$NR^{11c}$)$NR^{11a}R^{11b}$, —N($R^{11d}$)C(=$NR^{11c}$)$R^{11a}$, —N($R^{11c}$)$NR^{11a}R^{11b}$, —N($R^{11c}$)$OR^{11d}$; $C_{1-6}$alkyl, $C_{2-6}$alkenyl, aryl, heteroaryl, —$C_{3-8}$cycloalkyl, —$C_{3-8}$cycloalkenyl, heteromonocyclyl, and fused heterobicyclyl; each of aryl, heteroaryl, heteromonocyclyl and fused heterobicyclyl, optionally substituted with 1 to 3 $R^{11g}$; wherein each hetercyclyl comprises from 5 to 10 ring atoms, 1-4 of which are selected from the group consisting of N, O and S.

Each $R^{2a}$, $R^{4d}$, $R^9$ and $R^{11g}$ is a member independently selected from the group consisting of: H, halo, $C_{1-6}$alkyl, $C_{2-6}$alkenyl, $C_{2-6}$alkynyl, $C_{0-4}$alkyl$C_{3-8}$cycloalkyl, —$C_{1-4}$alkoxy, —O—$C_{0-2}$alkyl-$CF_3$, —$C_{0-2}$alkyl-$CF_3$, —$C_{0-2}$alkyl-CN, —$C_{0-2}$alkyl-$NO_2$, —$C_{0-2}$alkyl-$NR^{12a}R^{12b}$, —$C_{0-2}$alkyl-$SO_2NR^{12a}R^{12b}$, —$C_{0-2}$alkyl-$SO_2R^{12a}$, —$C_{0-2}$alkyl-$SOR^{12a}$, —$C_{0-2}$alkyl-$CF_3$, —$C_{0-2}$alkyl-$OR^{12a}$, —$C_{0-2}$alkyl-$SR^{12a}$, —O—$CH_2$—$CH_2$—$OR^{12a}$, —O—$CH_2$—$CO_2R^{12a}$, —N($R^{12a}$)—$CH_2$—$CH_2$—$OR^{12b}$, —$C_{0-2}$alkyl-C(O)NR $R^{12a}R^{12b}$, —$C_{0-2}$alkyl-$CO_2R^{12a}$, —$C_{0-2}$alkyl-N($R^{12a}$)—C(O)$R^{12b}$, —$C_{0-2}$alkyl-N($R^{12c}$)—C(O)$NR^{12a}R^{12b}$, —$C_{0-2}$alkyl-C(=$NR^{12c}$)$NR^{12a}R^{12b}$, —$C_{0-2}$alkyl-C(=$NR^{12a}$)$R^{12b}$, —$C_{0-2}$alkyl-N($R^{12d}$)C(=$NR^{12c}$)$NR^{12a}R^{12b}$, —$C_{0-2}$alkyl-N($R^{12a}$)—$SO_2$—$R^{12b}$) =O, =S, =$NR^{12a}$, 5- or 6-membered aryl, 5- or 6-membered heteroaryl and 5- to 7-membered heterocyclyl, each of which is optionally substituted with a member independently selected from the group consisting of halo, $CF_3$, $OCF_3$, $SCF_3$, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —$CONR^{12a}R^{12b}$, =O, =S, —OH, —CH and —$NO_2$; wherein each heteroaryl or heterocyclyl comprises 1 to 4 heteroatoms, independently selected from the group consisting of N, O and S.

Each of the symbols $R^{3a}$, $R^{3b}$, $R^{4a}$, $R^{4b}$, $R^{4c}$, $R^{11a}$, $R^{11b}$, $R^{11c}$, $R^{11d}$, $R^{11e}$, $R^{11f}$, $R^{12a}$, $R^{12b}$, $R^{12c}$ and $R^{12d}$ are members independently selected from the group consisting of: H, $C_{1-6}$alkyl, $C_{2-6}$alkenyl, $C_{2-6}$alkynyl, $C_{0-4}$alkyl$C_{3-8}$cycloalkyl, $C_{0-4}$alkylaryl, $C_{0-4}$alkyl-heteroaryl, —$C_{0-6}$alkyl-$COC_{1-4}$alkyl, —$C_{0-6}$alkyl-$SO_2$—$C_{1-4}$alkyl, —$C_{0-6}$alkyl-$SO_2$—N($C_{1-4}$alkyl, $C_{1-4}$alkyl, $C_{104}$alkyl, —$C_{0-6}$alkyl-N($C_{1-4}$alkyl, $C_{1-4}$alkyl) and —$C_{1-6}$alkyl-O—$C_{0-6}$alkyl, wherein 1-3 hydrogen atoms on the aryl or heteroaryl ring may be independently replaced with a member selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$C_{0-2}C_{1-4}$alkyl, —CON($C_{1-4}$alkyl, $C_{1-4}$alkyl), —OH, —CN and $NO_2$; or can be taken together with the nitrogen atom to which they are attached to form a 3-8 membered heterocyclyl group, comprising 1 to 4 heteroatoms selected from the group consisting of N, O and S, optionally substituted with 1 to 4 $R^{13}$ substituents selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-6}$alkyl, —CON($C_{1-4}$alkyl, $C_{1-4}$alkyl), =O, =S, —OH, —CN and $NO_2$.

Each of the symbols $R^{10a}$ and $R^{10b}$ is a member independently selected from the group consisting of: hydrogen, $C_{1-6}$alkyl, $C_{2-6}$alkenyl, $C_{2-6}$alkynyl, $C_{3-8}$cycloalkyl and $C_{0-4}$alkyl$C_{3-8}$cycloalkyl, —$C_{0-6}$alkyl-aryl, heteraryl and —$C_{0-6}$alkyl-heteroaryl; and wherein 1 to 3 carbon or nitrogen atoms of aryl and heteroaryl are substituted with 1 to 3 $R^{4d}$ substituents.

With the above formula are a number of specific embodiments of the invention. In one group of embodiments, $R^1$ and $R^3$ is H. In a specific group of embodiments, $R^2$ is aryl, optionally substituted with 1 to 3 $R^{2a}$. More preferably, $R^2$ is phenyl or thiophenyl. More preferably, $R^{2a}$ is halo. For these embodiments, a preferred group of embodiments are those in which $R^{2a}$ is attached to the phenyl ring at a position para to the rest of the molecule.

In one group of embodiments, $R^4$ and $R^5$ is a member independently selected from the group consisting of: hydrogen and —$C_{0-6}$alkyl-aryl, wherein 1 to 3 carbon or nitrogen atoms of aryl are substituted with 1 to 3 $R^{4d}$ substituents. More preferably $R^4$ is hydrogen and $R^5$ is phenyl. In a specific group of embodiments when $R^4$ and $R^5$ are different, the carbon bearing $R^5$ has the R-configuration. In another group of embodiments when $R^4$ and $R^5$ are different, the carbon bearing $R^5$ has the S-configuration. In another group of embodiments, each $R^{4d}$ is a member independently selected from the group consisting of halogen and $C_{0-2}$alkyl-$OR^{12a}$; and $R^{12a}$ is $C_{1-6}$alkyl.

In one group of embodiments, the compounds have the formula:

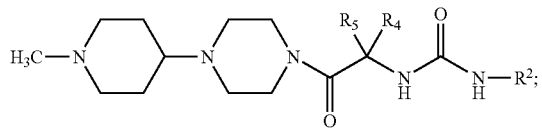

wherein $R^2$ is aryl, optionally substituted with 1 to 3 $R^{2a}$. In a specific group of embodiments, $R^2$ is aryl, optionally substituted with 1 to 3 $R^{2a}$. More preferably, $R^{2a}$ is phenyl. More preferably, $R^{2a}$ is halo. For these embodiments, a preferred group of embodiments are those in which $R^{2a}$ is attached to the phenyl ring at a position para to the rest of the molecule.

In one group of embodiments, $R^4$ and $R^5$ is a member independently selected from the group consisting of: hydrogen and —$C_{0-6}$alkyl-aryl, wherein 1 to 3 carbon or nitrogen atoms of aryl are substituted with 1 to 3 $R^{4d}$ substituents. More preferably $R^4$ is hydrogen and $R^5$ is phenyl. In a specific group of embodiments when $R^4$ and $R^5$ are different, the carbon bearing $R^5$ has the R-configuration. In another group of embodiments when $R^4$ and $R^5$ are different, the carbon bearing $R^5$ has the S-configuration. In another group of embodiments, each $R^{4d}$ is a member independently selected from the group consisting of halogen and $C_{0-2}$alkyl-$OR^{12a}$; and $R^{12a}$ is $C_{1-6}$alkyl.

In one group of embodiments, the compounds have the formula:

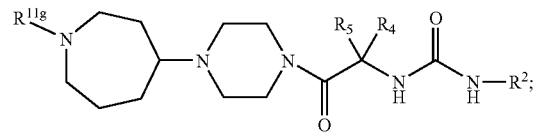

wherein $R^2$ is aryl, optionally substituted with 1 to 3 $R^{2a}$. In a specific group of embodiments, $R^2$ is aryl, optionally substituted with 1 to 3 $R^{2a}$. More preferably, $R^2$ is phenyl. More preferably, $R^{2a}$ is halo. For these embodiments, a preferred group of embodiments are those in which $R^{2a}$ is attached to the phenyl ring at a position para to the rest of the molecule.

In one group of embodiments, $R^4$ and $R^5$ is a member independently selected from the group consisting of: hydrogen and —$C_{0-6}$alkyl-aryl, wherein 1 to 3 carbon or nitrogen atoms of aryl are substituted with 1 to 3 $R^{4d}$ substituents. More preferably $R^4$ is hydrogen and $R^5$ is phenyl. In a specific group of embodiments when $R^4$ and $R^5$ are different, the carbon bearing $R^5$ has the R-configuration. In another group of embodiments when $R^4$ and $R^5$ are different, the carbon bearing $R^5$ has the S-configuration. In another group of embodiments, each $R^{4d}$ is a member independently selected from the group consisting of halogen and $C_{0-2}$lkyl-$OR^{12a}$; and $R^{12a}$ is $C_{1-6}$alkyl.

In one aspect, the present invention provides compounds having the formula:

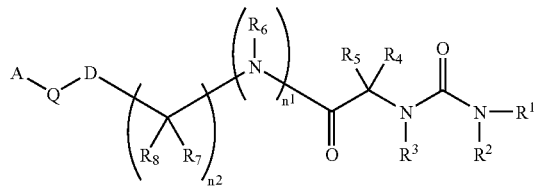

and pharmaceutically acceptable salts, hydrates, solvates and prodrugs thereof. In formula (III), $R^1$ is a member selected from the group consisting of: hydrogen, —$C_{1-6}$alkyl, —$C_{0-6}$alkyl-aryl, heteroaryl and —$C_{2-6}$alkenyl.

The symbol $R^2$ is a member selected from the group consisting of: —$C_{0-6}$alkyl-aryl, —$C_{3-8}$cycloalkylaryl, heteroaryl, —$C_{3-8}$cycloalkylheteroaryl, —$C_{3-8}$cycloalkyl, —$C_{3-8}$cycloalkenyl, heteromonocyclyl, fused heterobicyclyl and unfused heterobicyclyl, optionally substituted with from 1 to 3 $R^{2a}$ substituents, wherein each heterocyclyl comprises 5 to 12 ring atoms, 1 to 4 of which are members independently selected from the group consisting of N, O and S.

The symbol $R^3$ is a member selected from the group consisting of: hydrogen, $C_{1-6}$alkyl, $C_{2-6}$alkenyl, —$C_{3-8}$cycloalkyl, —$C_{0-4}$alkyl-$C_{3-8}$-cycloalkyl, —$C_{0-6}$alkyl-aryl, —$C_{0-6}$alkyl-heteroaryl, —$C_{0-6}$alkyl-heterocyclyl, —$C_{0-6}$alkyl-CO—$OR^{3a}$, —$C_{1-6}$alkyl-N($R^{3a}R^{3b}$), —$C_{1-6}$alkyl-O—$R^{3a}$, —$C_{1-6}$alkyl-S—$R^{3a}$, —$C_{0-6}$alkyl-C(O)—N($R^{3a}R^{3b}$) and —$C_{1-6}$alkyl-N($R^{3a}$)—C(O)$R^{3b}$.

Each $R^4$ and $R^5$ is a member independently selected from the group consisting of: hydrogen, —$C_{1-6}$alkyl, —$C_{2-6}$alkenyl, —$C_{2-6}$alkynyl, —$C_{3-8}$cycloalkyl, —$C_{0-4}$alkyl-$C_{3-8}$-cycloalkyl, $C_{1-6}$haloalkyl, —$C_{0-6}$alkyl-heteroaryl, —$C_{0-6}$alkyl-heterocyclyl, —$C_{0-6}$alkyl-CN, —$C_{0-6}$alkyl-NO$_2$, —$C_{1-6}$alkyl-O—$R^{4a}$, —$C_{1-6}$alkyl-S—$R^{4a}$, —$C_{1-6}$alkyl-SO$_2$—$R^{4a}$, —$C_{1-6}$alkyl-S(O)—$R^{4a}$, —$C_{0-6}$alkyl-CO—OR$^{4a}$, —$C_{0-6}$alkyl-C(O)—N(R$^{4a}$R$^{4b}$), —$C_{0-6}$alkyl-C(O) R$^{4a}$, —$C_{1-6}$alkyl-N(R$^{4a}$R$^{4b}$), —$C_{1-6}$alkyl-N(R$^{4a}$)—C(O) R$^{4b}$, —$C_{1-6}$alkyl-N(R$^{4a}$)—C(O)—N(R$^{4b}$R$^{4c}$), —$C_{1-6}$alkyl-(N)R$^{4a}$)—SO$_2$—R$^{4b}$, —$C_{1-6}$alkyl-SO$_2$—N(R$^{4a}$R$^{4b}$), —$C_{0-6}$alkyl-PO(—OR$^{4a}$)(—OR$^{4b}$), —$C_{1-6}$alkyl-N(R$^{4a}$)—PO(—$^{4b}$)(—OR$^{4c}$) and —$C_{0-6}$alkyl-aryl; or R$^4$ and R$^5$ can be taken together with the carbon atom to which they are attached to form a 3 to 8 membered cycloalkyl or heterocyclyl group; wherein each heterocyclyl is a 3 to 8 membered monocyclic ring or a 8-12 membered bicyclic ring, each comprising from 1 to 4 heteroatoms selected from the group consisting of O, N and S, and wherein 1 to 3 carbon or nitrogen atoms of aryl, heteroaryl and heterocyclyl are substituted with 1 to 3 R$^{4d}$ substituents.

The letter D is a member selected from the group consisting of: a direct bond, aryl, heteroaryl, $C_{3-8}$cycloalkyl, $C_{3-8}$cycloalkenyl, heteromonocyclyl, unfused heterobicyclyl, and fused heterobicyclyl; optionally substituted with 1 to 3 R$^9$ substituents, wherein each heterocyclyl comprises from 5 to 10 ring atoms, 1-4 of which are selected from the group consisting of N, O and S.

The symbol Q is selected from the group consisting of: a direct bond, —C(R$^{10a}$R$^{10b}$)—, —C(O)—, —C(S)—, —C(=NR$^{10a}$)—, —O—, —S—, —N(R$^{10a}$)—, —N(R$^{10a}$)CH$_2$—, —CH$_2$N(R$^{10a}$)—, —C(O)N(R$^{10a}$)—, —N(R$^{10a}$)C (O)—, —SO$_2$—, —SO—, —SO$_2$N(R$^{10a}$)—, and —N(R$^{10a}$)—SO$_2$—; and at least one of D and Q is not a direct bond.

The symbol A is dihydroimidazolyl, 1,4-diazepanyl, thiazolyl, oxazolyl, imidazolyl, pyrid-4-yl, 3-oxo-morpholin-4-yl, optionally substituted with 1 to 3 R$^{11g}$. In another embodiment the symbol A is 1-H-2-oxo-pyridyl, optionally substituted with 1 to 3 R$^{11g}$.

Each R$^{2a}$, R$^{4d}$, R$^9$ and R$^{11g}$ is a member independently selected from the group consisting of: H, halo, $C_{1-6}$alkyl, $C_{2-6}$alkenyl, $C_{2-6}$alkynyl, $C_{0-4}$alkylC$_{3-8}$cycloalkyl, —$C_{1-4}$alkoxy, —O—$C_{0-2}$alkyl-CF$_3$, —$C_{0-2}$alkyl-CF$_3$, —$C_{0-2}$alkyl-CN, —$C_{0-2}$alkyl-NO$_2$, —$C_{0-2}$alkyl-NR$^{12a}$R$^{12b}$, —$C_{0-2}$alkyl-SO$_2$NR$^{12a}$R$^{12b}$, —$C_{0-2}$alkyl-SO$_2$R$^{12a}$, —$C_{0-2}$alkyl-SOR$^{12a}$, —$C_{0-2}$alkyl-CF$_3$, —$C_{0-2}$alkyl-OR$^{12a}$, —$C_{0-2}$alkyl-SR$^{12a}$, —O—CH$_2$—CH$_2$—OR$^{12a}$, —O—CH$_2$—CO$_2$R$^{12a}$, —N(R$^{12a}$)—CH$_2$—CH$_2$—OR$^{12b}$, —$C_{0-2}$alkyl-C(O)NR$^{12a}$R$^{12b}$, —$C_{0-2}$alkyl-C$_{0-2}$R$^{12a}$, —$C_{0-2}$alkyl-N(R$^{12a}$)—C(O)R$^{12b}$, —$C_{0-2}$alkyl-N(R$^{12c}$)—C(O)NR$^{12a}$R$^{12b}$, —$C_{0-2}$alkyl-C(=NR$^{12c}$)NR$^{12a}$R$^{12b}$), —$C_{0-2}$alkyl-C(=NR$^{12a}$)R$^{12b}$, —$C_{0-2}$alkyl-N(R$^{12d}$)C (=NR$^{12c}$)NR$^{12a}$R$^{12b}$, —$C_{0-2}$alkyl-N(R$^{12a}$)—SO$_2$—R$^{12b}$, =O, =S, =NR$^{12a}$, 5- or 6-membered aryl, 5- or 6-membered heteroaryl and 5- to 7-membered heterocyclyl, each of which is optionally substituted with a member independently selected from the group consisting of halo, CF$_3$, OCF$_3$, SCF$_3$, $C_{1-6}$alkyl, $C_{2-6}$alkenyl, $C_{2-6}$alkynyl, $C_{0-4}$alkylC$_{3-8}$cycloalkyl, $C_{1-4}$alkoxy, —CO$_2$H, —CO$_2$C$_{1-4}$alkyl, —CONR$^{12a}$R$^{12b}$, =O, =S, —OH, —CN and —NO$_2$; wherein each heteroaryl or heterocyclyl comprises 1 to 4 heteroatoms, independently selected from the group consisting of N, O and S.

Each of the symbols R$^{3a}$, R$^{3b}$, R$^{4a}$, R$^{4b}$, R$^{4c}$R$^{12a}$, R$^{12b}$, R$^{12c}$ and R$^{12d}$ are members independently selected from the group consisting of: H, $C_{1-6}$alkyl, $C_{2-6}$alkenyl, $C_{2-6}$alkynyl, $C_{0-4}$alkylC$_{3-8}$cycloalkyl, $C_{0-4}$alkylaryl, $C_{0-4}$alkyl-heteroaryl, —$C_{0-6}$alkyl-COC$_{1-4}$alkyl, —$C_{0-6}$alkyl-CO$_2$C$_{1-4}$alkyl, —$C_{0-6}$alkyl-SO$_2$—C$_{1-4}$alkyl, —$C_{0-6}$alkyl-SO$_2$—N(C$_{1-4}$alkyl, C$_{1-4}$alkyl), —$C_{0-6}$alkyl-N(C$_{1-4}$alkyl, C$_{1-4}$alkyl) and —$C_{1-6}$alkyl-O—$C_{0-6}$alkyl, wherein 1-3 hydrogen atoms on the aryl or heteroaryl ring may be independently replaced with a member selected from the group consisting of halo, $C_{1-6}$alkyl, $C_{2-6}$alkenyl, $C_{2-6}$alkynyl, $C_{0-4}$alkylC$_{3-8}$cycloalkyl, $C_{1-4}$alkoxy, —CO$_2$H, —CO$_2$C$_{1-4}$alkyl, —CON(C$_{1-4}$alkyl, C$_{1-4}$alkyl), —OH, —CN and NO$_2$; or can be taken together with the nitrogen atom to which they are attached to form a 3-8 membered heterocyclyl group, comprising 1 to 4 heteroatoms selected from the group consisting of N, O and S, optionally substituted with 1 to 4 R$^{13}$ substituents selected from the group consisting of halo, $C_{1-6}$alkyl, $C_{2-6}$alkenyl, $C_{2-6}$alkynyl, $C_{0-4}$alkylC$_{3-8}$cycloalkyl, $C_{1-4}$alkoxy, —CO$_2$H, —CO$_2$C$^{1-4}$alkyl, —CON(C$_{1-4}$alkyl, C$_{1-4}$alkyl), =O, =S, —OH, —CN and NO$_2$.

Each of the symbols R$^6$, R$^7$, R$^8$, R$^{10a}$ and R$^{10b}$ is a member independently selected from the group consisting of: hydrogen, $C_{1-6}$alkyl, $C_{2-6}$alkenyl, $C_{2-6}$alkynyl, $C_{3-8}$cycloalkyl and $C_{0-4}$alkylC$_{3-8}$cycloalkyl, —$C_{0-6}$alkyl-aryl, hetaryl and —$C_{0-6}$alkyl-heteroaryl, or R$^4$ and R$^6$ can be taken together with the atoms to which they are attached to form a 5 to 12 membered heterocyclyl group; wherein each heterocyclyl is a 5 to 8 membered monocyclic ring or a 8-12 membered bicyclic ring, each comprising from 1 to 4 heteroatoms selected from the group consisting of O, N and S, and wherein 1 to 3 carbon or nitrogen atoms of aryl, heteroaryl and heterocyclyl are substituted with 1 to 3 R$^{4d}$ substituents. Each of the subscripts n1 and n2 is an integer of 0 to 1.

With the above formula are a number of specific embodiments of the invention. In one group of embodiments, R$^1$ and R$^3$ is H. In a specific group of embodiments, R$^2$ is aryl, optionally substituted with 1 to 3 R$^{2a}$. More preferably, R$^2$ is phenyl or thiophenyl. More preferably, R$^{2a}$ is independently selected from the group consisting of halo and $C_{2-6}$alkynyl. For these embodiments, a preferred group of embodiments are those in which R$^{2a}$ is attached to the phenyl or pyridyl ring at a position para to the rest of the molecule.

In one group of embodiments, each R$^4$ and R$^5$ is a member independently selected from the group consisting of: hydrogen, —$C_{1-6}$alkyl, —$C_{0-6}$alkyl-heteroaryl, —$C_{0-6}$alkyl-aryl, —$C_{0-6}$alkyl-CO—OR$^{4a}$, —$C_{0-6}$alkyl-C(O)—N(R$^{4a}$R$^{4b}$), —$C_{2-6}$alkynyl and —$C_{2-6}$alkynyl; or R$^4$ and R$^5$ can be taken together with the carbon atom to which they are attached to form a 3 to 12 membered cycloalkyl or heterocyclyl group; wherein each heterocyclyl is a 3 to 8 membered monocyclic ring or a 8-12 membered bicyclic ring, each comprising from 1 to 4 heteroatoms selected from the group consisting of O, N and S, and wherein 1 to 3 carbon or nitrogen atoms of aryl and heteroaryl are substituted with 1 to 3 R$^{4d}$ substituents. More preferably R$^4$ is hydrogen or phenyl; and R$^5$ is a member independently selected from the group consisting of hydrogen, isopropyl, t-butyl, isobutyl, benzyl, 2-indol-3-ylmethyl, 2-imidazol-4-ylmethyl, phenyl, 3-pyridyl, 2-thiophenyl, 3-thiophenyl, 2-benzyloxycarbonylmethyl, 2-carboxymethyl, 2-dimethylaminocarbonylmethyl, 2-(piperidin-1-yl-carbonylmethyl), 2-(morpholin-4-ylcarbonylmethyl), 2-(pyrrolidin-1-yl-carbonylmethyl), 2-[4-ethoxycarbonyl-piperidin-1-yl)carbonylmethyl], 2-(homopiperidin-1-ylcarbonylmethyl), 2-(benzylamino-carbonylmethyl), 2-(methylamino-carbonylmethyl), 2-(aminocarbonylmethyl), 2-(phenylamino-carbonylmethyl), benzodioxol-5-yl, 2-butynyl, 2-propynyl, and 2-propenyl or are taken together with the carbon atom to which they are attached to from a cyclopropyl ring. In a specific group of embodiments when R$^4$ and R$^5$ are different, the carbon bearing R$^5$ has the R-configuration. In another group of embodiments when R$^4$ and R$^5$ are different, the carbon bearing R$^5$ has the S-configuration. In another group of embodiments, each R$^{4d}$ is a member independently selected from the group consisting of halogen, —$C_{1-6}$alkyl, —O—$C_{0-2}$alkyl-$CF_3$ and $C_{0-2}$alkyl-$OR^{12a}$; and $R^{12a}$ is $C_{1-6}$alkyl or $C_{0-4}$alkylary.

In one group of embodiments, the subscript n1 is 0. In another group of embodiments the subscript n1 is 1.

In a specific group of embodiments $R^6$ is H or $R^4$ and $R^6$ can be taken together with the atoms to which they are attached to form a 5 to 12 membered heterocyclyl group; wherein each heterocyclyl is a 5 to 8 membered monocyclic ring or a 8-12 membered bicyclic ring, each comprising from 1 to 4 heteroatoms selected from the group consisting of O, N and S, and wherein 1 to 3 carbon or nitrogen atoms of aryl, heteroaryl and heterocyclyl are substituted with 1 to 3 $R^{4d}$ substituents. Within this embodiment, $R^4$ and $R^6$ are taken together with the atoms to which they are attached selected from the group having the formula:

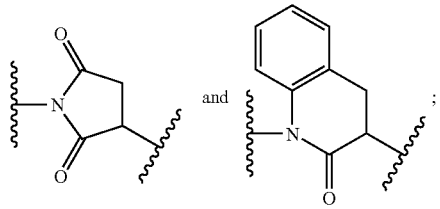

optionally substituted with 1 to 3 $R^{4d}$ substituents. In one group of embodiments, the subscript n2 is 0. In another group of embodiments the subscript n2 is 1.

In one group of embodiments, D is aryl or heteromonocyclyl, wherein heteromonocyclyl comprises from 5 to 7 ring atoms, 1 to 2 of which are N or O. More preferably, D is phenyl or piperidinyl.

In another group of embodiments, Q is a direct bond or —C(O)-More preferably, Q is attached to the phenyl or piperidinyl ring at a position para to the rest of the molecule.

In another group of embodiments, A is a member selected from the group consisting of: dihydroimidazolyl, 1,4-diazepanyl, thiazolyl and oxazolyl. In another group of embodiments, A is a member selected from the group consisting of: imidazolyl, pyrid-4-yl, 3-oxo-morpholin-4-yl. More preferably, A-Q-D-$(CR^7R^8)_{n2}$—$NR^6_{n1}$ is selected from the group consisting of:

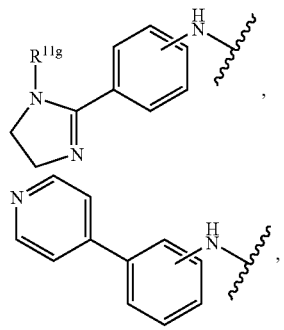

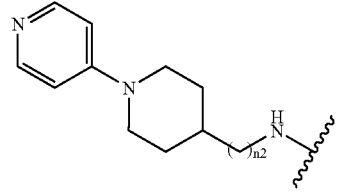

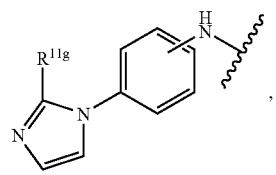

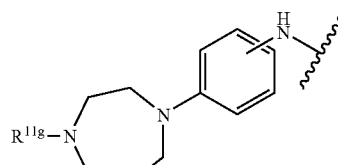

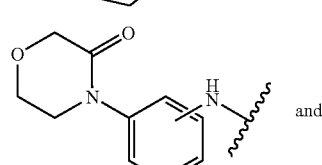

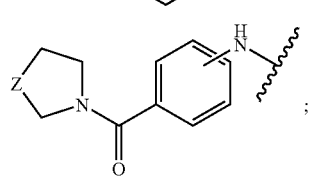

wherein Z is O or S; and the wavy line indicates the point of attachment to the rest of the molecule. Other embodiments are wherein A-Q-D-$(CR^7R^8)_{n2}$—$NR^6_{n1}$ is selected from the group consisting of:

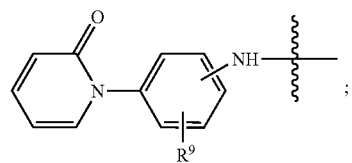

wherein and the wavy line indicates the point of attachment to the rest of the molecule. Other embodiments are wherein A-Q- is selected from the group consisting of:

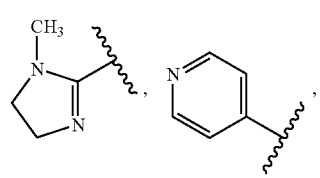

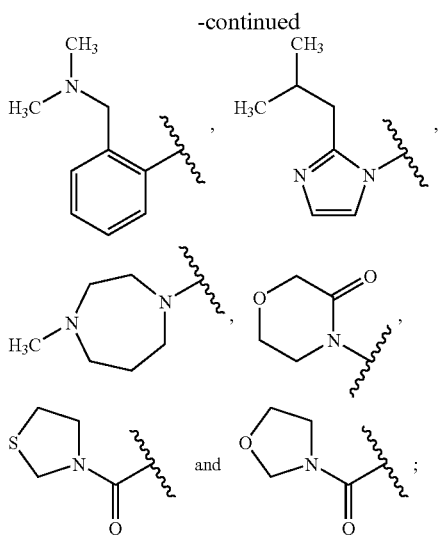

wherein the wavy line indicates the point of attachment to the rest of the molecule. Other embodiments are wherein A-Q- is:

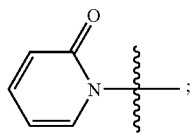

wherein the wavy line indicates the point of attachment to the rest of the molecule.

In other embodiments, compounds of formula I are provided which have the formula:

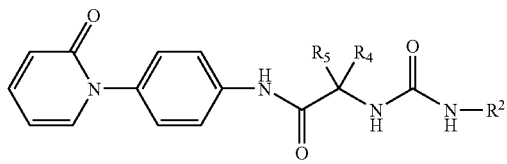

Within this group, specific embodiments are provided in which $R^2$ is aryl or heteroaryl, optionally substituted with 1 to 3 $R^{2a}$. Preferably, $R^2$ is selected from the group consisting of phenyl and benzofuranyl. Still further preferred are embodiments wherein each optional substituent $R^{2a}$ is independently selected from the group consisting of halo and $C_{1-6}$alkyl. Still further preferred are embodiments wherein $R^{2a}$ is attached to the phenyl ring at a position para to the rest of the molecule. Yet another group of embodiments are those in which each $R^4$ and $R^5$ is a member independently selected from the group consisting of: hydrogen, —$C_{1-6}$alkyl and —$C_{0-6}$alkyl-aryl. More preferably $R^4$ is hydrogen and $R^5$ is a member independently selected from the group consisting of hydrogen, isobutyl and phenyl. In a specific group of embodiments when $R^4$ and $R^5$ are different, the carbon bearing $R^5$ has the R-configuration. In another group of embodiments when $R^4$ and $R^5$ are different, the carbon bearing $R^5$ has the S-configuration.

In each of the above embodiments, any variables are meant to have their full scope w/reference to formulas (I), (II) and (III) unless indicated otherwise.

Within the present invention, the compounds provided in the examples below are each preferred embodiments, along with their pharmaceutically acceptable salts. Preferred examples of compounds of formula (I) include:

N-[4-(1-methyl-4,5-dihydro-1H-imidazol-2-yl)phenyl]-2-(4-chlorophenylaminocarbonylamino)-acetamide;

N-[4-(1-methyl-4,5-dihydro-1H-imidazol-2-yl)phenyl]-2-isopropyl-2-(4-chlorophenylaminocarbonylamino)-acetamide;

N-[4-(1-methyl-4,5-dihydro-1H-imidazol-2-yl)phenyl]-2-(1,1-dimethylethyl)-2-(4-chlorophenylaminocarbonylamino)-acetamide;

N-[4-(1-methyl-4,5-dihydro-1H-imidazol-2-yl)phenyl]-2-(2,2-dimethylpropyl)-2-(4-chlorophenylaminocarbonylamino)-acetamide;

N-[4-(1-methyl-4,5-dihydro-1H-imidazol-2-yl)phenyl]-2-benzyl-2-(4-chlorophenylaminocarbonylamino)-acetamide;

N-[4-(1-methyl-4,5-dihydro-1H-imidazol-2-yl)phenyl]-2-indol-3-ylmethyl-2-4-chlorophenylaminocarbonylamino)-acetamide;

N-[4-(1-methyl-4,5-dihydro-1H-imidazol-2-yl)phenyl]-2-imidazol-4-ylmethyl-2-(4-chlorophenylaminocarbonylamino)-acetamide;

N-[4-(1-methyl-4,5-dihydro-1H-imidazol-2-yl)phenyl]-2-(1-methyl-indol-3-ylmethyl)-2-(4-chlorophenylaminocarbonylamino)-acetamide;

N-[4-(1-methyl-4,5-dihydro-1H-imidazol-2-yl)phenyl]-2-pyridin-3-yl-2-(4-chlorophenylaminocarbonylamino)-acetamide;

N-[4-(1-methyl-4,5-dihydro-1H-imidazol-2-yl)phenyl]-2-(4-fluorophenyl)-2-(4-chlorophenylaminocarbonylamino)-acetamide;

N-[4-(1-methyl-4,5-dihydro-1H-imidazol-2-yl)phenyl]-2-(2-fluorophenyl)-2-(4-chlorophenylaminocarbonylamino)-acetamide;

N-[4-(1-methyl-4,5-dihydro-1H-imidazol-2-yl)phenyl]-2-(2-thienyl)-2-(4-chlorophenylaminocarbonylamino)-acetamide;

N-[4-(1-methyl-4,5-dihydro-1H-imidazol-2-yl)phenyl]-2-(3-thienyl)-2-(4-chlorophenylaminocarbonylamino)-acetamide;

N-[4-(1-methyl-4,5-dihydro-1H-imidazol-2-yl)phenyl]-2,2-diphenyl-2-(4-chlorophenylaminocarbonylamino)-acetamide;

N-[4-(1-methyl-4,5-dihydro-1H-imidazol-2-yl)phenyl]-1-(4-chlorophenylaminocarbonylamino)-1-cyclopropanecarboxamide;

N-[4-(1-methyl-4,5-dihydro-1H-imidazol-2-yl)phenyl]-2-phenyl-2-(4-chlorophenylaminocarbonylamino)-acetamide;

N-[4-(1-methyl-4,5-dihydro-1H-imidazol-2-yl)phenyl]-2-(2-thienyl)-2-(4-fluorophenylaminocarbonylamino)-acetamide;

N-[4-(1-methyl-4,5-dihydro-1H-imidazol-2-yl)phenyl]-2-(2-thienyl)-2-(4-ethynylphenylaminocarbonylamino)-acetamide;

N-[4-(dimethylaminoimino)phenyl]-2-(2-thienyl)-2-(4-chlorophenylamino-carbonylamino)-acetamide;

N-[4-(N-methyl-N-ethylaminoimino)phenyl]-2-(2-thienyl)-2-(4-chlorophenylaminocarbonylamino)-acetamide;

N-[4-(pyrrolidinylimino)phenyl]-2-(2-thienyl)-2-(4-chlorophenylamino-carbonylamino)-acetamide;

N-[4-(piperidinylimino)phenyl]-2-(2-thienyl)-2-(4-chlorophenylamino-carbonylamino)-acetamide;
N-[4-(dimethylaminoimino)phenyl]-2-phenyl-2-(4-chlorophenylamino-carbonylamino)-acetamide;
N-[4-(N-methyl-N-ethylaminoimino)phenyl]-2-phenyl-2-(4-chlorophenylaminocarbonylamino)-acetamide;
N-[4-(methylaminoimino)phenyl]-2-phenyl-2-(4-chlorophenylamino-carbonylamino)-acetamide;
N-[4-(N-methyl-N-allylaminoimino)phenyl]-2-phenyl-2-(4-chlorophenylaminocarbonylamino)-acetamide;
N-[4-(N-methyl-N-propargylaminoimino)phenyl]-2-phenyl-2-(4-chlorophenylaminocarbonylamino)-acetamide;
N-[4-(azetidin-1-ylimino)phenyl]-2-phenyl-2-(4-chlorophenylamino-carbonylamino)-acetamide;
N-[4-(pyrrolidin-1-ylimino)phenyl]-2-phenyl-2-(4-chlorophenylamino-carbonylamino)-acetamide;
N-[4-(1-methyl-4,5-dihydro-1H-imidazol-2-yl)phenyl]-2-(2-thienyl)-2-(4-bromophenylaminocarbonylamino)-acetamide;
(2S) N-[4-(1-methyl-4,5-dihydro-1H-imidazol-2-yl)phenyl]-2-phenyl-2-(4-chlorophenylaminocarbonylamino)-acetamide;
(2R) N-[4-(1-methyl-4,5-dihydro-1H-imidazol-2-yl)phenyl]-2-phenyl-2-(4-chlorophenylaminocarbonylamino)-acetamide;
N-[4-(dimethylaminoimino)-2-fluorophenyl]-2-phenyl-2-(4-chlorophenylaminocarbonylamino)-acetamide;
N-[4-(N-methyl-N-ethylaminoimino)-2-fluorophenyl]-2-phenyl-2-(4-chlorophenylaminocarbonylamino)-acetamide;
N-[4-(N-methyl-N-allylaminoimino)-2-fluorophenyl]-2-phenyl-2-(4-chlorophenylaminocarbonylamino)-acetamide;
N-[4-(N-methyl-N-propargylaminoimino)-2-fluorophenyl]-2-phenyl-2-(4-chlorophenylaminocarbonylamino)-acetamide;
N-(4-methylaminoimino-2-fluorophenyl)-2-phenyl-2-(4-chlorophenylamino-carbonylamino)-acetamide;
N-[4-(pyrrolidin-1-ylimino)-2-fluorophenyl]-2-phenyl-2-(4-chlorophenylaminocarbonylamino)-acetamide;
N-[4-(azetidin-1-ylimino)-2-fluorophenyl]-2-phenyl-2-(4-chlorophenylaminocarbonylamino)-acetamide;
N-[4-(1-methyl-4,5-dihydro-1H-imidazol-2-yl)phenyl]-2-(2-fluorophenyl)-2-(4-bromophenylaminocarbonylamino)-acetamide;
N-[4-(pyrrolidin-1-ylimino)phenyl]-2-(2-fluorophenyl)-2-(4-chlorophenylaminocarbonylamino)-acetamide;
N-[4-(piperidin-1-ylimino)phenyl]-2-(2-fluorophenyl)-2-(4-chlorophenylaminocarbonylamino)-acetamide;
N-[4-(dimethylaminoimino)phenyl]-2-(2-fluorophenyl)-2-(4-chlorophenylaminocarbonylamino)-acetamide;
N-[4-(pyrrolidin-1-ylimino)phenyl]-2-(2-fluorophenyl)-2-(4-bromophenylaminocarbonylamino)-acetamide;
N-[4-(piperidin-1-ylimino)phenyl]-2-(2-fluorophenyl)-2-(4-bromophenylaminocarbonylamino)-acetamide;
N-[4-(dimethylaminoimino)phenyl]-2-(2-fluorophenyl)-2-(4-bromophenylaminocarbonylamino)-acetamide;
N-[4-(2,2-dimethylhydrazinoimino)-2-fluorophenyl]-2-(2-fluorophenyl)-2-(4-chlorophenylaminocarbonylamino)-acetamide;
N-[4-(pyridin-4-yl)phenyl]-2-(2-fluorophenyl)-2-(4-chlorophenylaminocarbonylamino)-acetamide;
N-[4-(N-oxo-pyridin-4-yl)phenyl]-2-(2-fluorophenyl)-2-(4-chlorophenylaminocarbonylamino)-acetamide;
N-[4-(N-oxo-pyridin-2-yl)phenyl]-2-(2-fluorophenyl)-2-(4-chlorophenylaminocarbonylamino)-acetamide;
N-[4-(N-oxo-pyridin-2-yl)phenyl]-2-(2-fluorophenyl)-2-(4-bromophenylaminocarbonylamino)-acetamide;
N-(piperidin-4-ylmethyl)-2-(2-fluorophenyl)-2-(4-chlorophenylaminocarbonylamino)-acetamide;
N-[(N-acetimidyl-piperidin-4-yl)methyl]-2-(2-fluorophenyl)-2-(4-chlorophenylaminocarbonylamino)-acetamide;
N-[4-(2-dimethylaminomethyl-phenyl)phenyl]-2-(2-fluorophenyl)-2-(4-chlorophenylaminocarbonylamino)-acetamide;
N-[4-(2-dimethylaninomethyl-phenyl)-2-fluorophenyl]-2-(2-fluorophenyl)-2-(4-chlorophenylaminocarbonylamino)-acetamide;
N-[4-(2-dimethylaminomethyl-phenyl)-2-fluorophenyl]-2-(2-fluorophenyl)-2-(4-bromophenylaminocarbonylamino)-acetamide;
N-[4-(2-dimethylaminomethyl-imidazol-1-yl)-2-fluorophenyl]-2-(2-fluorophenyl)-2-(4-chlorophenylaminocarbonylamino)-acetamide;
(2S) N-[4-(1-methyl-4,5-dihydro-1H-imidazol-2-yl)phenyl]-2-benzyloxy-carbonylmethyl-2-(4-chlorophenylaminocarbonylamino)-acetamide;
(2S) N-[4-(1-methyl-4,5-dihydro-1H-imidazol-2-yl)phenyl]-2-carboxymethyl-2-(4-chlorophenylaminocarbonylamino)-acetamide;
(2R) N-[4-(1-methyl-4,5-dihydro-1H-imidazol-2-yl)phenyl]-2-benzyloxycarbonylmethyl-2-(4-chlorophenylaminocarbonylamino)-acetamide;
(2R) N-[4-(1-methyl-4,5-dihydro-1H-imidazol-2-yl)phenyl]-2-carboxymethyl-2-(4-chlorophenylaminocarbonylamino)-acetamide;
N-[4-(1-methyl-4,5-dihydro-1H-imidazol-2-yl)phenyl]-2-dimethylaminocarbonylmethyl-2-(4-chlorophenylaminocarbonylamino)-acetamide;
N-[4-(1-methyl-4,5-dihydro-1H-imidazol-2-yl)phenyl]-2-(piperidin-1-ylcarbonylmethyl)-2-(4-chlorophenylaminocarbonylamino)-acetamide;
N-[4-(1-methyl-4,5-dihydro-1H-imidazol-2-yl)phenyl]-2-(morpholin-4-ylcarbonylmethyl)-2-(4-chlorophenylaminocarbonylamino)-acetamide;
N-[4-(1-methyl-4,5-dihydro-1H-imidazol-2-yl)phenyl]-2-(pyrrolidin-1-yl-carbonylmethyl)-2-(4-chlorophenylaminocarbonylamino)-acetamide;
N-[4-(1-methyl-4,5-dihydro-1H-imidazol-2-yl)phenyl]-2-[4-ethoxycarbonyl-piperidin-1-yl)carbonylmethyl]-2-(4-chlorophenylaminocarbonylamino)-acetamide;
N-[4-(1-methyl-4,5-dihydro-1H-imidazol-2-yl)phenyl]-2-(homopiperidin-1-ylcarbonylmethyl)-2-(4-chlorophenylaminocarbonylamino)-acetamide;
N-[4-(1-methyl-4,5-dihydro-1H-imidazol-2-yl)phenyl]-2-(benzylamino-carbonylmethyl)-2-(4-chlorophenylaminocarbonylamino)-acetamide;
N-[4-(1-methyl-4,5-dihydro-1H-imidazol-2-yl)phenyl]-2-(methylamino-carbonylmethyl)-2-(4-chlorophenylaminocarbonylamino)-acetamide;
N-[4-(1-methyl-4,5-dihydro-1H-imidazol-2-yl)phenyl]-2-(aminocarbonylmethyl)-2-(4-chlorophenylaminocarbonylamino)-acetamide;
N-[4-(1-methyl-4,5-dihydro-1H-imidazol-2-yl)phenyl]-3-(4-chlorophenylaminocarbonylamino)-succinimide;
N-[4-(1-methyl-4,5-dihydro-1H-imidazol-2-yl)phenyl]-2-(phenylamino-carbonylmethyl)-2-(4-chlorophenylaminocarbonylamino)-acetamide;
N-[4-(1-methyl-4,5-dihydro-1H-imidazol-2-yl)phenyl]-2-(3-chlorophenyl)-2-(4-chlorophenylaminocarbonylamino)-acetamide;

N-[4-(1-methyl-4,5-dihydro-1H-imidazol-2-yl)phenyl]-2-(2-chlorophenyl)-2-4-chlorophenylaminocarbonylamino)-acetamide;
N-[4-(1-methyl-4,5-dihydro-1H-imidazol-2-yl)phenyl]-2-(benzo-1,3-dioxl-5-yl)-2-(4-chlorophenylaminocarbonylamino)-acetamide;
N-[4-(1-methyl-4,5-dihydro-1H-imidazol-2-yl)phenyl]-2-(2-bromophenyl)-2-(4-chlorophenylaminocarbonylamino)-acetamide;
N-[4-(N-oxo-pyridin-4-yl)phenyl]-2-(2-bromophenyl)-2-(4-chlorophenylaminocarbonylamino)-acetamide;
N-[4-(N-oxo-pyridin-2-yl)phenyl]-2-(2-bromophenyl)-2-(4-chlorophenylaminocarbonylamino)-acetamide;
N-[4-(dimethylaminoimino)phenyl]-2-(2-bromophenyl)-2-(4-chlorophenylaminocarbonylamino)-acetamide;
N-[4-(pyrrolidin-1-ylimino)phenyl]-2-(2-bromophenyl)-2-(4-chlorophenylaminocarbonylamino)-acetamide;
N-(1-isopropylpiperidin-4-yl)-2-(2-bromophenyl)-2-(4-chlorophenylamino-carbonylamino)-acetamide;
N-[4-(1-methylpiperidin-4-yl)piperazin-1-yl]-2-(2-bromophenyl)-2-(4-chlorophenylaminocarbonylamino)-acetamide;
N-[4-(1-methyl-4,5-dihydro-1H-imidazol-2-yl)phenyl]-2-(2-methylphenyl)-2-(4-chlorophenylaminocarbonylamino)-acetamide;
N-[4-(2-dimethylaminomethyl-imidazol-1-yl)-2-fluorophenyl]-2-(2-methylphenyl)-2-(4-chlorophenylaminocarbonylamino)-acetamide;
N-[4-(dimethylaminoimino)phenyl]-2-(2-methylphenyl)-2-(4-chlorophenylaminocarbonylamino)-acetamide;
N-[4-(pyrrolidin-1-ylimino)phenyl]-2-(2-methylphenyl)-2-(4-chlorophenylaminocarbonylamino)-acetamide;
N-[4-(N-oxo-pyridin-2-yl)phenyl]-2-(2-methylphenyl)-2-(4-chlorophenylaminocarbonylamino)-acetamide;
N-[4-(2-dimethylaminomethyl-phenyl)phenyl]-2-(2-methylphenyl)-2-(4-chlorophenylaminocarbonylamino)-acetamide;
N-(1-isopropylpiperidin-4-yl)-2-(2-methylphenyl)-2-(4-chlorophenylamino-carbonylamino)-acetamide;
N-[4-(1-methylpiperidin-4-yl)piperazin-1-yl]-2-(2-methylphenyl)-2-(4-chlorophenylaminocarbonylamino)-acetamide;
N-[4-(4-methyl-homopiperazinyl)phenyl]-2-(2-methylphenyl)-2-(4-chlorophenylaminocarbonylamino)-acetamide;
N-[1-(pyridin-4-yl)piperidin-4-yl]methyl-2-(2-methylphenyl)-2-(4-chlorophenylaminocarbonylamino)-acetamide;
N-[4-(pyrrolidin-1-ylcarbonyl)phenyl]-2-(2-methylphenyl)-2-(4-chlorophenylaminocarbonylamino)-acetamide;
N-[4-(3-oxo-morpholin-4-yl)phenyl]-2-(2-methylphenyl)-2-(4-chlorophenylaminocarbonylamino)-acetamide;
N-[4-(N-methyl-N-pyridin-4-yl-amino)phenyl]-2-(2-methylphenyl)-2-(4-chlorophenylaminocarbonylamino)-acetamide;
N-[4-(thiazolidin-3-ylcarbonyl)phenyl]-2-(2-methylphenyl)-2-(4-chlorophenylaminocarbonylamino)-acetamide;
N-[4-(oxazolidin-3-ylcarbonyl)phenyl]-2-(2-methylphenyl)-2-(4-chlorophenylaminocarbonylamino)-acetamide;
N-[4-(N-oxo-pyridin-2-yl)phenyl]-2-(2-chlorophenyl)-2-(4-chlorophenylaminocarbonylamino)-acetamide;
N-[4-(dimethylaminoimino)phenyl]-2-(2-chlorophenyl)-2-(4-chlorophenylaminocarbonylamino)-acetamide;
N-[4-(pyrrolidin-1-ylimino)phenyl]-2-(2-chlorophenyl)-2-(4-chlorophenylaminocarbonylamino)-acetamide;
N-[4-(4-methyl-homopiperazinyl)phenyl]-2-(2-chlorophenyl)-2-(4-chlorophenylaminocarbonylamino)-acetamide;
N-(1-isopropylpiperidin-4-yl)-2-(2-chlorophenyl)-2-(4-chlorophenylamino-carbonylamino)-acetamide;
N-[4-(1-methylpiperidin-4-yl)piperazin-1-yl]-2-(2-chlorophenyl)-2-(4-chlorophenylaminocarbonylamino)-acetamide;
N-[1-(pyridin-4-yl)piperidin-4-yl]methyl-2-(2-chlorophenyl)-2-(4-chlorophenylaminocarbonylamino)-acetamide;
N-[4-(1-methyl-4,5-dihydro-1H-imidazol-2-yl)phenyl]-2-(2-methoxyphenyl)-2-(4-chlorophenylaminocarbonylamino)-acetamide;
N-[4-(N-oxo-pyridin-2-yl)phenyl]-2-(2-methoxyphenyl)-2-(4-chlorophenylaminocarbonylamino)-acetamide;
N-[1-(pyridin-4-yl)piperidin-4-yl]methyl-2-(2-methoxyphenyl)-2-(4-chlorophenylaminocarbonylamino)-acetamide;
N-[4-(1-methylpiperidin-4-yl)piperazin-1-yl]-2-(2-methoxyphenyl)-2-(4-chlorophenylaminocarbonylamino)-acetamide;
N-(1-isopropylpiperidin-4-yl)-2-(2-methoxyphenyl)-2-(4-chlorophenylamino-carbonylamino)-acetamide;
N-[4-(4-methyl-homopiperazinyl)phenyl]-2-(2-methoxyphenyl)-2-(4-chlorophenylaminocarbonylamino)-acetamide;
N-[4-(dimethylaminoimino)phenyl]-2-(2-methoxyphenyl)-2-(4-chlorophenylaminocarbonylamino)-acetamide;
N-[4-(pyrrolidin-1-ylimino)phenyl]-2-(2-methoxyphenyl)-2-(4-chlorophenylaminocarbonylamino)-acetamide;
N-[4-(1-methyl-4,5-dihydro-1H-imidazol-2-yl)phenyl]-2-(2-iodophenyl)-2-(4-chlorophenylaminocarbonylamino)-acetamide;
N-[4-(N-oxo-pyridin-2-yl)phenyl]-2-(2-iodophenyl)-2-(4-chlorophenylamino-carbonylamino)-acetamide;
N-[4-(dimethylaminoimino)phenyl]-2-(2-iodophenyl)-2-(4-chlorophenylaminocarbonylamino)-acetamide;
N-[4-(pyrrolidin-1-ylimino)phenyl]-2-(2-iodophenyl)-2-(4-chlorophenylaminocarbonylamino)-acetamide;
N-[4-(1-methylpiperidin-4-yl)piperazin-1-yl]-2-(2-iodophenyl)-2-(4-chlorophenylaminocarbonylamino)-acetamide;
N-[4-(1-methyl-4,5-dihydro-1H-imidazol-2-yl)phenyl]-2-(4-bromophenyl)-2-(4-chlorophenylaminocarbonylamino)-acetamide;
N-[4-(1-methyl-4,5-dihydro-1H-imidazol-2-yl)phenyl]-2-(2-(4-trifluoromethoxyphenyl)-2-(4-chlorophenylaminocarbonylamino)-acetamide;
N-[4-(N-oxo-pyridin-2-yl)phenyl]-2-(2-trifluoromethoxyphenyl)-2-(4-chlorophenylaminocarbonylamino)-acetamide;
N-[4-(1-methyl-4,5-dihydro-1H-imidazol-2-yl)phenyl]-2-(2-trifluoromethylthiophenyl)-2-(4-chlorophenylaminocarbonylamino)-acetamide;
N-[4-(N-oxo-pyridin-2-yl)phenyl]-2-(2-trifluoromethylthiophenyl)-2-(4-chlorophenylaminocarbonylamino)-acetamide;
N-[4-(1-methyl-4,5-dihydro-1H-imidazol-2-yl)phenyl]-2-(2-phenoxyphenyl)-2-(4-chlorophenylaminocarbonylamino)-acetamide;
N-[4-(N-oxo-pyridin-2-yl)phenyl]-2-(2-phenoxyphenyl)-2-(4-chlorophenylaminocarbonylamino)-acetamide;
N-[4-(N-oxo-pyridin-2-yl)phenyl]-2-(2-methylthiophenyl)-2-(4-chlorophenylaminocarbonylamino)-acetamide;
N-[4-(1-methylpiperidin-4-yl)piperazin-1-yl]-2-(2-fluorophenyl)-2-(4-chlorophenylaminocarbonylamino)-acetamide;
N-[4-(1-methylpiperidin-4-yl)piperazin-1-yl]-2-phenyl-2-(4-chlorophenylaminocarbonylamino)-acetamide;
N-[4-(1-methyl-4,5-dihydro-1H-imidazol-2-yl)phenyl]-2-propargyl-2-(4-chlorophenylaminocarbonylamino)-acetamide;

N-[4-(1-methyl-4,5-dihydro-1H-imidazol-2-yl)phenyl]-2-(but-2-yn-1-yl)-2-(4-chlorophenylaminocarbonylamino)-acetamide;

N-[4-(N-oxo-pyridin-2-yl)phenyl]-2-(but-2-yn-1-yl)-2-(4-chlorophenylaminocarbonylamino)-acetamide;

N-[4-(1-methyl-4,5-dihydro-1H-imidazol-2-yl)phenyl]-2-allyl-2-(4-chlorophenylaminocarbonylamino)-acetamide;

N-[4-(N-oxo-pyridin-2-yl)phenyl]-2-allyl-2-(4-chlorophenylaminocarbonylamino)-acetamide;

1-[4-(dimethylaminoimino)phenyl]-3-(4-chlorophenylaminocarbonylamino)-3,4-dihydroquinolin-2-one;

1-[4-(pyrrolidinylimino)phenyl]-3-(4-chlorophenylaminocarbonylamino)-3,4-dihydroquinolin-2-one;

1-[4-(1-methyl-4,5-dihyrdo-1H-imidazol-2-yl)phenyl]-3-(4-chlorophenylaminocarbonylamino)-3,4-dihydroquinolin-2-one.

(2S) N-[4-(2-pyridon-1-yl)phenyl]-2-phenyl-2-(4-chlorophenylaminocarbonylamino)-acetamide;

(2R) N-[4-(2-pyridon-1-yl)phenyl]-2-phenyl-2-(4-chlorophenylaminocarbonylamino)-acetamide;

(2S) N-[4-(2-pyridon-1-yl)phenyl]-2-phenyl-2-(2-chlorothiophen-5-ylaminocarbonylamino)-acetamide;

(2R) N-[4-(2-pyridon-1-yl)-2-fluorophenyl]-2-phenyl-2-(4-chlorophenylaminocarbonylamino)-acetamide;

(2R) 4-(2-piperidinon-1-yl)piperidin-1-yl-2-phenyl-2-(4-chlorophenylaminocarbonylamino)-acetamide;

(2R) 4-(3-morpholinon-4-yl)piperidin-1-yl-2-phenyl-2-(4-chlorophenylaminocarbonylamino)-acetamide;

(2R) 4-(2-pyridon-1-yl)piperidin-1-yl-2-phenyl-2-(4-chlorophenylaminocarbonylamino)-acetamide;

4-(3-morpholinon-4-yl)piperidin-1-yl-2-(2-fluorophenyl)-2-(4-chlorophenylaminocarbonylamino)-acetamide;

4-(3-morpholinon-4-yl)piperidin-1-yl-2-(2-chlorophenyl)-2-(4-chlorophenylaminocarbonylamino)-acetamide;

4-(3-morpholinon-4-yl)piperidin-1-yl-2-(2-bromophenyl)-2-(4-chlorophenylaminocarbonylamino)-acetamide;

4-(3-morpholinon-4-yl)piperidin-1-yl-2-(2-methylphenyl)-2-(4-chlorophenylaminocarbonylamino)-acetamide;

4-(3-morpholinon-4-yl)piperidin-1-yl-2-(2-methoxyphenyl)-2-(4-chlorophenylaminocarbonylamino)-acetamide;

4-(2-piperidinon-1-yl)piperidin-1-yl-2-(2-fluorophenyl)-2-(4-chlorophenylaminocarbonylamino)-acetamide;

4-(2-piperidinon-1-yl)piperidin-1-yl-2-(2-methoxyphenyl)-2-(4-chlorophenylaminocarbonylamino)-acetamide;

4-(4-methyl-2-piperazinon-1-yl)piperidin-1-yl-2-(2-methoxyphenyl)-2-(4-chlorophenylaminocarbonylamino)-acetamide;

4-(homopiperidin-4-yl)piperazin-1-yl-2-(2-methoxyphenyl)-2-(4-chlorophenylaminocarbonylamino)-acetamide;

4-(1-methylhomopiperidin-4-yl)piperazin-1-yl-2-(2-methoxyphenyl)-2-(4-chlorophenylaminocarbonylamino)-acetamide;

(2R) 4-(4-methylhomopiperazin-1-yl)piperidin-1-yl-2-phenyl-2-(4-chlorophenylaminocarbonylamino)-acetamide;

(2R) 4-(1-methylpiperidin-4-yl)piperidin-1-yl-2-phenyl-2-(4-chlorophenylaminocarbonylamino)-acetamide; and (2R) 4-(1-methylpiperidin-4-yl)homopiperazin-1-yl-2-phenyl-2-(4-chlorophenylaminocarbonylamino)-acetamide.

All the preferred, more preferred, and most preferred compounds listed above are selective inhibitors of Factor Xa.

Compositions

The present invention further provides compositions comprising one or more compounds of formula (I), (II) or (III) or a tautomer or a pharmaceutically acceptable salt thereof, and a pharmaceutically acceptable carrier. It will be appreciated that the compounds of formula (I), (II) or (III) in this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the compounds of formula (I), (II) or (III), similar to metabolically labile esters or carbamates, which are capable of producing the parent compounds of formula (I), (II) or (III) in vivo, are within the scope of this invention.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Furthermore, the basic nitrogen-containing groups may be quatemized with agents like lower alkyl halides, such as methyl, ethyl, propyl and butyl chlorides, bromides and iodides; dialkyl sulfates, such as dimethyl, diethyl, dibutyl and diamyl sulfates, long chain halides, such as decyl, lauryl, myristyl and stearyl chlorides, bromides and iodides; aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system, etc.), increase oral availability, increase solubility to allow administration by injection, alter metabolism and alter rate of excretion.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

Pharmaceutical formulations may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

Pharmaceutically acceptable carriers that may be used in these compositions include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously. The formulations of the invention may be designed as short-acting, fast-releasing, or long-acting. Still further, compounds can be administered in a local rather than systemic means, such as administration (e.g., injection) as a sustained release formulation.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The pharmaceutical compositions of this invention may be in any orally acceptable dosage form, including capsules, tablets, aqueous suspensions or solutions. In the case of tablets for oral use, carriers that are commonly used include lactose and corn starch. Lubricating agents, such as magnesium stearate, are also typically added. For a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be in a topical form, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include mineral oil, sorbitan monostearate, polysorbate 60, cetyl esters, wax, cetyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative, such as benzylalkonium chloride. Alternatively, for ophthalmic uses, the pharmaceutical compositions may be formulated in an ointment, such as petrolatum.

The pharmaceutical compositions of this invention may also be administered by nasal aerosol or inhalation. Such compositions are prepared according to techniques known in the art of pharmaceutical formulation and may be prepared as solutions in saline, employing benzyl alcohol or other suitable preservatives, absorption promoters to enhance bioavailability, fluorocarbons and/or other conventional solubilizing or dispersing agents.

Any of the above dosage forms containing effective amounts are within the bounds of routine experimentation and within the scope of the invention. A therapeutically effective dose may vary depending upon the route of administration and dosage form. The preferred compound or compounds of the invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

Besides those representative dosage forms described above, pharmaceutically acceptable excipients and carriers and dosage forms are generally known to those skilled in the art and are included in the invention. It should be understood that a specific dosage and treatment regimen for any particular patient will depend upon a variety of factors, including the activity of the specific compound employed, the age, body weight, general health, sex and diet of the patient, and the time of administration, rate of excretion, drug combination, judgment of the treating physician and severity of the particular disease being treated. The amount of active ingredient(s) will also depend upon the particular compound and other therapeutic agent, if present, in the composition.

Methods of Use

The invention provides methods of inhibiting or decreasing Factor Xa activity as well as treating or ameliorating a Factor Xa associated state, symptom, disorder or disease in a patient in need thereof (e.g., human or non-human). "Treating" within the context of the invention means an alleviation of symptoms associated with a disorder or disease, or halt of further progression or worsening of those symptoms, or prevention or prophylaxis of the disease or disorder.

The term "mammal" includes organisms which express Factor Xa. Examples of mammals include mice, rats, cows, sheep, pigs, goats, horses, bears, monkeys, dogs, cats and, preferably, humans. Transgenic organisms which express Factor Xa are also included in this definition.

The inventive methods comprise administering an effective amount of a compound or composition described herein to a mammal or non-human animal. As used herein, "effective amount" of a compound or composition of the invention includes those amounts that antagonize or inhibit Factor Xa. An amount which antagonizes or inhibits Factor Xa is detectable, for example, by any assay capable of determining Factor Xa activity, including the one described below as an illustrative testing method. Effective amounts may also include those amounts which alleviate symptoms of a Factor Xa associated disorder treatable by inhibiting Factor Xa. Accordingly, "antagonists of Factor Xa" include compounds which interact with the Factor Xa and modulate, e.g., inhibit or decrease, the ability of a second compound, e.g., another Factor Xa ligand, to interact with the Factor Xa. The Factor Xa binding compounds are preferably antagonists of Factor Xa. The language "Factor Xa binding compound" (e.g., exhibits binding affinity to the receptor) includes those compounds which interact with Factor Xa resulting in modulation of the activity of Factor Xa. Factor Xa binding compounds may be identified using an in vitro (e.g., cell and non-cell based) or in vivo method. A description of an in vitro method is provided below.

The amount of compound present in the methods and compositions described herein should be sufficient to cause a detectable decrease in the severity of the disorder, as measured by any of the assays described in the examples. The amount of Factor Xa modulator needed will depend on the effectiveness of the modulator for the given cell type and the length of time required to treat the disorder. In certain embodiments, the compositions of this invention may further comprise another therapeutic agent. When a second agent is used, the second agent may be administered either as a separate dosage form or as part of a single dosage form with the compounds or compositions of this invention. While one or more of the inventive compounds can be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the two or more therapeutic agents concurrently or sequentially. The agents may be administered in any order. Alternatively, the multiple therapeutic agents can be combined into a single composition that can be administered to the patient. For instance, a single pharmaceutical composition could comprise the compound or pharmaceutically acceptable salt or solvate according to the formula I, another therapeutic agent (e.g., methotrexate) or a pharmaceutically acceptable salt or solvate thereof, and a pharmaceutically acceptable excipient or carrier.

The invention comprises a compound having the formula I, a method for making an inventive compound, a method for making a pharmaceutical composition from at least one inventive compound and at least one pharmaceutically acceptable carrier or excipient, and a method of using one or more inventive compounds to treat a variety of disorders, symptoms and diseases (e.g., inflammatory, autoimmune, neurological, neurodegenerative, oncology and cardiovascular), such as RA, osteoarthritis, irritable bowel disease IBD, asthma, chronic obstructive pulmonary disease COPD and MS. The inventive compounds and their pharmaceutically acceptable salts and/or neutral compositions may be formulated together with a pharmaceutically acceptable excipient or carrier and the resulting composition may be administered in vivo to mammals, such as men, women and animals, to treat a variety of disorders, symptoms and diseases. Furthermore, the inventive compounds can be used to prepare a medicament that is useful for treating a variety of disorders, symptoms and diseases.

Kits

Still another aspect of this invention is to provide a kit comprising separate containers in a single package, wherein the inventive pharmaceutical compounds, compositions and/or salts thereof are used in combination with pharmaceutically acceptable carriers to treat states, disorders, symptoms and diseases where Factor Xa plays a role.

EXAMPLES

Example 1

N-[4-(1-methyl-4,5-dihydro-1H-imidazol-2-yl)phenyl]-2-(4-chlorophenylaminocarbonylamino)-acetamide

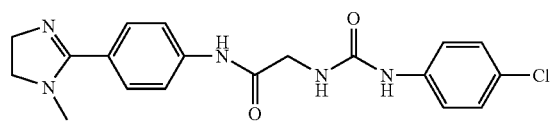

To a solution of N-Boc-glycine (1.75 g, 10.0 mmol) and 4-aminobenzonitrile (1.18 g, 10.0 mmol) in $CH_2Cl_2$ (10 mL), EDC (1.95 g, 10.2 mmol) was added. The mixture was stirred at room temperature overnight. The product was collected as a white precipitate by filtration (2.46 g). MS 276.1 (M+H) and 298.1 (M+Na).

To a solution of the nitrile compound (400 mg, 1.45 mmol) in pyridine (10 mL) and TEA (1.0 mL), H2S gas was bubbled until saturation was reached. The solution was then stirred at room temperature overnight. It was concentrated in vacuo. The residue was dissolved in acetone (8 mL). Iodomethane (0.903 mL, 14.5 mmol) was added. It was heated at reflux for 30 min, then concentrated in vacuo. The residue was dissolved in MeOH (12 mL). To the solution, a pre-mixed N-methylethylenediamine (0.637 mL, 7.34 mmol) and HOAc (0.630 mL, 11.0 mmol) were added. The mixture was heated at reflux for 30 min. It was then stirred at room temperature overnight. After being concentrated in vacuo, the residue was purified by HPLC to give white powder (258 mg).

A solution of the N-Boc compound (110 mg, 0.331 mmol) in TFA (5 mL) was stirred at room temperature for 1 h. It was the concentrated in vacuo. The residue was dissolved in THF (4 mL). To the solution, 4-chlorophenyl isocyanate (53 mg, 0.35 mmol) was added. The mixture was stirred at room temperature overnight. It was then concentrated in vacuo. The residue was purified by HPLC to give the titled compound as a powder (35 mg) MS 386.1 and 388.1 (M+H, Cl pattern).

Example 2

N-[4-(1-methyl-4,5-dihydro-1H-imidazol-2-yl)phenyl]-2-isopropyl-2-(4-chlorophenylaminocarbonylamino)-acetamide

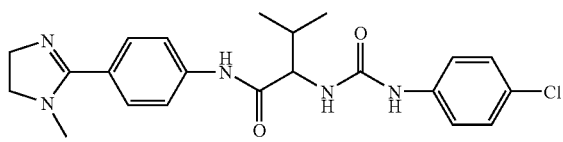

To a solution of N-Boc-valine (DL, 217 mg, 1.00 mmol) and 4-aminobenzonitrile (118 mg, 1.00 mmol) in pyridine (5 mL) cooled in an ice-bath, POCl3 (0.186 mL, 2.00 mmol) was added. The mixture was stirred at room temperature overnight. EtOAc and H2O were added. The organic layer was separated, dried over Na2SO4, concentrated in vacuo to give a solid (260 mg) MS 340.2 (M+Na).

To a solution of the nitrile compound (260 mg, 0.820 mmol) in anhydrous MeOH (5 mL) cooled in an ice-bath, HCl gas was bubbled through until saturation was reached. The mixture was then stirred at room temperature overnight. It was concentrated in vacuo. The residue was dissolved in anhydrous MeOH (6 mL). To the solution, N-methylethylenediamine (0.360 mL, 4.10 mmol) was added. The mixture was heated at reflux for 2 h. It was then concentrated in vacuo. The residue was purified by HPLC to give an oil (90 mg). MS 275.2 (M+H).

To a solution of the oil (45 mg, 0.16 mmol) and TEA (0.050 mL, 0.36 mmol) in THF (4 mL), 4-chlorophenyl isocyanate (33 mg, 0.21 mmol) was added. The mixture was stirred at room temperature overnight. It was then concentrated in vacuo. The residue was purified by HPLC to give a powder (20 mg). 428.2 and 430.2 (M+H, Cl pattern).

Example 3

N-[4-(1-methyl-4,5-dihydro-1H-imidazol-2-yl)phenyl]-2-(1,1-dimethylethyl)-2-(4-chlorophenylaminocarbonylamino)-acetamide

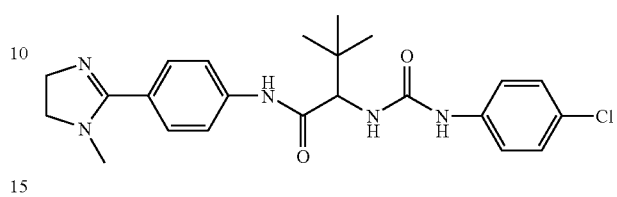

A. 4-(1-Methyl-4,5-dihydro-1H-imidazol-2-yl)-phenylamine

To a solution of 4-aminobenzonitrile (5.1 g, 43 mmol) in dry methanol (60 mL) at 0 C, hydrogen chloride gas was bubbled through until saturation was reached. The mixture was then stirred at room temperature overnight. It was concentrated in vacuo. The residue was dissolved in dry methanol (60 mL). To the solution, N-methyl ethylenediamine (19 mL, 216 mmol) was added. The mixture was then heated to reflux for 3 h. After being cooled in fridge overnight, the precipitated product was collected by filtration, then was dried on vacuum to give white solids (3.7 g). MS 176.0 (M+H).

B. N-[4-(1-methyl-4,5-dihydro-1H-imidazol-2-yl)phenyl]-2-(1,1-dimethylethyl)-2-(4-chlorophenylaminocarbonylamino)-acetamide To a solution of DL-tert-leucine (43 mg, 0.33 mmol) in DMF (2 mL), 4-chlorophenyl isocyanate (50 mg, 0.33 mmol) was added. The mixture was then stirred at room temperature overnight. To the reaction mixture, 4-(1-Methyl-4,5-dihydro-1H-imidazol-2-yl)-phenylamine (150 mg, 0.86 mmol) and H2O (0.5 mL, to solubilize the amine) were added. To the solution, EDC (127 mg, 0.66 mmol) was added. After being stirred at room temperature overnight, the solution was concentrated in vacuo. The residue was purified by HPLC to give the titled compound as a powder (35 mg). MS 442.1 and 444.1 (M+H, Cl pattern).

Example 4

N-[4-(1-methyl-4,5-dihydro-1H-imidazol-2-yl)phenyl]-2-(2,2-dimethylpropyl)-2-(4-chlorophenylaminocarbonylamino)-acetamide

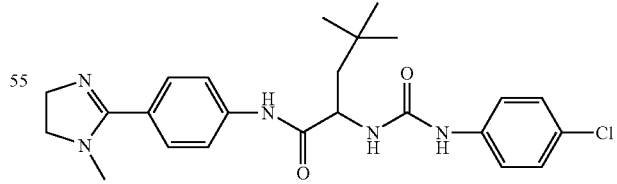

To a solution of DL-γ-methylleucine (48 mg, 0.33 mmol) in DMF (2 mL), 4-chlorophenyl isocyanate (50 mg, 0.33 mmol) was added. The mixture was then stirred at room temperature overnight. To the reaction mixture, 4-(1-Methyl-4,5-dihydro-1H-imidazol-2-yl)-phenylamine (150 mg, 0.86 mmol) and H2O (0.5 mL, to solubilize the amine) were added. To the solution, EDC (127 mg, 0.66 mmol) was added. After being stirred at room temperature overnight, the solution was concentrated in vacuo. The residue was purified by HPLC to give the titled compound as a powder (77 mg). MS 456.2 and 458.2 (M+H, Cl pattern).

Example 5

N-[4-(1-methyl-4,5-dihydro-1H-imidazol-2-yl)phenyl]-2-benzyl-2-(4-chlorophenylaminocarbonylamino)-acetamide

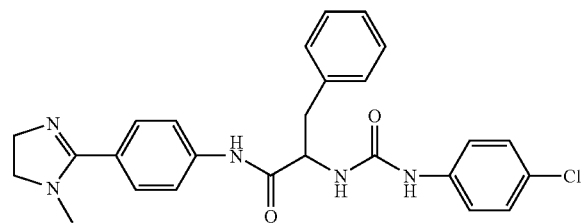

To a solution of DL-phenylalanine (83 mg, 0.50 mmol) in DMF (6 mL), 4-chlorophenyl isocyanate (77 mg, 0.50 mmol) was added. The mixture was then stirred at room temperature overnight. To the reaction mixture, 4-(1-Methyl-4,5-dihydro-1H-imidazol-2-yl)-phenylamine (180 mg, 1.02 mmol) and H₂O (1 mL, to solubilize the amine) were added. To the solution, EDC (200 mg, 1.04 mmol) was added. After being stirred at room temperature overnight, the solution was concentrated in vacuo. The residue was purified by HPLC to give the titled compound as a powder (96 mg). MS 476.1 and 478.1 (M+H, Cl pattern).

Example 6

N-[4-(1-methyl-4,5-dihydro-1H-imidazol-2-yl)phenyl]-2-indol-3-ylmethyl-2-(4-chlorophenylaminocarbonylamino)-acetamide

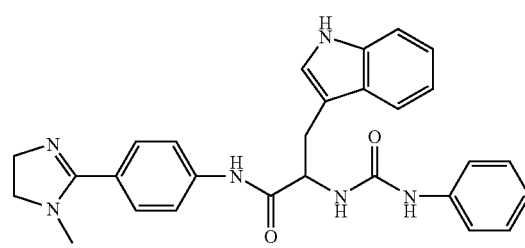

To a solution of DL-tryptophan (102 mg, 0.50 mmol) in DMF (6 mL), 4-chlorophenyl isocyanate (77 mg, 0.50 mmol) was added. The mixture was then stirred at room temperature overnight. To the reaction mixture, 4-(1-Methyl-4,5-dihydro-1H-imidazol-2-yl)-phenylamine (180 mg, 1.02 mmol) and H₂O (1 mL, to solubilize the amine) were added. To the solution, EDC (200 mg, 1.04 mmol) was added. After being stirred at room temperature overnight, the solution was concentrated in vacuo. The residue was purified by HPLC to give the titled compound as a powder (200 mg). MS 515.2 and 517.2 (M+H, Cl pattern).

Example 7

N-[4-(1-methyl-4,5-dihydro-1H-imidazol-2-yl)phenyl]-2-imidazol-4-ylmethyl-2-(4-chlorophenylaminocarbonylamino)-acetamide

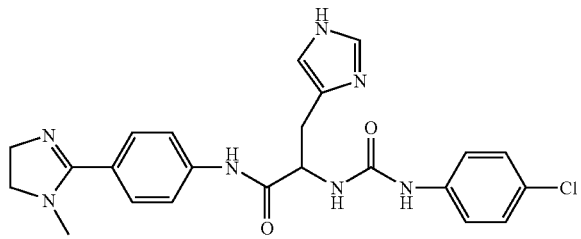

To a solution of DL-histidine (155 mg, 1.00 mmol) in 1N NaOH (5 mL), a solution of 4-chlorophenyl isocyanate (173 mg, 1.13 mmol) in dioxane (5 mL) was added. The mixture was then stirred at room temperature overnight. It was then concentrated in vacuo. The residue was purified by HPLC to give a powder (47 mg).

To a solution of the powder (45 mg, 0.15 mmol) and 4-(1-Methyl-4,5-dihydro-1H-imidazol-2-yl)-phenylamine (51 mg, 0.29 mmol) in DMF (2 mL) and H₂O (0.5 mL), EDC (112 mg, 0.58 mmol) was added. After being stirred at room temperature overnight, the mixture was concentrated in vacuo. The residue was purified by HPLC to give the titled compound as a powder (10 mg). MS 466.2 and 468.2 (M+H, Cl pattern).

Example 8

N-[4-(1-methyl-4,5-dihydro-1H-imidazol-2-yl)phenyl]-2-(1-methyl-indol-3-ylmethyl)-2-(4-chlorophenylaminocarbonylamino)-acetamide

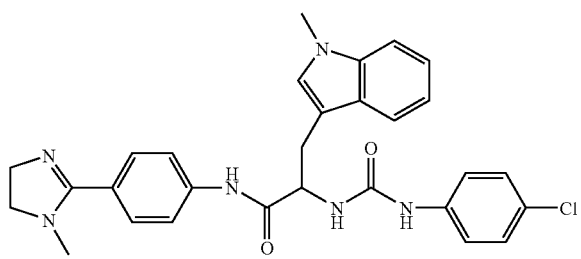

To a solution of DL-1-methyl-tryptophan (71 mg, 0.33 mmol) in DMF (4 mL), 4-chlorophenyl isocyanate (50 mg, 0.33 mmol) was added. The mixture was then stirred at room temperature overnight. It was filtered. To the filtrate, 4-(1-Methyl-4,5-dihydro-1H-imidazol-2-yl)-phenylamine (150 mg, 0.86 mmol) and H₂O (0.5 mL, to solubilize the amine) were added. To the solution, EDC (127 mg, 0.66 mmol) was added. After being stirred at room temperature overnight, the solution was concentrated in vacuo. The residue was purified by HPLC to give the titled compound as a powder (108 mg). MS 529.2 and 531.2 (M+H, Cl pattern).

Example 9

N-[4-(1-methyl-4,5-dihydro-1H-imidazol-2-yl)phenyl]-2-pyridin-3-yl-2-(4-chlorophenylaminocarbonylamino)-acetamide

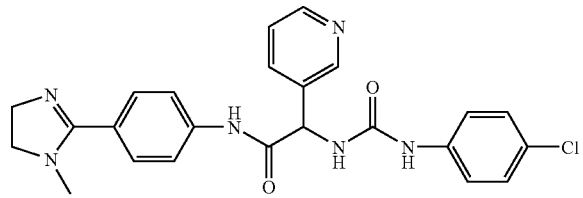

To a solution of DL-3-pyridyl-aminoacetic acid hydrochloride (307 mg, 1.63 mmol) and DIEA (0.283 mL, 1.63 mmol) in DMF (10 mL), 4-chlorophenyl isocyanate (253 mg, 1.65 mmol) was added. The mixture was then stirred at room temperature overnight. It was then concentrated in vacuo. The residue was purified by HPLC to give a powder (155 mg). MS 306.0 and 308.0 (M+H, Cl pattern).

To a solution of the powder (93 mg, 0.30 mmol) and 4-(1-Methyl-4,5-dihydro-1H-imidazol-2-yl)-phenylamine (10-6 mg, 0.60 mmol) in DMF (4 mL) and H$_2$O (1 mL), EDC (232 mg, 1.21 mmol) was added. After being stirred at room temperature overnight, the mixture was concentrated in vacuo. The residue was purified by HPLC to give the titled compound as a white powder (110 mg). MS 463.1 and 465.1 (M+H, Cl pattern).

Example 10

N-[4-(1-methyl-4,5-dihydro-1H-imidazol-2-yl)phenyl]-2-(4-fluorophenyl)-2-(4-chlorophenylaminocarbonylamino)-acetamide

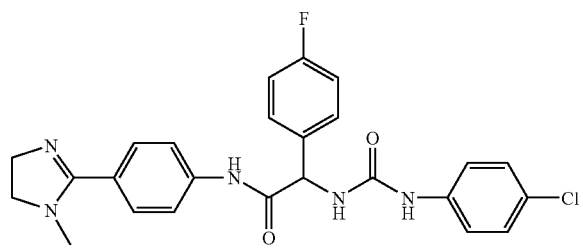

To a solution of 4-fluorophenyl glycine (288 mg, 1.70 mmol) in DMF (5 mL), 4-chlorophenyl isocyanate (262 mg, 1.70 mmol) was added. The mixture was then stirred at room temperature overnight. It was concentrated in vacuo. The residue was purified by HPLC to give a powder (210 mg). MS 323.1 and 325.1 (M+H, Cl pattern).

To a solution of the powder (52 mg, 0.16 mmol) and 4-(1-Methyl-4,5-dihydro-1H-imidazol-2-yl)-phenylamine (64 mg, 0.37 mmol) in DMF (3 mL) and H$_2$O (1 mL), EDC (64 mg, 0.33 mmol) was added. After being stirred at room temperature for 2 h, the mixture was concentrated in vacuo. The residue was purified by HPLC to give the titled compound as a white powder (28 mg). MS 480.1 and 482.1 (M+H, Cl pattern).

Example 11

N-[4-(1-methyl-4,5-dihydro-1H-imidazol-2-yl)phenyl]-2-(2-fluorophenyl)-2-(4-chlorophenylaminocarbonylamino)-acetamide

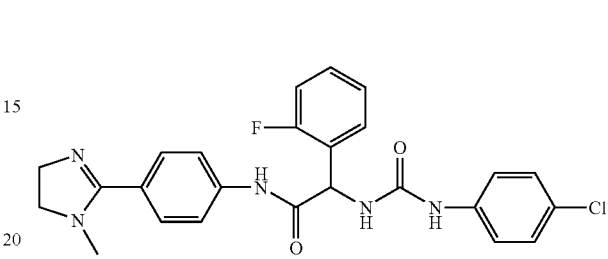

To a solution of 2-fluorophenyl glycine (288 mg, 1.70 mmol) in DMF (8 mL), 4-chlorophenyl isocyanate (262 mg, 1.70 mmol) was added. The mixture was then stirred at room temperature overnight. It was concentrated in vacuo. The residue was purified by HPLC to give a powder (150 mg). MS 323.1 and 325.1 (M+H, Cl pattern).

To a solution of the powder (52 mg, 0.16 mmol) and 4-(1-Methyl-4,5-dihydro-1H-imidazol-2-yl)-phenylamine (64 mg, 0.37 mmol) in DMF (3 mL) and H$_2$O (1 mL), EDC (64 mg, 0.33 mmol) was added. After being stirred at room temperature for 3 h, the mixture was concentrated in vacuo. The residue was purified by HPLC to give the titled compound as a white powder (50 mg). MS 480.1 and 482.1 (M+H, Cl pattern).

Example 12

N-[4-(1-methyl-4,5-dihydro-1H-imidazol-2-yl)phenyl]-2-(2-thienyl)-2-(4-chlorophenylaminocarbonylamino)-acetamide

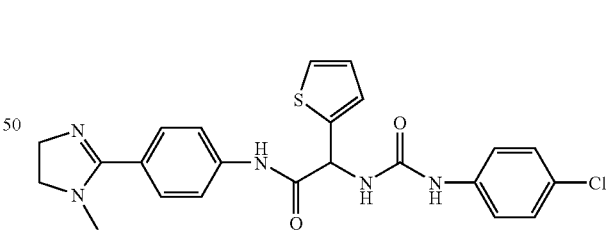

To a solution of 2-thienyl glycine (278 mg, 1.77 mmol) in DMF (8 mL), 4-chlorophenyl isocyanate (270 mg, 1.76 mmol) was added. The mixture was then stirred at room temperature overnight. It was concentrated in vacuo. The residue was purified by HPLC to give a powder (110 mg). MS 311.0 and 313.0 (M+H, Cl pattern).

To a solution of the powder (52 mg, 0.17 mmol) and 4-(1-Methyl-4,5-dihydro-1H-imidazol-2-yl)-phenylamine (64 mg, 0.37 mmol) in DMF (3 mL) and H$_2$O (1 mL), EDC (64 mg, 0.33 mmol) was added. After being stirred at room temperature for 3 h, the mixture was concentrated in vacuo. The residue was purified by HPLC to give the titled compound as a white powder (53 mg). MS 468.1 and 470.1 (M+H, Cl pattern).

Example 13

N-[4-(1-methyl-4,5-dihydro-1H-imidazol-2-yl)phenyl]-2-(3-thienyl)-2-(4-chlorophenylaminocarbonylamino)-acetamide

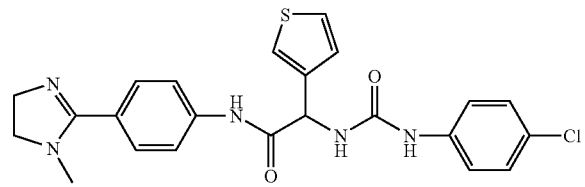

To a solution of 3-thienyl glycine (240 mg, 1.53 mmol) in DMF (5 mL), 4-chlorophenyl isocyanate (234 mg, 1.52 mmol) was added. The mixture was then stirred at room temperature overnight. It was concentrated in vacuo. The residue was purified by HPLC to give a powder (170 mg).

To a solution of the powder (55 mg, 0.18 mmol) and 4-(1-Methyl-4,5-dihydro-1H-imidazol-2-yl)-phenylamine (66 mg, 0.38 mmol) in DMF (3 mL) and $H_2O$ (1 mL), EDC (66 mg, 0.34 mmol) was added. After being stirred at room temperature for 3 h, the mixture was concentrated in vacuo. The residue was purified by HPLC to give the titled compound as a white powder (75 mg). MS 468.1 and 470.1 (M+H, Cl pattern).

Example 14

N-[4-(1-methyl-4,5-dihydro-1H-imidazol-2-yl)phenyl]-2,2-diphenyl-2-(4-chlorophenylaminocarbonylamino)-acetamide

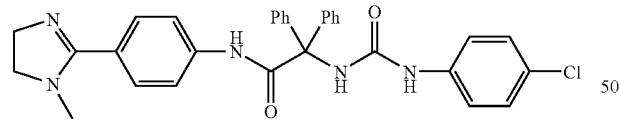

To a solution of diphenyl glycine (353 mg, 1.56 mmol) in DMF (5 mL), 4-chlorophenyl isocyanate (235 mg, 1.53 mmol) was added. The mixture was then stirred at room temperature overnight. It was concentrated in vacuo. The residue was dissolved in CH3CN (8 mL). When $H_2O$ (8 mL) was added, solids precipitated out as the desired product, which were collected by filtration (160 mg). MS 381.0 and 383.0 (M+H, Cl pattern).

To a solution of the solid (100 mg, 0.262 mmol) and 4-(1-Methyl-4,5-dihydro-1H-imidazol-2-yl)-phenylamine (92 mg, 0.53 mmol) in DMF (8 mL) and $H_2O$ (2 mL), EDC (197 mg, 1.03 mmol) was added. After being stirred at room temperature overnight, the mixture was concentrated in vacuo.

The residue was purified by HPLC to give the titled compound as a white powder (25 mg). MS 538.3 and 540.3 (M+H, Cl pattern).

Example 15

N-[4-(1-methyl-4,5-dihydro-1H-imidazol-2-yl)phenyl]-1-(4-chlorophenylaminocarbonylamino)-1-cyclopropanecarboxamide

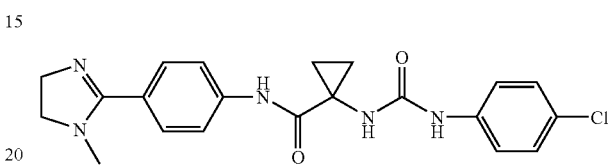

To a solution of 1-amino-1-cyclopropanecarboxylic acid (204 mg, 2.02 mmol) in 1N NaOH (6 mL), a solution of 4-chlorophenyl isocyanate (465 mg, 3.03 mmol) in dioxane (5 mL) was added. The mixture was then stirred at room temperature overnight. The mixture was washed with Et2O. The aqueous layer was separated, and acidified with 4N HCl to pH 1-2. The product was extracted with EtOAc. The EtOAc solution was dried over $Na_2SO_4$, then concentrated in vacuo to give a solid (210 mg).

To a solution of the solid (51 mg, 0.20 mmol) and 4-(1-Methyl-4,5-dihydro-1H-imidazol-2-yl)-phenylamine (69 mg, 0.40 mmol) in DMF (4 mL) and $H_2O$ (1 mL), EDC (151 mg, 0.79 mmol) was added. After being stirred at room temperature overnight, the mixture was concentrated in vacuo. The residue was purified by HPLC to give the titled compound as a powder (10 mg). MS 412.24 and 414.15 (N+H, Cl pattern).

Example 16

N-[4-(1-methyl-4,5-dihydro-1H-imidazol-2-yl)phenyl]-2-phenyl-2-(4-chlorophenylaminocarbonylamino)-acetamide

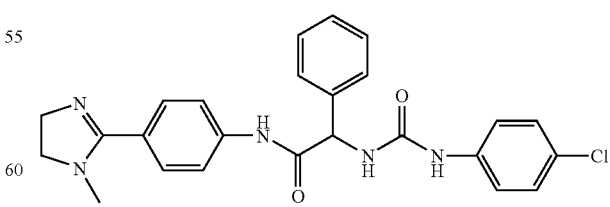

The titled compound was prepared analogously as described in Example 10, starting from DL-phenyl glycine in the place of 4-fluorophenyl glycine. MS 462.1 and 464.1 (M+H, Cl pattern).

Example 17

N-[4-(1-methyl-4,5-dihydro-1H-imidazol-2-yl)phenyl]-2-(2-thienyl)-2-(4-fluorophenylaminocarbonylamino)-acetamide

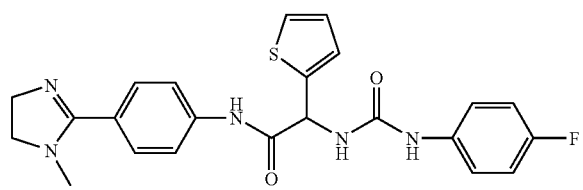

The titled compound was prepared analogously as described in Example 12, starting from 4-fluorophenylisocyanate in the place of 4-chlorophenylisocyanate. MS 452.1 (M+H).

Example 18

N-[4-(1-methyl-4,5-dihydro-1H-imidazol-2-yl)phenyl]-2-(2-thienyl)-2-(4-ethynylphenylaminocarbonylamino)-acetamide

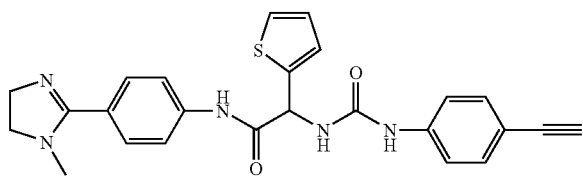

The titled compound was prepared analogously as described in Example 12, starting from 4-ethynylphenylisocyanate in the place of 4-chlorophenylisocyanate. MS 458.1 (M+H).

4-Ethynylphenylisocyanate was prepared from reaction of 4-ethynylaniline with one equivalent of carbonyldiimidazole in $CH_2Cl_2$.

Example 19

N-[4-(dimethylaminoimino)phenyl]-2-(2-thienyl)-2-(4-chlorophenylamino-carbonylamino)-acetamide

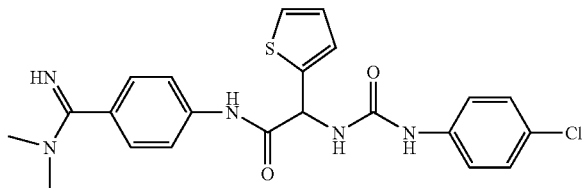

To a solution of 2-thienyl glycine (785 mg, 5.00 mmol) in DMF (10 mL), 4-chlorophenyl isocyanate (765 mg, 5.00 mmol) was added. The mixture was then stirred at room temperature for 3 h. It was concentrated in vacuo. The residue was purified by HPLC to give a powder (1.06 g).

To a solution of the powder (1.00 g, 3.23 mmol) and 4-aminobenzonitrile (0.380 g, 3.22 mmol) in DMF (10 mL), EDC (1.24 g, 6.46 mmol) was added. The mixture was stirred at room temperature overnight. It was then concentrated in vacuo. The residue was purified by HPLC to give a solid (1.22 g). MS 411.0 and 413.0 (M+H, Cl pattern).

To a solution of the nitrile compound (500 mg, 1.22 mmol) in pyridine (10 mL) and TEA (1.0 mL), H2S gas was bubbled until saturation was reached. The solution was then stirred at room temperature overnight. It was concentrated in vacuo. The residue was dissolved in acetone (8 mL). Iodomethane (0.380 mL, 6.10 mmol) was added. It was heated at reflux for 30 min, then concentrated in vacuo. The residue was dissolved in MeOH (20 mL). To a fifth of the solution (4 mL, 0.24 mmol), a pre-mixed dimethylamine (2M in THF, 0.61 mL, 1.22 mmol) and HOAc (0.11 mL, 1.92 mmol) were added. The mixture was then stirred at room temperature overnight. After being concentrated in vacuo, the residue was purified by HPLC to give a white powder (25 mg). MS 456.1 and 458.1 (M+H, Cl pattern).

Example 20

N-[4-(N-methyl-N-ethylaminoimino)phenyl]-2-(2-thienyl)-2-(4-chlorophenylaminocarbonylamino)-acetamide To the thioimidate solution in MeOH (4 mL, 0.24 mmol) from Example 19, a pre-mixed N-methyl-N-ethylamine (0.11 mL, 1.28 mmol) and HOAc (0.11 mL, 1.92 mmol) were added. The mixture was then stirred at room temperature overnight. After being concentrated in vacuo, the residue was purified by HPLC to give a white powder (8 mg). MS 470.1 and 472.1 (M+H, Cl pattern).

Example 21

N-[4-(pyrrolidinylimino)phenyl]-2-(2-thienyl)-2-(4-chlorophenylamino-carbonylamino)-acetamide To the thioimidate solution in MeOH (4 mL, 0.24 mmol) from Example 19, a pre-mixed pyrrolidine (0.11 mL, 1.32 mmol) and HOAc (0.11 mL, 1.92 mmol) were added. The mixture was then stirred at room temperature overnight. After being concentrated in vacuo, the residue was purified by HPLC to give a white powder (24 mg). MS 482.1 and 484.1 (M+H, Cl pattern).

Example 22

N-[4-(piperidinylimino)phenyl]-2-(2-thienyl)-2-(4-chlorophenylamino-carbonylamino)-acetamide

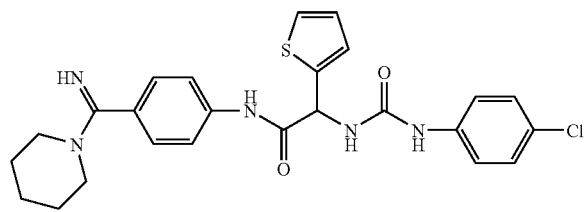

To the thioimidate solution in MeOH (4 mL, 0.24 mmol) from Example 19, a pre-mixed piperidine (0.12 mL, 1.21 mmol) and HOAc (0.11 mL, 1.92 mmol) were added. The mixture was then stirred at room temperature overnight. After being concentrated in vacuo, the residue was purified by HPLC to give a white powder (21 mg). MS 496.1 and 498.1 (M+H, Cl pattern).

Example 23

N-[4-(dimethylaminoimino)phenyl]-2-phenyl-2-(4-chlorophenylamino-carbonylamino)-acetamide

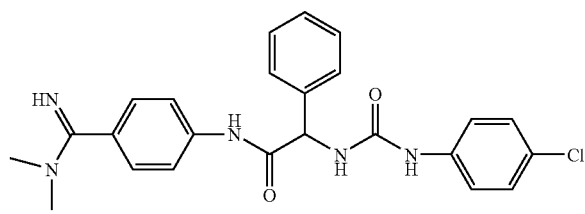

The titled compound was prepared analogously as described in Example 19, starting from phenyl glycine in the place of 2-thienyl glycine. MS 450.2 and 452.1 (M+H, Cl pattern).

Example 24

N-[4-(N-methyl-N-ethylaminoimino)phenyl]-2-phenyl-2-(4-chlorophenylaminocarbonylamino)-acetamide

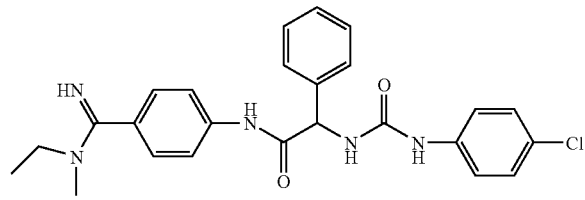

The titled compound was prepared analogously as described in Example 19, starting from phenyl glycine in the place of 2-thienyl glycine, and using N-methyl-N-ethylamine in the place of dimethylamine. MS 464.1 and 466.2 (M+H, Cl pattern).

Example 25

N-[4-(methylaminoimino)phenyl]-2-phenyl-2-(4-chlorophenylamino-carbonylamino)-acetamide

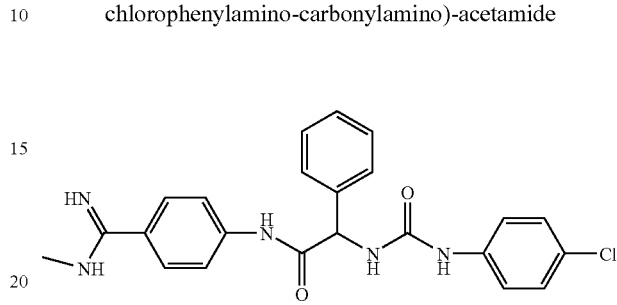

The titled compound was prepared analogously as described in Example 19, starting from phenylglycine in the place of 2-thienylglycine, and using methylamine in the place of dimethylamine. MS 436.1 and 438.1 (M+H, Cl pattern).

Example 26

N-[4-(N-methyl-N-allylaminoimino)phenyl]-2-phenyl-2-(4-chlorophenylaminocarbonylamino)-acetamide

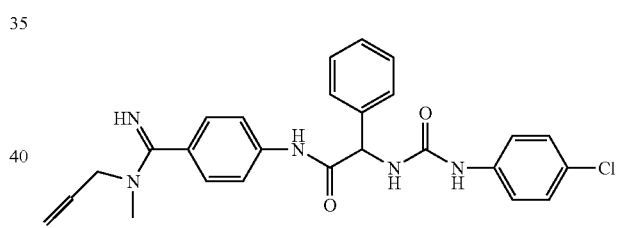

The titled compound was prepared analogously as described in Example 19, starting from phenylglycine in the place of 2-thienylglycine, and using N-methyl-N-allylamine in the place of dimethylamine. MS 476.2 and 478.2 (M+H, Cl pattern).

Example 27

N-[4-(N-methyl-N-propargylaminoimino)phenyl]-2-phenyl-2-(4-chlorophenylaminocarbonylamino)-acetamide

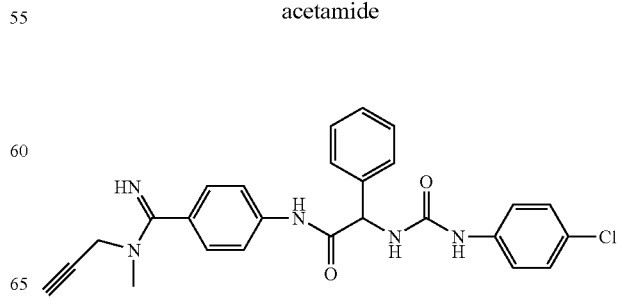

The titled compound was prepared analogously as described in Example 19, starting from phenylglycine in the place of 2-thienylglycine, and using N-methyl-N-propargylamine in the place of dimethylamine. MS 474.2 and 476.2 (M+H, Cl pattern).

Example 28

N-[4-(azetidin-1-ylimino)phenyl]-2-phenyl-2-(4-chlorophenylamino-carbonylamino)-acetamide

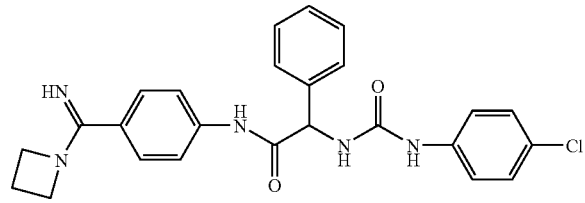

The titled compound was prepared analogously as described in Example 19, starting from phenylglycine in the place of 2-thienylglycine, and using azetidine in the place of dimethylamine. MS 462.1 and 464.2 (M+H, Cl pattern).

Example 29

N-[4-(pyrrolidin-1-ylimino)phenyl]-2-phenyl-2-(4-chlorophenylamino-carbonylamino)-acetamide

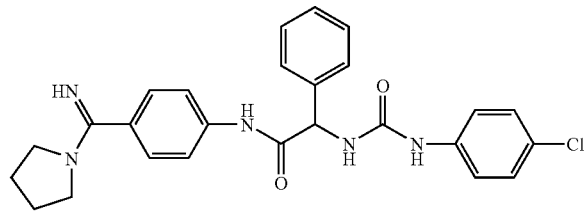

The titled compound was prepared analogously as described in Example 19, starting from phenylglycine in the place of 2-thienylglycine, and using pyrrolidine in the place of dimethylamine. MS 476.2 and 478.2 (M+H, Cl pattern).

Example 30

N-[4-(1-methyl-4,5-dihydro-1H-imidazol-2-yl)phenyl]-2-(2-thienyl)-2-(4-bromophenylaminocarbonylamino)-acetamide

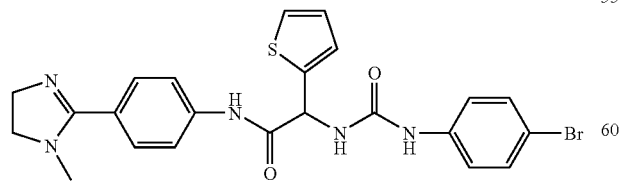

The titled compound was prepared analogously as described in Example 12, starting from 4-bromophenylisocyanate in the place of 4-chlorophenylisocyanate. MS 512.0 and 514.0 (M+H, Br pattern).

Example 31

(2S) N-[4-(1-methyl-4,5-dihydro-1H-imidazol-2-yl)phenyl]-2-phenyl-2-(4-chlorophenylaminocarbonylamino)-acetamide

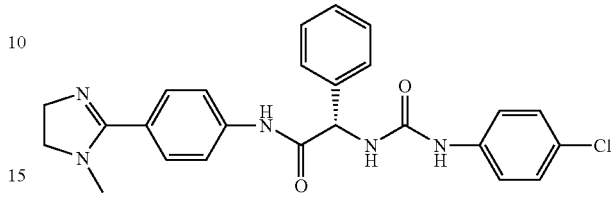

The titled compound was prepared analogously as described in Example 10, starting from L-phenylglycine in the place of 4-fluorophenyl glycine. MS 462.1 and 464.1 (M+H, Cl pattern).

Example 32

(2R) N-[4-(1-methyl-4,5-dihydro-1H-imidazol-2-yl)phenyl]-2-phenyl-2-(4-chlorophenylaminocarbonylamino)-acetamide

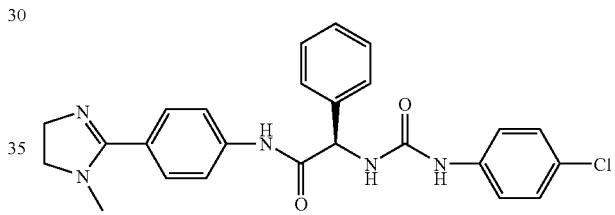

The titled compound was prepared analogously as described in Example 10, starting from D-phenylglycine in the place of 4-fluorophenyl glycine. MS 462.1 and 464.1 (M+H, Cl pattern).

Example 33

N-[4-(dimethylaminoimino)-2-fluorophenyl]-2-phenyl-2-(4-chlorophenylaminocarbonylamino)-acetamide

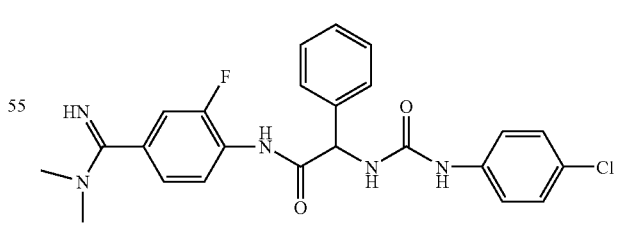

A. 4-amino-3-fluoro-benzonitrile

A mixture of 2-fluoro-4-iodoaniline (10.0 g, 42.2 mmol) and CuCN (7.56 g, 84.4 mmol) in DMF (40 mL) was heated at reflux for 5 h. After being cooled down, EtOAc and 1N HCl were added. The mixture was filtered through celite. The organic phase was separated, washed sequentially with 1N HCl and brine. It was then dried over MgSO₄, concentrated in vacuo to give a brown solid (5.69 g), which was pure enough for the next step. MS 137.1 (M+H).

B. N-[4-(dimethylaminoimino)-2-fluorophenyl]-2-phenyl-2-(4-chlorophenylaminocarbonylamino)-acetamide To a solution of DL-phenylglycine (2.51 g, 10.0 mmol) and 4-amino-3-fluoro-benzonitrile (1.36 g, 10.0 mmol) in pyridine (25 mL) cooled in an ice-bath, POCl₃ (2.30 mL, 25.0 mmol) was added. The mixture was stirred for 3 h. EtOAc and H₂O were added. The organic layer was separated, washed with brine, dried over MgSO₄, concentrated in vacuo to give a solid (3.15 g), which was pure enough for the next step.

To a solution of the solid (1.50 g, 4.06 mmol) in CH₂Cl₂ (10 mL), TFA (6 mL) was added. After it was stirred for 30 min, it was then concentrated in vacuo. The residue was dissolved in THF (15 mL). To the solution, TEA (1.09 mL, 7.84 mmol) was added, followed by addition of 4-chlorophenylisocyanate (0.626 g, 4.07 mmol). After being stirred at room temperature overnight, the mixture was concentrated in vacuo. The residue was purified by HPLC to give a powder (0.842 g). MS 423.1 (M+H) and 445.1 (M+Na).

To a solution of the powder (0.842 g, 1.99 mmol) in pyridine (10 mL) and TEA (1.0 mL), H₂S gas was bubbled until saturation was reached. The solution was then stirred at room temperature overnight. It was concentrated in vacuo. The residue was dissolved in acetone (10 mL). Iodomethane (0.620 mL, 9.95 mmol) was added. It was heated at reflux for 30 min, then concentrated in vacuo. The residue was dissolved in MeOH (28 mL). To a seventh of the solution (4 mL, 0.284 mmol), a pre-mixed dimethylamine (2M in THF, 0.713 mL, 1.42 mmol) and HOAc (0.122 mL, 2.14 mmol) were added. The mixture was then stirred at room temperature overnight. After being concentrated in vacuo, the residue was purified by HPLC to give white powder (15 mg). MS 468.2 and 470.1 (M+H, Cl pattern).

Example 34

N-[4-(N-methyl-N-ethylaminoimino)-2-fluorophenyl]-2-phenyl-2-(4-chlorophenylaminocarbonylamino)-acetamide

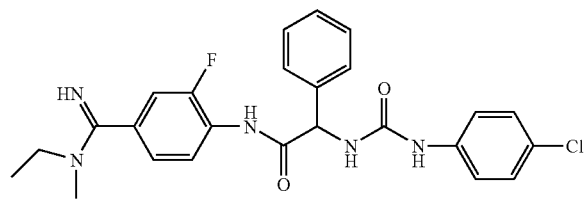

To the thioimidate solution in MeOH (4 mL, 0.284 mmol) from Example 33, a pre-mixed N-methyl-N-ethylamine (0.123 mL, 1.43 mmol) and HOAc (0.122 mL, 2.14 mmol) were added. The mixture was then stirred at room temperature overnight. After being concentrated in vacuo, the residue was purified by HPLC to give a white powder (21 mg). MS 482.2 and 484.2 (M+H, Cl pattern).

Example 35

N-[4-(N-methyl-N-allylaminoimino)-2-fluorophenyl]-2-phenyl-2-(4-chlorophenylaminocarbonylamino)-acetamide

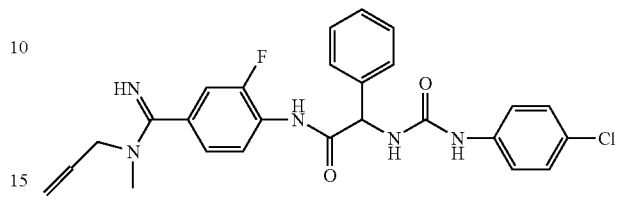

To the thioimidate solution in MeOH (4 mL, 0.284 mmol) from Example 33, a pre-mixed N-methyl-N-allylamine (0.136 mL, 1.43 mmol) and HOAc (0.122 mL, 2.14 mmol) were added. The mixture was then stirred at room temperature overnight. After being concentrated in vacuo, the residue was purified by HPLC to give a white powder (9 mg). MS 494.2 and 496.2 (M+H, Cl pattern).

Example 36

N-[4-(N-methyl-N-propargylaminoimino)-2-fluorophenyl]-2-phenyl-2-(4-chlorophenylaminocarbonylamino)-acetamide

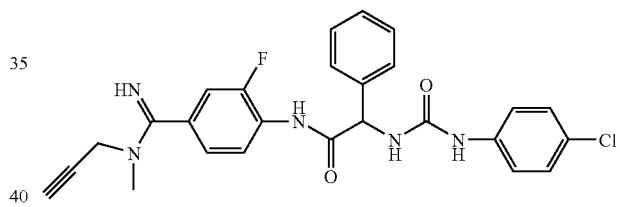

To the thioimidate solution in MeOH (4 mL, 0.284 mmol) from EXAMPLE 33, a pre-mixed N-methyl-N-propargylamine (0.119 mL, 1.43 mmol) and HOAc (0.122 mL, 2.14 mmol) were added. The mixture was then stirred at room temperature overnight. After being concentrated in vacuo, the residue was purified by HPLC to give a white powder (21 mg). MS 492.2 and 494.2 (M+H, Cl pattern).

Example 37

N-(4-methylaminoimino-2-fluorophenyl)-2-phenyl-2-(4-chlorophenylamino-carbonylamino)-acetamide

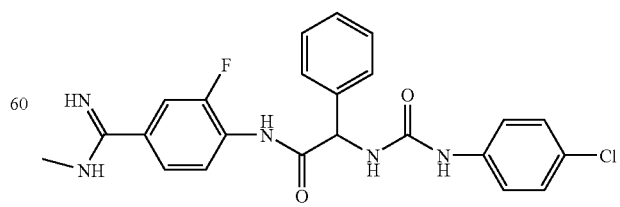

To the thioimidate solution in MeOH (4 mL, 0.284 mmol) from EXAMPLE 33, a pre-mixed methylamine (2M in THF, 0.713 mL, 1.43 mmol) and HOAc (0.122 mL, 2.14 mmol) were added. The mixture was then stirred at room temperature overnight. After being concentrated in vacuo, the residue was purified by HPLC to give a white powder (18 mg). MS 454.1 and 456.1 (M+H, Cl pattern).

Example 38

N-[4-(pyrrolidin-1-ylimino)-2-fluorophenyl]-2-phenyl-2-(4-chlorophenylaminocarbonylamino)-acetamide

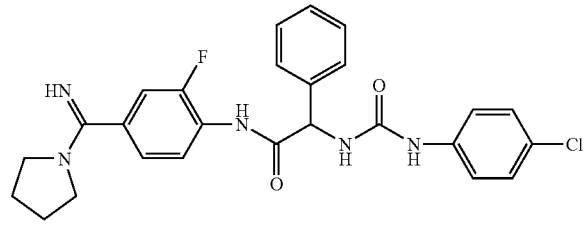

To the thioimidate solution in MeOH (4 mL, 0.284 mmol) from EXAMPLE 33, a pre-mixed pyrrolidine (0.119 mL, 1.43 mmol) and HOAc (0.122 mL, 2.14 mmol) were added. The mixture was then stirred at room temperature overnight. After being concentrated in vacuo, the residue was purified by HPLC to give a white powder (17 mg). MS 494.1 and 496.2 (M+H, Cl pattern).

Example 39

N-[4-(azetidin-1-ylimino)-2-fluorophenyl]-2-phenyl-2-(4-chlorophenylaminocarbonylamino)-acetamide

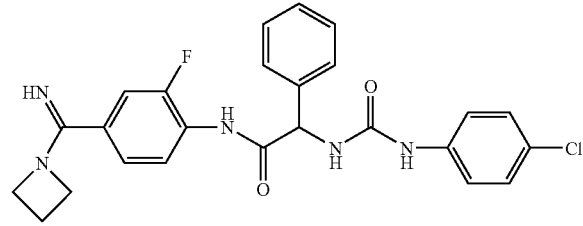

To the thioimidate solution in MeOH (4 mL, 0.284 mmol) from EXAMPLE 33, a pre-mixed azetidine (0.096 mL, 1.43 mmol) and HOAc (0.122 mL, 2.14 mmol) were added. The mixture was then stirred at room temperature overnight. After being concentrated in vacuo, the residue was purified by HPLC to give a white powder (24 mg). MS 480.1 and 482.1 (M+H, Cl pattern).

Example 40

N-[4-(1-methyl-4,5-dihydro-1H-imidazol-2-yl)phenyl]-2-(2-fluorophenyl)-2-(4-bromophenylaminocarbonylamino)-acetamide

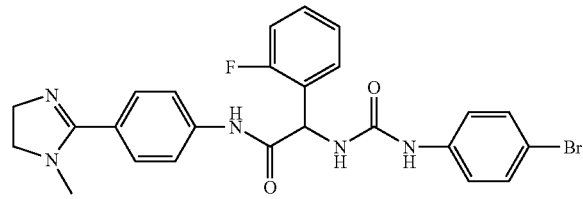

The titled compound was prepared analogously as described in EXAMPLE 11, using 4-bromophenylisocyanate in the place of 4-chlorophenylisocyanate. MS 524.0 and 526.0 (M+H, Br pattern).

Example 41

N-[4-(pyrrolidin-1-ylimino)phenyl]-2-(2-fluorophenyl)-2-(4-chlorophenylaminocarbonylamino)-acetamide

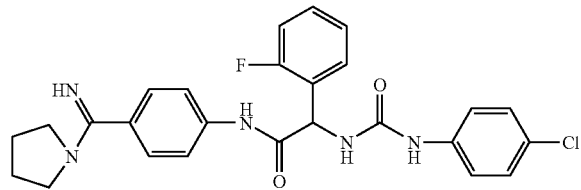

To a solution of 2-fluorophenylglycine (0.592 g, 3.50 mmol) in DMF (10 mL), 4-chlorophenylisocyanate (0.540 g, 3.52 mmol) was added. The mixture was stirred at room temperature overnight. To the solution, 4-aminobenzonitrile (0.418 g, 3.54 mmol) was added, followed by addition of EDC (0.803 g, 4.19 mmol). After being stirred at room temperature overnight, the mixture was concentrated in vacuo. The residue was purified by a flash silica gel column using EtOAc/Hexanes (10-20% EtOAc) as eluents to give a solid (0.260 g). MS 445.0 and 447.0 (M+Na, Cl pattern).

To a solution of the solid (260 mg, 0.615 mmol) in pyridine (8 mL) and TEA (0.8 mL), H$_2$S gas was bubbled until saturation was reached. The solution was then stirred at room temperature overnight. It was concentrated in vacuo. The residue was dissolved in acetone (10 mL). Iodomethane (0.383 mL, 6.15 mmol) was added. It was heated at reflux for 30 min, then concentrated in vacuo. The residue was dissolved in MeOH (12 mL). To one third of the solution (4 mL, 0.205 mmol), a pre-mixed pyrrolidine and 1.5 eq. HOAc (0.5 M in THF, 2.0 mL, 1.0 mmol) were added. The mixture was then stirred at room temperature overnight. After being concentrated in vacuo, the residue was purified by HPLC to give white powder (42 mg). MS 494.1 and 496.1 (M+H, Cl pattern).

Example 42

N-[4-(piperidin-1-ylimino)phenyl]-2-(2-fluorophenyl)-2-(4-chlorophenylaminocarbonylamino)-acetamide

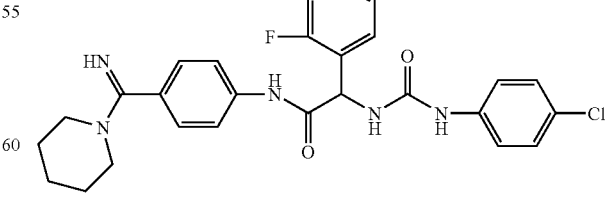

To the thioimidate solution in MeOH (4 mL, 0.205 mmol) from EXAMPLE 42, a pre-mixed piperidine and 1.5 eq. HOAc (0.5 M in THF, 2.0 mL, 1.0 mmol) were added. The mixture was then stirred at room temperature overnight. After being concentrated in vacuo, the residue was purified by HPLC to give white powder (28 mg). MS 508.1 and 510.1 (M+H, Cl pattern).

Example 43

N-[4-(dimethylaminoimino)phenyl]-2-(2-fluorophenyl)-2-(4-chlorophenylaminocarbonylamino)-acetamide

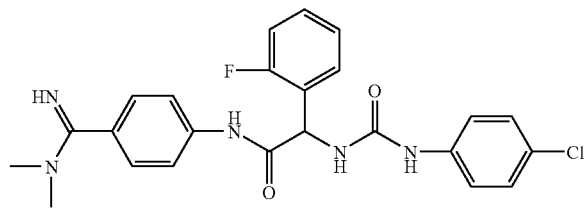

To the thioimidate solution in MeOH (4 mL, 0.205 mmol) from EXAMPLE 42, a pre-mixed dimethylamine and 1.5 eq. HOAc (0.5 M in THF, 2.0 mL, 1.0 mmol) were added. The mixture was then stirred at room temperature overnight. After being concentrated in vacuo, the residue was purified by HPLC to give white powder (43 mg). MS 468.1 and 470.1 (M+H, Cl pattern).

Example 44

N-[4-(pyrrolidin-1-ylimino)phenyl]-2-(2-fluorophenyl)-2-(4-bromophenylaminocarbonylamino)-acetamide

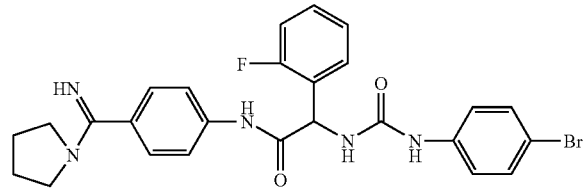

The titled compound was prepared analogously as described in EXAMPLE 41, using 4-bromophenylisocyanate in the place of 4-chlorophenylisocyanate. MS 538.0 and 540.0 (M+H, Br pattern).

Example 45

N-[4-(piperidin-1-ylimino)phenyl]-2-(2-fluorophenyl)-2-(4-bromophenylaminocarbonylamino)-acetamide

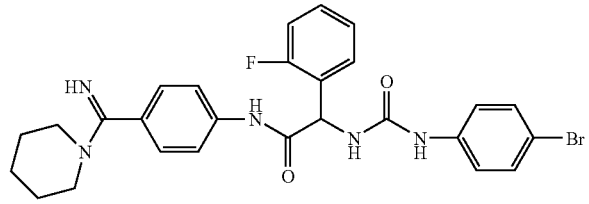

The titled compound was prepared analogously as described in EXAMPLE 42, using 4-bromophenylisocyanate in the place of 4-chlorophenylisocyanate. MS 552.0 and 554.0 (M+H, Br pattern).

Example 46

N-[4-(dimethylaminoimino)phenyl]-2-(2-fluorophenyl)-2-(4-bromophenylaminocarbonylamino)-acetamide

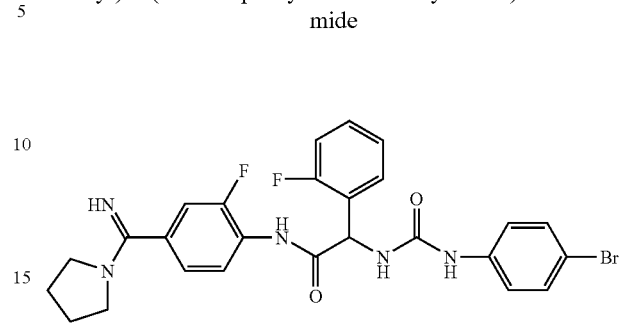

The titled compound was prepared analogously as described in EXAMPLE 43, using 4-bromophenylisocyanate in the place of 4-chlorophenylisocyanate. MS 512 and 514 (M+H, Br pattern).

Example 47

N-[4-(pyrrolidin-1-ylimino)-2-fluorophenyl]-2-(2-fluorophenyl)-2-(4-chlorophenylaminocarbonylamino)-acetamide

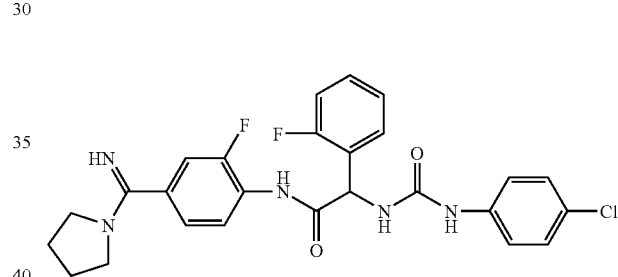

The titled compound was prepared analogously as described in EXAMPLE 33, starting from DL-2-fluorophenylglycine in the place of DL-phenylglycine, and using pyrrolidine in the place of dimethylamine. MS 512.0 and 514.0 (M+H, Cl pattern).

Example 48

N-[4-(2,2-dimethylhydrazinoimino)-2-fluorophenyl]-2-(2-fluorophenyl)-2-(4-chlorophenylaminocarbonylamino)-acetamide

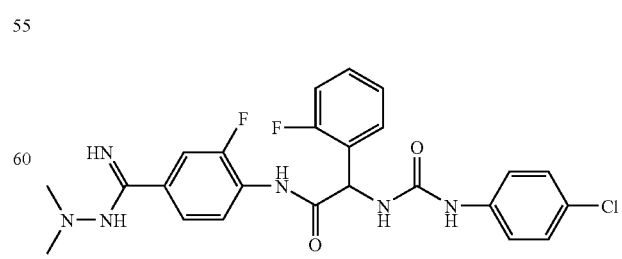

The titled compound was prepared analogously as described in EXAMPLE 33, starting from DL-2-fluorophenylglycine in the place of DL-phenylglycine, and using N,N-dimethylhydrazine in the place of dimethylamine. MS 501.1 and 503.1 (M+H, Cl pattern).

Example 49

N-[4-(pyridin-4-yl)phenyl]-2-(2-fluorophenyl)-2-(4-chlorophenylaminocarbonylamino)-acetamide

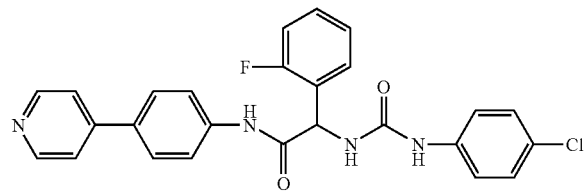

A. Preparation of 4-(pyridin-4-yl)phenylamine

To a solution of 4-(4,4,5,5-tetramethyl-1,3,2-dioxaborolan-2-yl)aniline (1.33 g, 6.07 mmol) in toluene (20 mL) and n-butanol (7 mL), a solution of 4-bromopyridine hydrochloride (0.608 g, 3.13 mmol) and $Cs_2CO_3$ (3.0-6 g, 9.39 mmol) in $H_2O$ (15 mL) was added. The mixture was degassed three times with Ar/vacuum cycle before being charged with $Pd(Ph_3P)_4$ (0.270 g, 0.230 mmol, 7% mol). It was then heated at reflux under Ar overnight. The reaction mixture was allowed to cool at room temperature, and then in an ice-bath. The precipitates were collected, dried on vacuum to give a solid (0.420 g). MS 171.0 (M+H)

B. Preparation of N-[4-(pyridin-4-yl)phenyl]-2-(2-fluorophenyl)-2-(4-chlorophenylaminocarbonylamino)-acetamide To a solution of 2-fluorophenylglycine (0.157 g, 0.930 mmol) in DMF (4 mL), 4-chlorophenylisocyanate (0.143 g, 0.930 mmol) was added. The mixture was stirred at room temperature overnight. To the solution, 4-(pyridin-4-yl)phenylamine (0.150 g, 0.880 mmol) was added, followed by addition of EDC (0.339 g, 1.77 mmol). The mixture was then stirred at room temperature overnight. It was concentrated in vacuo. The residue was dissolved in $CH_3CN$. $H_2O$ was then added to induce precipitation. The precipitates were collected by filtration (0.215 g). MS 475.1 and 477.1 (M+H, Cl pattern).

Example 50

N-[4-(N-oxo-pyridin-4-yl)phenyl]-2-(2-fluorophenyl)-2-(4-chlorophenylaminocarbonylamino)-acetamide

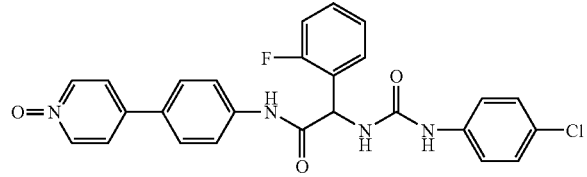

To a solution of N-[4-(pyridin-4-yl)phenyl]-2-(2-fluorophenyl)-2-(4-chlorophenylaminocarbonylamino)-acetamide (from EXAMPLE 49, 210 mg, 0.442 mmol) in acetone (10 mL), mCPBA (ca.70%, 650 mg, 2.63 mmol) was added. After the mixture was stirred at room temperature overnight, it was concentrated in vacuo. The residue was purified by HPLC to give a powder (115 mg). MS 491.1 and 493.0 (M+H, Cl pattern).

Example 51

N-[4-(N-oxo-pyridin-2-yl)phenyl]-2-(2-fluorophenyl)-2-(4-chlorophenylaminocarbonylamino)-acetamide

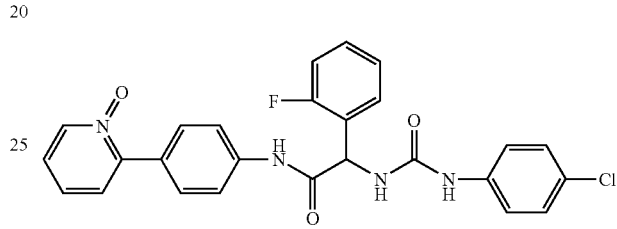

To a solution of 2-fluorophenylglycine (79 mg, 0.466 mmol) in DMF (4 mL), 4-chlorophenylisocyanate (72 mg, 0.466 mmol) was added. The mixture was stirred at room temperature overnight. To the solution, a solution of 4-(N-oxo-pyridin-2-yl)phenylamine hydrochloride (104 mg, 0.466 mmol) in DMF (3 mL) and $H_2O$ (2 mL) was added, followed by addition of EDC (135 mg, 0.704 mmol). The mixture was then stirred at room temperature overnight. It was concentrated in vacuo. The residue was purified by HPLC to give a powder (25 mg). MS 491.0 and 493.0 (M+H, Cl pattern).

Example 52

N-[4-(N-oxo-pyridin-2-yl)phenyl]-2-(2-fluorophenyl)-2-(4-bromophenylaminocarbonylamino)-acetamide

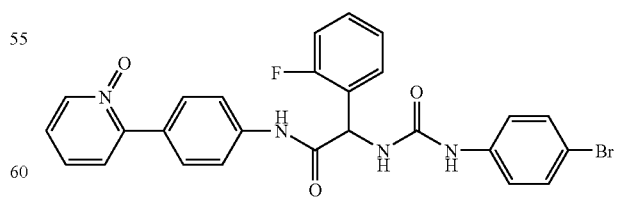

The titled compound was analogously prepared as described in EXAMPLE 51, using 4-bromophenylisocyanate in the place of 4-chlorophenylisocyanate. MS 535.0 and 537.0 (M+H, Br pattern).

Example 53

N-(piperidin-4-ylmethyl)-2-(2-fluorophenyl)-2-(4-chlorophenylaminocarbonylamino)-acetamide

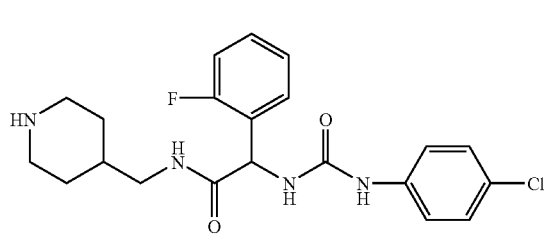

To a solution of 2-fluorophenylglycine (59 mg, 0.35 mmol) in DMF (4 mL), 4-chlorophenylisocyanate (54 mg, 0.35 mmol) was added. The mixture was stirred at room temperature overnight. To the solution, a solution of N-BOC-aminomethylpiperidine hydrochloride (105 mg, 0.42 mmol) and TEA (0.150 mL, 1.08 mmol) in DMF (4 mL) was added, followed by addition of BOP (239 mg, 0.54 mmol). The mixture was then stirred at room temperature overnight. EtOAc and H$_2$O were added. The organic layer was separated, dried over Na$_2$SO$_4$, concentrated in vacuo.

The residue was dissolved in TFA (5 mL). After being stirred for 1 h, the solution was concentrated in vacuo. The residue was purified by HPLC to give a white powder (100 mg). MS 419.1 and 421.1 (M+H, Cl pattern).

Example 54

N-[(N-acetimidyl-piperidin-4-yl)methyl]-2-(2-fluorophenyl)-2-(4-chlorophenylaminocarbonylamino)-acetamide

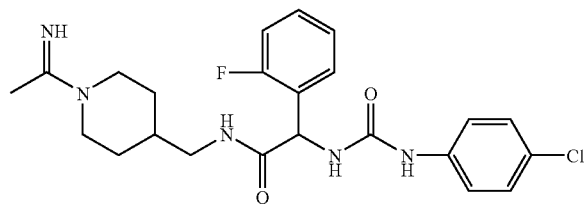

A solution of N-(piperidin-4-ylmethyl)-2-(2-fluorophenyl)-2-(4-chlorophenylaminocarbonylamino)-acetamide (from EXAMPLE 53, 70 mg, 0.17 mmol), ethyl acetimidate hydrochloride (40 mg, 0.32 mmol) and TEA (0.070 mL, 0.50 mmol) in EtOH (3 mL) was stirred at room temperature overnight. It was then concentrated in vacuo. The residue was purified by HPLC to give the titled compound as a white powder (37 mg). MS 460.1 and 462.1 (M+H, Cl pattern).

Example 55

N-[4-(2-dimethylaminomethyl-phenyl)phenyl]-2-(2-fluorophenyl)-2-(4-chlorophenylaminocarbonylamino)-acetamide

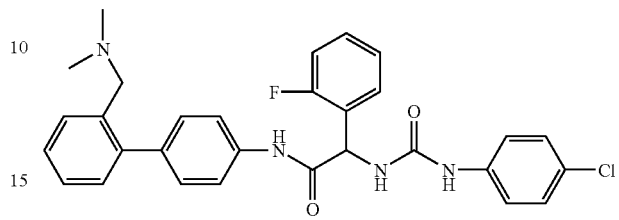

A. 4-(2-dimethylaminomethyl-phenyl)phenylamine

To a solution of 2-dimethylaminomethyl-bromobenzene (588 mg, 2.75 mmol) and 4-(4,4,5,5-tetramethyl-1,3,2-dioxaborolan-2-yl)aniline (560 mg, 2.56 mmol) in toluene (10 mL) and n-BuOH (3 mL), Cs$_2$CO$_3$ (2.50 g, 7.67 mmol) in H$_2$O (5 mL) was added, followed by addition of Pd(Ph$_3$P)$_4$ (200 mg, 0.17 mmol, 6%). The mixture was then heated at reflux for 4 h. EtOAc and H$_2$O were added. The organic layer was separated, filtered, dried over Na$_2$SO$_4$, concentrated in vacuo. The residue was purified by a silica gel flash column using 50% EtOAc/hexanes (containing 1% TEA) as eluent to give a solid (300 mg). MS 182.0 (M—Me2N).

B. 2-(2-fluorophenyl)-2-(4-chlorophenylaminocarbonylamino)-acetic acid

A mixture of 2-fluorophenylglycine (1.18 g, 6.98 mmol) and 4-chlorophenylisocyanate (1.10 g, 7.16 mmol) in DMF (20 mL) was stirred at room temperature overnight. After being concentrated in vacuo, the residue was purified by HPLC to give a white solid (1.60 g).

C. Preparation of N-[4-(2-dimethylaminomethyl-phenyl)phenyl]-2-(2-fluorophenyl)-2-(4-chlorophenylaminocarbonylamino)-acetamide To a solution of 2-(2-fluorophenyl)-2-(4-chlorophenylaminocarbonylamino)-acetic acid (60 mg, 0.19 mmol) and 4-(2-dimethylaminomethyl-phenyl)phenylamine (50 mg, 0.22 mmol) in pyridine (3 mL) cooled in an ice-bath, POCl$_3$ (0.034 mL, 0.37 mmol) was added. After being stirred at room temperature overnight, the mixture was concentrated in vacuo. The residue was purified by HPLC to give the titled compound as a powder (8 mg). MS 531.1 and 533.1 (M+H, Cl pattern).

Example 56

N-[4-(2-dimethylaminomethyl-phenyl)-2-fluorophenyl]-2-(2-fluorophenyl)-2-(4-chlorophenylaminocarbonylamino)-acetamide

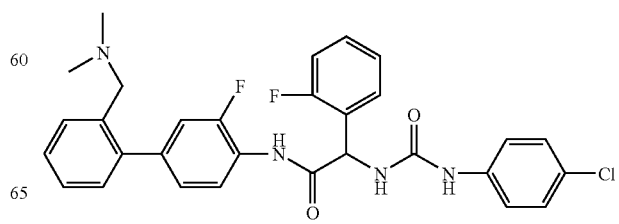

A. Preparation of 4-(2-dimethylaminomethyl-phenyl)-2-fluoro-phenylamine

To a solution of 2-dimethylaminomethyl-bromobenzene (1.93 g, 9.02 mmol) and 4-(4,4,5,5-tetramethyl-1,3,2-dioxaborolan-2-yl)aniline (4.42 g, 18.6 mmol) in toluene (40 mL) and n-BuOH (10 mL), $Cs_2CO_3$ (8.80 g, 27.0 mmol) in $H_2O$ (20 mL) was added, followed by addition of $Pd(Ph_3P)_4$ (0.556 g, 0.480 mmol). The mixture was then heated at reflux overnight. EtOAc and $H_2O$ were added. The organic layer was separated, filtered, dried over $Na_2SO_4$, concentrated in vacuo. The residue was purified by a silica gel flash column using 50% EtOAc/hexanes (containing 1% TEA) as eluent to give an oil (0.537 g). MS 245.1 (M+H).

B. Preparation of N-[4-(2-dimethylaminomethyl-phenyl)-2-fluorophenyl]-2-(2-fluorophenyl)-2-(4-chlorophenylaminocarbonylamino)-acetamide To a solution of 2-(2-fluorophenyl)-2-(4-chlorophenylaminocarbonylamino)-acetic acid (from EXAMPLE 55, 90 mg, 0.28 mmol) and 4-(2-dimethylaminomethyl-phenyl)-2-fluoro-phenylamine (80 mg, 0.33 mmol) in pyridine (3 mL) cooled in an ice-bath, $POCl_3$ (0.050 mL, 0.55 mmol) was added. After being stirred at room temperature overnight, the mixture was concentrated in vacuo. The residue was purified by HPLC to give the titled compound as a powder (38 mg). MS 549.1 and 551.2 (M+H, Cl pattern).

Example 57

N-[4-(2-dimethylaminomethyl-phenyl)-2-fluorophenyl]-2-(2-fluorophenyl)-2-(4-bromophenylaminocarbonylamino)-acetamide

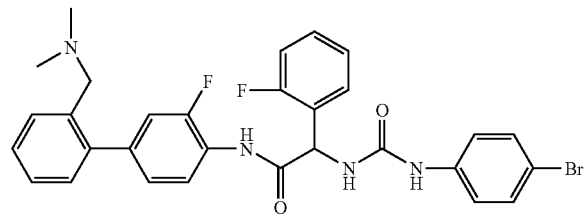

The titled compound was prepared analogously as described in EXAMPLE 56, using 2-(2-fluorophenyl)-2-(4-bromophenylaminocarbonylamino)-acetic acid in the place of 2-(2-fluorophenyl)-2-(4-chlorophenylaminocarbonylamino)-acetic acid. MS 593.0 and 595.1 (M+H, Br pattern).

Example 58

N-[4-(2-dimethylaminomethyl-imidazol-1-yl)-2-fluorophenyl]-2-(2-fluorophenyl)-2-(4-chlorophenylaminocarbonylamino)-acetamide

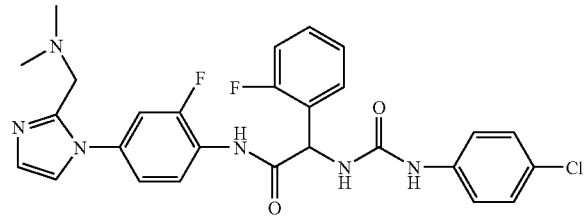

A. Preparation of 4-(2-dimethylaminomethyl-imidazol-1-yl)-2-fluorophenylamine

To suspension of 2-imidazolecarboxaldehyde (1.06 g, 11.0 mmol) and dimethylamine (2M in THF, 7 mL, 14 mmol) in MeOH (10 mL) and HOAc (7 mL), $NaBH_3CN$ (1.04 g, 16.5 mmol) was added. The reaction mixture was then stirred at room temperature overnight, during which time the suspension became clear. The solution was concentrated in vacuo, and the residue was partitioned between 1N NaOH and nBuOH. The nBuOH solution was separated, concentrated in vacuo to give gum-like residue (0.89 g), which was pure enough for the next reaction. MS 126.1 (M+H)

A suspension of the residue (0.790 g, 6.32 mmol), 2-fluoro-4-iodoaniline (1.24 g, 5.23 mmol), $K_2CO_3$ (0.794 g, 5.75 mmol) and 8-hydroxyquinoline (114 mg, 0.786 mmol) in DMSO (20 mL) was degassed with vacuum/Ar cycle (3×), before being charged with CuI (170 mg, 0.895 mmol). The mixture was then heated at 130 C overnight. EtOAc and 14% $NH_4OH$ were added. The organic layer was separated, filtered, dried over $Na_2SO_4$, concentrated in vacuo. The residue was purified by HPLC to give an oil, which was then dissolved in EtOAc. The EtOAc solution was washed with sat. $NaHCO_3$ to remove TFA, dried over $Na_2SO_4$, concentrated in vacuo to give a solid (0.32 g). MS 235.1 (M+H) and 190.0 (M—$Me_2N$).

B. Preparation of N-[4-(2-dimethylaminomethyl-imidazol-1-yl)-2-fluorophenyl]-2-(2-fluorophenyl)-2-(4-chlorophenylaminocarbonylamino)-acetamide To a solution of 2-(2-fluorophenyl)-2-(4-chlorophenylaminocarbonylamino)-acetic acid (from EXAMPLE 55, 62 mg, 0.19 mmol) and 4-(2-dimethylaminomethyl-imidazol-1-yl)-2-fluorophenylamine (45 mg, 0.19 mmol) in pyridine (3 mL) cooled in an ice-bath, $POCl_3$ (0.035 mL, 0.38 mmol) was added. After being stirred at room temperature overnight, the mixture was concentrated in vacuo. The residue was purified by HPLC to give the titled compound as a powder (19 mg). MS 539.1 and 541.1 (M+H, Cl pattern).

Example 59

2S) N-[4-(1-methyl-4,5-dihydro-1H-imidazol-2-yl)phenyl]-2-benzyloxy-carbonylmethyl-2-(4-chlorophenylaminocarbonylamino)-acetamide

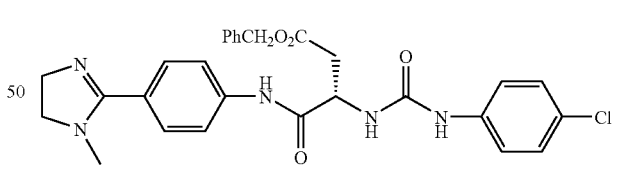

A mixture of L-aspartic acid γ-benzyl ester (327 mg, 1.47 mmol) and 4-chlorophenyl isocyanate (230 mg, 1.50 mmol) in DMF (12 mL) was stirred at room temperature overnight. It was then filtered. A small portion of the filtrate (2 mL, 0.20 mmol) was taken to mix with 4-(1-Methyl-4,5-dihydro-1H-imidazol-2-yl)-phenylamine (from EXAMPLE 3, 70 mg, 0.40 mmol) and $H_2O$ (0.5 mL). To the resulted solution, EDC (77 mg, 0.40 mmol) was added. After being stirred at room temperature overnight, the mixture was concentrated in vacuo. The residue was purified by HPLC to give the titled compound as a white powder (85 mg). MS 534.1 and 536.1 (M+H, Cl pattern).

Example 60

(2S) N-[4-(1-methyl-4,5-dihydro-1H-imidazol-2-yl)phenyl]-2-carboxymethyl-2-(4-chlorophenylaminocarbonylamino)-acetamide

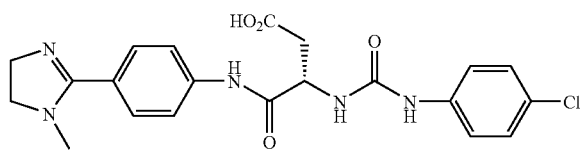

To a solution of (2S) N-[4-(1-methyl-4,5-dihydro-1H-imidazol-2-yl)phenyl]-2-benzyloxycarbonylmethyl-2-(4-chlorophenylaminocarbonylamino)-acetamide (from EXAMPLE 59, 60 mg, 0.11 mmol) in MeOH (3 mL) at room temperature, 1N aq. NaOH (0.50 mL) was added. After being stirred at room temperature overnight, the mixture was concentrated in vacuo. The residue (after being neutralized to acidic with TFA) was purified by HPLC to give the titled compound as a powder (26 mg). MS

Example 61

(2R) N-[4-(1-methyl-4,5-dihydro-1H-imidazol-2-yl)phenyl]-2-benzyloxycarbonylmethyl-2-(4-chlorophenylaminocarbonylamino)-acetamide

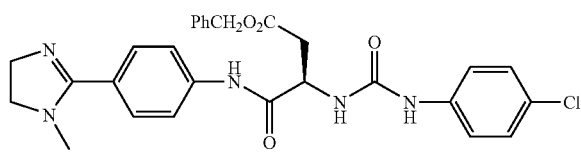

The titled compound was prepared analogously as described in EXAMPLE 59, using D-aspartic acid γ-benzyl ester in the place of the L-isomer. MS 534.1 and 546.1 (M+H, Cl pattern).

Example 62

(2R) N-[4-(1-methyl-4,5-dihydro-1H-imidazol-2-yl)phenyl]-2-carboxymethyl-2-(4-chlorophenylaminocarbonylamino)-acetamide

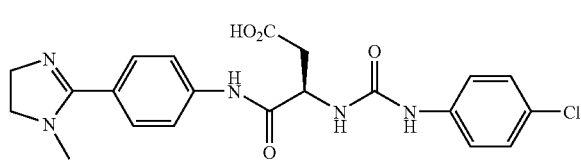

The titled compound was prepared analogously as described in EXAMPLE 60, using (2R) N-[4-(1-methyl-4,5-dihydro-1H-imidazol-2-yl)phenyl]-2-benzyloxycarbonylmethyl-2-(4-chlorophenylaminocarbonylamino)-acetamide in the place of the S isomer.

Example 63

N-[4-(1-methyl-4,5-dihydro-1H-imidazol-2-yl)phenyl]-2-dimethylaminocarbonylmethyl-2-(4-chlorophenylaminocarbonylamino)-acetamide

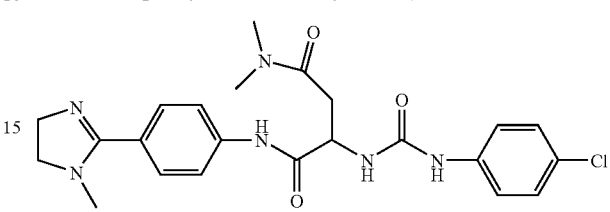

To a solution of 1:1 mixture of the R and S isomers of N-[4-(1-methyl-4,5-dihydro-1H-imidazol-2-yl)phenyl]-2-carboxymethyl-2-(4-chlorophenylaminocarbonylamino)-acetamide (from EXAMPLEs 60 and 62, 45 mg, 0.10 mmol) and dimethylamine (2N in THF, 0.25 mL, 0.50 mmol) in DMF (2 mL), BOP (100 mg, 0.22 mmol) was added. After being stirred at room temperature overnight, the mixture was concentrated in vacuo. The residue was purified by HPLC to give the titled compound as a powder (25 mg). MS 471.1 and 473.1 (M+H, Cl pattern).

Example 64

N-[4-(1-methyl-4,5-dihydro-1H-imidazol-2-yl)phenyl]-2-(piperidin-1-ylcarbonylmethyl)-2-(4-chlorophenylaminocarbonylamino)-acetamide

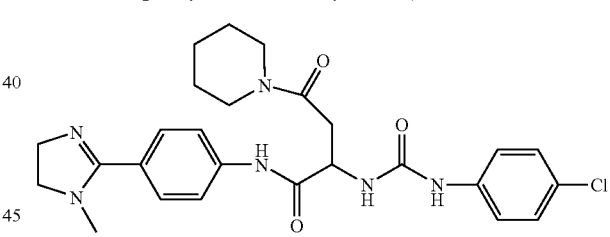

The titled compound was prepared analogously as described in EXAMPLE 63, using piperidine in the place of dimethylamine. MS 511.1 and 513.2 (M+H, Cl pattern).

Example 65

N-[4-(1-methyl-4,5-dihydro-1H-imidazol-2-yl)phenyl]-2-(morpholin-4-ylcarbonylmethyl)-2-(4-chlorophenylaminocarbonylamino)-acetamide

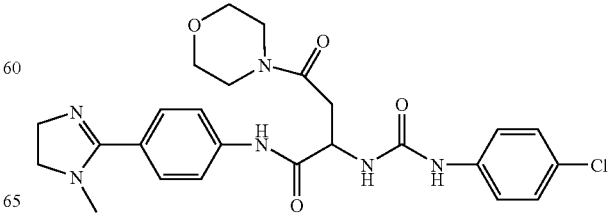

The titled compound was prepared analogously as described in EXAMPLE 63, using morpholine in the place of dimethylamine. MS 513.2 and 515.1 (M+H, Cl pattern).

Example 66

N-[4-(1-methyl-4,5-dihydro-1H-imidazol-2-yl)phenyl]-2-(pyrrolidin-1-yl-carbonylmethyl)-2-(4-chlorophenylaminocarbonylamino)-acetamide

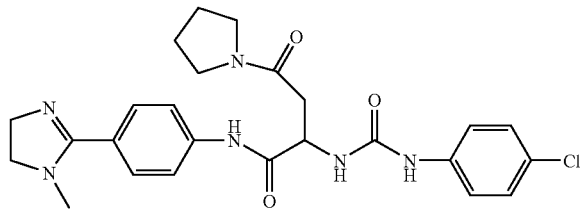

The titled compound was prepared analogously as described in EXAMPLE 63, using pyrrolidine in the place of dimethylamine. MS 497.2 and 499.1 (M+H, Cl pattern).

Example 67

N-[4-(1-methyl-4,5-dihydro-1H-imidazol-2-yl)phenyl]-2-[4-ethoxycarbonyl-piperidin-1-yl)carbonylmethyl]-2-(4-chlorophenylaminocarbonylamino)-acetamide

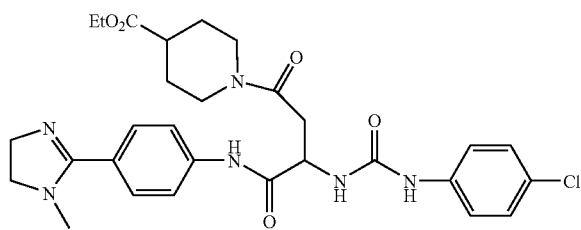

The titled compound was prepared analogously as described in EXAMPLE 63, using ethyl isonipecotate in the place of dimethylamine. MS 583.2 and 585.2 (M+H, Cl pattern).

Example 68

N-[4-(1-methyl-4,5-dihydro-1H-imidazol-2-yl)phenyl]-2-(homopiperidin-1-ylcarbonylmethyl)-2-(4-chlorophenylaminocarbonylamino)-acetamide

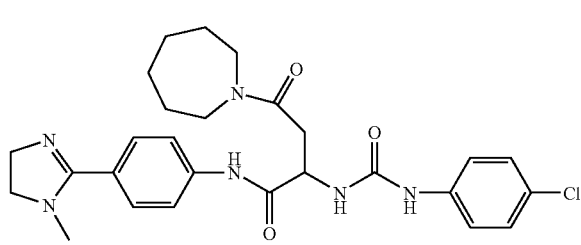

The titled compound was prepared analogously as described in EXAMPLE 63, using homopiperidine in the place of dimethylamine. MS 525.2 and 527.3 (M+H, Cl pattern).

Example 69

N-[4-(1-methyl-4,5-dihydro-1H-imidazol-2-yl)phenyl]-2-(benzylamino-carbonylmethyl)-2-(4-chlorophenylaminocarbonylamino)-acetamide

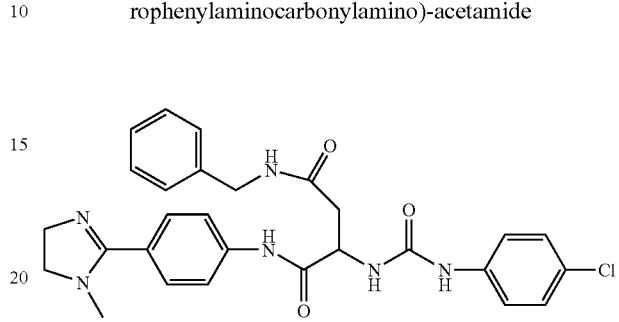

The titled compound was prepared analogously as described in EXAMPLE 63, using benzylamine in the place of dimethylamine. MS 533.2 and 535.1 (M+H, Cl pattern).

Example 70

N-[4-(1-methyl-4,5-dihydro-1H-imidazol-2-yl)phenyl]-2-(methylamino-carbonylmethyl)-2-(4-chlorophenylaminocarbonylamino)-acetamide

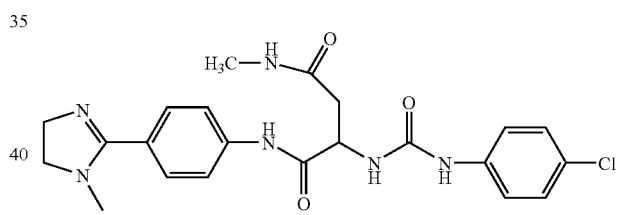

The titled compound was prepared analogously as described in EXAMPLE 63, using methylamine in the place of dimethylamine. MS 457.1 and 459.1 (M+H, Cl pattern).

Example 71

N-[4-(1-methyl-4,5-dihydro-1H-imidazol-2-yl)phenyl]-2-(aminocarbonylmethyl)-2-(4-chlorophenylaminocarbonylamino)-acetamide

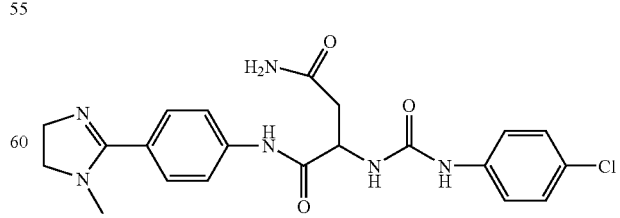

The titled compound was prepared analogously as described in EXAMPLE 63, using ammonia in the place of dimethylamine. MS 443.1 and 445.1 (M+H, Cl pattern).

Example 72

N-[4-(1-methyl-4,5-dihydro-1H-imidazol-2-yl)phenyl]-3-(4-chlorophenylaminocarbonylamino)-succinimide

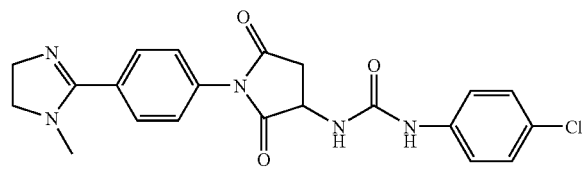

The titled compound was prepared by surprise during an attempted synthesis of N-[4-(1-methyl-4,5-dihydro-1H-imidazol-2-yl)phenyl]-2-(phenylamino carbonylmethyl)-2-(4-chlorophenylaminocarbonylamino)-acetamide, which was not obtained by the following procedure. However, it was synthesized by the procedure described in EXAMPLE 73.

To a solution of 1:1 mixture of the R and S isomers of N-[4-(1-methyl-4,5-dihydro-1H-imidazol-2-yl)phenyl]-2-carboxymethyl-2-(4-chlorophenylaminocarbonylamino)-acetamide (from EXAMPLEs 60 and 62, 45 mg, 0.10 mmol), aniline hydrochloride (65 mg, 0.50 mmol) and TEA (0.10 mL, 0.72 mmol) in DMF (2 mL), BOP (100 mg, 0.22 mmol) was added. After being stirred at room temperature overnight, the mixture was concentrated in vacuo. The residue was purified by HPLC to give the cyclized compound as a powder (30 mg). MS 426.1 and 428.1 (M+H, Cl pattern). 1H NMR (400 MHz, CD$_3$OD) δ 7.79 (d, 9 Hz, 2H), 7.68 (d, 9 Hz, 2H), 7.33 (d, 11 Hz, 2H), 7.21 (d, 11 Hz, 2H), 4.60-4.50 (m, 1H), 4.18-4.05 (m, 2H), 4.05-3.95 (m, 2H), 3.30-3.10 (m, 1H), 3.15 (s, 3H), 2.96-2.88 (M, 1H).

Example 73

N-[4-(1-methyl-4,5-dihydro-1H-imidazol-2-yl)phenyl]-2-(phenylamino-carbonylmethyl)-2-(4-chlorophenylaminocarbonylamino)-acetamide

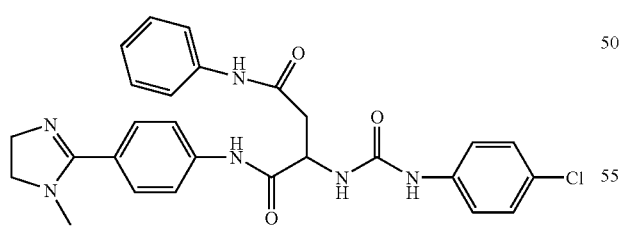

To a solution of 1:1 mixture of the R and S isomers of N-[4-(1-methyl-4,5-dihydro-1H-imidazol-2-yl)phenyl]-2-carboxymethyl-2-(4-chlorophenylaminocarbonylamino)-acetamide (from EXAMPLEs 60 and 62, 45 mg, 0.10 mmol) and aniline hydrochloride (28 mg, 0.22 mmol) in pyridine (2 mL) cooled in an ice-bath, POCl$_3$ (0.040 mL, 0.44 mmol) was added. After being stirred at room temperature overnight, the mixture was concentrated in vacuo. The residue was purified by HPLC to the titled compound as a powder (12 mg). MS 519.1 and 521.1 (M+H, Cl pattern).

Example 74

N-[4-(1-methyl-4,5-dihydro-1H-imidazol-2-yl)phenyl]-2-(3-chlorophenyl)-2-(4-chlorophenylaminocarbonylamino)-acetamide

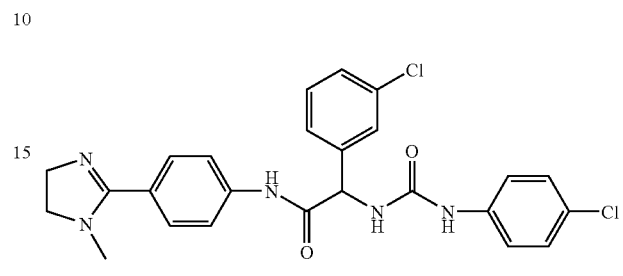

To a solution of NaCN (349 mg, 7.12 mmol) in H$_2$O (15 mL), was added a solution of 3-chlorobenzaldehyde (0.807 mL, 7.12 mmol), 4-methoxybenzylamine (0.929 mL, 7.12 mmol) and conc. HCl (0.593 mL, 7.12 mmol) in MeOH (15 mL). The mixture was then stirred at room temperature for 48 h. The white precipitates were collected by filtration (2.0 g).

A suspension of the white solid (1.00 g, 3.49 mmol) in 6N HCl (16 mL) was heated at reflux overnight. The reaction mixture was then filtered. The filtrate was concentrated in vacuo to give the 3-chlorophenylglycine as a solid (0.44 g). MS 186.0 and 188.0 (M+H, Cl pattern).

A solution of 3-chlorophenylglycine (240 mg, 1.29 mmol) and 4-chlorophenyl isocyanate (244 mg, 1.59 mmol) in DMF (5 mL) was stirred at room temperature overnight. After being concentrated in vacuo, the residue was purified by HPLC to the urea acid as a white powder (55 mg).

To a solution of the powder (45 mg, 0.13 mmol) and 4-(1-Methyl-4,5-dihydro-1H-imidazol-2-yl)-phenylamine (from EXAMPLE 3, 35 mg, 0.20 mmol) in DMF (4 mL) and H$_2$O (0.5 mL), EDC (84 mg, 0.44 mmol) was added. After being stirred at room temperature overnight, the mixture was concentrated in vacuo. The residue was purified by HPLC to give the tilted compound as a white powder (23 mg). MS 496.1 and 498.1 (M+H, 2Cl pattern).

Example 75

N-[4-(1-methyl-4,5-dihydro-1H-imidazol-2-yl)phenyl]-2-(2-chlorophenyl)-2-(4-chlorophenylaminocarbonylamino)-acetamide

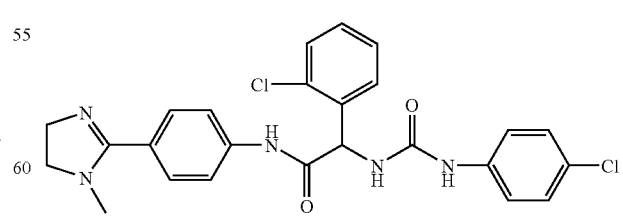

The titled compound was prepared analogously as described in EXAMPLE 74, starting with 2-chlorobenzaldehyde in the place of 3-chlorobenzaldehyde. MS 496.1 and 498.1 (M+H, 2Cl pattern).

Example 76

N-[4-(1-methyl-4,5-dihydro-1H-imidazol-2-yl)phenyl]-2-(benzo-1,3-dioxl-5-yl)-2-(4-chlorophenylaminocarbonylamino)-acetamide

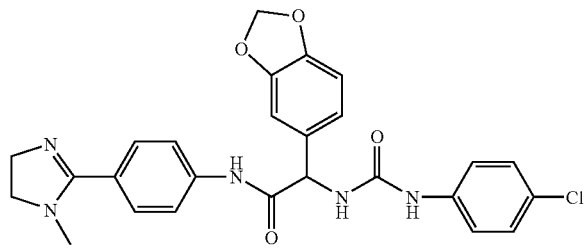

The titled compound was prepared analogously as described in EXAMPLE 74, starting with piperonal in the place of 3-chlorobenzaldehyde. MS 506.1 and 508.1 (M+H, Cl pattern).

Example 77

N-[4-(1-methyl-4,5-dihydro-1H-imidazol-2-yl)phenyl]-2-(2-bromophenyl)-2-(4-chlorophenylaminocarbonylamino)-acetamide

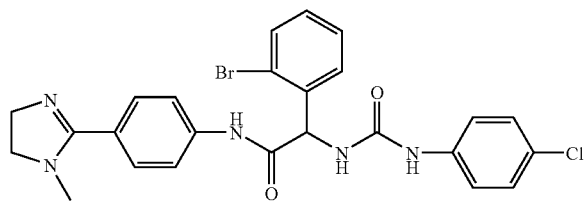

A. Preparation of 2-(2-bromophenyl)-2-(4-chlorophenylaminocarbonylamino)-acetic acid An improved Strecker synthesis procedure was used to prepare the required 2-bromophenylglycine (ref: Mai, K & Patil, G., Tetra. Lett. 25, 4583, 1984).

A mixture of 2-bromobenzaldehyde (1.00 mL, 8.57 mmol), trimethylsilyl cyanide (1.42 mL, 10.7 mmol) and catalytic amount of ZnI2 (ca.10 mg) was stirred at room temperature for 2 h. A solution of methanolic ammonia (ca.7 N, 6.0 mL, 42 mmol) was added. The mixture was then warmed to 40 C and stirred at that temperature for 3 h. The mixture was concentrated in vacuo. The residue was taken up in ether (40 mL). The solution was dried over $Na_2SO_4$, and then filtered. To the filtrate, 4N HCl in dioxane (2 mL) was added. The precipitated product was collected as brownish gum-like oil (0.90 g). MS 211.0 and 212.9 (M+H, Br pattern).

A mixture of the oil (0.890 g, 3.60 mmol) in 6N HCl (15 mL) was heated at reflux for 3 h. It was then concentrated in vacuo to give a solid (0.905 g).

A solution of the solid (0.900 g, 3.38 mmol) and 4-chlorophenyl isocyanate (0.690 g, 4.49 mmol) in DMF (15 mL) was stirred at room temperature overnight. After being concentrated in vacuo, the reaction mixture was purified by HPLC to give the urea acid as a powder (0.680 g). MS 382.9 and 385.0 (M+H, Cl+Br pattern).

B. N-[4-(1-methyl-4,5-dihydro-1H-imidazol-2-yl)phenyl]-2-(2-bromophenyl)-2-(4-chlorophenylaminocarbonylamino)-acetamide To a solution of the urea acid (77 mg, 0.20 mmol) and 4-(1-Methyl-4,5-dihydro-1H-imidazol-2-yl)-phenylamine (from EXAMPLE 3, 70 mg, 0.40 mmol) in DMF (5 mL) and $H_2O$ (1 mL), EDC (78 mg, 0.40 mmol) was added. After being stirred at room temperature overnight, the mixture was concentrated in vacuo. The residue was purified by HPLC to give the titled compound as a powder (110 mg). MS 540.0 and 542.0 (M+H, Cl+Br pattern).

Example 78

N-[4-(N-oxo-pyridin-4-yl)phenyl]-2-(2-bromophenyl)-2-(4-chlorophenylaminocarbonylamino)-acetamide

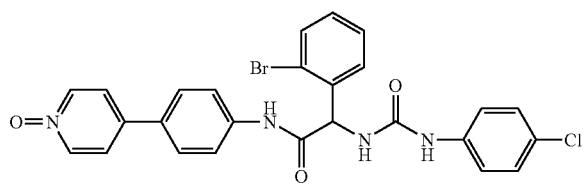

The titled compound was prepared analogously as described in EXAMPLEs 49 and 50, starting from 2-(2-bromophenyl)-2-(4-chlorophenylaminocarbonylamino)-acetic acid and 4-(pyridine-4-yl)phenylamine. MS 551.0, 552.0, 553.0 and 554.0 (M+H, Cl+Br pattern).

Example 79

N-[4-(N-oxo-pyridin-2-yl)phenyl]-2-(2-bromophenyl)-2-(4-chlorophenylaminocarbonylamino)-acetamide

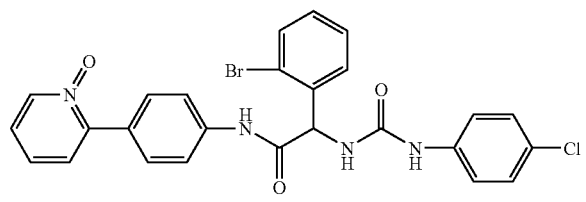

The titled compound was prepared analogously as describe in EXAMPLE 51, using 2-(2-bromophenyl)-2-(4-chlorophenylaminocarbonylamino)-acetic acid and 4-(N-oxo-pyridin-2-yl)phenylamine hydrochloride. MS 551.0 and 553.0 (M+H, Cl+Br pattern).

Example 80

N-[4-(dimethylaminoimino)phenyl]-2-(2-bromophenyl)-2-(4-chlorophenylaminocarbonylamino)-acetamide

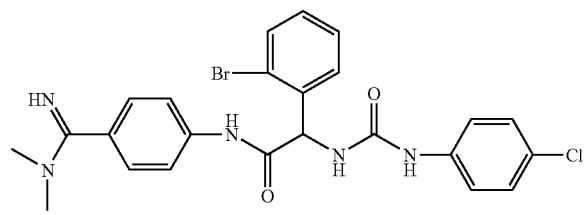

A. Preparation of 4-(dimethylaminoimino)phenylamine

To a solution of 4-aminobenzonitrile (5.1 g, 43 mmol) in dry methanol (70 mL) at 0 C, hydrogen chloride gas was bubbled through until saturation was reached. The mixture was then stirred at room temperature overnight. It was concentrated in vacuo. The residue was suspended in dry methanol (80 mL). To the solution, dimethylamine (2M in THF, 120 mL, 240 mmol) was added. The mixture was then heated to reflux for 30 min, during which time the mixture became clear. It was then stirred at room temperature overnight. It was concentrated in vacuo. The residue was dissolved in methanol (140 mL). To the solution, $Et_2O$ (140 mL) was added. After being cooled in fridge overnight, the precipitated product was collected by filtration. It was then dried on vacuum to give white solids (5.6 g). MS 164 (M+H).

B. N-[4-(dimethylaminoimino)phenyl]-2-(2-bromophenyl)-2-(4-chlorophenylamino-carbonylamino)-acetamide To a solution of 2-(2-bromophenyl)-2-(4-chlorophenylaminocarbonylamino)-acetic acid (from EXAMPLE 77, 60 mg, 0.16 mmol) and 4-(dimethylaminoimino)phenylamine (51 mg, 0.31 mmol) in DMF (4 mL) and $H_2O$ (1 mL), EDC (120 mg, 0.62 mmol) was added. After being stirred at room temperature for 2 h, the mixture was concentrated in vacuo. The residue was purified by HPLC to give the titled compound as a powder (40 mg). MS 528.2 and 530.2 (M+H, Cl+Br pattern).

Example 81

N-[4-(pyrrolidin-1-ylimino)phenyl]-2-(2-bromophenyl)-2-(4-chlorophenylaminocarbonylamino)-acetamide

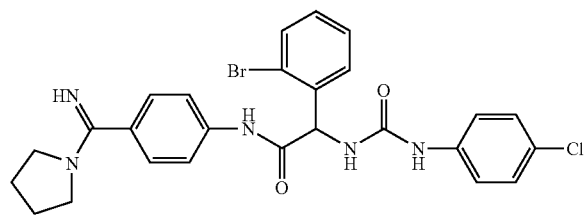

A. 4-(pyrrolidin-1-ylimino)phenylamine

To a solution of 4-aminobenzonitrile (5.1 g, 43 mmol) in dry methanol (70 mL) at 0 C, hydrogen chloride gas was bubbled through until saturation was reached. The mixture was then stirred at room temperature overnight. It was concentrated in vacuo. The residue was suspended in dry methanol (80 mL). To the solution, pyrrolidine (22 mL, 264 mmol) was added. The mixture was then heated to reflux for 30 min, during which time the mixture became clear. It was then stirred at room temperature overnight. It was concentrated in vacuo. The residue was dissolved in methanol (90 mL). To the solution, $Et_2O$ (170 mL) was added. After being cooled in fridge overnight, the precipitated product was collected by filtration. It was then dried on vacuum to give white solids (4.5 g). MS 190 (M+H).

B. N-[4-(pyrrolidin-1-ylimino)phenyl]-2-(2-bromophenyl)-2-(4-chlorophenylamino-carbonylamino)-acetamide To a solution of 2-(2-bromophenyl)-2-(4-chlorophenylaminocarbonylamino)-acetic acid (from EXAMPLE 77, 60 mg, 0.16 mmol) and 4-(pyrrolidin-1-ylimino)phenylamine (60 mg, 0.31 mmol) in DMF (4 mL) and $H_2O$ (1 mL), EDC (120 mg, 0.62 mmol) was added. After being stirred at room temperature for 2 h, the mixture was concentrated in vacuo. The residue was purified by HPLC to give the titled compound as a powder (70 mg). MS 554.2 and 556.2 (M+H, Cl+Br pattern).

Example 82

N-(1-isopropylpiperidin-4-yl)-2-(2-bromophenyl)-2-(4-chlorophenylamino-carbonylamino)-acetamide

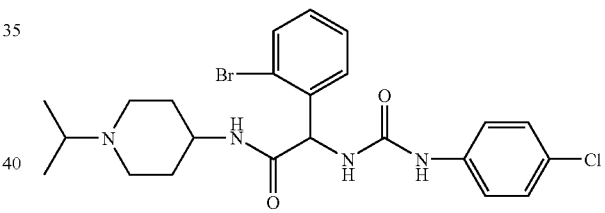

A. 1-isopropyl-4-aminopiperidine

To a solution of 4-N-Boc-aminopiperidine (1.50 g, 7.49 mmol) and acetone (2.8 mL, 37.5 mmol) in MeOH (10 mL) and HOAc (0.5 mL), $NaBH_3CN$ (1.89 g, 15.0 mmol) was added. The mixture was stirred at room temperature for 6 h. It was then concentrated in vacuo. The residue was purified by a flash column using $MeOH/CH_2Cl_2/NH_3$ (5/95/1) as eluents to afford an off-white solid (1.5 g). MS 244.4 (M+H)

The solid (1.0 g, 4.1 mmol) was dissolved in 4 N HCl in dioxane (10 mL). The solution was stirred at room temperature for 3 h. It was then concentrated in vacuo to give the desired product as hydrochloride salt (0.71 g).

B. Preparation of N-(1-isopropylpiperidin-4-yl)-2-(2-bromophenyl)-2-(4-chlorophenyl-aminocarbonylamino)-acetamide To a solution of 2-(2-bromophenyl)-2-(4-chlorophenylaminocarbonylamino)-acetic acid (from EXAMPLE 77, 60 mg, 0.16 mmol), 1-isopropyl-4-aminopiperidine (60 mg, 0.31 mmol) and TEA (0.087 mL, 0.62 mmol) in DMF (3 mL), BOP (103 mg, 0.23 mmol) was added. After being stirred at room temperature overnight, the mixture was concentrated in vacuo. The residue was purified HPLC to give the titled compound as a powder (63 mg). MS 507.1 and 509.1 (M+H, Cl+Br pattern).

Example 83

N-[4-(1-methylpiperidin-4-yl)piperazin-1-yl]-2-(2-bromophenyl)-2-(4-chlorophenylaminocarbonylamino)-acetamide

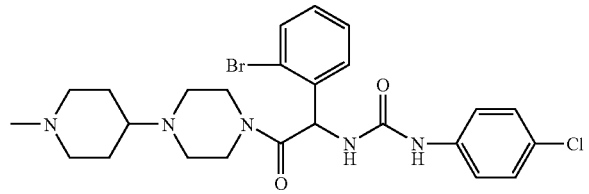

To a solution of 2-(2-bromophenyl)-2-(4-chlorophenylaminocarbonylamino)-acetic acid (from EXAMPLE 77, 30 mg, 0.078 mmol), 1-(1-methylpiperidin-4-yl)piperazine (purchased from Oakwood products, 21 mg, 0.11 mmol) and TEA (0.0-44 mL, 0.31 mmol) in DMF (3 mL), BOP (69 mg, 0.16 mmol) was added. After being stirred at room temperature for 1 h, the mixture was concentrated in vacuo. The residue was purified by HPLC to give the titled compound as a powder (39 mg). MS 548.3 and 550.3 (M+H, Cl+Br pattern).

Example 84

N-[4-(1-methyl-4,5-dihydro-1H-imidazol-2-yl)phenyl]-2-(2-methylphenyl)-2-(4-chlorophenylaminocarbonylamino)-acetamide

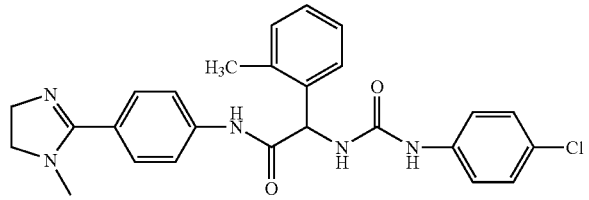

The titled compound was prepared analogously as described in EXAMPLE 77, using o-tolualdehyde in the place of 2-bromobenzaldehyde. MS 476.1 and 478.2 (M+H, Cl pattern).

Example 85

N-[4-(2-dimethylaminomethyl-imidazol-1-yl)-2-fluorophenyl]-2-(2-methylphenyl)-2-(4-chlorophenylaminocarbonylamino)-acetamide

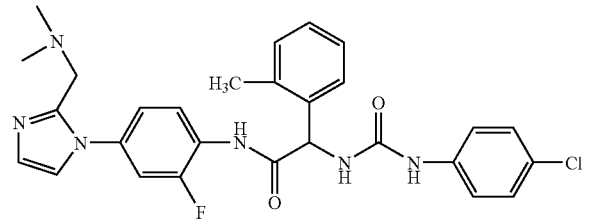

The titled compound was prepared analogously as described in EXAMPLE 58, using 2-(2-methylphenyl)-2-(4-chlorophenylaminocarbonylamino)-acetic acid in the place of 2-(2-fluorophenyl)-2-(4-chlorophenylaminocarbonylamino)-acetic acid. MS 535.4 and 537.4 (M+H, Cl pattern).

Example 86

N-[4-(dimethylaminoimino)phenyl]-2-(2-methylphenyl)-2-(4-chlorophenylaminocarbonylamino)-acetamide

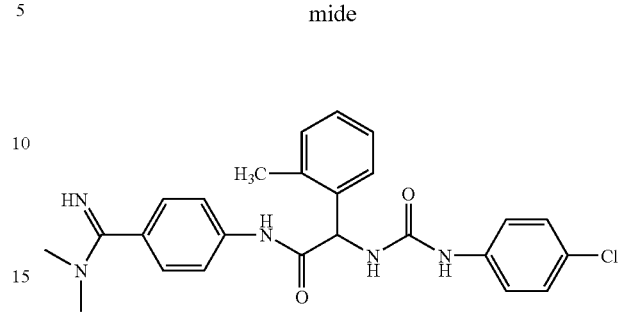

The titled compound was prepared analogously as described in EXAMPLE 80, using 2-(2-methylphenyl)-2-(4-chlorophenylaminocarbonylamino)-acetic acid in the place of 2-(2-bromophenyl)-2-(4-chlorophenylaminocarbonylamino)-acetic acid. MS 464.4 and 466.4 (M+H, Cl pattern).

Example 87

N-[4-(pyrrolidin-1-ylimino)phenyl]-2-(2-methylphenyl)-2-(4-chlorophenylaminocarbonylamino)-acetamide

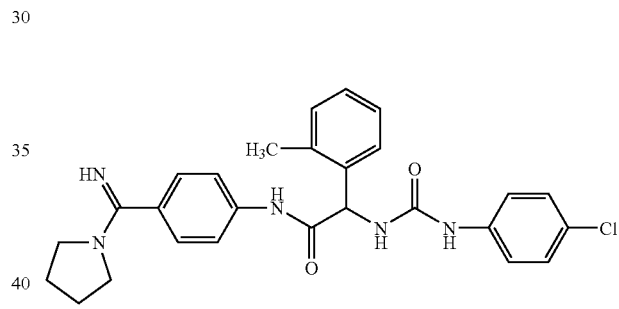

The titled compound was prepared analogously as described in EXAMPLE 81, using 2-(2-methylphenyl)-2-(4-chlorophenylaminocarbonylamino)-acetic acid in the place of 2-(2-bromophenyl)-2-(4-chlorophenylaminocarbonylamino)-acetic acid. MS 490.4 and 492.4 (M+H, Cl pattern).

Example 88

N-[4-(N-oxo-pyridin-2-yl)phenyl]-2-(2-methylphenyl)-2-(4-chlorophenylaminocarbonylamino)-acetamide

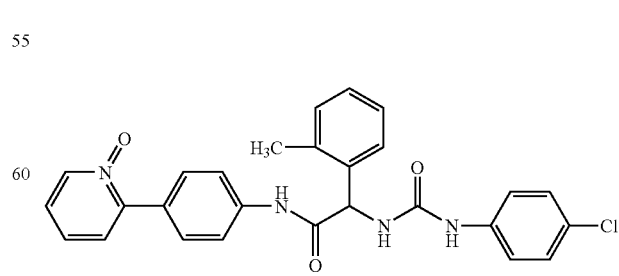

The titled compound was prepared analogously as describe in EXAMPLE 51, using 2-(2-methylphenyl)-2-(4-chlorophe-

Example 89

N-[4-(2-dimethylaminomethyl-phenyl)phenyl]-2-(2-methylphenyl)-2-(4-chlorophenylaminocarbonylamino)-acetamide

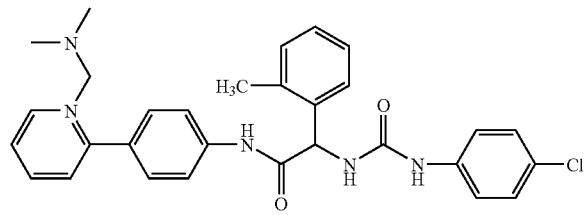

The titled compound was prepared analogously as describe in EXAMPLE 55, using 2-(2-methylphenyl)-2-(4-chlorophenylaminocarbonylamino)-acetic acid and 4-(2-dimethylaminomethyl-phenyl)phenylamine MS 527.7 and 529.6 (M+H, Cl pattern).

Example 90

N-(1-isopropylpiperidin-4-yl)-2-(2-methylphenyl)-2-(4-chlorophenylamino-carbonylamino)-acetamide

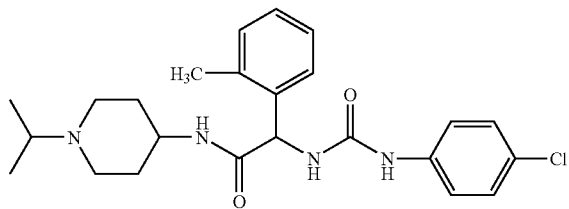

The titled compound was prepared analogously as describe in EXAMPLE 82, using 2-(2-methylphenyl)-2-(4-chlorophenylaminocarbonylamino)-acetic acid and 1-isopropyl-4-aminopiperidine. MS 443.2 and 445.2 (M+H, Cl pattern).

Example 91

N-[4-(1-methylpiperidin-4-yl)piperazin-1-yl]-2-(2-methylphenyl)-2-(4-chlorophenylaminocarbonylamino)-acetamide

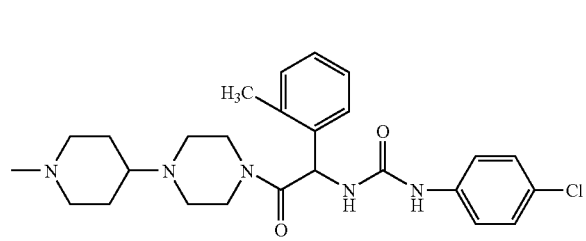

The titled compound was prepared analogously as describe in EXAMPLE 83, using 2-(2-methylphenyl)-2-(4-chlorophenylaminocarbonylamino)-acetic acid in the place of 2-(2-bromophenyl)-2-(4-chlorophenylaminocarbonylamino)-acetic acid. MS 484.6 and 486.6 (M+H, Cl pattern).

Example 92

N-[4-(4-methyl-homopiperazinyl)phenyl]-2-(2-methylphenyl)-2-(4-chlorophenylaminocarbonylamino)-acetamide

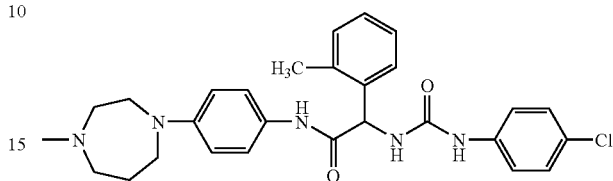

A. 4-(4-methyl-homopiperazinyl)phenylamine

A mixture of 1-fluoro-4-nitrobenzene (1.00 g, 7.09 mmol), 1-methylhomopiperazine (0.882 mL, 7.09 mmol) and $K_2CO_3$ (1.96 g, 14.2 mmol) in DMF (8 mL) was heated at 100 C for 7 h. After cooling to room temperature, $H_2O$ and EtOAc were added. The organic layer was separated, dried over $MgSO_4$, and concentrated in vacuo. The residue was diluted with $H_2O$, and acidified with 4N HCl to pH=1-2. The aqueous solution was then washed with EtOAc, neutralized with 5 N NaOH to pH=9. The aqueous solution was concentrated in vacuo. The product in the residue was taken up in MeOH. The insoluble inorganic salt was filtered off, the filtrate was concentrated in vacuo to give a solid (0.88 g). MS 236.1 (M+H)

A mixture of the solid (0.80 g, 3.4 mmol) and Pd—C (5%, 0.080 g) in MeOH (10 mL) was stirred under balloon $H_2$ overnight. It was then filtered, and the filtrate was concentrated in vacuo to give the desired product as an oil (0.59 g).

B. N-[4-(4-methyl-homopiperazinyl)phenyl]-2-(2-methylphenyl)-2-(4-chlorophenylamino-carbonylamino)-acetamide To a solution of 2-(2-methylphenyl)-2-(4-chlorophenylaminocarbonylamino)-acetic acid (from EXAMPLE 84, 40 mg, 0.13 mmol) and 4-(4-methyl-homopiperazinyl)phenylamine (61 mg, 0.25 mmol) in DMF (3 mL) and $H_2O$ (1 mL), EDC (96 mg, 0.50 mmol) was added. After being stirred at room temperature for 2 h, the mixture was concentrated in vacuo. The residue was purified by HPLC to give the titled compound as a powder (25 mg). MS 506.2 and 508.2 (M+H, Cl pattern).

Example 93

N-[1-(pyridin-4-yl)piperidin-4-yl]methyl-2-(2-methylphenyl)-2-(4-chlorophenylaminocarbonylamino)-acetamide

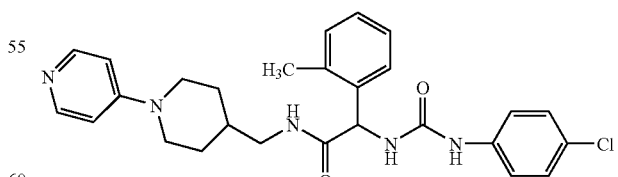

A. 4-[1-(pyridin-4-yl)piperidinyl]methylamine hydrochloride

To a solution of 4-N-Boc-aminomethyl piperidine (1.32 g, 6.17 mmol) and sodium t-butoxide (0.741 g, 7.71 mmol) in dioxane (10 mL), 4-bromopyridine hydrochloride (1.00 g, 5.14 mmol) in H₂O (2 mL) was added, then Pd2 (dba)3 (47 mg, 0.05 mmol) and BINAP (96 mg, 0.15 mmol) were added. The mixture was stirred at 80 C for 8 h. The mixture was filtered, and the filtrate was concentrated in vacuo. The residue was purified by HPLC to give the desired product (1.2 g).

Alternatively, a mixture of 4-N-Boc-aminomethyl piperidine (132 mg, 0.617 mmol), 4-bromopyridine hydrochloride (100 mg, 0.514 mmol) and K₂CO₃ (142 mg, 1.03 mmol) in DMF (5 mL) was heated at 80 C overnight. A clean product was also obtained.

The product (120 mg) was dissolved in 4 N HCl in dioxane (3 mL). The solution was stirred at room temperature for 2 h. It was then concentrated in vacuo to give the titled compound (100 mg). MS 192.3 (M+H).

B. Preparation of N-[1-(pyridin-4-yl)piperidin-4-yl]methyl-2-(2-methylphenyl)-2-(4-chlorophenylaminocarbonylamino)-acetamide To a solution of 2-(2-methylphenyl)-2-(4-chlorophenylaminocarbonylamino)-acetic acid (from EXAMPLE 84, 30 mg, 0.094 mmol), 4-[1-(pyridin-4-yl)piperidinyl]methylamine hydrochloride (36 mg, 0.19 mmol) and TEA (0.052 mL, 0.37 mmol) in DMF (3 mL), BOP (62 mg, 0.14 mmol) was added. After being stirred at room temperature for 2 h, the mixture was concentrated in vacuo. The residue was purified by HPLC to give the titled compound as a powder (15 mg). MS 492.4 and 494.4 (M+H, Cl pattern).

Example 94

N-[4-(pyrrolidin-1-ylcarbonyl)phenyl]-2-(2-methylphenyl)-2-(4-chlorophenylaminocarbonylamino)-acetamide

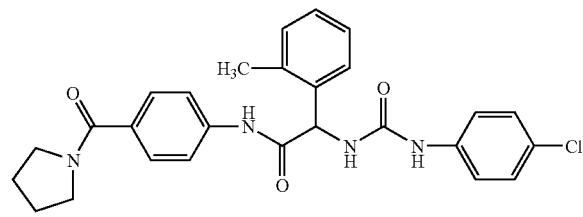

A. 4-(pyrrolidinylcarbonyl)phenylamine hydrochloride

To a suspension of 4-nitrobenzoyl chloride (18.5 g, 100 mmol) in CH₂Cl₂ (200 mL) cooled in ice-bath, a solution of pyrrolidine (8.30 mL, 100 mmol) and TEA (28.0 mL, 200 mmol) in CH₂Cl₂ (50 mL) was added dropwise. After being stirred at room temperature overnight, the reaction solution was washed sequentially with sat. NaHCO₃, H₂O, 1N HCl, H₂O, dried over MgSO₄, concentrated in vacuo to give a solid (15 g), which was pure enough for the next reaction.

A mixture of the solid (10 g, 45 mmol) and Pd—C (10%, 0.80 g) in MeOH (200 mL) containing 4N HCl (12 mL) was hydrogenated under 50 psi on a Parr shaker overnight. It was then filtered, and the filtrate was concentrated in vacuo to give the titled compound as a solid. MS 191.1 (M+H).

B. N-[4-(pyrrolidin-1-ylcarbonyl)phenyl]-2-(2-methylphenyl)-2-(4-chlorophenylaminocarbonylamino)-acetamide To a solution of 2-(2-methylphenyl)-2-(4-chlorophenylaminocarbonylamino)-acetic acid (50 mg, 0.16 mmol) and 4-(pyrrolidinylcarbonyl)phenylamine hydrochloride (43 mg, 0.19 mmol) in pyridine (3 mL) cooled in ice-bath, POCl₃ (0.028 mL, 0.31 mmol) was added. The mixture was stirred at room temperature overnight. It was then concentrated in vacuo. The residue was purified by HPLC to give the titled compound as a white powder (15 mg). MS 491.4 and 493.4 (M+H, Cl pattern).

Example 95

N-[4-(3-oxo-morpholin-4-yl)phenyl]-2-(2-methylphenyl)-2-(4-chlorophenylaminocarbonylamino)-acetamide

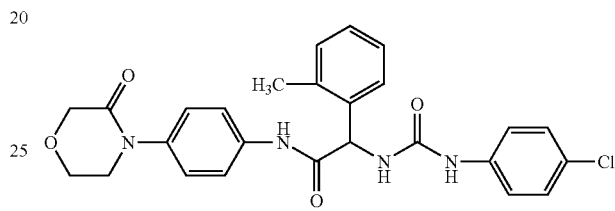

A. Preparation of 3-morpholinone

NaH (60%, 3.2 g, 80 mmol) in a flask was washed with hexane. To the flask cooled in an ice-bath, a solution of ethanolamine (4.4 mL, 73 mmol) in dioxane (40 mL) was added. The mixture was heated at reflux for 10 min until no H₂ gas evolved. The thick slurry was then cooled in an ice-bath, and a solution of ethyl chloroacetate (8.9 g, 73 mmol) in dioxane (15 mL) was added. The reaction mixture was heated at reflux for 1 h. It was then filtered. The filtrate was concentrated in vacuo to give an oil, which was purified by a short flash column, eluted with EtOAc/MeOH (95/5) to give a white solid (1.9 g).

B. Preparation of 4-(3-oxo-morpholin-4-yl)phenylamine

To a blue solution of 3-morpholinone (250 mg, 2.48 mmol), 4-iodoaniline (650 mg, 2.97 mmol), CuI (47 mg, 0.25 mmol) and N,N'-dimethylethylenediamine (0.040 mL, 0.372 mmol) in dioxane (5 mL) in a pressure bottle, K₂CO₃ (683 mg, 4.95 mmol) was added. The mixture was heated at 110 C overnight. After being cooled to room temperature, the crude dark solution was loaded to two preparative TLC plates, eluted with EtOAc/MeOH (95/5) to give the desired product as off-white solid (240 mg). MS 193.1 (M+H).

C. Preparation of N-[4-(3-oxo-morpholin-4-yl)phenyl]-2-(2-methylphenyl)-2-(4-chlorophenylaminocarbonylamino)-acetamide To a solution of 2-(2-methylphenyl)-2-(4-chlorophenylaminocarbonylamino)-acetic acid (26 mg, 0.082 mmol) and 4-(3-oxo-morpholin-4-yl)phenylamine (23 mg, 0.12 mmol) in DMF (3 mL), EDC (39 mg, 0.20 mmol) was added. The reaction mixture was stirred at room temperature overnight. It was then concentrated in vacuo. The residue was purified by HPLC to give the titled compound as a white powder (27 mg). MS 493.2 and 495.2 (M+H, Cl pattern).

Example 96

N-[4-(N-methyl-N-pyridin-4-yl-amino)phenyl]-2-(2-methylphenyl)-2-(4-chlorophenylaminocarbonylamino)-acetamide

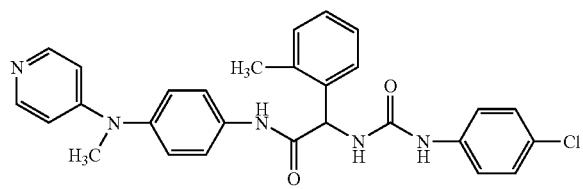

A. 4-(N-methyl-N-pyridin-4-yl-amino)phenylamine

A mixture of 4-methylaminopyridine (427 mg, 3.95 mmol), 1-fluoro-nitrobenzene (0.472 mL, 4.45 mmol) and $Cs_2CO_3$ (2.0 g, 6.1 mmol) in DMF (9 mL) was heated at 80 C for 3 h. It was then filtered, and the filtrate was concentrated in vacuo. The residue was purified by HPLC to give an oil (230 mg). MS 230.0 (M+H).

A mixture of the oil (110 mg, 0.480 mmol) and Pd—C (5%, 35 mg) in MeOH (5 mL) was stirred under balloon $H_2$ for 4 h. It was then filtered, and the filtrate was concentrated in vacuo to give the titled compound (94 mg). MS 200.2 (M+H).

B. Preparation of N-[4-(N-methyl-N-pyridin-4-yl-amino)phenyl]-2-(2-methylphenyl)-2-(4-chlorophenylaminocarbonylamino)-acetamide To a solution of 2-(2-methylphenyl)-2-(4-chlorophenylaminocarbonylamino)-acetic acid (53 mg, 0.17 mmol) and 4-(N-methyl-N-pyridin-4-yl-amino)phenylamine (47 mg, 0.24 mmol) in DMF (3 mL), EDC (73 mg, 0.38 mmol) was added. The reaction mixture was stirred at room temperature overnight. It was then concentrated in vacuo. The residue was purified by HPLC to give the titled compound as a white powder (28 mg). MS 500.2 and 502.2 (M+H, Cl pattern).

Example 97

N-[4-(thiazolidin-3-ylcarbonyl)phenyl]-2-(2-methylphenyl)-2-(4-chlorophenylaminocarbonylamino)-acetamide

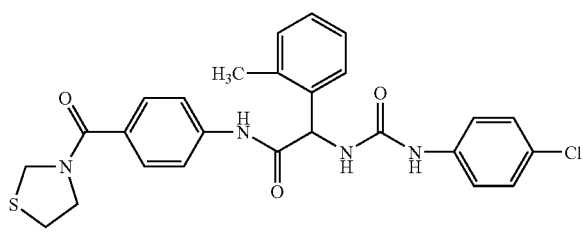

A. Preparation of 4-(thiazolidin-3-ylcarbonyl)phenylamine

To a suspension of 4-nitrobenzoic acid (1.00 g, 5.99 mmol) in $CH_2Cl_2$ (15 mL) and DMF (4 drops) at room temperature, oxalyl chloride (0.628 mL, 7.19 mmol) was added. The reaction mixture was then stirred for 4 h, during which time the suspension became clear. After being concentrated in vacuo, the residue was dissolved in $CH_2Cl_2$ (15 mL). To the solution, thiazolidine (0.471 mL, 5.99 mmol) and TEA (1.67 mL, 12.0 mmol) were added. It was stirred overnight. The $CH_2Cl_2$ solution was washed with 1N HCl, $H_2O$, and sat. $NaHCO_3$, then dried over $Na_2SO_4$, concentrated in vacuo to give an oil (1.12 g).

A mixture of the oil (1.12 g, 4.71 mmol) and Pd—C (5%, 180 mg) in $CH_2Cl_2$ (5 mL) and MeOH (10 mL) containing TFA (5 drops) was hydrogenated at 45 psi on a Parr shaker for 3 days. The mixture was then filtered, and the filtrate was concentrated in vacuo. One half of the residue was purified by HPLC to give an oil (151 mg). MS 209.0 (M+H) and 231.0 (M+Na).

B. Preparation of N-[4-(thiazolidin-3-ylcarbonyl)phenyl]-2-(2-methylphenyl)-2-(4-chlorophenylaminocarbonylamino)-acetamide To a solution of 2-(2-methylphenyl)-2-(4-chlorophenylaminocarbonylamino)-acetic acid (46 mg, 0.14 mmol) and 4-(thiazolidin-3-ylcarbonyl)phenylamine (30 mg, 0.14 mmol) in DMF (2 mL), EDC (54 mg, 0.28 mmol) was added. The reaction mixture was stirred at room temperature overnight. It was then concentrated in vacuo. The residue was purified by HPLC to give the titled compound as a white powder (15 mg). MS 509.2 and 511.2 (M+H, Cl pattern).

Example 98

N-[4-(oxazolidin-3-ylcarbonyl)phenyl]-2-(2-methylphenyl)-2-(4-chlorophenylaminocarbonylamino)-acetamide

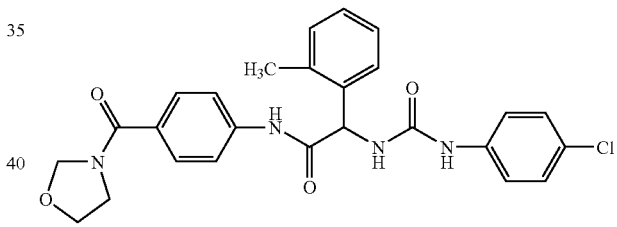

A. 4-(oxazolidin-3-ylcarbonyl)phenylamine

To a suspension of 4-nitrobenzoic acid (2.00 g, 12.0 mmol) in $CH_2Cl_2$ (30 mL) and DMF (5 drops) at room temperature, oxalyl chloride (1.25 mL, 14.3 mmol) was added. It was then stirred overnight. The solution was concentrated in vacuo.

To a solution of ethanolamine (0.866 mL, 14.3 mmol) and TEA (3.9 mL, 28.0 mmol) in $CH_2Cl_2$ (15 mL) at room temperature, a solution of the acid chloride (12 mmol) in $CH_2Cl_2$ (8 mL) was added. After being stirred for 1 h, the reaction mixture was concentrated in vacuo. One third of the residue was purified by HPLC to give a white solid (0.62 g). MS 211.0 (M+H).

A mixture of the solid (230 mg, 1.10 mmol), dimethoxymethane (0.58 mL, 6.6 mmol) and $P_2O_5$ (600 mg, 4.23 mmol) in $CHCl_3$ (5 mL) was heated at 70 C for 4 h. $CHCl_3$ and 1 N HCl were added. The $CHCl_3$ solution was separated, washed with brine, dried over $Na_2SO_4$, concentrated in vacuo to give an oil (138 mg). MS 223.0 (M+H).

A mixture of the oil (138 mg) and Pd—C (5%, 33 mg) in MeOH (5 mL) was stirred under balloon $H_2$ overnight. It was then filtered, and the filtrate was concentrated in vacuo to give titled compound as an oil (105 mg). MS 193.0 (M+H).

B. N-[4-(oxazolidin-3-ylcarbonyl)phenyl]-2-(2-methylphenyl)-2-(4-chlorophenylamino-carbonylamino)-acetamide To a solution of 2-(2-methylphenyl)-2-(4-chlorophenylaminocarbonylamino)-acetic acid (44 mg, 0.14 mmol) and 4-(oxazolidin-3-ylcarbonyl)phenylamine (25 mg, 0.13 mmol) in DMF (3 mL), EDC (75 mg, 0.39 mmol) was added. The reaction mixture was stirred at room temperature overnight. It was then concentrated in vacuo. The residue was purified by HPLC to give the titled compound as a white powder (20 mg). MS 493.2 and 495.2 (M+H, Cl pattern).

Example 99

N-[4-(N-oxo-pyridin-2-yl)phenyl]-2-(2-chlorophenyl)-2-(4-chlorophenylaminocarbonylamino)-acetamide

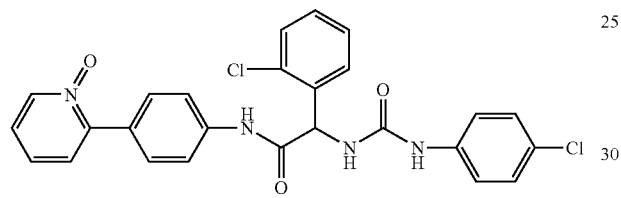

The titled compound was analogously prepared as described in Example 51, using 2-(2-chlorophenyl)-2-(4-chlorophenylaminocarbonylamino)-acetic acid and 4-(N-oxo-pyridin-2-yl)phenylamine hydrochloride. MS 507.1, 508.1, 509.1 and 510.1 (M+H, 2Cl pattern).

Example 100

N-[4-(dimethylaminoimino)phenyl]-2-(2-chlorophenyl)-2-(4-chlorophenylaminocarbonylamino)-acetamide

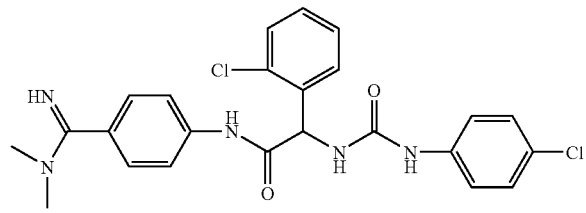

The titled compound was prepared analogously as described in Example 80, using 2-(2-chlorophenyl)-2-(4-chlorophenylaminocarbonylamino)-acetic acid in the place of 2-(2-bromophenyl)-2-(4-chlorophenylaminocarbonylamino)-acetic acid. MS 484.5, 485.6, 486.5 and 487.6 (M+H, 2Cl pattern).

Example 101

N-[4-(pyrrolidin-1-ylimino)phenyl]-2-(2-chlorophenyl)-2-(4-chlorophenylaminocarbonylamino)-acetamide

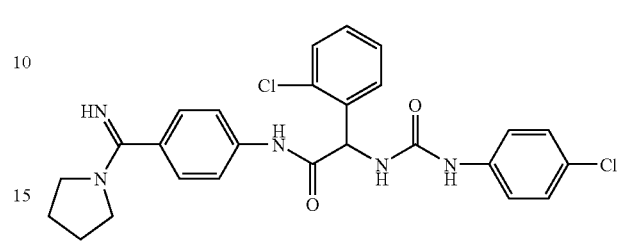

The titled compound was prepared analogously as described in Example 81, using 2-(2-chlorophenyl)-2-(4-chlorophenylaminocarbonylamino)-acetic acid in the place of 2-(2-bromophenyl)-2-(4-chlorophenylaminocarbonylamino)-acetic acid. MS 510.6, 511.6, 512.6 and 513.6 (M+H, 2Cl pattern).

Example 102

N-[4-(4-methyl-homopiperazinyl)phenyl]-2-(2-chlorophenyl)-2-(4-chlorophenylaminocarbonylamino)-acetamide

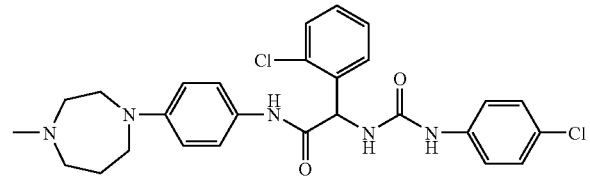

The titled compound was prepared analogously as described in Example 92, using 2-(2-chlorophenyl)-2-(4-chlorophenylaminocarbonylamino)-acetic acid in the place of 2-(2-methylphenyl)-2-(4-chlorophenylaminocarbonylamino)-acetic acid. MS 526.2, 527.2, 528.2 and 529.2 (M+H, 2Cl pattern).

Example 103

N-(1-isopropylpiperidin-4-yl)-2-(2-chlorophenyl)-2-(4-chlorophenylamino-carbonylamino)-acetamide

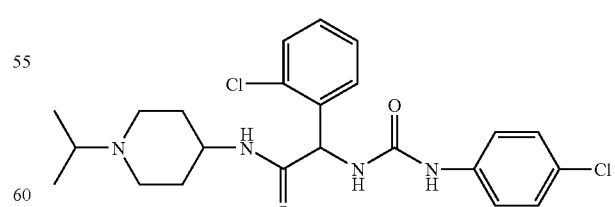

The titled compound was prepared analogously as describe in Example 82, using 2-(2-chlorophenyl)-2-(4-chlorophenylaminocarbonylamino)-acetic acid and 1-isopropyl-4-aminopiperidine. MS 463.1, 464.1, 465.1 and 466.1 (M+H, 2Cl pattern).

Example 104

N-[4-(1-methylpiperidin-4-yl)piperazin-1-yl]-2-(2-chlorophenyl)-2-(4-chlorophenylaminocarbonylamino)-acetamide

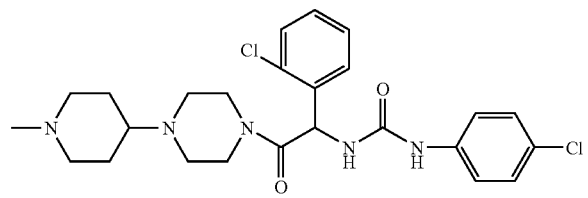

The titled compound was prepared analogously as describe in Example 83, using 2-(2-chlorophenyl)-2-(4-chlorophenylaminocarbonylamino)-acetic acid in the place of 2-(2-bromophenyl)-2-(4-chlorophenylaminocarbonylamino)-acetic acid. MS 504.4, 505.4, 506.4 and 507.4 (M+H, 2Cl pattern).

Example 105

N-[1-(pyridin-4-yl)piperidin-4-yl]methyl-2-(2-chlorophenyl)-2-(4-chlorophenylaminocarbonylamino)-acetamide

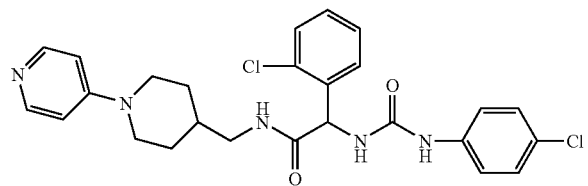

The titled compound was prepared analogously as described in Example 93, using 2-(2-chlorophenyl)-2-(4-chlorophenylaminocarbonylamino)-acetic acid in the place of 2-(2-methylphenyl)-2-(4-chlorophenylaminocarbonylamino)-acetic acid. MS 512.3, 513.3, 514.3 and 515.3 (M+H, 2Cl pattern).

Example 106

N-[4-(1-methyl-4,5-dihydro-1H-imidazol-2-yl)phenyl]-2-(2-methoxyphenyl)-2-(4-chlorophenylaminocarbonylamino)-acetamide

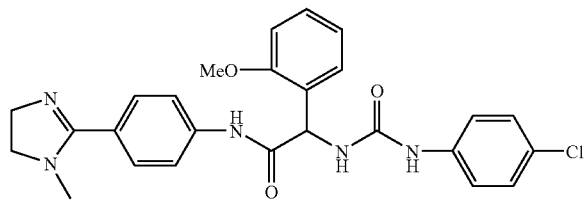

The titled compound was prepared analogously as described in Example 77, using o-anisaldehyde in the place of 2-bromobenzaldehyde. MS 492.1 and 494.1 (M+H, Cl pattern).

Example 107

N-[4-(N-oxo-pyridin-2-yl)phenyl]-2-(2-methoxyphenyl)-2-(4-chlorophenylaminocarbonylamino)-acetamide

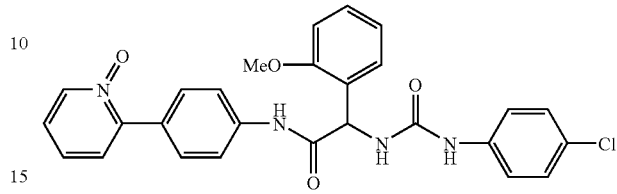

The titled compound was prepared analogously as describe in Example 51, using 2-(2-methoxyphenyl)-2-(4-chlorophenylaminocarbonylamino)-acetic acid and 4-(N-oxo-pyridin-2-yl)phenylamine hydrochloride. MS 503.1 and 505.2 (M+H, Cl pattern).

Example 108

N-[1-(pyridin-4-yl)piperidin-4-yl]methyl-2-(2-methoxyphenyl)-2-(4-chlorophenylaminocarbonylamino)-acetamide

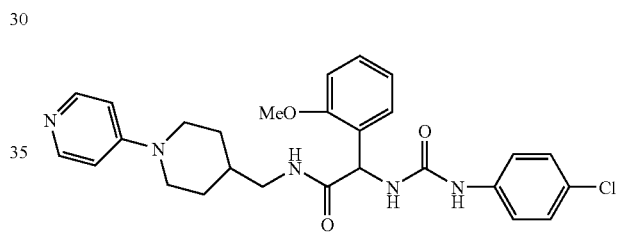

The titled compound was prepared analogously as described in Example 93, using 2-(2-methoxyphenyl)-2-(4-chlorophenylaminocarbonylamino)-acetic acid in the place of 2-(2-methylphenyl)-2-(4-chlorophenylaminocarbonylamino)-acetic acid. MS 508.4 and 510.4 (M+H, Cl pattern).

Example 109

N-[4-(1-methylpiperidin-4-yl)piperazin-1-yl]-2-(2-methoxyphenyl)-2-(4-chlorophenylaminocarbonylamino)-acetamide

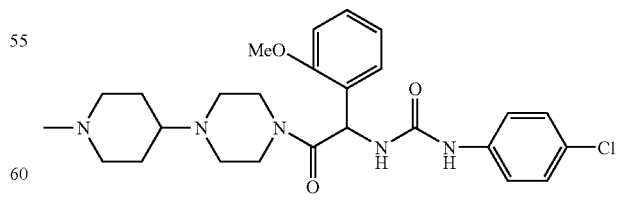

The titled compound was prepared analogously as describe in Example 83, using 2-(2-methoxyphenyl)-2-(4-chlorophenylaminocarbonylamino)-acetic acid in the place of 2-(2-bromophenyl)-2-(4-chlorophenylaminocarbonylamino)-acetic acid. MS 500.4 and 502.4 (M+H, Cl pattern).

Example 110

N-(1-isopropylpiperidin-4-yl)-2-(2-methoxyphenyl)-2-(4-chlorophenylamino-carbonylamino)-acetamide

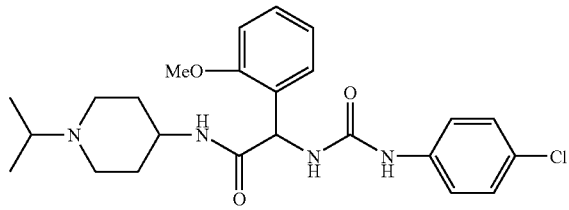

The titled compound was prepared analogously as describe in Example 82, using 2-(2-methoxyphenyl)-2-(4-chlorophenylaminocarbonylamino)-acetic acid and 1-isopropyl-4-aminopiperidine. MS 460.2 and 462.2 (M+H, Cl pattern).

Example 111

N-[4-(4-methyl-homopiperazinyl)phenyl]-2-(2-methoxyphenyl)-2-(4-chlorophenylaminocarbonylamino)-acetamide

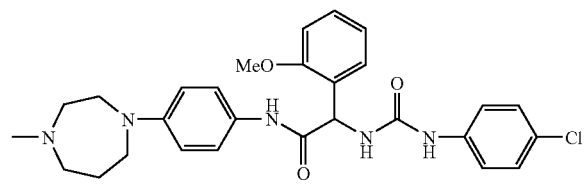

The titled compound was prepared analogously as described in Example 92, using 2-(2-methoxyphenyl)-2-(4-chlorophenylaminocarbonylamino)-acetic acid in the place of 2-(2-methylphenyl)-2-(4-chlorophenylaminocarbonylamino)-acetic acid. MS 522.2 and 524.2 (M+H, Cl pattern).

Example 112

N-[4-(dimethylaminoimino)phenyl]-2-(2-methoxyphenyl)-2-(4-chlorophenylaminocarbonylamino)-acetamide

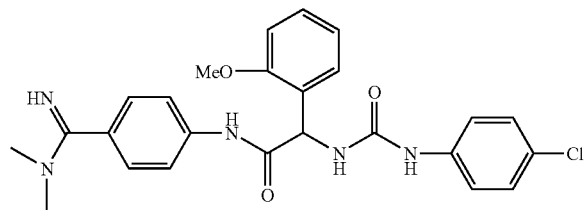

The titled compound was prepared analogously as described in Example 80, using 2-(2-methoxyphenyl)-2-(4-chlorophenylaminocarbonylamino)-acetic acid in the place of 2-(2-bromophenyl)-2-(4-chlorophenylaminocarbonylamino)-acetic acid. MS 480.3 and 482.3 (M+H, Cl pattern).

Example 113

N-[4-(pyrrolidin-1-ylimino)phenyl]-2-(2-methoxyphenyl)-2-(4-chlorophenylaminocarbonylamino)-acetamide

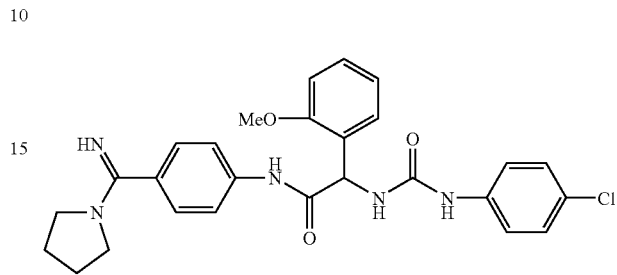

The titled compound was prepared analogously as described in Example 81, using 2-(2-methoxyphenyl)-2-(4-chlorophenylaminocarbonylamino)-acetic acid in the place of 2-(2-bromophenyl)-2-(4-chlorophenylaminocarbonylamino)-acetic acid. MS 506.4 and 508.4 (M+H, Cl pattern).

Example 114

N-[4-(1-methyl-4,5-dihydro-1H-imidazol-2-yl)phenyl]-2-(2-iodophenyl)-2-(4-chlorophenylaminocarbonylamino)-acetamide

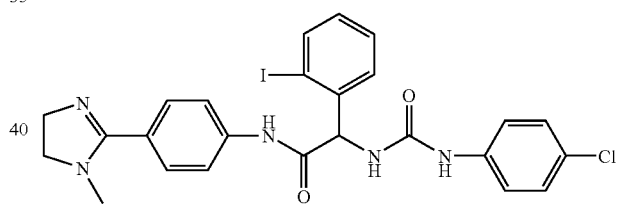

The titled compound was prepared analogously as described in Example 77, using 2-iodobenzaldehyde in the place of 2-bromobenzaldehyde. MS 588.5 and 590.6 (M+H, Cl pattern).

Example 115

N-[4-(N-oxo-pyridin-2-yl)phenyl]-2-(2-iodophenyl)-2-(4-chlorophenylamino-carbonylamino)-acetamide

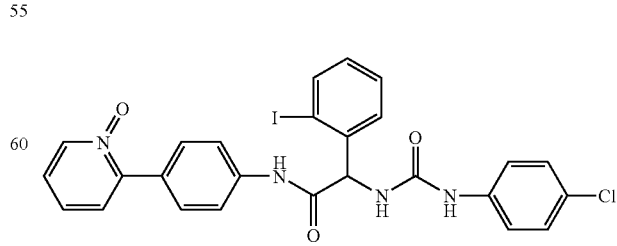

The titled compound was prepared analogously as describe in Example 51, using 2-(2-iodophenyl)-2-(4-chlorophenylaminocarbonylamino)-acetic acid and 4-(N-oxo-pyridin-2-yl)phenylamine hydrochloride. MS 599.5 and 601.5 (M+H, Cl pattern).

Example 116

N-[4-(dimethylaminoimino)phenyl]-2-(2-iodophenyl)-2-(4-chlorophenylaminocarbonylamino)-acetamide

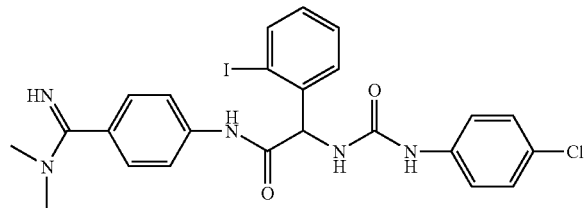

The titled compound was prepared analogously as described in Example 80, using 2-(2-iodophenyl)-2-(4-chlorophenylaminocarbonylamino)-acetic acid in the place of 2-(2-bromophenyl)-2-(4-chlorophenylaminocarbonylamino)-acetic acid. MS 576.2 and 578.2 (M+H, Cl pattern).

Example 117

N-[4-(pyrrolidin-1-ylimino)phenyl]-2-(2-iodophenyl)-2-(4-chlorophenylaminocarbonylamino)-acetamide

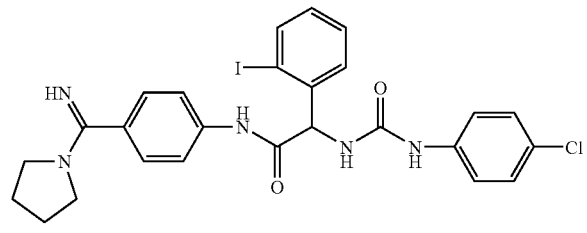

The titled compound was prepared analogously as described in Example 81, using 2-(2-iodophenyl)-2-(4-chlorophenylaminocarbonylamino)-acetic acid in the place of 2-(2-bromophenyl)-2-(4-chlorophenylaminocarbonylamino)-acetic acid. MS 602.2 and 604.2 (M+H, Cl pattern).

Example 118

N-[4-(1-methylpiperidin-4-yl)piperazin-1-yl]-2-(2-iodophenyl)-2-(4-chlorophenylaminocarbonylamino)-acetamide

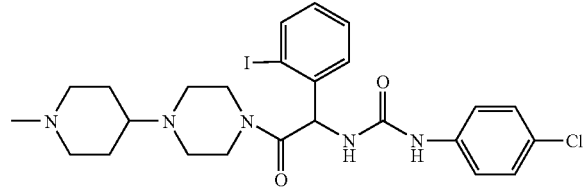

The titled compound was prepared analogously as describe in Example 83, using 2-(2-iodophenyl)-2-(4-chlorophenylaminocarbonylamino)-acetic acid in the place of 2-(2-bromophenyl)-2-(4-chlorophenylaminocarbonylamino)-acetic acid. MS 596.3 and 598.3 (M+H, Cl pattern).

Example 119

N-[4-(1-methyl-4,5-dihydro-1H-imidazol-2-yl)phenyl]-2-(4-bromophenyl)-2-(4-chlorophenylaminocarbonylamino)-acetamide

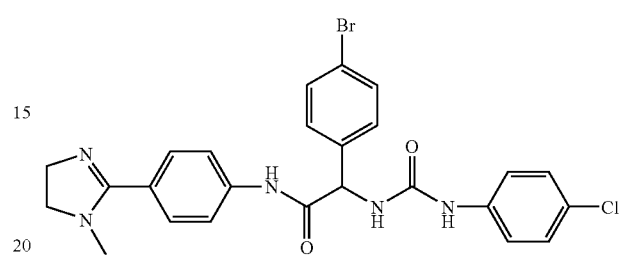

The titled compound was prepared analogously as described in Example 77, using 4-bromobenzaldehyde in the place of 2-bromobenzaldehyde. MS 540.5 and 542.5 (M+H, Cl+Br pattern).

Example 120

N-[4-(1-methyl-4,5-dihydro-1H-imidazol-2-yl)phenyl]-2-(2-trifluoromethoxyphenyl)-2-(4-chlorophenylaminocarbonylamino)-acetamide

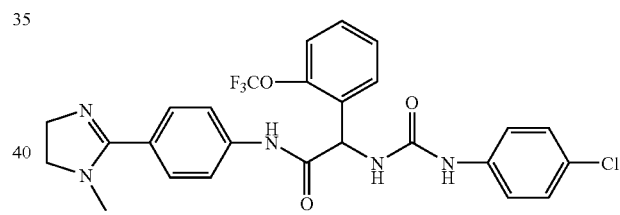

The titled compound was prepared analogously as described in Example 77, using 2-trifluoromethoxybenzaldehyde in the place of 2-bromobenzaldehyde. MS 546.6 and 548.6 (M+H, Cl pattern).

Example 121

N-[4-(N-oxo-pyridin-2-yl)phenyl]-2-(2-trifluoromethoxyphenyl)-2-(4-chlorophenylaminocarbonylamino)-acetamide

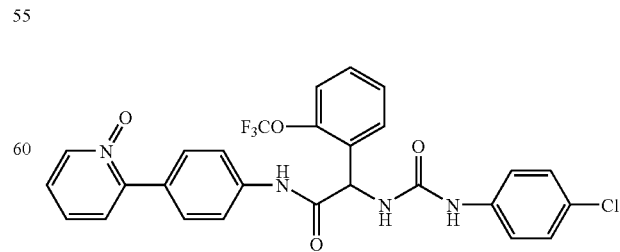

The titled compound was prepared analogously as describe in Example 51, using 2-(2-trifluoromethoxyphenyl)-2-(4- chlorophenylaminocarbonylamino)-acetic acid and 4-(N-oxo-pyridin-2-yl)phenylamine hydrochloride. MS 557.6 and 559.6 (M+H, Cl pattern).

Example 122

N-[4-(1-methyl-4,5-dihydro-1H-imidazol-2-yl)phenyl]-2-(2-trifluoromethylthiophenyl)-2-(4-chlorophenylaminocarbonylamino)-acetamide

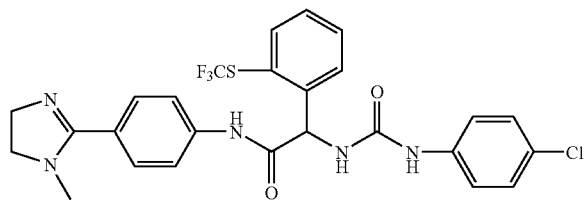

The titled compound was prepared analogously as described in EXAMPLE 77, using 2-trifluoromethylthiobenzaldehyde in the place of 2-bromobenzaldehyde. MS 562.6 and 564.6 (M+H, Cl pattern).

Example 123

N-[4-(N-oxo-pyridin-2-yl)phenyl]-2-(2-trifluoromethylthiophenyl)-2-(4-chlorophenylaminocarbonylamino)-acetamide

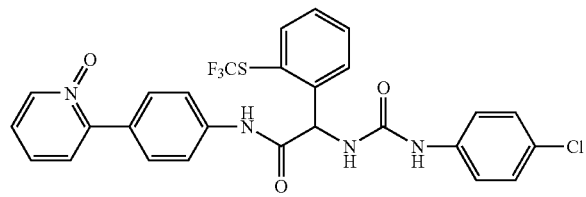

The titled compound was prepared analogously as describe in Example 51, using 2-(2-trifluoromethylthiophenyl)-2-(4-chlorophenylaminocarbonylamino)-acetic acid and 4-(N-oxo-pyridin-2-yl)phenylamine hydrochloride. MS 573.5 and 575.5 (M+H, Cl pattern).

Example 124

N-[4-(1-methyl-4,5-dihydro-1H-imidazol-2-yl)phenyl]-2-(2-phenoxyphenyl)-2-(4-chlorophenylaminocarbonylamino)-acetamide

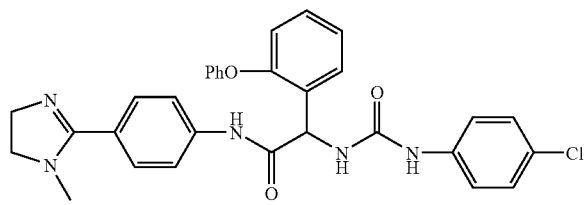

The titled compound was prepared analogously as described in Example 77, using 2-phenoxybenzaldehyde in the place of 2-bromobenzaldehyde. MS 554.7 and 556.7 (M+H, Cl pattern).

Example 125

N-[4-(N-oxo-pyridin-2-yl)phenyl]-2-(2-phenoxyphenyl)-2-(4-chlorophenylaminocarbonylamino)-acetamide

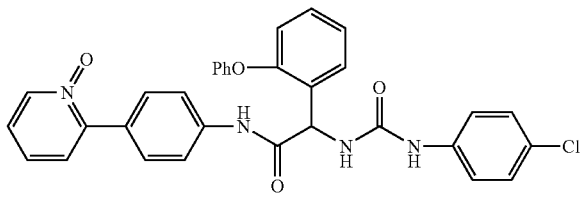

The titled compound was prepared analogously as describe in Example 51, using 2-(2-phenoxyphenyl)-2-(4-chlorophenylaminocarbonylamino)-acetic acid and 4-(N-oxo-pyridin-2-yl)phenylamine hydrochloride. MS 565.6 and 567.6 (M+H, Cl pattern).

Example 126

N-[4-(N-oxo-pyridin-2-yl)phenyl]-2-(2-methylthiophenyl)-2-(4-chlorophenylaminocarbonylamino)-acetamide

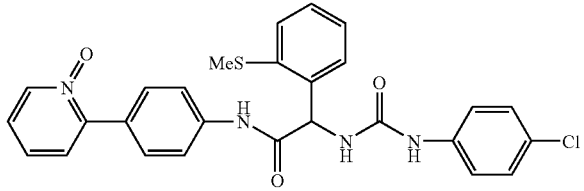

The titled compound was prepared analogously as described in Example 77, using 2-methylthiobenzaldehyde in the place of 2-bromobenzaldehyde, and 4-(N-oxo-pyridin-2-yl)phenylamine hydrochloride in the place of 4-(1-Methyl-4,5-dihydro-1H-imidazol-2-yl)-phenylamine. MS 519.1 and 521.1 (M+H, Cl pattern).

Example 127

N-[4-(1-methylpiperidin-4-yl)piperazin-1-yl]-2-(2-fluorophenyl)-2-(4-chlorophenylaminocarbonylamino)-acetamide

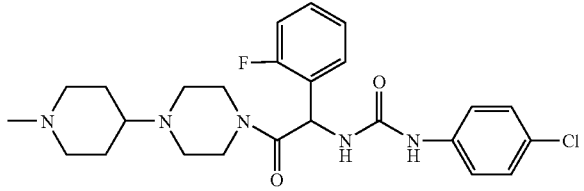

The titled compound was prepared analogously as describe in Example 83, using 2-(2-fluorophenyl)-2-(4-chlorophenylaminocarbonylamino)-acetic acid (from Example 55) in the place of 2-(2-bromophenyl)-2-(4-chlorophenylaminocarbonylamino)-acetic acid. MS 488.2 and 490.2 (M+H, Cl pattern).

Example 128

N-[4-(1-methylpiperidin-4-yl)piperazin-1-yl]-2-phenyl-2-(4-chlorophenylaminocarbonylamino)-acetamide

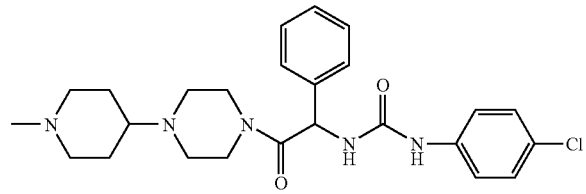

The titled compound was prepared analogously as describe in Example 83, using 2-phenyl-2-(4-chlorophenylaminocarbonylamino)-acetic acid (from Example 16) in the place of 2-(2-bromophenyl)-2-(4-chlorophenylaminocarbonylamino)-acetic acid. MS 470.2 and 472.2 (M+H, Cl pattern).

Example 129

N-[4-(1-methyl-4,5-dihydro-1H-imidazol-2-yl)phenyl]-2-propargyl-2-(4-chlorophenylaminocarbonylamino)-acetamide

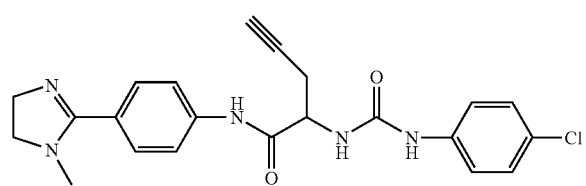

The titled compound was prepared analogously as described in Example 59, using DL-propargylglycine in the place of L-aspartic acid γ-benzyl ester. MS 424.1 and 426.1 (M+H, Cl pattern).

Example 130

N-[4-(1-methyl-4,5-dihydro-1H-imidazol-2-yl)phenyl]-2-(but-2-yn-1-yl)-2-(4-chlorophenylaminocarbonylamino)-acetamide

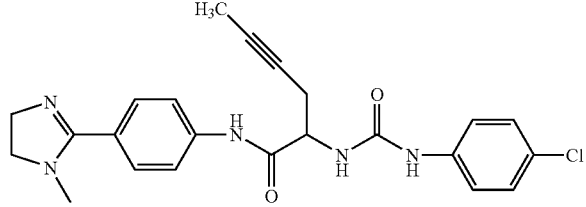

A. 2-(but-2-yn-1-yl)-2-(4-chlorophenylaminocarbonylamino)-acetic acid

To a mixture of N-(diphenylmethylene)glycine t-butyl ester (300 mg, 1.02 mmol) in $CH_2Cl_2$ (4 mL) and aq. 5N NaOH (4 mL), 1-bromo-2-butyne (0.107 mL, 1.22 mmol) was added, followed by addition of tetrabutylammonium bromide (164 mg, 0.508 mmol). After being stirred at room temperature overnight, $H_2O$ and $CH_2Cl_2$ were added. The $CH_2Cl_2$ layer was separated, dried over $MgSO_4$, concentrated in vacuo to give a solid (330 mg), which was pure enough for the next step.

A mixture of the solid (330 mg, 0.950 mmol) in $CHCl_3$ (10 mL) and aq. 5N HCl (10 mL) was stirred at room temperature for 3 h. $H_2O$ (20 mL) was added. The aqueous layer was separated, washed with $CHCl_3$, concentrated in vacuo to give a solid (110 mg), which was pure enough for the next step. MS 128.2 (M+H).

To a solution of the solid (110 mg, 0.866 mmol) in 1N aq. NaOH (3 mL), a solution of 4-chlorophenyl isocyanate (200 mg, 1.30 mmol) in dioxane (3 mL) was added. The mixture was stirred at room temperature for 16 h. $H_2O$ (20 mL) was added. The aqueous layer was washed with $Et_2O$, acidified with 4N HCl to pH 1-2. The product was extracted with EtOAc. The EtOAc solution was dried over $Na_2SO_4$, concentrated in vacuo. The residue was purified by HPLC to give the urea acid as a white powder (207 mg). MS 303.3 and 305.2 (M+Na, Cl pattern)

B. N-[4-(1-methyl-4,5-dihydro-1H-imidazol-2-yl)phenyl]-2-(but-2-yn-1-yl)-2-(4-chlorophenylaminocarbonylamino)-acetamide To a solution of the urea acid (60 mg, 0.21 mmol) and 4-(1-Methyl-4,5-dihydro-1H-imidazol-2-yl)-phenylamine (from Example 3, 75 mg, 0.43 mmol) in DMF (4 mL) and $H_2O$ (1 mL), EDC (219 mg, 0.86 mmol) was added. After being stirred at room temperature for 2 h, the mixture was concentrated in vacuo. The residue was purified by HPLC to give the titled compound as a white powder (46 mg). MS 438.5 and 440.5 (M+H, Cl pattern).

Example 131

N-[4-(N-oxo-pyridin-2-yl)phenyl]-2-(but-2-yn-1-yl)-2-(4-chlorophenylaminocarbonylamino)-acetamide

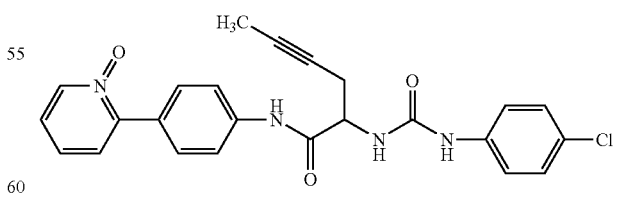

The titled compound was prepared analogously as describe in Example 51, using 2-(but-2-yn-1-yl)-2-(4-chlorophenylaminocarbonylamino)-acetic acid (from Example 130) and 4-(N-oxo-pyridin-2-yl)phenylamine hydrochloride. MS 449.5 and 451.5 (M+H, Cl pattern).

Example 132

N-[4-(1-methyl-4,5-dihydro-1H-imidazol-2-yl)phenyl]-2-allyl-2-(4-chlorophenylaminocarbonylamino)-acetamide

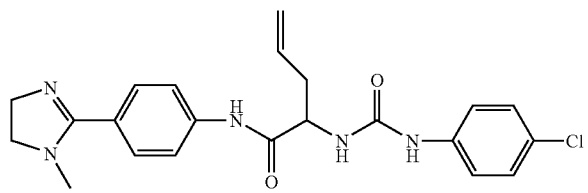

The titled compound was prepared analogously as describe in Example 130, starting with allyl bromide in the place of 1-bromo-2-butyne. MS 426.5 and 428.5 (M+H, Cl pattern).

Example 133

N-[4-(N-oxo-pyridin-2-yl)phenyl]-2-allyl-2-(4-chlorophenylaminocarbonylamino)-acetamide

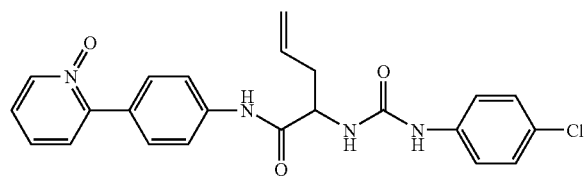

The titled compound was prepared analogously as describe in Example 51, using 2-allyl-2-(4-chlorophenylaminocarbonylamino)-acetic acid (from Example 132) and 4-(N-oxo-pyridin-2-yl)phenylamine hydrochloride. MS 437.5 and 439.5 (M+H, Cl pattern).

Example 134

1-[4-(dimethylaminoimino)phenyl]-3-(4-chlorophenylaminocarbonylamino)-3,4-dihydroquinolin-2-one

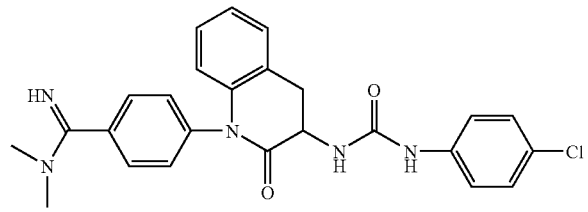

A mixture of 3,4-dihydroquinolin-2-one (1.00 g, 6.80 mmol), 4-iodobenzonitrile (1.71 g, 7.47 mmol), CuI (0.129 g, 0.680 mmol), 1,2-diaminocyclohexane (0.038 mL, 3.10 mmol) and $K_3PO_4$ (2.90 g, 13.7 mmol) in dioxane (10 mL) in a sealed thick-wall flask was heated at 110 C overnight. After cooling to room temperature, the mixture was filtered. The filtrate was concentrated in vacuo. The residue was purified by a flash column using EtOAc/hexane (15-40%) as eluents to give a white solid (0.690 g).

To a solution of the solid (0.250 g, 1.00 mmol) in THF (6 mL) at −78 C, LDA (1.8 M, 0.70 mL, 1.26 mmol) was added. After 15 min, a solution of triisopropylbenzenesulfonyl azide (0.464 g, 1.50 mmol) in THF (2 mL) was added. After being stirred at −78 C for 1 h, the mixture was removed to room temperature, and was stirred at that temperature overnight. Aqueous $NH_4Cl$ and EtOAc were added. The organic layer was separated, washed with brine, dried over $Na_2SO_4$, concentrated in vacuo. The residue was purified by a flash column using EtOAc/hexane (10-20%) as eluents to give a solid (0.110 g).

To a solution of the solid (0.100 g, 0.346 mmol) in THF (4 mL), $Ph_3P$ (0.180 g, 0.687 mmol) was added, followed by addition of $H_2O$ (0.050 mL, 2.78 mmol). After being stirred at room temperature overnight, the solution was concentrated in vacuo. To a solution of the residue in DMF (5 mL), 4-chlorophenyl isocyanate (0.080 g, 0.52 mmol) was added. After being stirred at room temperature overnight, the solution was concentrated in vacuo. The residue was purified by HPLC to give a solid (0.092 g). MS 417.3 and 419.3 (M+H, Cl pattern).

To a solution of the nitrile compound (0.080 g, 0.19 mmol) in pyridine (7 mL) and TEA (0.7 mL), $H_2S$ gas was bubbled until saturation was reached. The solution was then stirred at room temperature overnight. It was concentrated in vacuo. The residue was dissolved in acetone (8 mL). Iodomethane (0.100 mL, 1.61 mmol) was added. It was heated at reflux for 3 h, then concentrated in vacuo. The residue was dissolved in MeOH (12 mL). To a third of the solution (4 mL, 0.063 mmol), a pre-mixed dimethylamine (2M in THF, 0.22 mL, 0.44 mmol) and HOAc (0.040 mL, 0.70 mmol) were added. The mixture was heated to reflux for 1 h, then was stirred at room temperature overnight. After being concentrated in vacuo, the residue was purified by HPLC to give a white powder (15 mg). MS 462.3 and 464.3 (M+H, Cl pattern).

Example 135

1-[4-(pyrrolidinylimino)phenyl]-3-(4-chlorophenylaminocarbonylamino)-3,4-dihydroquinolin-2-one

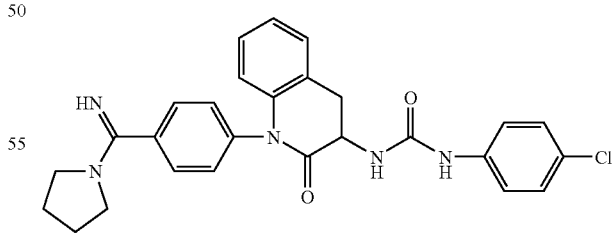

To the thioimidate solution in MeOH (4 mL, 0.063 mmol) from Example 134, a pre-mixed pyrrolidine (0.037 mL, 0.44 mmol) and HOAc (0.040 mL, 0.70 mmol) were added. The mixture was heated to reflux for 1 h, then was stirred at room temperature overnight. After being concentrated in vacuo, the residue was purified by HPLC to give a white powder (15 mg). MS 488.3 and 490.3 (M+H, Cl pattern).

Example 136

1-[4-(1-methyl-4,5-dihyrdo-1H-imidazol-2-yl)phenyl]-3-(4-chlorophenylaminocarbonylamino)-3,4-dihydroquinolin-2-one

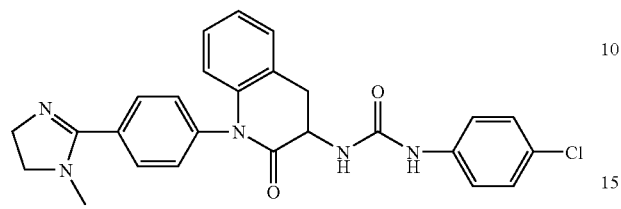

To the thioimidate solution in MeOH (4 mL, 0.063 mmol) from Example 134, a pre-mixed N-methylethylenediamine (0.039 mL, 0.44 mmol) and HOAc (0.080 mL, 1.4 mmol) were added. The mixture was heated to reflux for 1 h, then was stirred at room temperature overnight. After being concentrated in vacuo, the residue was purified by HPLC to give a white powder (15 mg). MS 474.3 and 476.3 (M+H, Cl pattern).

Example 137

Preparation of (2S) N-[4-(2-pyridon-1-yl)phenyl]-2-phenyl-2-(4-chlorophenylaminocarbonylamino)-acetamide

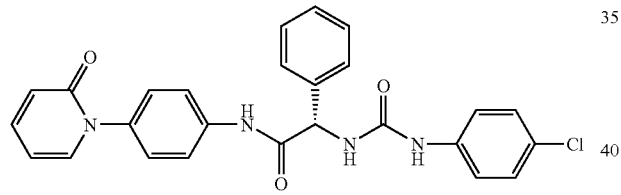

A. Preparation of 4-(2-pyridon-1-yl)phenylamine

A mixture of 4-iodoaniline (1.00 g, 4.57 mmol), 2-hydroxypyridine (0.477 g, 5.02 mmol), 8-hydroxyquinoline (0.110 g, 0.759 mmol) and $K_2CO_3$ (0.945 g, 6.85 mmol) in DMSO (10 mL) was degassed with Ar before being charged with CuI (0.145 g, 0.763 mmol). The mixture in a sealed tube was then heated at 130° C. overnight. Water and nBuOH were added. The mixture was filtered. The nBuOH phase was separated, and concentrated in vacuo to give a solid (0.666 g), which was pure enough for subsequent reactions. MS 187.3 (M+H).

B. Preparation of (2S) N-[4-(2-pyridon-1-yl)phenyl]-2-phenyl-2-(4-chlorophenylaminocarbonylamino)-acetamide To a solution of (L) N-BOC-phenylglycine (126 mg, 0.500 mmol) and 4-(2-pyridon-1-yl)phenylamine (102 mg, 0.548 mmol) in DMF (3 mL), EDC (144 mg, 0.750 mmol) was added. The mixture was stirred at room temperature for 1 h. Water (10 mL) was added to induce precipitation. The precipitate was collected by filtration to give the amide (61 mg). MS 420.2 (M+H).

The amide (61 mg, 0.15 mmol) was dissolved in TFA (4 mL). After being stirred at room temperature for 1 h, TFA was removed in vacuo. The residue was partitioned between EtOAc and aq. 5% $NaHCO_3$. The EtOAc phase was separated, dried over $Na_2SO_4$, concentrated in vacuo to give a solid (35 mg).

To a solution of the solid (17 mg, 0.053 mmol) in $CH_3CN$ (2 mL), 4-chlorophenylisocyanate (20 mg, 0.13 mmol) was added. After being stirred at room temperature for 30 min, the mixture was purified by HPLC to give the titled compound (10 mg). MS 473.2 and 475.2 (M+H, Cl pattern)

Example 138

Preparation of (2R) N-[4-(2-pyridon-1-yl)phenyl]-2-phenyl-2-(4-chlorophenylaminocarbonylamino)-acetamide

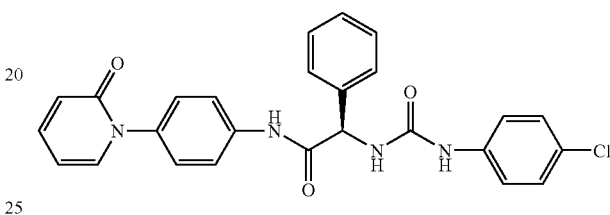

The titled compound was prepared analogously to the procedure described in Example 137, using (D) N-BOC-phenylglycine in the place of (L) N-BOC-phenylglycine. MS 473.2 and 475.2 (M+H, Cl pattern).

Example 139

Preparation of (2S) N-[4-(2-pyridon-1-yl)phenyl]-2-phenyl-2-(2-chlorothiophen-5-ylaminocarbonylamino)-acetamide

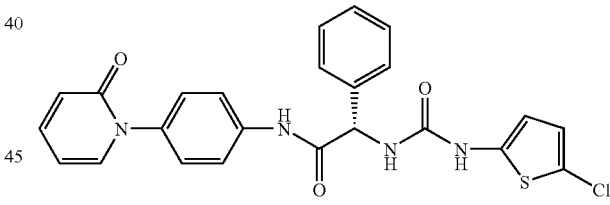

A. Preparation of 2-chlorothiophene-5-isocyanate

To a suspension of 5-chloro-2-thiophenecarboxylic acid (650 mg, 4.00 mmol) in $CH_2Cl_2$ (8 mL) containing 3 drops of DMF, oxalyl chloride (0.700 mL, 8.00 mmol) was added. The suspension became clear after 10 min of stirring. After being stirred for 1 h, the mixture was concentrated in vacuo. The residue was dissolved in toluene (8 mL). $NaN_3$ (540 mg, 8.31 mmol) was added. The mixture was stirred at room temperature overnight. It was then filtered. The filtrate was heated at 100 C for 3 h. The solution was filtered, and used in the next reaction.

B. Preparation of (2S) N-[4-(2-pyridon-1-yl)phenyl]-2-phenyl-2-(2-chlorothiophen-5-ylaminocarbonylamino)-acetamide The titled compound was prepared analogously to the procedure described in step B of Example 137, using 2-chlorothiophene-5-isocyanate in the place of 4-chlorophenylisocyanate. MS 479.2 and 481.2 (M+H, Cl pattern).

Example 140

Preparation of (2R) N-[4-(2-pyridon-1-yl)-2-fluorophenyl]-2-phenyl-2-(4-chlorophenylaminocarbonylamino)-acetamide

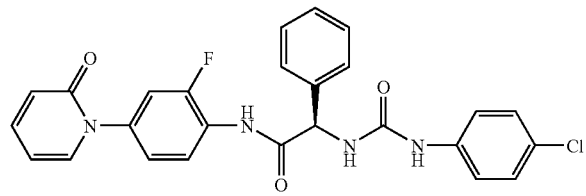

A. Preparation of 4-(2-pyridon-1-yl)-2-fluorophenylamine

A mixture of 2-fluoro-4-iodoaniline (1.08 g, 4.56 mmol), 2-hydroxypyridine (0.477 g, 5.02 mmol), 8-hydroxyquinoline (0.110 g, 0.759 mmol) and $K_2CO_3$ (0.945 g, 6.85 mmol) in DMSO (10 mL) was degassed with Ar before being charged with CuI (0.145 g, 0.763 mmol). The mixture in a sealed tube was then heated at 130° C. overnight. Water and nBuOH were added. The mixture was filtered. The nBuOH phase was separated, and concentrated in vacuo to give a solid (0.902 g), which was pure enough for subsequent reactions. MS 205.2 (M+H).

B. Preparation of (2R) N-[4-(2-pyridon-1-yl)-2-fluorophenyl]-2-phenyl-2-(4-chlorophenylaminocarbonylamino)-acetamide The titled compound was prepared analogously to the procedure described in Example 138, using 4-(2-pyridon-1-yl)-2-fluorophenylamine in the place of 4-(2-pyridon-1-yl)phenylamine. MS 488.7 and 490.7 (M–H, Cl pattern).

Example 141

Preparation of (2R) 4-(2-piperidinon-1-yl)piperidin-1-yl-2-phenyl-2-(4-chlorophenylaminocarbonylamino)-acetamide

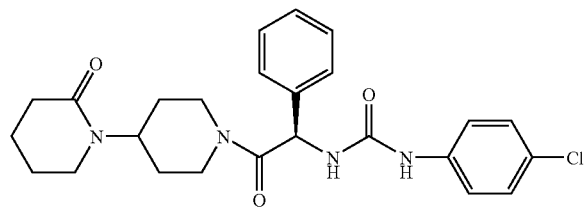

A. Preparation of 4-(2-pyridon-1-yl)pyridine

A mixture of 4-bromopyridine hydrochloride (778 mg, 4.00 mmol), 2-hydroxypyridine (388 mg, 4.08 mmol), $K_3PO_4$ (1.70 g, 8.00 mmol) and 1,2-trans-diaminocyclohexane (200 uL, 1.60 mmol) in dioxane (10 mL).was degassed with Ar before being charged with CuI (152 mg, 0.80 mmol). The mixture in a sealed tube was heated at 110° C. overnight. The mixture was then applied to a silica gel column, which was eluted with $CH_2Cl_2$/MeOH (95/5) to give the desired product (205 mg). MS 173.5 (M+H).

B. Preparation of 4-(2-piperidinon-1-yl)piperidine

A solution of 4-(2-pyridon-1-yl)pyridine (186 mg, 1.08 mmol) and $PtO_2$ (100 mg) in HOAc (8 mL) was hydrogenated under 40 psi on a Parr shaker overnight. The mixture was filtered through Celite. The filtrate was concentrated in vacuo. To the residue, aqueous 1N HCl (3 mL) was added. The solution was then concentrated in vacuo to give the desired product as hydrochloride salt (231 mg). MS 183.5 (M+H)

C. Preparation of (2R) 4-(2-piperidinon-1-yl)piperidin-1-yl-2-phenyl-2-(4-chlorophenylaminocarbonylamino)-acetamide To a solution of(D) N-BOC phenylglycine (32 mg, 0.13 mmol), 4-(2-piperidinon-1-yl)piperidine hydrochloride (22 mg, 0.10 mmol) and triethylamine (0.070 mL, 0.50 mmol) in DMF (1.0 mL), BOP (66 mg, 0.15 mmol) was added. The mixture was stirred at room temperature for 20 min. Water and EtOAc were added. The EtOAc phase was separated, washed with 5% $NaHCO_3$, dried over $Na_2SO_4$, and concentrated in vacuo to give the amide (51 mg). MS 416.5 (M+H).

The amide (51 mg, 0.12 mmol) was dissolved in TFA (4.0 mL). After being stirred at room temperature for 15 min, the TFA was removed in vacuo. The residue was dissolved in $CH_3CN$ (2.0 mL). To the solution, 4-chlorophenylisocyanate (27 mg, 0.18 mmol) and triethylamine (0.050 mL, 0.36 mmol) were added. After being stirred for 30 min, the mixture was purified by HPLC to give the titled compound (15 mg). MS 469.2 and 471.3 (M+H, Cl pattern).

Example 142

Preparation of (2R) 4-(3-morpholinon-4-yl)piperidin-1-yl-2-phenyl-2-(4-chlorophenylaminocarbonylamino)-acetamide

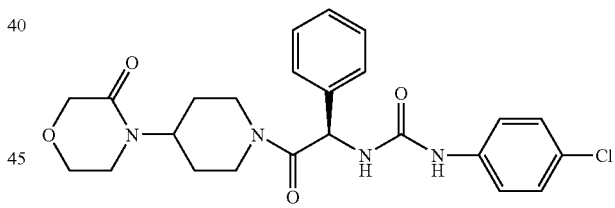

A. Preparation of 4-(3-morpholinon-4-yl)piperidine

A mixture of 4-bromopyridine hydrochloride (778 mg, 4.00 mmol), 3-morpholinone (404 mg, 4.00 mmol), $K_3PO_4$ (1.70 g, 8.00 mmol) and 1,2-trans-diaminocyclohexane (200 uL, 1.60 mmol) in dioxane (10 mL) was degassed with Ar before being charged with CuI (152 mg, 0.80 mmol). The mixture in a sealed tube was heated at 110° C. overnight. The mixture was applied to a silica gel column, which was then eluted with 2-5% MeOH in $CH_2Cl_2$ to give the desired product (85 mg). MS 179.5 (M+H).

A solution of the compound (85 mg, 0.48 mmol) and $PtO_2$ (50 mg) in HOAc (8 mL) was hydrogenated under 40 psi on a Parr shaker overnight. The mixture was filtered through Celite. The filtrate was concentrated in vacuo. To the residue, aqueous 1N HCl (3 mL) was added. The solution was then concentrated in vacuo to give the desired product as hydrochloride salt (91 mg). MS 185.2 (M+H).

101

B. Preparation of (2R) 4-(3-morpholinon-4-yl)piperidin-1-yl-2-phenyl-2-(4-chlorophenylaminocarbonylamino)-acetamide The titled compound was prepared analogously to the procedure described in Example 141, using 4-(3-morpholinon-4-yl)piperidine hydrochloride in the place of 4-(2-piperidinon-1-yl)piperidine hydrochloride. MS 471.0 and 473.0 (M+H, Cl pattern).

Example 143

Preparation of (2R) 4-(2-pyridon-1-yl)piperidin-1-yl-2-phenyl-2-(4-chlorophenylaminocarbonylamino)-acetamide

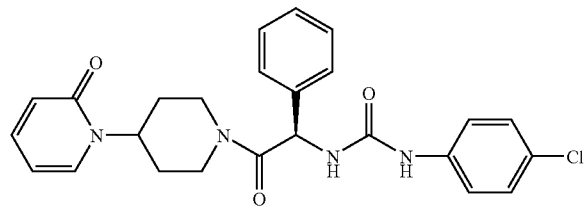

A. Preparation of 4-(2-pyridon-1-yl)piperidine

To a solution of t-butyl 4-hydroxypiperidine carboxylate (1.02 g, 5.07 mmol) in $CH_2Cl_2$ (10 mL) and pyridine (4 mL) at room temperature, methanesulfonyl chloride (1.00 mL, 12.9 mmol) was added. The mixture was stirred at room temperature overnight. Water and $CH_2Cl_2$ were added. The organic phase was separated, washed with 5% $NaHCO_3$, 1N HCl and brine, then it was dried over $Na_2SO_4$, concentrated in vacuo to give a white solid (1.35 g).

A mixture of the white solid (550 mg, 1.97 mmol), 2-hydroxypyridine (207 mg, 2.18 mmol) and $Cs_2CO_3$ (1.37 g, 4.20 mmol) in DMF (10 mL) was heated at 100° C. for 2 h. After being cooled to room temperature, the mixture was filtered. The filtrate was then purified by RP-HPLC to give the desired compound as a minor product (62 mg). MS 223.3 (M-tBu+H) and 279.5 (M+H).

The compound (62 mg) was dissolved in trifluoroacetic acid (6 mL). After being stirred for 30 min, the trifluoroacetic acid was removed in vacuo. The residue was dissolved in $H_2O$ (5 mL), 6N HCl (0.5 mL) was added. The aqueous solution was then lyophilized to give the titled compound as hydrochloride salt (47 mg).

B. Preparation of (2R) 4-(2-pyridon-1-yl)piperidin-1-yl-2-phenyl-2-(4-chlorophenylaminocarbonylamino)-acetamide The titled compound was prepared analogously to the procedure described in Example 141, using 4-(2-pyridon-1-yl)piperidine hydrochloride in the place of 4-(2-piperidinon-1-yl)piperidine hydrochloride. MS 465.0 and 467.0 (M+H, Cl pattern).

102

Example 144

Preparation of 4-(3-morpholinon-4-yl)piperidin-1-yl-2-(2-fluorophenyl)-2-(4-chlorophenylaminocarbonylamino)-acetamide

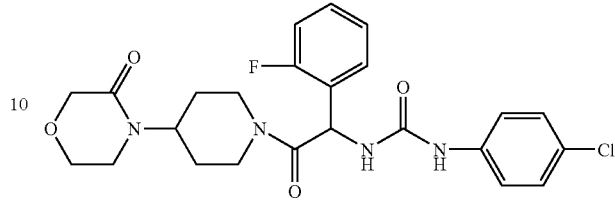

To a solution of 2-(2-fluorophenyl)-2-(4-chlorophenylaminocarbonylamino)-acetic acid (50 mg, 0.15 mmol), 4-(3-morpholinon-4-yl)piperidine hydrochloride (45 mg, 0.20 mmol) and triethylamine (0.086 mL, 0.62 mmol) in DMF (1.0 mL, containing 0.10 mL of $H_2O$ to solubilize the piperidine hydrochloride), BOP (100 mg, 0.23 mmol) was added. After being stirred at room temperature for 30 min, the mixture was purified by HPLC to give the titled compound (20 mg). MS 489.4 and 491.4 (M+H, Cl pattern).

Example 145

Preparation of 4-(3-morpholinon-4-yl)piperidin-1-yl-2-(2-chlorophenyl)-2-(4-chlorophenylaminocarbonylamino)-acetamide

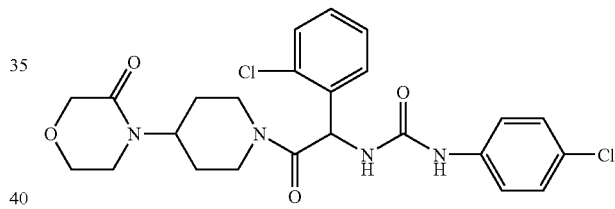

The titled compound was prepared analogously to the procedure described in Example 144, using 2-(2-chlorophenyl)-2-(4-chlorophenylaminocarbonylamino)-acetic acid in the place of 2-(2-fluorophenyl)-2-(4-chlorophenylaminocarbonylamino)-acetic acid. MS 505.4 and 507.4 (M+H, 2Cl pattern).

Example 146

Preparation of 4-(3-morpholinon-4-yl)piperidin-1-yl-2-(2-bromophenyl)-2-(4-chlorophenylaminocarbonylamino)-acetamide

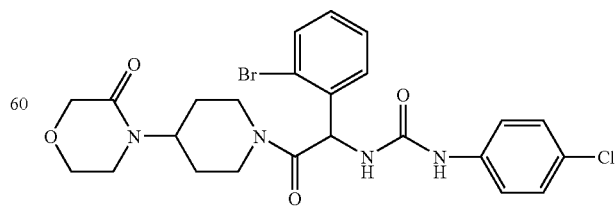

The titled compound was prepared analogously to the procedure described in Example 144, using 2-(2-bromophenyl)-

Example 147

Preparation of 4-(3-morpholinon-4-yl)piperidin-1-yl-2-(2-methylphenyl)-2-(4-chlorophenylaminocarbonylamino)-acetamide

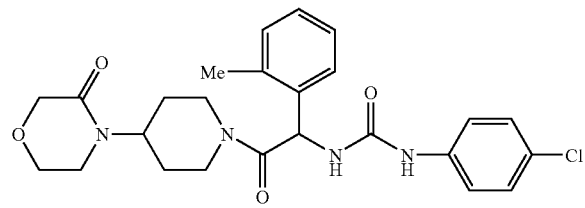

The titled compound was prepared analogously to the procedure described in Example 144, using 2-(2-methylphenyl)-2-(4-chlorophenylaminocarbonylamino)-acetic acid in the place of 2-(2-fluorophenyl)-2-(4-chlorophenylaminocarbonylamino)-acetic acid. MS 485.4 and 487.4 (M+H, Cl pattern).

Example 148

Preparation of 4-(3-morpholinon-4-yl)piperidin-1-yl-2-(2-methoxyphenyl)-2-(4-chlorophenylaminocarbonylamino)-acetamide

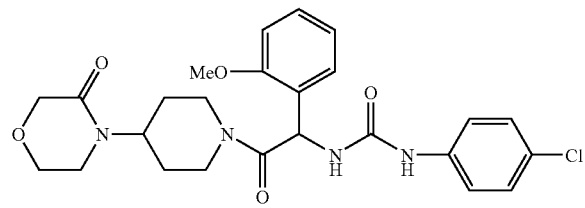

The titled compound was prepared analogously to the procedure described in Example 144, using 2-(2-methoxyphenyl)-2-(4-chlorophenylaminocarbonylamino)-acetic acid in the place of 2-(2-fluorophenyl)-2-(4-chlorophenylaminocarbonylamino)-acetic acid. MS 501.4 and 503.4 (M+H, Cl pattern).

Example 149

Preparation of 4-(2-piperidinon-1-yl)piperidin-1-yl-2-(2-fluorophenyl)-2-(4-chlorophenylaminocarbonylamino)-acetamide

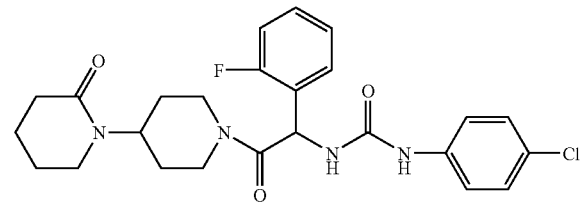

To a solution of 2-(2-fluorophenyl)-2-(4-chlorophenylaminocarbonylamino)-acetic acid (45 mg, 0.14 mmol), 4-(2-piperidinon-1-yl)piperidine hydrochloride (40 mg, 0.18 mmol) and triethylamine (0.085 mL, 0.61 mmol) in DMF (1.0 mL, containing 0.050 mL of $H_2O$ to solubilize the piperidine hydrochloride), BOP (100 mg, 0.23 mmol) was added. After being stirred at room temperature for 30 min, the mixture was purified by HPLC to give the titled compound (20 mg). MS 487.3 and 489.3 (M+H, Cl pattern).

Example 150

Preparation of 4-(2-piperidinon-1-yl)piperidin-1-yl-2-(2-methoxyphenyl)-2-(4-chlorophenylaminocarbonylamino)-acetamide

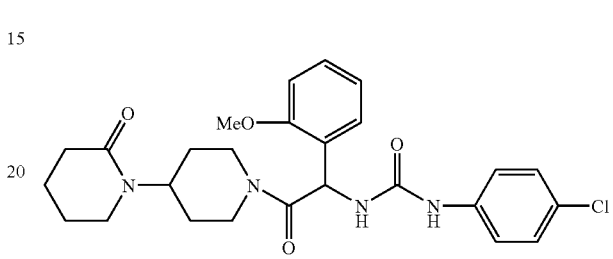

The titled compound was prepared analogously to the procedure described in Example 149, using 2-(2-methoxyphenyl)-2-(4-chlorophenylaminocarbonylamino)-acetic acid in the place of 2-(2-fluorophenyl)-2-(4-chlorophenylaminocarbonylamino)-acetic acid. MS 499.2 and 501.2 (M+H, Cl pattern).

Example 151

Preparation of 4-(4-methyl-2-piperazinon-1-yl)piperidin-1-yl-2-(2-methoxyphenyl)-2-(4-chlorophenylaminocarbonylamino)-acetamide

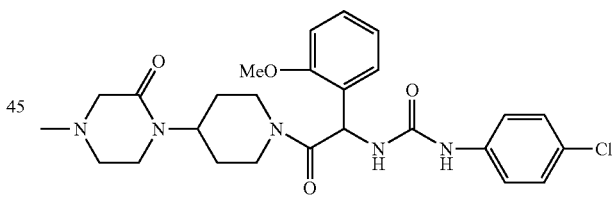

A. Preparation of 4-(4-methyl-2-piperazinon-1-yl)piperidine

To a solution of 2-piperazinone (200 mg, 2.00 mmol) and HCHO (37% aq., 0.200 mL, 2.69 mmol) in MeOH (6 mL) at room temperature, $NaBH_3CN$ (162 mg, 2.57 mmol) was added. After being stirred at room temperature overnight, the solution was concentrated in vacuo. The residue was partitioned between 5% aq. $NaHCO_3$ and nBuOH. The nBuOH phase was separated, concentrated in vacuo to give the 4-methyl-2-piperazinone as a semi-solid (118 mg). MS 115.5 (M+H).

A mixture of 4-iodopyridine (218 mg, 1.06 mmol), 4-methyl-2-piperazinone (106 mg, 0.929 mmol), $K_3PO_4$ (425 mg, 2.00 mmol) and 1,2-trans-diaminocyclohexane (0.050 mL, 0.41 mmol) in anhydrous dioxane (3.0 mL) was degassed with Ar before being charged with CuI (40 mg, 0.21 mmol).

The mixture in a sealed tube was heated at 110° C. overnight. The mixture was purified by a prep-TLC using MeOH/CH₂Cl₂ (10/90) as solvents to give 1-(pyridin-4-yl)-4-methyl-2-piperazinone (42 mg). MS 192.5 (M+H).

A mixture of 1-(pyridin-4-yl)-4-methyl-2-piperazinone (12 mg, 0.063 mmol) and PtO₂ (49 mg) in HOAc (6.0 mL) was hydrogenated on a Parr shaker under 40 psi for 3 days. The mixture was filtered through celite. The filtrate was concentrated in vacuo. The residue was dissolved in 1N HCl (5.0 mL). The solution was then concentrated in vacuo to give the titled compound as hydrochloride salt (12 mg). MS 198.5 (M+H).

B. Preparation of 4-(4-methyl-2-piperazinon-1-yl)piperidin-1-yl-2-(2-methoxyphenyl)-2-(4-chlorophenylaminocarbonylamino)-acetamide The titled compound was prepared analogously to the procedure described in Example 150, using 4-(4-methyl-2-piperazinon-1-yl)piperidine in the place of 4-(2-piperidinon-1-yl)piperidine. MS 514.2 and 516.3 (M+H, Cl pattern).

Example 152

Preparation of 4-(homopiperidin-4-yl)piperazin-1-yl-2-(2-methoxyphenyl)-2-(4-chlorophenylaminocarbonylamino)-acetamide

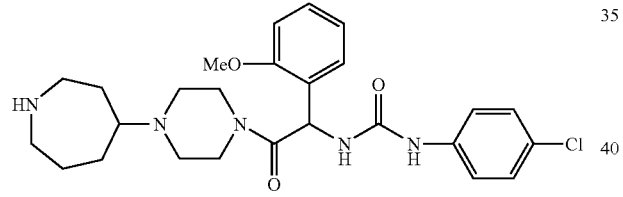

To a solution of 2-(2-methoxyphenyl)-2-(4-chlorophenylaminocarbonylamino)-acetic acid (134 mg, 0.400 mmol), piperazine (190 mg, 2.21 mmol) and triethylamine (0.200 mL, 1.44 mmol) in DMF (6.0 mL), BOP (260 mg, 0.587 mmol) was added. After being stirred at room temperature for 30 min, EtOAc and 5% aq. NaHCO₃ were added. The organic phase was separated, and concentrated in vacuo. The residue was purified by HPLC to give the amide as a white powder (156 mg).

To a solution of the amide (156 mg, 0.39 mmol) and N-BOC-hexahydro-1H-azepin-4-one (101 mg, 0.47 mmol) in MeOH (2.0 mL), NaBH₃CN (45 mg, 0.71 mmol) was added. The solution was stirred at room temperature overnight. More azepinone (65 mg, 0.31 mmol) and NaBH₃CN (45 mg, 0.71 mmol) were added. After being stirred for another day, water and EtOAc were added. The organic phase was separated, and concentrated in vacuo. The residue was dissolved in TFA (8.0 mL). After being stirred for 1 h, TFA was removed in vacuo. The residue was purified by HPLC to give the titled compound (158 mg). MS 500.3 and 502.2 (M+H, Cl pattern).

Example 153

Preparation of 4-(1-methylhomopiperidin-4-yl)piperazin-1-yl-2-(2-methoxyphenyl)-2-(4-chlorophenylaminocarbonylamino)-acetamide

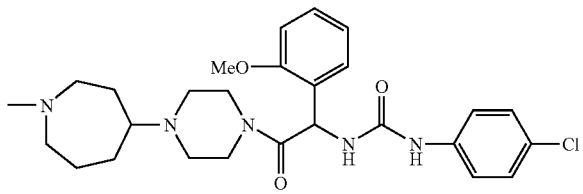

To a solution of 4-(homopiperidin-4-yl)piperazin-1-yl-2-(2-methoxyphenyl)-2-(4-chlorophenylaminocarbonylamino)-acetamide (150 mg, 0.30 mmol) and HCHO (37% aq., 0.067 mL, 0.90 mmol) in MeOH (5.0 mL), NaBH₃CN (57 mg, 0.90 mmol) was added. After being stirred at room temperature overnight, the mixture was purified by HPLC to give the titled compound (40 mg). MS 514.5 qnd 516.5 (M+H, Cl pattern).

Example 154

Preparation of (2R) 4-(4-methylhomopiperazin-1-yl)piperidin-1-yl-2-phenyl-2-(4-chlorophenylaminocarbonylamino)-acetamide

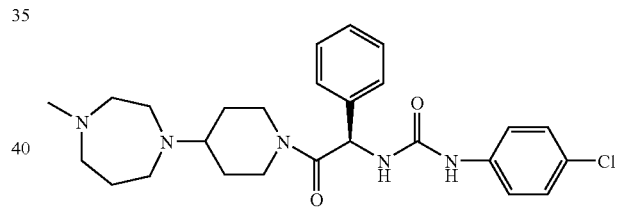

To a solution of (D) N-BOC phenylglycine (100 mg, 0.400 mmol), triethylamine (0.200 mL, 1.44 mmol) and 4-piperidone hydrate hydrochloride (67 mg, 0.436 mmol) in DMF (3.0 mL), BOP (230 mg, 0.520 mmol) was added. After being stirred at room temperature overnight, water and EtOAc were added. The organic phase was separated, washed with 1N HCl, then with 5% NaHCO₃ and brine. The solution was dried over Na₂SO₄, and concentrated in vacuo to give the amide (130 mg). MS 233.5 (M–tBu+H).

To a solution of the amide (130 mg, 0.39 mmol) and 1-methylhomopiperazine (0.045 mL, 0.36 mmol) in MeOH (4.0 mL), NaBH₃CN (33 mg, 0.52 mmol) was added. After being stirred at room temperature overnight, the mixture was purified by HPLC to give a white powder (90 mg). MS 431.5 (M+H).

The white powder (90 mg, 0.21 mmol) was dissolved in TFA (3.0 mL). After being stirred at room temperature for 30 min, TFA was removed in vacuo. The residue was dissolved in CH₃CN (4.0 mL), and triethylamine (0.200 mL, 1.44 mmol) was added. To the solution, 4-chlorophenylisocyanate (53 mg, 0.35 mmol) was added. After being stirred for 1 h, the mixture was purified by HPLC to give the titled compound (20 mg). MS 484.2 and 486.2 (M+H, Cl pattern).

Example 155

Preparation of (2R) 4-(1-methylpiperidin-4-yl)piperidin-1-yl-2-phenyl-2-(4-chlorophenylaminocarbonylamino)-acetamide

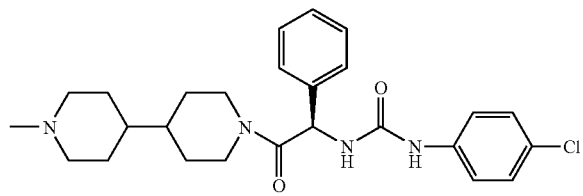

To a solution of (D) N-BOC phenylglycine (100 mg, 0.40 mmol), 4,4'-bipiperidine dihydrochloride (482 mg, 2.00 mmol) and triethylamine (0.70 mL, 5.0 mmol) in DMF (6.0 mL) and H$_2$O (3.0 mL), BOP (355 mg, 0.80 mmol) was added. After being stirred at room temperature for 1 h, the mixture was purified by HPLC to give the amide (160 mg). MS 402.5 (M+H).

To a solution of the amide (160 mg, 0.40 mmol) and HCHO (37% aq, 0.178 mL, 2.39 mmol) in MeOH (6.0 mL), NaBH$_3$CN (151 mg, 2.39 mmol) was added. After being stirred at room temperature overnight, the mixture was concentrated in vacuo. The residue was dissolved in TFA (6.0 mL). After being stirred for 2 h, TFA removed in vacuo. The residue was dissolved in CH$_3$CN (6 mL). To the solution, 4-chlorophenylisocyanate (90 mg, 0.58 mmol) was added. After 30 min of stirring, the mixture was purified by HPLC to give the titled compound (32 mg). MS 469.5 and 471.5 (M+H, Cl pattern).

Example 156

Preparation of (2R) 4-(1-methylpiperidin-4-yl)homopiperazin-1-yl-2-phenyl-2-(4-chlorophenylaminocarbonylamino)-acetamide

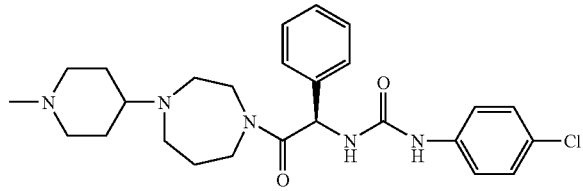

To a solution of (D) N-BOC phenylglycine (100 mg, 0.400 mmol) and triethylamine (0.200 mL, 1.44 mmol) in DMF (3.0 mL), BOP (230 mg, 0.520 mmol) was added. After 30 min of stirring, the solution was added to a solution of homopiperazine (200 mg, 2.00 mmol) in DMF (2.0 mL). After being stirred at room temperature for 1 h, the mixture was concentrated in vacuo. The residue was purified by HPLC to give the amide (91 mg). MS 334.5 (M+H).

To a solution of the amide (91 mg, 0.27 mmol) and 1-methyl-4-piperidone (0.040 mL, 0.33 mmol) in MeOH (4.0 mL), NaBH$_3$CN (26 mg, 0.41 mmol) was added. After being stirred at room temperature overnight, more 1-methyl-4-piperidone (0.040 mL, 0.33 mmol) and NaBH$_3$CN (26 mg, 0.41 mmol) were added. The mixture was stirred for another day, then it was concentrated in vacuo. The residue was dissolved in TFA (6.0 mL). After being stirred for 30 min, TFA was removed in vacuo. The residue was dissolved in CH$_3$CN (5.0 mL), and triethylamine (0.400 mL, 2.88 mmol) was added. To the solution, 4-chlorophenylisocyanate (62 mg, 0.40 mmol) was added. The mixture was stirred for 30 min before it was purified by HPLC to give the titled compound (25 mg).

Example 157

This example illustrates methods for evaluating the compounds of the invention, along with results obtained for such assays. The in vitro and in vivo Factor Xa isoform activities of the inventive compounds can be determined by various procedures known in the art, such as a test for their ability to inhibit the activity of the Factor Xa isoform. The potent affinities for Factor Xa isoform exhibited by the inventive compounds can be measured by an IC$_{50}$ value (in nM). The IC$_{50}$ value is the concentration (in nM) of the compound required to provide 50% inhibition of Factor Xa isoform. The smaller the IC$_{50}$ value, the more active (potent) is a compound for inhibiting Factor Xa isoform.

An in vitro assay for detecting and measuring inhibition activity against Factor Xa is as follows:

IC$_{50}$ and Ki Determinations:

Substrate:
The substrate S-2765 (Z-D-Arg-Gly-Arg-pNA.HCl) was obtained from Diapharma (West Chester, Ohio).

Enzyme:
The human plasma protein factor Xa was purchased from Haematologic Technologies (Essex Junction, Vt.).

Methods
IC$_{50}$ Determinations
All assays, which are performed in 96-well microtiter plates, measure proteolytic activity of the enzyme (factor Xa) by following cleavage of paranitroanilide substrate. The assay buffer used for proteolytic assays was Tris buffered saline (20 mM Tris, 150 mM NaCl, 5 mM CaCl$_2$, 0.1% Bovine serum albumin (BSA), 5% Dimethly Sulfoxide (DMSO) pH 7.4). In a 96-well microtiter plate, inhibitor was serially diluted to give a range of concentrations from 0.01 nM to 10 µM (final). Duplicate sets of wells were assayed and control wells without inhibitor were included. Enzyme was added to each well, (fXa concentration=1nM), the plate was shaken for 5 seconds and then incubated for 5 minutes at room temperature. S2765 was added (100 µM final) and the plate was shaken for 5 seconds (final liquid volume in each well was 200 µl). The degree of substrate hydrolysis was measured at 405 nm on a Thermomax plate reader (Molecular Devices, Sunnyvale, Calif.) for 2 minutes. The initial velocities (mOD/min), for each range of inhibitor concentrations, were fitted to a four parameter equation using Softmax data analysis software. The parameter C, derived from the resulting curve-fit, corresponded to the concentration for half maximal inhibition (IC$_{50}$).

K$_i$ Determination
The assay buffer for this series of assays was Hepes buffered saline (20 mM Hepes, 150 mM NaCl, 5 mM CaCl$_2$, 0.1% PEG-8000, pH 7.4). In a 96-well microtiter plate, inhibitor was serially diluted in a duplicate set of wells to give a range of final concentrations from 5 pM to 3 µM final. Controls without inhibitor (8 wells) were included. The enzyme, fXa (1 nM final) was added to the wells. The substrate S-2765 (200 µM final) was added and the degree of substrate hydrolysis was measured at 405 nm on a Thermomax plate reader for 5 minutes, using Softmax software. Initial velocities (mOD/ min) were analyzed by non-linear least squares regression in the Plate Ki software (BioKin Ltd, Pullman, Wash.) (Literature reference: Kusmic P, Sideris S, Cregar L M, Elrod K C, Rice K D, Janc J. High-throughput screening of enzyme inhibitors: Automatic determination of tight-binding inhibition constants. *Anal. Biochemistry* 2000, 281:62-67). The model used for fitting the inhibitor dose-response curves was the Morrison equation. An apparent $K_i(Ki^*)$ was determined. The overall $K_i$ was calculated using the following equation:

$$Ki = \frac{Ki*}{1 + \frac{[S]}{Km}}$$

where [S] is substrate concentration (200 µM) and $K_m$, the Michaelis constant for S2765.

The hERG (Human ether-a-go-go Related Gene Protein) Membrane Binding Assay

Human embryonic kidney (HEK293) cells stably transfected with hERG cDNA were used for preparation of membranes (Literature reference: Zhou, Z., Gong, Q., Ye, B., Fan, Z., Makielski, C., Robertson, G., January, C T., Properties of hERG stably expressed in HEK293 cells studied at physiological temperature. *Biophys. J*, 1998, 74:230-241). The assay buffer was comprised of 50 mM Tris, 10 mM KCl, 1 mM $MgCl_2$, pH 7.4. Competition assays for hERG binding were performed, in a 96 well plate, with 50 µL $^3$H-dofetilide, at a concentration of 3.5 nM (final concentration of 0.01% ethanol). Test compound was added at final concentrations of 100 µM, 33.33 µM, 11.11 µM, 3.70 µM, 1.23 µM, 0.41 µM, 0.14 µM, 0.046 µM, 0.015 µM, and 0.005 µM (1.0% DMSO). Each compound was run in duplicate on each of two plates. Total binding was determined by addition of 50 µL of assay buffer in place of compound. Non-specific binding was determined by addition of 50 µL of 50 µM terfenadine in place of test compound. All assays were initiated by addition of 150 µL of membrane homogenates (15 ug protein/well as final concentration) to the wells (total volume=250 µL per well), and the plates were incubated at room temperature for 80 minutes on a shaking platform. All assays were terminated by vacuum filtration on to glass fiber filters, followed by two washes with cold assay buffer. The filter plates were dried at 55° C. for 90 minutes, after which, Microscint 0 (50 µL) was added to each well of the dried filter plate. The plates were counted on a Packard Topcount (Perkin Elmer, Boston, Mass.) using a one minute protocol. Scintillation reading (counts per minute, CPM) data generated by the Packard TopCount was used to calculate the percent inhibition of $^3$H-dofetilide binding, for each compound at each concentration, using the total binding control value corrected for non-specific binding. The $IC_{50}$ value was calculated from the percent inhibition curve generated using Excel XL Fit software (Microsoft). The equilibrium dissociation constant ($K_i$) was calculated using the equation of Cheng and Prusoff (see "Relationship between the inhibition constant ($K_i$) and the concentration of inhibitor which causes 50 per cent inhibition ($I_{50}$) of an enzymatic reaction," *Biochem Pharmacol.*, 1973, 22(23):3099-108.

$$K_i = IC_{50}/[1+([L]/K_D)].$$

A compound can be run through this assay and its corresponding $IC_{50}$ inhibition value can be calculated from the assay data.

The following examples exhibited Factor Xa $IC_{50}$ values less than or equal to 100 nM: 1, 2, 5-8, 10-13, 16, 19-47, 51, 52, 55-59, 74-77, 79-81, 83-89, 91-133, 136-145, 148-150, 152, 153 and 155.

The following examples exhibited Factor Xa $IC_{50}$ values greater than 100 nM and less than 500 nM: 3, 9, 15, 17, 18, 48-50, 54, 61, 62, 70, 72, 73, 78, 134, 146, 147 and 154.

The following examples exhibited Factor Xa $IC_{50}$ values greater than or equal to 500 nM: 4, 14, 53, 60, 63-69, 71, 82, 90, 103, 110, 135, 151 and 156.

The present invention provides a number of embodiments. It is apparent that the examples may be altered to provide other embodiments of this invention. Therefore, it will be appreciated that the scope of this invention is to be defined by the appended claims rather than by the specific embodiments, which have been represented by way of example.

What is claimed is:

1. A compound having the formula:

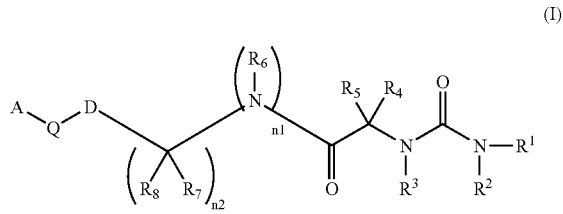

(I)

wherein:

$R^1$ is hydrogen;

$R^2$ is a member selected from the group consisting of: aryl, and heteroaryl, optionally substituted with from 1 to 3 $R^{2a}$ substituents;

$R^3$ is a member selected from the group consisting of: hydrogen and —$C_{0-6}$alky-aryl;

each $R^4$ and $R^5$ is a member independently selected from the group consisting of: hydrogen,—$C_{1-6}$alkyl, —$C_{2-6}$alkenyl, —$C_{2-6}$alkynyl,—$C_{0-6}$alkyl-heteroaryl, —$C_{0-6}$alkyl-heterocyclyl, —$C_{0-6}$alkyl-CO—$OR^{4a}$, —$C_{0-6}$alkyl-C(O)—N($R^{4a}R^{4b}$),—$C_{0-6}$alkyl-C(O)$R^{4a}$, and —$C_{0-6}$alkyl-aryl; or $R^4$ and $R^5$ can be taken together with the carbon atom to which they are attached to form a 3 to 8 membered cycloalkyl group; and wherein 1 to 3 carbon or nitrogen atoms of aryl, heteroaryl and heterocyclyl are substituted with 1 to 3 $R^{4d}$ substituents;

D is a member selected from the group consisting of: aryl, and heteromonocyclyl; optionally substituted with 1 to 3 $R^9$ substituents, wherein heterocyclyl comprises from 5 to 10 ring atoms, 1-4 of which are selected from the group consisting of N, O and S;

Q is selected from the group consisting of: a direct bond, —C($R^{10a}R^{10b}$)—, —C(O)—, —C(S)—, —C(=$NR^{10a}$)—, —O—, —S—, —N($R^{10a}$)—, —N($R^{10a}$)$CH_2$—, —$CH_2$N($R^{10a}$)—, —C(O)N ($R^{10a}$)—, —N($R^{10a}$)C(O)—, —SO—, —$SO_2$N ($R^{10a}$)—, and —N($R^{10a}$)—$SO_2$—;

A is selected from the group consisting of: —$NR^{11c}R^{11d}$, —C(=$NR^{11c}$)$NR^{11a}R^{11b}$, —C(=$NR^{11e}R^{11f}$) $NR^{11a}R^{11b}$, —N($R^{11d}$)C(=$NR^{11c}$)$NR^{11a}R^{11b}$, —N($R^{11d}$)C(=$NR^{11c}$)$R^{11a}$, —N($R^{11c}$)$NR^{11a}R^{11b}$, —N($R^{11c}$)$OR^{11d}$, $C_{1-6}$alkyl, $C_{2-6}$alkenyl, pyridyl-oxide, pyridinyl, pyrrolidinyl, homopiperazinyl, piperazinyl and morpholinyl each optionally substituted with 1 to 3 $R^{11g}$;

each $R^{2a}$, $R^{4d}$, $R^9$ and $R^{11g}$ is a member independently selected from the group consisting of: H, halo, $C_{1-6}$alkyl, $C_{2-6}$alkenyl, $C_{2-6}$alkynyl, $C_{0-4}$alkyl$C_{3-8}$cycloalkyl, —$C_{1-4}$alkoxy, —O—$C_{0-2}$alkyl-$CF_3$, —$C_{0-2}$alkyl-$CF_3$, —$C_{0-2}$alkyl-CN, —$C_{0-2}$alkyl-$NO_2$, —$C_{0-2}$alkyl-$NR^{12a}R^{12b}$, —$C_{0-2}$alkyl-$SO_2NR^{12a}R^{12b}$, —$C_{0-2}$alkyl-$SO_2R^{12a}$, —$C_{0-2}$alkyl-$SOR^{12a}$, —$C_{0-2}$alkyl-$CF_3$, —$C_{0-2}$alkyl-$OR^{12a}$, —$C_{0-2}$alkyl-$SR^{12a}$, —O—$CH_2$—$CH_2$—$OR^{12a}$, —O—$CH_2$—$CO_2R^{12a}$, —$N(R^{12a})$—$CH_2$—$CH_2$—$OR^{12b}$, —$C_{0-2}$alkyl-C(O)$NR^{12a}R^{12b}$, —$C_{0-2}$alkyl-$CO_2R^{12a}$, —$C_{0-2}$alkyl-$N(R^{12a})$—C(O)$R^{12b}$, —$C_{0-2}$alkyl-$N(R^{12c})$—C(O)$NR^{12a}R^{12b}$, —$C_{0-2}$alkyl-C(=$NR^{12c}$)$NR^{12a}R^{12b}$, —$C_{0-2}$alkyl-C(=$NR^{12a}$)$R^{12b}$, —$C_{0-2}$alkyl-$N(R^{12d})$C(=$NR^{12c}$)$NR^{12a}R^{12b}$, —$C_{0-2}$alkyl-$N(R^{12a})$—$SO_2$—$R^{12b}$, =O, =S, =$NR^{12a}$, 5- or 6-membered aryl, 5- or 6-membered heteroaryl and 5- to 7-membered heterocyclyl, each of which is optionally substituted with a member independently selected from the group consisting of halo, $CF_3$, $OCF_3$, $SCF_3$, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —$CONR^{12a}R^{12b}$, =O, =S, —OH, —CN and —$NO_2$; wherein each heteroaryl or heterocyclyl comprises 1 to 4 heteroatoms, independently selected from the group consisting of N, O and S, each $R^{3a}$,$R^{3b}$,$R^{4a}$,$R^{4b}$,$R^{12a}$,$R^{12b}$,$R^{12c}$ and $R^{12d}$ are members independently selected from the group consisting of: H, $C_{1-6}$alkyl, $C_{2-6}$alkenyl, $C_{2-6}$alkynyl, $C_{0-4}$alkyl $C_{3-8}$cycloalkyl, $C_{0-4}$alkylaryl, $C_{0-4}$alkyl-heteroaryl, —$C_{0-6}$alkyl-$COC_{1-4}$alkyl, —$C_{0-6}$alkyl-$CO_2C_{1-4}$alkyl, —$C_{0-6}$alkyl-$SO_2$—$C_{1-4}$alkyl, —$C_{0-6}$alkyl-$SO_2$—N($C_{1-4}$alkyl, $C_{1-4}$alkyl), —$C_{0-6}$alkyl-N($C_{1-4}$alkyl, $C_{1-4}$alkyl) and —$C_{1-6}$alkyl-O—$C_{0-6}$alkyl, wherein 1-3 hydrogen atoms on the aryl or heteroaryl ring may be independently replaced with a member selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{4\text{-alkoxy}}$,—$CO_2H$, —$CO_2C_{1-4}$alkyl, —CON($C_{1-4}$alkyl, $C_{1-4}$alkyl), —OH, —CN and $NO_2$; or can be taken together with the nitrogen atom to which they are attached to form a 3-8 membered heterocyclyl group, comprising 1 to 4 heteroatoms selected from the group consisting of N, O and S, optionally substituted with 1 to 4 $R^{13}$ substituents selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —CON($C_{1-4}$alkyl, $C_{1-4}$alkyl), —OH, —CN and $NO_2$;

each $R^6$, $R^7$, $R^8$, $R^{10a}$ and $R^{10b}$ is a member independently selected from the group consisting of: hydrogen, $C_{1-6}$alkyl, $C_{2-6}$alkenyl, $C_{2-6}$alkynyl, $C_{3-8}$cycloalkyl and $C_{0-4}$alkyl$C_{3-8}$cycloalkyl, —$C_{0-6}$alkyl-aryl, heteraryl and —$C_{0-6}$alkyl-heteroaryl, or $R^4$ and $R^6$ can be taken together with the atoms to which they are attached to form a 5 to 12 membered heterocyclyl group; wherein each heterocyclyl is a 5 to 8 membered monocyclic ring or a 8-12 membered bicyclic ring, each comprising from 1 to 4 heteroatoms selected from the group consisting of O, N and S, and wherein 1 to 3 carbon or nitrogen atoms of aryl, heteroaryl and heterocyclyl are substituted with 1 to 3 $R^{4d}$ substituents;

each $R^{11a}$, $R^{11b}$, $R^{11c}$, $R^{11d}$, $R^{11e}$ and $R^{11f}$ are members independently selected from the group consisting of: H, $C_{1-6}$alkyl, $C_{2-6}$alkenyl, $C_{2-6}$alkynyl, $C_{0-4}$alkyl$C_{3-8}$cycloalkyl, $C_{0-4}$alkylaryl, $C_{0-4}$alkyl-heteroaryl, —$C_{0-6}$alkyl-$COC_{1-4}$alkyl, —$C_{0-6}$alkyl-$CO_2C_{1-4}$alkyl, —$C_{0-6}$alkyl-$SO_2$—$C_{1-4}$alkyl, —$C_{0-6}$alkyl-$SO_2$—$NR^{12a}R^{12b}$, —$C_{0-6}$alkyl-$NR^{12a}R^{12b}$ and —$C_{1-6}$alkyl-O—$C_{0-6}$alkyl, wherein 1-3 hydrogen atoms on the aryl or heteroaryl ring may be independently replaced with a member selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —CON($C_{1-4}$alkyl, $C_{1-4}$alkyl), —OH, —CN and $NO_2$; or each $R^{11a}$ and $R^{11b}$ can be taken together with the nitrogen atom to which they are attached to form a 3-8 membered heterocyclyl group, comprising 1 to 4 heteroatoms selected from the group consisting of N, O and S, optionally substituted with 1 to 4 $R^{13}$ substituents selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —CON($C_{1-4}$alkyl, $C_{1-4}$alkyl), =O, =S, —OH, —CN and $NO_2$; or each $R^{11e}$ and $R^{11f}$ can be taken together with the nitrogen atom to which they are attached to form a 3-8 membered heterocyclyl group, comprising 1 to 4 heteroatoms selected from the group consisting of N, O and S, optionally substituted with 1 to 4 $R^{13}$ substituents selected from the group consisting of halo, $C_{1-6}$alkyl, $C_{2-6}$alkenyl, $C_{2-6}$alkynyl, $C_{0-4}$alkyl$C_{3-8}$cycloalkyl, $C_{1-4}$alkoxy, —$CO_2H$, —$CO_2C_{1-4}$alkyl, —CON($C_{1-4}$alkyl , $C_{1-4}$alkyl), =O, =S, —OH, —CN and $NO_2$;

each subscript n1 and n2 is an integer of 0 to 1; and pharmaceutically acceptable salts, solvates, hydrates, and prodrugs thereof.

2. A compound of claim 1, wherein $R^1$ and $R^3$ is H.

3. A compound of claim 1, wherein $R^2$ is aryl, optionally substituted with 1 to 3 $R^{2a}$.

4. A compound of claim 3, wherein $R^2$ is thiophenyl.

5. A compound of claim 3, wherein $R^2$ is phenyl.

6. A compound of claim 4, wherein each optional substituent $R^{2a}$ is independently selected from the group consisting of halo and $C_{2-6}$alkynyl.

7. A compound of claim 6, wherein $R^{2a}$ is attached to the phenyl ring at a position para to the rest of the molecule.

8. A compound of claim 1, wherein $R^4$ and $R^5$ is a member independently selected from the group consisting of: hydrogen, —$C_{0-6}$alkyl-heteroaryl, —$C_{0-6}$alkyl-aryl and —$C_{2-6}$alkynyl, wherein each heterocyclyl is a 3 to 8 membered monocyclic ring or a 8-12 membered bicyclic ring, each comprising from 1 to 4 heteroatoms selected from the group consisting of O, N and S, and wherein 1 to 3 carbon or nitrogen atoms of aryl and heteroaryl are substituted with 1 to 3 $R^{4d}$ substituents.

9. A compound of claim 8, wherein $R^4$ is hydrogen and $R^5$ is a member independently selected from the group consisting of hydrogen, 2-thiophenyl, phenyl and 2-butynyl.

10. A compound of claim 1, wherein when $R^4$ and $R^5$ are different the carbon bearing $R^5$ has the R— configuration.

11. A compound of claim 1, wherein when $R^4$ and $R^5$ are different the carbon bearing $R^5$ has the S— configuration.

12. A compound of claim 1, wherein each $R^{4d}$ is a member independently selected from the group consisting of halogen, —$C_{1-6}$alkyl, —O—$C_{0-2}$alkyl-$CF_3$ and $C_{0-2}$alkyl-$OR^{12a}$; and $R^{12a}$ is $C_{1-6}$alkyl or $C_{0-4}$alkylaryl.

13. A compound of claim 1, wherein n1 is 0.

14. A compound of claim 1, wherein n1 is 1.

15. A compound of claim 1, wherein $R^6$ is H.

16. A compound of claim 15, wherein $R^4$ and $R^6$ are taken together with the atoms to which they are attached selected from the group having the formula:

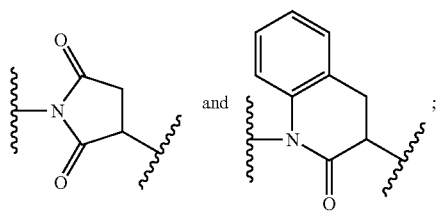

optionally substituted with 1 to 3 $R^{4d}$ substituents.

17. A compound of claim 1, wherein n2 is 0.

18. A compound of claim 1, n2 is 1.

19. A compound of claim 1, wherein each $R^7$ and $R^8$ is H.

20. A compound of claim 1, wherein D is aryl or heteromonocyclyl, wherein each heteromonocyclyl comprises from 5 to 7 ring atoms, 1 to 2 of which are N or O.

21. A compound of claim 20, wherein D is homopiperazinyl.

22. A compound of claim 20, wherein D is phenyl, piperidinyl or piperazinyl.

23. A compound of claim 1, wherein Q is selected from the group consisting of a direct bond, —C(=NH)—, C(O)— and —N($R^{10a}$); and $R^{10a}$ is $C_{1-6}$alkyl.

24. A compound of claim 23, wherein D is phenyl, piperidinyl or piperazinyl; and Q is attached to the phenyl, piperidinyl or piperazinyl ring at a position para to the rest of the molecule.

25. A compound of claim 1, wherein A is a member selected from the group consisting of pyridinyl, pyrrolidinyl, homopiperazinyl, piperazinyl and morpholinyl.

26. A compound of claim 1, wherein A is selected from the group consisting of: —$NR^{11c}R^{11d}$, —C(=$NR^{11c}$)$NR^{11a}R^{11b}$, —C(=$NR^{11e}R^{11f}$)$NR^{11a}R^{11b}$, —N($R^{11c}$)$NR^{11a}R^{11b}$, $C_{1-6}$alkyl and pyridyl-oxide.

27. A compound of claim 26, wherein each $R^{11a}$ and $R^{11b}$ is independently selected from the group consisting of H, $C_{1-6}$alkyl, $C_{2-6}$alkenyl, $C_{2-6}$alkynyl and —$C_{0-6}$alkyl-$NR^{12a}R^{12b}$ or each $R^{11a}$ and $R^{11b}$ can be taken together with the nitrogen atom to which they are attached to form a 3-8 membered heterocyclyl group, comprising 1 to 4 heteroatoms selected from the group consisting of N, O and S.

28. A compound of claim 1, wherein A-Q-D-$(CR^7R^8)_{n2}$—$NR^6_{n1}$ is selected from the group consisting of:

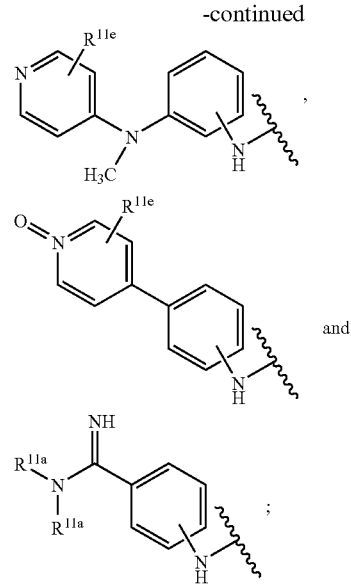

wherein the wavy line indicates the point of attachment to the rest of the molecule.

29. A compound of claim 1, wherein A-Q-D-$(CR^7R^8)_{n2}$—$NR^6_{n1}$ is selected from the group consisting of:

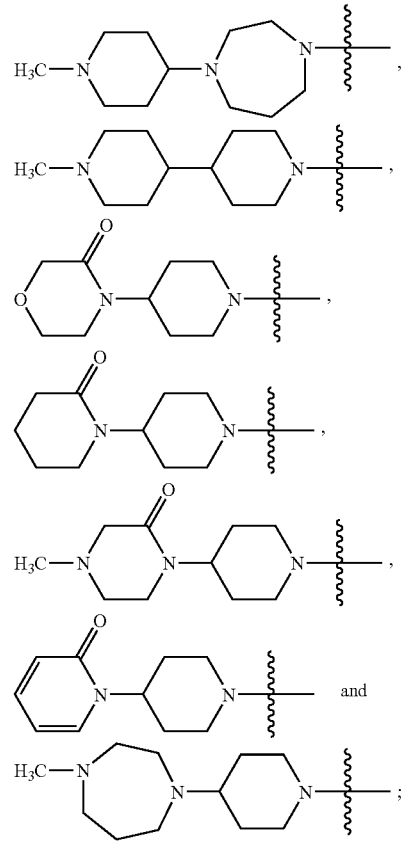

wherein the wavy line indicates the point of attachment to the rest of the molecule.

30. A compound of claim 28, wherein A-Q- is selected from the group consisting of:

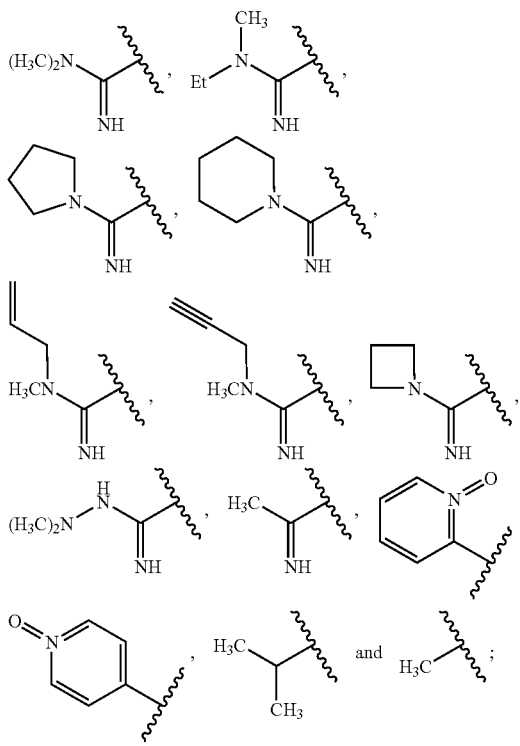

wherein the wavy line indicates the point of attachment to the rest of the molecule.

31. A compound of claim 28, wherein A-Q- is selected from the group consisting of:

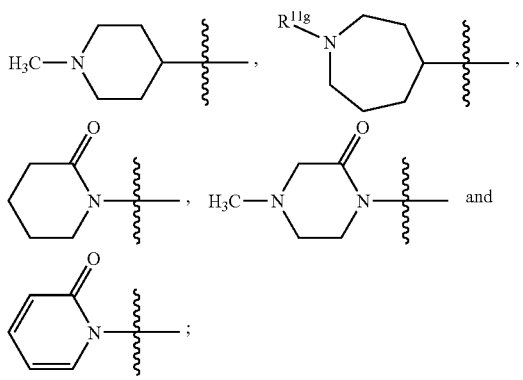

wherein the wavy line indicates the point of attachment to the rest of the molecule.

32. A compound of claim 28, wherein each $R^{11a}$ and $R^{11b}$ is independently selected from the group consisting of H, $C_{1-6}$alkyl, $C_{2-6}$alkenyl, $C_{2-6}$alkynyl and —$C_{0-6}$alkyl-$NR^{12a}R^{12b}$ or each $R^{11a}$ and $R^{11b}$ can be taken together with the nitrogen atom to which they are attached to form a 3-8 membered heterocyclyl group, comprising 1 to 4 heteroatoms selected from the group consisting of N, O and S.

33. A compound selected from the group consisting of: N-[4-(1-methyl-4,5-dihydro-1H-imidazol-2-yl)phenyl]-2-(4-chlorophenylaminocarbonylamino)-acetamide; N-[4-(1-methyl-4,5-dihydro-1H-imidazol-2-yl)phenyl]-2-isopropyl-2-(4-chlorophenylaminocarbonylamino)-acetamide; N-[4-(1-methyl-4,5-dihydro-1H-imidazol-2-yl)phenyl]-2-(1,1-dimethylethyl)-2-(4-chlorophenylaminocarbonylamino)-acetamide; N-[4-(1-methyl-4,5-dihydro-1H-imidazol-2-yl)phenyl]-2-(2,2-dimethylpropyl)-2-(4-chlorophenylaminocarbonylamino)-acetamide; N-[4-(1-methyl-4,5-dihydro-1H-imidazol-2-yl)phenyl]-2-benzyl-2-(4-chlorophenylaminocarbonylamino)-acetamide; N-[4-(1-methyl-4,5-dihydro-1H-imidazol-2-yl)phenyl]-2-indol-3-ylmethyl-2-(4-chlorophenylaminocarbonylamino)-acetamide; N-[4-(1-methyl-4,5-dihydro-1H-imidazol-2-yl)phenyl]-2-imidazol-4-ylmethyl-2-(4-chlorophenylaminocarbonylamino)-acetamide; N-[4-(1-methyl-4,5-dihydro-1H-imidazol-2-yl)phenyl]-2-(1-methyl-indol-3-ylmethyl)-2-(4-chlorophenylaminocarbonylamino)-acetamide; N-[4-(1-methyl-4,5-dihydro-1H-imidazol-2-yl)phenyl]-2-pyridin-3-yl-2-(4-chlorophenylaminocarbonylamino)-acetamide; N-[4-(1-methyl-4,5-dihydro-1H-imidazol-2-yl)phenyl]-2-(4-fluorophenyl)-2-(4-chlorophenylaminocarbonylamino)-acetamide; N-[4-(1-methyl-4,5-dihydro-1H-imidazol-2-yl)phenyl]-2-(2-fluorophenyl)-2-(4-chlorophenylaminocarbonylamino)-acetamide; N-[4-(1-methyl-4,5-dihydro-1H-imidazol-2-yl)phenyl]-2-(2-thienyl)-2-(4-chlorophenylaminocarbonylamino)-acetamide; N-[4-(1-methyl-4,5-dihydro-1H-imidazol-2-yl)phenyl]-2-(3-thienyl)-2-(4-chlorophenylaminocarbonylamino)-acetamide; N-[4-(1-methyl-4,5-dihydro-1H-imidazol-2-yl)phenyl]-2,2-diphenyl-2-(4-chlorophenylaminocarbonylamino)-acetamide; N-[4-(1-methyl-4,5-dihydro-1H-imidazol-2-yl)phenyl]-1-(4-chlorophenylaminocarbonylamino)-1-cyclopropanecarboxamide; N-[4-(1-methyl-4,5-dihydro-1H-imidazol-2-yl)phenyl]-2-phenyl-2-(4-chlorophenylaminocarbonylamino)-acetamide; N-[4-(1-methyl-4,5-dihydro-1H-imidazol-2-yl)phenyl]-2-(2-thienyl)-2-(4-fluorophenylaminocarbonylamino)-acetamide; N-[4-(1-methyl-4,5-dihydro-1H-imidazol-2-yl)phenyl]-2-(2-thienyl)-2-(4-ethynylphenylaminocarbonylamino)-acetamide; N-[4-(dimethylaminoimino)phenyl]-2-(2-thienyl)-2-(4-chlorophenylamino-carbonylamino)-acetamide; N-[4-(N-methyl-N-ethylaminoimino)phenyl]-2-(2-thienyl)-2-(4-chlorophenylaminocarbonylamino)-acetamide; N-[4-(pyrrolidinylimino)phenyl]-2-(2-thienyl)-2-(4-chlorophenylamino-carbonylamino)-acetamide; N-[4-(piperidinylimino)phenyl]-2-(2-thienyl)-2-(4-chlorophenylamino-carbonylamino)-acetamide; N-[4-(dimethylaminoimino)phenyl]-2-phenyl-2-(4-chlorophenylamino-carbonylamino)-acetamide; N-[4-(N-methyl-N-ethylaminoimino)phenyl]-2-phenyl-2-(4-chlorophenylaminocarbonylamino)-acetamide; N-[4-(methylaminoimino)phenyl]-2-phenyl-2-(4-chlorophenylamino-carbonylamino)-acetamide; N-[4-(N-methyl-N-allylaminoimino)phenyl]-2-phenyl-2-(4-chlorophenylaminocarbonylamino)-acetamide; N-[4-(N-methyl-N-propargylaminoimino)phenyl]-2-phenyl-2-(4-chlorophenylaminocarbonylamino)-acetamide; N-[4-(azetidin-1-ylimino)phenyl]-2-phenyl-2-(4-chlorophenylamino-carbonylamino)-acetamide; N-[4-(pyrrolidin-1-ylimino)phenyl]-2-phenyl-2-(4-chlorophenylamino-carbonylamino)-acetamide; N-[4-(1-methyl-4,5-dihydro-1H-imidazol-2-yl)phenyl]-2-(2-thienyl)-2-(4-bromophenylaminocarbonylamino)-acetamide; (2S) N-[4-(1-methyl-4,5-dihydro-1H-imidazol-2-yl)phenyl]-2-phenyl-2-(4-chlorophenylaminocarbonylamino)-acetamide; (2R) N-[4-

(1-methyl-4,5-dihydro-1H-imidazol-2-yl)phenyl]-2-phenyl-2-(4-chlorophenylaminocarbonylamino)-acetamide; N-[4-(dimethylaminoimino)-2-fluorophenyl]-2-phenyl-2-(4-chlorophenylaminocarbonylamino)-acetamide; N-[4-(N-methyl-N-ethylaminoimino)-2-fluorophenyl]-2-phenyl-2-(4-chlorophenylaminocarbonylamino)-acetamide; N-[4-(N-methyl-N-allylaminoimino)-2-fluorophenyl]-2-phenyl-2-(4-chlorophenylaminocarbonylamino)-acetamide; N-[4-(N-methyl-N-propargylaminoimino)-2-fluorophenyl]-2-phenyl-2-(4-chlorophenylaminocarbonylamino)-acetamide; N-(4-methylaminoimino-2-fluorophenyl)-2-phenyl-2-(4-chlorophenylamino-carbonylamino)-acetamide; N-[4-(pyrrolidin-1-ylimino)-2-fluorophenyl]-2-phenyl-2-(4-chlorophenylaminocarbonylamino)-acetamide; N-[4-(azetidin-1-ylimino)-2-fluorophenyl]-2-phenyl-2-(4-chlorophenylaminocarbonylamino)-acetamide; N-[4-(1-methyl-4,5-dihydro-1H-imidazol-2-yl)phenyl]-2-(2-fluorophenyl)-2-(4-bromophenylaminocarbonylamino)-acetamide; N-[4-(pyrrolidin-1-ylimino)phenyl]-2-(2-fluorophenyl)-2-(4-chlorophenylaminocarbonylamino)-acetamide; N-[4-(piperidin-1-ylimino)phenyl]-2-(2-fluorophenyl)-2-(4-chlorophenylaminocarbonylamino)-acetamide; N-[4-(dimethylaminoimino)phenyl]-2-(2-fluorophenyl)-2-(4-chlorophenylaminocarbonylamino)-acetamide; N-[4-(pyrrolidin-1-ylimino)phenyl]-2-(2-fluorophenyl)-2-(4-bromophenylaminocarbonylamino)-acetamide; N-[4-(piperidin-1-ylimino)phenyl]-2-(2-fluorophenyl)-2-(4-bromophenylaminocarbonylamino)-acetamide; N-[4-(dimethylaminoimino)phenyl]-2-(2-fluorophenyl)-2-(4-bromophenylaminocarbonylamino)-acetamide; N-[4-(2,2-dimethylhydrazinoimino)-2-fluorophenyl]-2-(2-fluorophenyl)-2-(4-chlorophenylaminocarbonylamino)-acetamide; N-[4-(pyridin-4-yl)phenyl]-2-(2-fluorophenyl)-2-(4-chlorophenylaminocarbonylamino)-acetamide; N-[4-(N-oxo-pyridin-4-yl)phenyl]-2-(2-fluorophenyl)-2-(4-chlorophenylaminocarbonylamino)-acetamide; N-[4-(N-oxo-pyridin-2-yl)phenyl]-2-(2-fluorophenyl)-2-(4-chlorophenylaminocarbonylamino)-acetamide; N-[4-(N-oxo-pyridin-2-yl)phenyl]-2-(2-fluorophenyl)-2-(4-bromophenylaminocarbonylamino)-acetamide; N-(piperidin-4-ylmethyl)-2-(2-fluorophenyl)-2-(4-chlorophenylaminocarbonylamino)-acetamide; N-[(N-acetimidyl-piperidin-4-yl)methyl]-2-(2-fluorophenyl)-2-(4-chlorophenylaminocarbonylamino)-acetamide; N-[4-(2-dimethylaminomethyl-phenyl)phenyl]-2-(2-fluorophenyl)-2-(4-chlorophenylaminocarbonylamino)-acetamide; N-[4-(2-dimethylaminomethyl-phenyl)-2-fluorophenyl]-2-(2-fluorophenyl)-2-(4-chlorophenylaminocarbonylamino)-acetamide; N-[4-(2-dimethylaminomethyl-phenyl)-2-fluorophenyl]-2-(2-fluorophenyl)-2-(4-bromophenylaminocarbonylamino)-acetamide; N-[4-(2-dimethylaminomethyl-imidazol-1-yl)-2-fluorophenyl]-2-(2-fluorophenyl)-2-(4-chlorophenylaminocarbonylamino)-acetamide; (2S) N-[4-(1-methyl-4,5-dihydro-1H-imidazol-2-yl)phenyl]-2-benzyloxy-carbonylmethyl-2-(4-chlorophenylaminocarbonylamino)-acetamide; (2S) N-[4-(1-methyl-4,5-dihydro-1H-imidazol-2-yl)phenyl]-2-carboxymethyl-2-(4-chlorophenylaminocarbonylamino)-acetamide; 2R) N-[4-(1-methyl-4,5-dihydro-1H-imidazol-2-yl)phenyl]-2-benzyloxycarbonylmethyl-2-(4-chlorophenylaminocarbonylamino)-acetamide; (2R) N-[4-(1-methyl-4,5-dihydro-1H-imidazol-2-yl)phenyl]-2-carboxymethyl-2-(4-chlorophenylaminocarbonylamino)-acetamide; N-[4-(1-methyl-4,5-dihydro-1H-imidazol-2-yl)phenyl]-2-dimethylaminocarbonylmethyl-2-(4-chlorophenylaminocarbonylamino)-acetamide; N-[4-(1-methyl-4,5-dihydro-1H-imidazol-2-yl)phenyl]-2-(piperidin-1-ylcarbonylmethyl)-2-(4-chlorophenylaminocarbonylamino)-acetamide; N-[4-(1-methyl-4,5-dihydro-1H-imidazol-2-yl)phenyl]-2-(morpholin-4-ylcarbonylmethyl)-2-(4-chlorophenylaminocarbonylamino)-acetamide; N-[4-(1-methyl-4,5-dihydro-1H-imidazol-2-yl)phenyl]-2-(pyrrolidin-1-yl-carbonylmethyl)-2-(4-chlorophenylaminocarbonylamino)-acetamide; N-[4-(1-methyl-4,5-dihydro-1H-imidazol-2-yl)phenyl]-2-[4-ethoxycarbonyl-piperidin-1-yl)carbonylmethyl]-2-(4-chlorophenylaminocarbonylamino)-acetamide; N-[4-(1-methyl-4,5-dihydro-1H-imidazol-2-yl)phenyl]-2-(homopiperidin-1-ylcarbonylmethyl)-2-(4-chlorophenylaminocarbonylamino)-acetamide; N-[4-(1-methyl-4,5-dihydro-1H-imidazol-2-yl)phenyl]-2-(benzylamino-carbonylmethyl)-2-(4-chlorophenylaminocarbonylamino)-acetamide; N-[4-(1-methyl-4,5-dihydro-1H-imidazol-2-yl)phenyl]-2-(methylamino-carbonylmethyl)-2-(4-chlorophenylaminocarbonylamino)-acetamide; N-[4-(1-methyl-4,5-dihydro-1H-imidazol-2-yl)phenyl]-2-(aminocarbonylmethyl)-2-(4-chlorophenylaminocarbonylamino)-acetamide; N-[4-(1-methyl-4,5-dihydro-1H-imidazol-2-yl)phenyl]-3-(4-chlorophenylaminocarbonylamino)-succinimide; N-[4-(1-methyl-4,5-dihydro-1H-imidazol-2-yl)phenyl]-2-(phenylamino-carbonylmethyl)-2-(4-chlorophenylaminocarbonylamino)-acetamide; N-[4-(1-methyl-4,5-dihydro-1H-imidazol-2-yl)phenyl]-2-(3-chlorophenyl)-2-(4-chlorophenylaminocarbonylamino)-acetamide; N-[4-(1-methyl-4,5-dihydro-1H-imidazol-2-yl)phenyl]-2-(2-chlorophenyl)-2-(4-chlorophenylaminocarbonylamino)-acetamide; N-[4-(1-methyl-4,5-dihydro-1H-imidazol-2-yl)phenyl]-2-(benzo-1,3-dioxl-5-yl)-2-(4-chlorophenylaminocarbonylamino)-acetamide; N-[4-(1-methyl-4,5-dihydro-1H-imidazol-2-yl)phenyl]-2-(2-bromophenyl)-2-(4-chlorophenylaminocarbonylamino)-acetamide; N-[4-(N-oxo-pyridin-4-yl)phenyl]-2-(2-bromophenyl)-2-(4-chlorophenylaminocarbonylamino)-acetamide; N-[4-(N-oxo-pyridin-2-yl)phenyl]-2-(2-bromophenyl)-2-(4-chlorophenylaminocarbonylamino)-acetamide; N-[4-(dimethylaminoimino)phenyl]-2-(2-bromophenyl)-2-(4-chlorophenylaminocarbonylamino)-acetamide; N-[4-(pyrrolidin-1-ylimino)phenyl]-2-(2-bromophenyl)-2-(4-chlorophenylaminocarbonylamino)-acetamide; N-(1-isopropylpiperidin-4-yl)-2-(2-bromophenyl)-2-(4-chlorophenylamino-carbonylamino)-acetamide; N-[4-(1-methylpiperidin-4-yl)piperazin-1-yl]-2-(2-bromophenyl)-2-(4-chlorophenylaminocarbonylamino)-acetamide; N-[4-(1-methyl-4,5-dihydro-1H-imidazol-2-yl)phenyl]-2-(2-methylphenyl)-2-(4-chlorophenylaminocarbonylamino)-acetamide; N-[4-(2-dimethylaminomethyl-imidazol-1-yl)-2-fluorophenyl]-2-(2-methylphenyl)-2-(4-chlorophenylaminocarbonylamino)-acetamide; N-[4-(dimethylaminoimino)phenyl]-2-(2-methylphenyl)-2-(4-chlorophenylaminocarbonylamino)-acetamide; N-[4-(pyrrolidin-1-ylimino)phenyl]-2-(2-methylphenyl)-2-(4-chlorophenylaminocarbonylamino)-acetamide; N-[4-(N-oxo-pyridin-2-yl)phenyl]-2-(2-methylphenyl)-2-(4-chlorophenylaminocarbonylamino)-acetamide; N-[4-(2-dimethylaminomethyl-phenyl)phenyl]-2-(2-methylphenyl)-2-(4-chlorophenylaminocarbonylamino)-acetamide; N-(1-isopropylpiperidin-4-yl)-2-(2-methylphenyl)-2-(4-chlorophenylamino-carbonylamino)-acetamide; N-[4-(1-methylpiperidin-4-yl)piperazin-1-yl]-2-(2-methylphenyl)-2-

(4-chlorophenylaminocarbonylamino)-acetamide; N-[4-(4-methyl-homopiperazinyl)phenyl]-2-(2-methylphenyl)-2-(4-chlorophenylaminocarbonylamino)-acetamide; N-[1-(pyridin-4-yl)piperidin-4-yl]methyl-2-(2-methylphenyl)-2-(4-chlorophenylaminocarbonylamino)-acetamide; N-[4-(pyrrolidin-1-ylcarbonyl)phenyl]-2-(2-methylphenyl)-2-(4-chlorophenylaminocarbonylamino)-acetamide; N-[4-(3-oxo-morpholin-4-yl)phenyl]-2-(2-methylphenyl)-2-(4-chlorophenylaminocarbonylamino)-acetamide; N-[4-(N-methyl-N-pyridin-4-yl-amino)phenyl]-2-(2-methylphenyl)-2-(4-chlorophenylaminocarbonylamino)-acetamide; N-[4-(thiazolidin-3-ylcarbonyl)phenyl]-2-(2-methylphenyl)-2-(4-chlorophenylaminocarbonylamino)-acetamide; N-[4-(oxazolidin-3-ylcarbonyl)phenyl]-2-(2-methylphenyl)-2-(4-chlorophenylaminocarbonylamino)-acetamide; N-[4-(N-oxo-pyridin-2-yl)phenyl]-2-(2-chlorophenyl)-2-(4-chlorophenylaminocarbonylamino)-acetamide; N-[4-(dimethylaminoimino)phenyl]-2-(2-chlorophenyl)-2-(4-chlorophenylaminocarbonylamino)-acetamide; N-[4-(pyrrolidin-1-ylimino)phenyl]-2-(2-chlorophenyl)-2-(4-chlorophenylaminocarbonylamino)-acetamide; N-[4-(4-methyl-homopiperazinyl)phenyl]-2-(2-chlorophenyl)-2-(4-chlorophenylaminocarbonylamino)-acetamide; N-(1-isopropylpiperidin-4-yl)-2-(2-chlorophenyl)-2-(4-chlorophenylamino-carbonylamino)-acetamide; N-[4-(1-methylpiperidin-4-yl)piperazin-1-yl]-2-(2-chlorophenyl)-2-(4-chlorophenylaminocarbonylamino)-acetamide; N-[1-(pyridin-4-yl)piperidin-4-yl]methyl-2-(2-chlorophenyl)-2-(4-chlorophenylaminocarbonylamino)-acetamide; N-[4-(1-methyl-4,5-dihydro-1H-imidazol-2-yl)phenyl]-2-(2-methoxyphenyl)-2-(4-chlorophenylaminocarbonylamino)-acetamide; N-[4-(N-oxo-pyridin-2-yl)phenyl]-2-(2-methoxyphenyl)-2-(4-chlorophenylaminocarbonylamino)-acetamide; N-[1-(pyridin-4-yl)piperidin-4-yl]methyl-2-(2-methoxyphenyl)-2-(4-chlorophenylaminocarbonylamino)-acetamide; N-[4-(1-methylpiperidin-4-yl)piperazin-1-yl]-2-(2-methoxyphenyl)-2-(4-chlorophenylaminocarbonylamino)-acetamide; N-(1-isopropylpiperidin-4-yl)-2-(2-methoxyphenyl)-2-(4-chlorophenylamino-carbonylamino)-acetamide; N-[4-(4-methyl-homopiperazinyl)phenyl]-2-(2-methoxyphenyl)-2-(4-chlorophenylaminocarbonylamino)-acetamide; N-[4-(dimethylaminoimino)phenyl]-2-(2-methoxyphenyl)-2-(4-chlorophenylaminocarbonylamino)-acetamide; N-[4-(pyrrolidin-1-ylimino)phenyl]-2-(2-methoxyphenyl)-2-(4-chlorophenylaminocarbonylamino)-acetamide; N-[4-(1-methyl-4,5-dihydro-1H-imidazol-2-yl)phenyl]-2-(2-iodophenyl)-2-(4-chlorophenylaminocarbonylamino)-acetamide; N-[4-(N-oxo-pyridin-2-yl)phenyl]-2-(2-iodophenyl)-2-(4-chlorophenylamino-carbonylamino)-acetamide; N-[4-(dimethylaminoimino)phenyl]-2-(2-iodophenyl)-2-(4-chlorophenylaminocarbonylamino)-acetamide; N-[4-(pyrrlidin-1-ylimino)phenyl]-2-(2-iodophenyl)-2-(4-chlorophenylaminocarbonylamino)-acetamide; N-[4-(1-methylpiperidin-4-yl)piperazin-1-yl]-2-(2-iodophenyl)-2-(4-chlorophenylaminocarbonylamino)-acetamide; N-[4-(1-methyl-4,5-dihydro-1H-imidazol-2-yl)phenyl]-2-(4-bromophenyl)-2-(4-chlorophenylaminocarbonylamino)-acetamide; N-[4-(1-methyl-4,5-dihydro-1H-imidazol-2-yl)phenyl]-2-(2-trifluoromethoxyphenyl)-2-(4-chlorophenylaminocarbonylamino)-acetamide; N-[4-(N-oxo-pyridin-2-yl)phenyl]-2-(2-trifluoromethoxyphenyl)-2-(4-chlorophenylaminocarbonylamino)-acetamide; N-[4-(1-methyl-4,5-dihydro-1H-imidazol-2-yl)phenyl]-2-(2-trifluoromethylthiophenyl)-2-(4-chlorophenylaminocarbonylamino)-acetamide; N-[4-(N-oxo-pyridin-2-yl)phenyl]-2-(2-trifluoromethylthiophenyl)-2-(4-chlorophenylaminocarbonylamino)-acetamide; N-[4-(1-methyl-4,5-dihydro-1H-imidazol-2-yl)phenyl]-2-(2-phenoxyphenyl)-2-(4-chlorophenylaminocarbonylamino)-acetamide; N-[4-(N-oxo-pyridin-2-yl)phenyl]-2-(2-phenoxyphenyl)-2-(4-chlorophenylaminocarbonylamino)-acetamide; N-[4-(N-oxo-pyridin-2-yl)phenyl]-2-(2-methythiophenyl)-2-(4-chlorophenylaminocarbonylamino)-acetamide; N-[4-(1-methylpiperidin-4-yl)piperazin-1-yl]-2-(2-fluorophenyl)-2-(4-chlorophenylaminocarbonylamino)-acetamide; N-[4-(1-methylpiperidin-4-yl)piperazin-1-yl]-2-phenyl-2-(4-chlorophenylaminocarbonylamino)-acetamide; N-[4-(1-methyl-4,5-dihydro-1H-imidazol-2-yl)phenyl]-2-propargyl-2-(4-chlorophenylaminocarbonylamino)-acetamide; N-[4-(1-methyl-4,5-dihydro-1H-imidazol-2-yl)phenyl]-2-(but-2-yn-1-yl)-2-(4-chlorophenylaminocarbonylamino)-acetamide; N-[4-(N-oxo-pyridin-2-yl)phenyl]-2-(but-2-yn-1-yl)-2-(4-chlorophenylaminocarbonylamino)-acetamide; N-[4-(1-methyl-4,5-dihydro-1H-imidazol-2-yl)phenyl]-2-allyl-2-(4-chlorophenylaminocarbonylamino)-acetamide; N-[4-(N-oxo-pyridin-2-yl)phenyl]-2-allyl-2-(4-chlorophenylaminocarbonylamino)-acetamide; 1-[4-(dimethylaminoimino)phenyl]-3-(4-chlorophenylaminocarbonylamino)-3,4-dihydroquinolin-2-one; 1-[4-(pyrrolidinylimino)phenyl]-3-(4-chlorophenylaminocarbonylamino)-3,4-dihydroquinolin-2-one; 1-[4-(1-methyl-4,5-dihyrdo-1H-imidazol-2-yl)phenyl]-3-(4-chlorophenylaminocarbonylamino)-3,4-dihydroquinolin-2-one; (2S) N-[4-(2-pyridon-1-yl)phenyl]-2-phenyl-2-(4-chlorophenylaminocarbonylamino)-acetamide; (2R) N-[4-(2-pyridon-1-yl)phenyl]-2-phenyl-2-(4-chlorophenylaminocarbonylamino)-acetamide; (2S) N-[4-(2-pyridon-1-yl)phenyl]-2-phenyl-2-(2-chlorothiophen-5-ylaminocarbonylamino)-acetamide; (2R) N-[4-(2-pyridon-1-yl)-2-fluorophenyl]-2-phenyl-2-(4-chlorophenylaminocarbonylamino)-acetamide; (2R) 4-(2-piperidinon-1-yl)piperidin-1-yl-2-phenyl-2-(4-chlorophenylaminocarbonylamino)-acetamide; (2R) 4-(3-morpholinon-4-yl)piperidin-1-yl-2-phenyl-2-(4-chlorophenylaminocarbonylamino)-acetamide; (2R) 4-(2-pyridon-1-yl)piperidin-1-yl-2-phenyl-2-(4-chlorophenylaminocarbonylamino)-acetamide; 4-(3-morpholinon-4-yl)piperidin-1-yl-2-(2-fluorophenyl)-2-(4-chlorophenylaminocarbonylamino)-acetamide; 4-(3-morpholinon-4-yl)piperidin-1-yl-2-(2-chlorophenyl)-2-(4-chlorophenylaminocarbonylamino)-acetamide; 4-(3-morpholinon-4-yl)piperidin-1-yl-2-(2-bromophenyl)-2-(4-chlorophenylaminocarbonylamino)-acetamide; 4-(3-morpholinon-4-yl)piperidin-1-yl-2-(2-methylphenyl)-2-(4-chlorophenylaminocarbonylamino)-acetamide; 4-(3-morpholinon-4-yl)piperidin-1-yl-2-(2-methoxyphenyl)-2-(4-chlorophenylaminocarbonylamino)-acetamide; 4-(2-piperidinon-1-yl)piperidin-1-yl-2-(2-fluorophenyl)-2-(4-chlorophenylaminocarbonylamino)-acetamide; 4-(2-piperidinon-1-yl)piperidin-1-yl-2-(2-methoxyphenyl)-2-(4-chlorophenylaminocarbonylamino)-acetamide; 4-(4-methyl-2-piperazinon-1-yl)piperidin-1-yl-2-(2-methoxyphenyl)-2-(4-chlorophenylaminocarbonylamino)-acetamide; 4-(homopiperidin-4-yl)piperazin-1-yl-2-(2-methoxyphenyl)-2-(4-chlorophenylaminocarbonylamino)-acetamide; 4-(1-methylhomopiperidin-4-yl)piperazin-1-yl-2-(2-methoxyphenyl)-2-(4-chlorophenylaminocarbonylamino)-acetamide; (2R) 4-(4-methylhomopiperazin-1-yl)piperidin-1-yl- 2-phenyl-2-(4-chlorophenylaminocarbonylamino)-acetamide; (2R) 4-(1-methylpiperidin-4-yl)piperidin-1-yl-2-phenyl-2-(4-chlorophenylaminocarbonylamino)-acetamide; and (2R) 4-(1-methylpiperidin-4-yl)homopiperazin-1-yl-2-phenyl-2-(4-chlorophenylaminocarbonylamino)-acetamide.

34. A composition comprising a pharmaceutically acceptable excipient and a compound of claim 1.

* * * * *